(12) United States Patent
Kim et al.

(10) Patent No.: US 11,378,572 B2
(45) Date of Patent: Jul. 5, 2022

(54) THERAPEUTIC AGENT FOR IMMUNE CELL MIGRATION-CAUSED DISEASE AND METHOD FOR SCREENING SAME

(71) Applicant: ZYMEDI CO., LTD., Incheon (KR)

(72) Inventors: Sunghoon Kim, Seoul (KR); Nam Hoon Kwon, Gyeonggi-do (KR); Jin Young Lee, Seoul (KR); Kun Ho Kim, Gyeonggi-do (KR)

(73) Assignee: Zymedi Co., Ltd., Incheon (KR)

( * ) Notice: Subject to any disclaimer, the term of this patent is extended or adjusted under 35 U.S.C. 154(b) by 0 days.

(21) Appl. No.: 16/716,085

(22) Filed: Dec. 16, 2019

(65) Prior Publication Data
US 2020/0141923 A1 May 7, 2020

Related U.S. Application Data

(63) Continuation of application No. PCT/KR2018/006820, filed on Jun. 18, 2018.

(30) Foreign Application Priority Data

Jun. 16, 2017 (KR) ........................ 10-2017-0076718

(51) Int. Cl.
*G01N 33/50* (2006.01)
*A61K 31/428* (2006.01)
*C07K 16/40* (2006.01)

(52) U.S. Cl.
CPC ....... *G01N 33/5029* (2013.01); *A61K 31/428* (2013.01); *C07K 16/40* (2013.01)

(58) Field of Classification Search
CPC ... G01N 33/5029; A61K 31/428; C07K 16/40
See application file for complete search history.

(56) References Cited

FOREIGN PATENT DOCUMENTS

KR      10-1453141 B1    10/2014
WO    WO 2011-153277 A2  12/2011

OTHER PUBLICATIONS

English Translation of International Search Report corresponding to International Patent Application No. PCT/KR2018/006820 dated Jan. 31, 2019.
NCBI Reference Sequence D32053.1 "mRNA for Lysyl tRNA Synthetase [*Homo sapiens*]," accessed Sep. 4, 1997.
Kim, "Chemical inhibition of prometastatic lysyl-tRNA synthetase-laminin receptor interaction," Nature Chemical Biology, vol. 10, No. 1 pp. 29-34 (2014).
Cho, "Characterization of the interaction between lysyl-tRNA synthetase and laminin receptor by NMR," FEBS Letters, vol. 588, No. 17, pp. 2851-2858 (2014).
NCBI Reference Sequence: AAH04132.1 "Lysyl-tRNA synthetase [*Homo sapiens*]," accessed Jul. 15, 2006.
International Preliminary Report on Patentability corresponding to International Patent Application No. PCT/KR2018/006820 dated Jun. 2, 2020.
English Translation of the Written Opinion of the International Searching Authority corresponding to International Patent Application No. PCT/KR2018/006820 dated Jan. 31, 2019.

*Primary Examiner* — J. E. Angell
(74) *Attorney, Agent, or Firm* — Jenkins, Wilson, Taylor & Hunt, P.A.

(57) ABSTRACT

The present invention relates to a therapeutic agent for immune cell migration-caused disease and a method for screening the same and, more particularly, to a pharmaceutical composition comprising a KRS inhibitor (or expression or activity inhibitor) as an effective ingredient for preventing or treating an immune cell migration-related disease, a method for controlling the migration of immune cells by regulating a level of KRS in immune cells, a cell membrane site-specific moiety level of KRS or the migration of KRS to the cell membrane, and a method for screening a therapeutic agent for immune cell migration-caused disease, using KRS. According to the present invention, the migration of immune cells can be controlled by means of KRS, which can find very useful applications in the prevention, alleviation, and treatment of immune cell migration-related disease.

5 Claims, 44 Drawing Sheets
(35 of 44 Drawing Sheet(s) Filed in Color)
Specification includes a Sequence Listing.

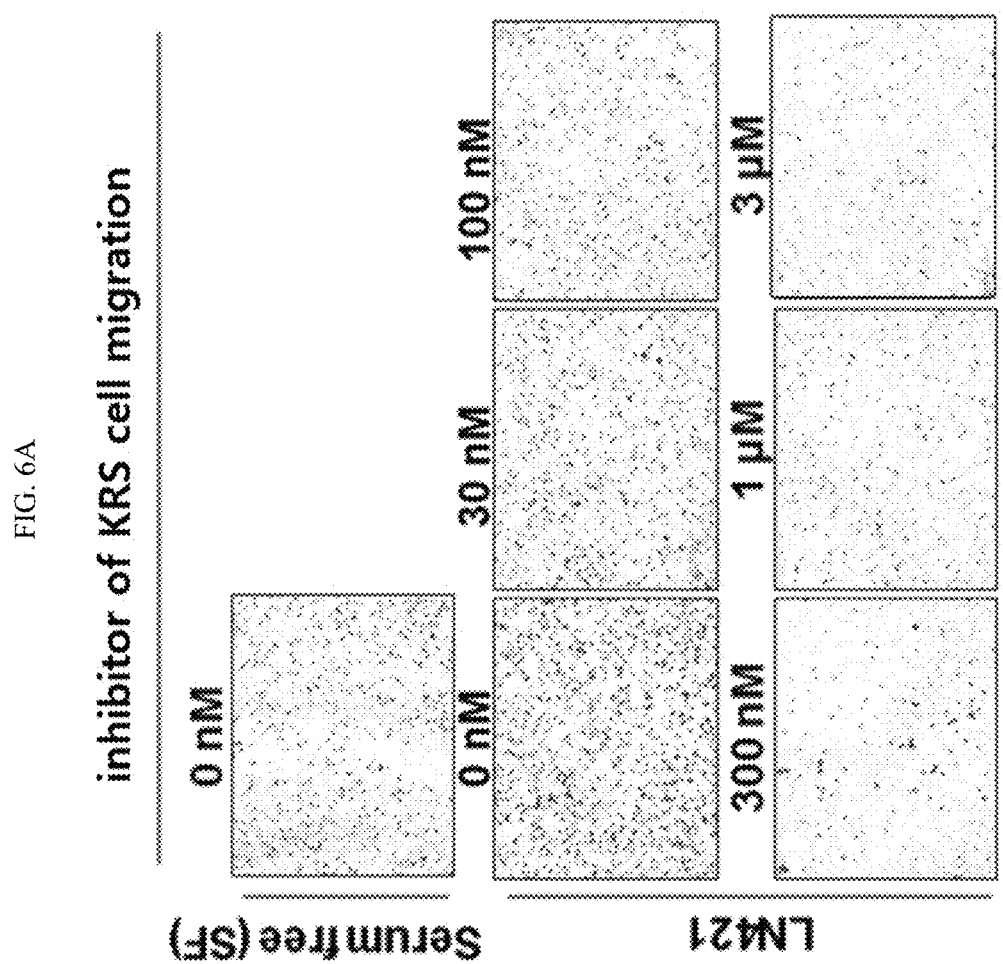

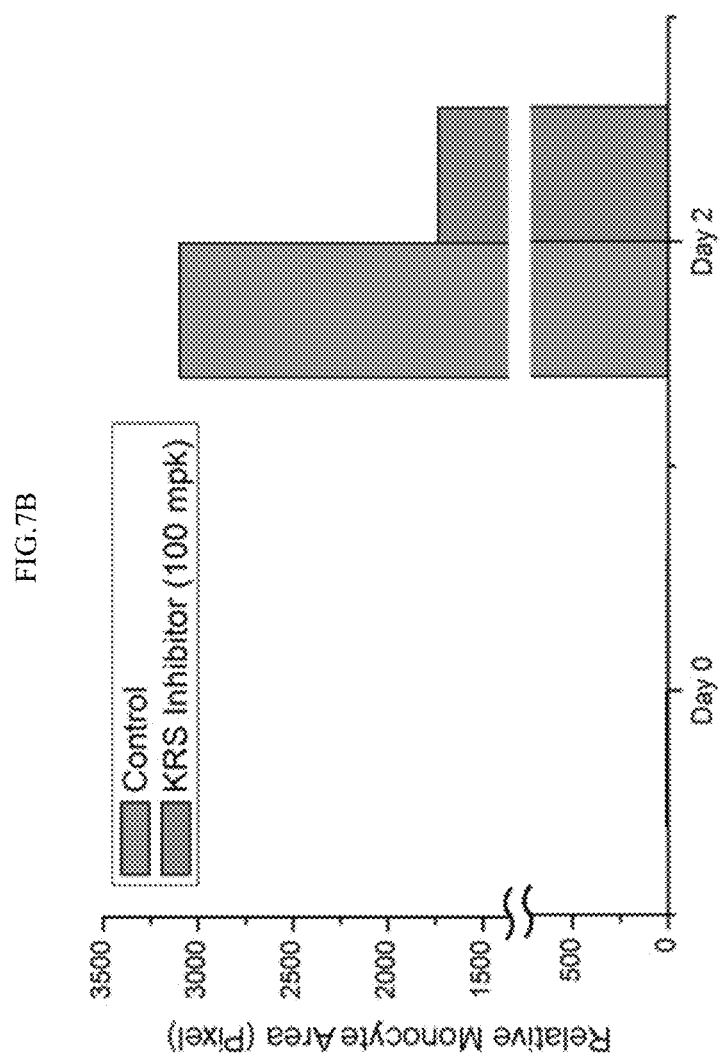

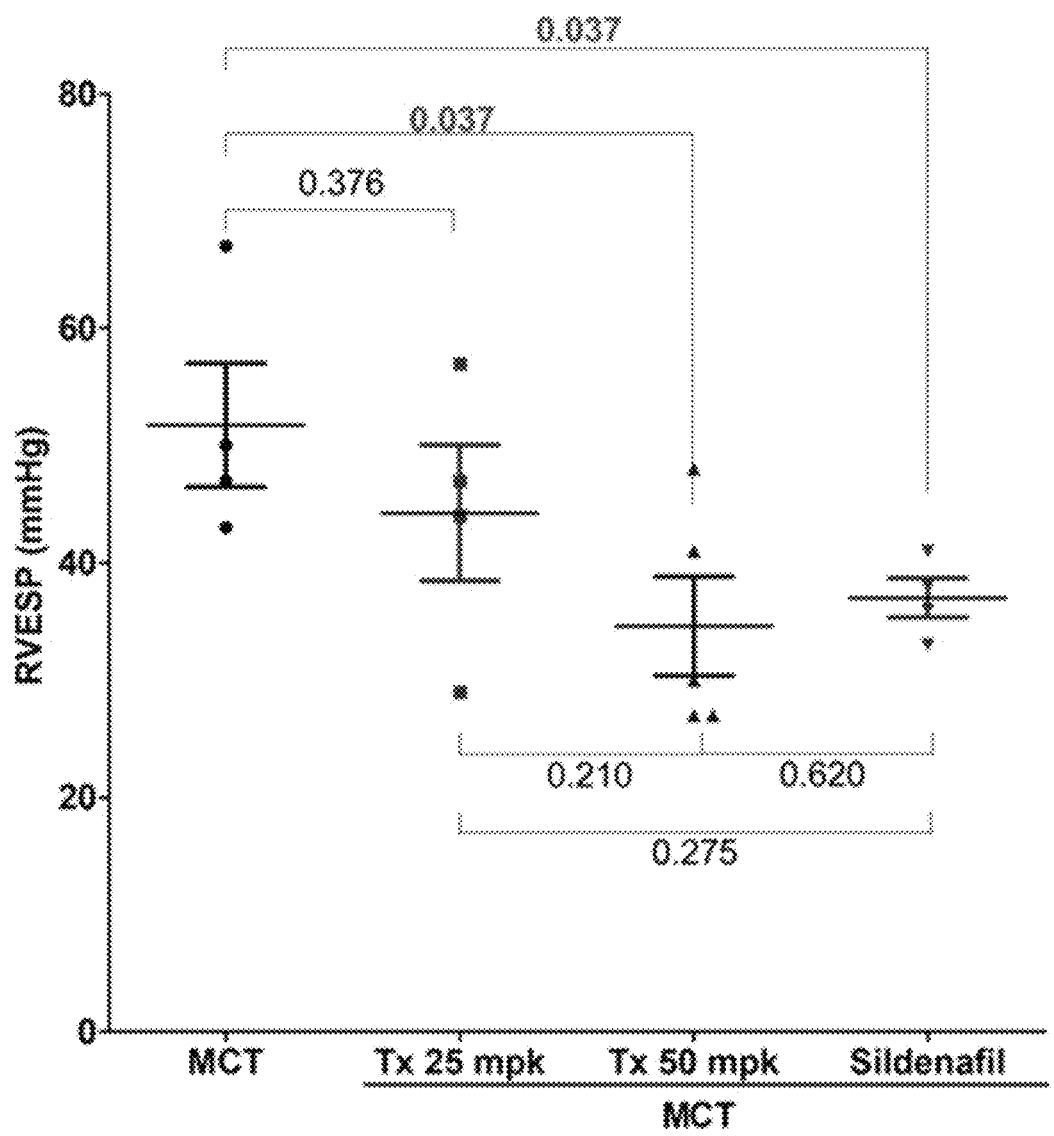

SEQUENCE LISTING

```
<160> NUMBER OF SEQ ID NOS: 24

<210> SEQ ID NO 1
<211> LENGTH: 597
<212> TYPE: PRT
<213> ORGANISM: Artificial Sequence
<220> FEATURE:
<223> OTHER INFORMATION: Amino acid sequence of Kyl-tRNA synthetase
      (KRS, Homo sapiens)_Genbank Accession No. NP_005539.1

<400> SEQUENCE: 1

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
                20                  25                  30

Val Ala Glu Lys Glu Ala Lys Gln Lys Glu Leu Ser Glu Lys Gln Leu
            35                  40                  45

Ser Gln Ala Thr Ala Ala Thr Asn His Thr Thr Asp Asn Gly Val
        50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
                100                 105                 110

Ser His Leu Gln Pro Gly Asp His Leu Thr Asp Ile Thr Leu Lys Val
            115                 120                 125

Ala Gly Arg Ile His Ala Lys Arg Ala Ser Gly Gly Lys Leu Ile Phe
        130                 135                 140

Tyr Asp Leu Arg Gly Glu Gly Val Lys Leu Gln Val Met Ala Asn Ser
145                 150                 155                 160

Arg Asn Tyr Lys Ser Glu Glu Glu Phe Ile His Ile Asn Asn Lys Leu
                165                 170                 175

Arg Arg Gly Asp Ile Ile Gly Val Gln Gly Asn Pro Gly Lys Thr Lys
                180                 185                 190

Lys Gly Glu Leu Ser Ile Ile Pro Tyr Glu Ile Thr Leu Leu Ser Pro
            195                 200                 205

Cys Leu His Met Leu Pro His Leu His Phe Gly Leu Lys Asp Lys Glu
        210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255
```

Phe Leu Asp Glu Leu Gly Phe Leu Glu Ile Glu Thr Pro Met Met Asn
              260                 265                 270

Ile Ile Pro Gly Gly Ala Val Ala Lys Pro Phe Ile Thr Tyr His Asn
          275                 280                 285

Glu Leu Asp Met Asn Leu Tyr Met Arg Ile Ala Pro Glu Leu Tyr His
          290                 295                 300

Lys Met Leu Val Val Gly Gly Ile Asp Arg Val Tyr Glu Ile Gly Arg
305                 310                 315                 320

Gln Phe Arg Asn Glu Gly Ile Asp Leu Thr His Asn Pro Glu Phe Thr
              325                 330                 335

Thr Cys Glu Phe Tyr Met Ala Tyr Ala Asp Tyr His Asp Leu Met Glu
              340                 345                 350

Ile Thr Glu Lys Met Val Ser Gly Met Val Lys His Ile Thr Gly Ser
          355                 360                 365

Tyr Lys Val Thr Tyr His Pro Asp Gly Pro Glu Gly Gln Ala Tyr Asp
          370                 375                 380

Val Asp Phe Thr Pro Pro Phe Arg Arg Ile Asn Met Val Glu Glu Leu
385                 390                 395                 400

Glu Lys Ala Leu Gly Met Lys Leu Pro Glu Thr Asn Leu Phe Glu Thr
              405                 410                 415

Glu Glu Thr Arg Lys Ile Leu Asp Asp Ile Cys Val Ala Lys Ala Val
              420                 425                 430

Glu Cys Pro Pro Pro Arg Thr Thr Ala Arg Leu Leu Asp Lys Leu Val
              435                 440                 445

Gly Glu Phe Leu Glu Val Thr Cys Ile Asn Pro Thr Phe Ile Cys Asp
450                 455                 460

His Pro Gln Ile Met Ser Pro Leu Ala Lys Trp His Arg Ser Lys Glu
465                 470                 475                 480

Gly Leu Thr Glu Arg Phe Glu Leu Phe Val Met Lys Lys Glu Ile Cys
              485                 490                 495

Asn Ala Tyr Thr Glu Leu Asn Asp Pro Met Arg Gln Arg Gln Leu Phe
          500                 505                 510

Glu Glu Gln Ala Lys Ala Lys Ala Ala Gly Asp Asp Glu Ala Met Phe
      515                 520                 525

Ile Asp Glu Asn Phe Cys Thr Ala Leu Glu Tyr Gly Leu Pro Pro Thr
530                 535                 540

Ala Gly Trp Gly Met Gly Ile Asp Arg Val Ala Met Phe Leu Thr Asp
545                 550                 555                 560

Ser Asn Asn Ile Lys Glu Val Leu Leu Phe Pro Ala Met Lys Pro Glu
              565                 570                 575

Asp Lys Lys Glu Asn Val Ala Thr Thr Asp Thr Leu Glu Ser Thr Thr
              580                 585                 590

Val Gly Thr Ser Val
          595

<210> SEQ ID NO 2
<211> LENGTH: 1794
<212> TYPE: DNA
<213> ORGANISM: Artificial Sequence
<220> FEATURE:
<223> OTHER INFORMATION: DNA sequence of KRS

<400> SEQUENCE: 2
atggcggccg tgcaggcggc cgaggtgaaa gtggatggca gcgagccgaa actgagcaag      60
aatgagctga agagacgcct gaaagctgag aagaaagtag cagagaagga ggccaaacag     120

```
aaagagctca gtgagaaaca gctaagccaa gccactgctg ctgccaccaa ccacaccact    180
gataatggtg tgggtcctga ggaagagagc gtggacccaa atcaatacta caaaatccgc    240
agtcaagcaa ttcatcagct gaaggtcaat ggggaagacc catacccaca caagttccat    300
gtagacatct cactcactga cttcatccaa aaatatagtc acctgcagcc tggggatcac    360
ctgactgaca tcaccttaaa ggtggcaggt aggatccatg ccaaaagagc ttctggggga    420
aagctcatct tctatgatct tcgaggagag ggggtgaagt tgcaagtcat ggccaattcc    480
agaaattata aatcagaaga agaatttatt catattaata caaactgcg tcggggagac    540 ataattggag ttcaggggaa tcctggtaaa accaagaagg gtgagctgag catcattccg    600
tatgagatca cactgctgtc tccctgtttg catatgttac ctcatcttca ctttgggctc    660
aaagacaagg aaacaaggta tcgccagaga tacttggact tgatcctgaa tgactttgtg    720
aggcagaaat ttatcatccg ctctaagatc atcacatata taagaagttt cttagatgag    780
ctgggattcc tagagattga aactcccatg atgaacatca tcccagggg agccgtggcc    840 aagcctttca tcacttatca caacgagctg acatgaact tatatatgag aattgctcca    900
gaactctatc ataagatgct tgtggttggt ggcatcgacc gggtttatga aattggacgc    960
cagttccgga atgaggggat tgatttgacg cacaatcctg agttcaccac ctgtgagttc   1020
tacatggcct atgcagacta tcacgatctc atggaaatca cggagaagat ggtttcaggg   1080
atggtgaagc atattacagg cagttacaag gtcacctacc acccagatgg cccagagggc   1140
caagcctacg atgttgactt cacccccacc ttccggcgaa tcaacatggt agaagagctt   1200
gagaaagccc tggggatgaa gctgccagaa acgaacctct ttgaaactga agaaactcgc   1260
aaaattcttg atgatatctg tgtggcaaaa gctgttgaat gccctccacc tcggaccaca   1320
gccaggctcc ttgacaagct tgttggggag ttcctggaag tgacttgcat caatcctaca   1380
ttcatctgtg atcacccaca gataatgagc cctttggcta atggcaccg ctctaaagag   1440 ggtctgactg agcgctttga gctgtttgtc atgaagaaag agatatgcaa tgcgtatact   1500
gagctgaatg atcccatgcg gcagcggcag cttttttgaag aacaggccaa ggccaaggct   1560
gcaggtgatg atgaggccat gttcatagat gaaaacttct gtactgccct ggaatatggg   1620 ctgccccca cagctggctg gggcatgggc attgatcgag tcgccatgtt tctcacggac   1680
tccaacaaca tcaaggaagt acttctgttt cctgccatga aacccgaaga caagaaggag   1740
aatgtagcaa ccactgatac actggaaagc acaacagttg gcacttctgt ctag          1794
```

<210> SEQ ID NO 3
<211> LENGTH: 1176
<212> TYPE: PRT
<213> ORGANISM: Artificial Sequence
<220> FEATURE:
<223> OTHER INFORMATION: Amino acid sequence of LRS (Homo sapiens)

<400> SEQUENCE: 3

```
Met Ala Glu Arg Lys Gly Thr Ala Lys Val Asp Phe Leu Lys Lys Ile
1               5                   10                  15

Glu Lys Glu Ile Gln Gln Lys Trp Asp Thr Glu Arg Val Phe Glu Val
            20                  25                  30

Asn Ala Ser Asn Leu Glu Lys Gln Thr Ser Lys Gly Lys Tyr Phe Val
        35                  40                  45

Thr Phe Pro Tyr Pro Tyr Met Asn Gly Arg Leu His Leu Gly His Thr
    50                  55                  60
```

```
Phe Ser Leu Ser Lys Cys Glu Phe Ala Val Gly Tyr Gln Arg Leu Lys
 65                  70                  75                  80

Gly Lys Cys Cys Leu Phe Pro Phe Gly Leu His Cys Thr Gly Met Pro
                 85                  90                  95

Ile Lys Ala Cys Ala Asp Lys Leu Lys Arg Glu Ile Glu Leu Tyr Gly
            100                 105                 110

Cys Pro Pro Asp Phe Pro Asp Glu Glu Glu Glu Glu Glu Glu Thr Ser
        115                 120                 125

Val Lys Thr Glu Asp Ile Ile Ile Lys Asp Lys Ala Lys Gly Lys Lys
    130                 135                 140

Ser Lys Ala Ala Ala Lys Ala Gly Ser Ser Lys Tyr Gln Trp Gly Ile
145                 150                 155                 160

Met Lys Ser Leu Gly Leu Ser Asp Glu Glu Ile Val Lys Phe Ser Glu
                165                 170                 175

Ala Glu His Trp Leu Asp Tyr Phe Pro Pro Leu Ala Ile Gln Asp Leu
            180                 185                 190

Lys Arg Met Gly Leu Lys Val Asp Trp Arg Arg Ser Phe Ile Thr Thr
        195                 200                 205

Asp Val Asn Pro Tyr Tyr Asp Ser Phe Val Arg Trp Gln Phe Leu Thr
    210                 215                 220

Leu Arg Glu Arg Asn Lys Ile Lys Phe Gly Lys Arg Tyr Thr Ile Tyr
225                 230                 235                 240

Ser Pro Lys Asp Gly Gln Pro Cys Met Asp His Asp Arg Gln Thr Gly
                245                 250                 255

Glu Gly Val Gly Pro Gln Glu Tyr Thr Leu Leu Lys Leu Lys Val Leu
            260                 265                 270

Glu Pro Tyr Pro Ser Lys Leu Ser Gly Leu Lys Gly Lys Asn Ile Phe
        275                 280                 285

Leu Val Ala Ala Thr Leu Arg Pro Glu Thr Met Phe Gly Gln Thr Asn
    290                 295                 300

Cys Trp Val Arg Pro Asp Met Lys Tyr Ile Gly Phe Glu Thr Val Asn
305                 310                 315                 320

Gly Asp Ile Phe Ile Cys Thr Gln Lys Ala Ala Arg Asn Met Ser Tyr
                325                 330                 335

Gln Gly Phe Thr Lys Asp Asn Gly Val Val Pro Val Val Lys Glu Leu
            340                 345                 350

Met Gly Glu Glu Ile Leu Gly Ala Ser Leu Ser Ala Pro Leu Thr Ser
        355                 360                 365

Tyr Lys Val Ile Tyr Val Leu Pro Met Leu Thr Ile Lys Glu Asp Lys
    370                 375                 380

Gly Thr Gly Val Val Thr Ser Val Pro Ser Asp Ser Pro Asp Asp Ile
385                 390                 395                 400

Ala Ala Leu Arg Asp Leu Lys Lys Lys Gln Ala Leu Arg Ala Lys Tyr
                405                 410                 415

Gly Ile Arg Asp Asp Met Val Leu Pro Phe Glu Pro Val Pro Val Ile
            420                 425                 430

Glu Ile Pro Gly Phe Gly Asn Leu Ser Ala Val Thr Ile Cys Asp Glu
        435                 440                 445

Leu Lys Ile Gln Ser Gln Asn Asp Arg Glu Lys Leu Ala Glu Ala Lys
    450                 455                 460

Glu Lys Ile Tyr Leu Lys Gly Phe Tyr Glu Gly Ile Met Leu Val Asp
465                 470                 475                 480

Gly Phe Lys Gly Gln Lys Val Gln Asp Val Lys Lys Thr Ile Gln Lys
```

```
                485                 490                 495
Lys Met Ile Asp Ala Gly Asp Ala Leu Ile Tyr Met Glu Pro Glu Lys
                500                 505                 510

Gln Val Met Ser Arg Ser Ser Asp Glu Cys Val Val Ala Leu Cys Asp
                515                 520                 525

Gln Trp Tyr Leu Asp Tyr Gly Glu Glu Asn Trp Lys Lys Gln Thr Ser
                530                 535                 540

Gln Cys Leu Lys Asn Leu Glu Thr Phe Cys Glu Glu Thr Arg Arg Asn
545                 550                 555                 560

Phe Glu Ala Thr Leu Gly Trp Leu Gln Glu His Ala Cys Ser Arg Thr
                565                 570                 575

Tyr Gly Leu Gly Thr His Leu Pro Trp Asp Glu Gln Trp Leu Ile Glu
                580                 585                 590

Ser Leu Ser Asp Ser Thr Ile Tyr Met Ala Phe Tyr Thr Val Ala His
                595                 600                 605

Leu Leu Gln Gly Gly Asn Leu His Gly Gln Ala Glu Ser Pro Leu Gly
                610                 615                 620

Ile Arg Pro Gln Gln Met Thr Lys Glu Val Trp Asp Tyr Val Phe Phe
625                 630                 635                 640

Lys Glu Ala Pro Phe Pro Lys Thr Gln Ile Ala Lys Glu Lys Leu Asp
                645                 650                 655

Gln Leu Lys Gln Glu Phe Glu Phe Trp Tyr Pro Val Asp Leu Arg Val
                660                 665                 670

Ser Gly Lys Asp Leu Val Pro Asn His Leu Ser Tyr Tyr Leu Tyr Asn
                675                 680                 685

His Val Ala Met Trp Pro Glu Gln Ser Asp Lys Trp Pro Thr Ala Val
                690                 695                 700

Arg Ala Asn Gly His Leu Leu Leu Asn Ser Glu Lys Met Ser Lys Ser
705                 710                 715                 720

Thr Gly Asn Phe Leu Thr Leu Thr Gln Ala Ile Asp Lys Phe Ser Ala
                725                 730                 735

Asp Gly Met Arg Leu Ala Leu Ala Asp Ala Gly Asp Thr Val Glu Asp
                740                 745                 750

Ala Asn Phe Val Glu Ala Met Ala Asp Ala Gly Ile Leu Arg Leu Tyr
                755                 760                 765

Thr Trp Val Glu Trp Val Lys Glu Met Val Ala Asn Trp Asp Ser Leu
                770                 775                 780

Arg Ser Gly Pro Ala Ser Thr Phe Asn Asp Arg Val Phe Ala Ser Glu
785                 790                 795                 800

Leu Asn Ala Gly Ile Ile Lys Thr Asp Gln Asn Tyr Glu Lys Met Met
                805                 810                 815

Phe Lys Glu Ala Leu Lys Thr Gly Phe Phe Glu Phe Gln Ala Ala Lys
                820                 825                 830

Asp Lys Tyr Arg Glu Leu Ala Val Glu Gly Met His Arg Glu Leu Val
                835                 840                 845

Phe Arg Phe Ile Glu Val Gln Thr Leu Leu Leu Ala Pro Phe Cys Pro
                850                 855                 860

His Leu Cys Glu His Ile Trp Thr Leu Leu Gly Lys Pro Asp Ser Ile
865                 870                 875                 880

Met Asn Ala Ser Trp Pro Val Ala Gly Pro Val Asn Glu Val Leu Ile
                885                 890                 895

His Ser Ser Gln Tyr Leu Met Glu Val Thr His Asp Leu Arg Leu Arg
                900                 905                 910
```

-continued

```
Leu Lys Asn Tyr Met Met Pro Ala Lys Gly Lys Lys Thr Asp Lys Gln
        915                 920                 925

Pro Leu Gln Lys Pro Ser His Cys Thr Ile Tyr Val Ala Lys Asn Tyr
    930                 935                 940

Pro Pro Trp Gln His Thr Thr Leu Ser Val Leu Arg Lys His Phe Glu
945                 950                 955                 960

Ala Asn Asn Gly Lys Leu Pro Asp Asn Lys Val Ile Ala Ser Glu Leu
                965                 970                 975

Gly Ser Met Pro Glu Leu Lys Lys Tyr Met Lys Lys Val Met Pro Phe
            980                 985                 990

Val Ala Met Ile Lys Glu Asn Leu Glu Lys Met Gly Pro Arg Ile Leu
        995                1000                1005

Asp Leu Gln Leu Glu Phe Asp Glu Lys Ala Val Leu Met Glu Asn
   1010                1015                1020

Ile Val Tyr Leu Thr Asn Ser Leu Glu Leu Glu His Ile Glu Val
   1025                1030                1035

Lys Phe Ala Ser Glu Ala Glu Asp Lys Ile Arg Glu Asp Cys Cys
   1040                1045                1050

Pro Gly Lys Pro Leu Asn Val Phe Arg Ile Glu Pro Gly Val Ser
   1055                1060                1065

Val Ser Leu Val Asn Pro Gln Pro Ser Asn Gly His Phe Ser Thr
   1070                1075                1080

Lys Ile Glu Ile Arg Gln Gly Asp Asn Cys Asp Ser Ile Ile Arg
   1085                1090                1095

Arg Leu Met Lys Met Asn Arg Gly Ile Lys Asp Leu Ser Lys Val
   1100                1105                1110

Lys Leu Met Arg Phe Asp Asp Pro Leu Leu Gly Pro Arg Arg Val
   1115                1120                1125

Pro Val Leu Gly Lys Glu Tyr Thr Glu Lys Thr Pro Ile Ser Glu
   1130                1135                1140

His Ala Val Phe Asn Val Asp Leu Met Ser Lys Lys Ile His Leu
   1145                1150                1155

Thr Glu Asn Gly Ile Arg Val Asp Ile Gly Asp Thr Ile Ile Tyr
   1160                1165                1170

Leu Val His
   1175

<210> SEQ ID NO 4
<211> LENGTH: 1823
<212> TYPE: PRT
<213> ORGANISM: Artificial Sequence
<220> FEATURE:
<223> OTHER INFORMATION: Amino acid sequence of Laminin subunit alpha-4
      (Homo sapiens)

<400> SEQUENCE: 4

Met Ala Leu Ser Ser Ala Trp Arg Ser Val Leu Pro Leu Trp Leu Leu
1               5                  10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
```

```
                65                  70                  75                  80
        Pro Cys Asp Cys Asn Gly Asn Ser Asn Glu Cys Leu Asp Gly Ser Gly
                            85                  90                  95
        Tyr Cys Val His Cys Gln Arg Asn Thr Thr Gly Glu His Cys Glu Lys
                            100                 105                 110
        Cys Leu Asp Gly Tyr Ile Gly Asp Ser Ile Arg Gly Ala Pro Gln Phe
                            115                 120                 125
        Cys Gln Pro Cys Pro Cys Pro Leu Pro His Leu Ala Asn Phe Ala Glu
                    130                 135                 140
        Ser Cys Tyr Arg Lys Asn Gly Ala Val Arg Cys Ile Cys Asn Glu Asn
        145                 150                 155                 160
        Tyr Ala Gly Pro Asn Cys Glu Arg Cys Ala Pro Gly Tyr Tyr Gly Asn
                            165                 170                 175
        Pro Leu Leu Ile Gly Ser Thr Cys Lys Lys Cys Asp Cys Ser Gly Asn
                    180                 185                 190
        Ser Asp Pro Asn Leu Ile Phe Glu Asp Cys Asp Glu Val Thr Gly Gln
                    195                 200                 205
        Cys Arg Asn Cys Leu Arg Asn Thr Thr Gly Phe Lys Cys Glu Arg Cys
                210                 215                 220
        Ala Pro Gly Tyr Tyr Gly Asp Ala Arg Ile Ala Lys Asn Cys Ala Val
        225                 230                 235                 240
        Cys Asn Cys Gly Gly Gly Pro Cys Asp Ser Val Thr Gly Glu Cys Leu
                            245                 250                 255
        Glu Glu Gly Phe Glu Pro Pro Thr Gly Met Asp Cys Pro Thr Ile Ser
                    260                 265                 270
        Cys Asp Lys Cys Val Trp Asp Leu Thr Asp Ala Leu Arg Leu Ala Ala
                275                 280                 285
        Leu Ser Ile Glu Glu Gly Lys Ser Gly Val Leu Ser Val Ser Ser Gly
                    290                 295                 300
        Ala Ala Ala His Arg His Val Asn Glu Ile Asn Ala Thr Ile Tyr Leu
        305                 310                 315                 320
        Leu Lys Thr Lys Leu Ser Glu Arg Glu Asn Gln Tyr Ala Leu Arg Lys
                            325                 330                 335
        Ile Gln Ile Asn Asn Ala Glu Asn Thr Met Lys Ser Leu Leu Ser Asp
                            340                 345                 350
        Val Glu Leu Val Glu Lys Glu Asn Gln Ala Ser Arg Lys Gly Gln
                    355                 360                 365
        Leu Val Gln Lys Glu Ser Met Asp Thr Ile Asn His Ala Ser Gln Leu
                    370                 375                 380
        Val Glu Gln Ala His Asp Met Arg Asp Lys Ile Gln Glu Ile Asn Asn
        385                 390                 395                 400
        Lys Met Leu Tyr Tyr Gly Glu Glu His Glu Leu Ser Pro Lys Glu Ile
                            405                 410                 415
        Ser Glu Lys Leu Val Leu Ala Gln Lys Met Leu Glu Glu Ile Arg Ser
                    420                 425                 430
        Arg Gln Pro Phe Phe Thr Gln Arg Glu Leu Val Asp Glu Glu Ala Asp
                    435                 440                 445
        Glu Ala Tyr Glu Leu Leu Ser Gln Ala Glu Ser Trp Gln Arg Leu His
                    450                 455                 460
        Asn Glu Thr Arg Thr Leu Phe Pro Val Val Leu Glu Gln Leu Asp Asp
        465                 470                 475                 480
        Tyr Asn Ala Lys Leu Ser Asp Leu Gln Glu Ala Leu Asp Gln Ala Leu
                            485                 490                 495
```

```
Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
        515                 520                 525

Val Val Asn Met Ser Leu Ser Thr Ser Ala Asp Ser Leu Thr Thr Pro
    530                 535                 540

Arg Leu Thr Leu Ser Glu Leu Asp Asp Ile Ile Lys Asn Ala Ser Gly
545                 550                 555                 560

Ile Tyr Ala Glu Ile Asp Gly Ala Lys Ser Glu Leu Gln Val Lys Leu
                565                 570                 575

Ser Asn Leu Ser Asn Leu Ser His Asp Leu Val Gln Glu Ala Ile Asp
            580                 585                 590

His Ala Gln Asp Leu Gln Gln Glu Ala Asn Glu Leu Ser Arg Lys Leu
        595                 600                 605

His Ser Ser Asp Met Asn Gly Leu Val Gln Lys Ala Leu Asp Ala Ser
    610                 615                 620

Asn Val Tyr Glu Asn Ile Val Asn Tyr Val Ser Glu Ala Asn Glu Thr
625                 630                 635                 640

Ala Glu Phe Ala Leu Asn Thr Thr Asp Arg Ile Tyr Asp Ala Val Ser
                645                 650                 655

Gly Ile Asp Thr Gln Ile Ile Tyr His Lys Asp Glu Ser Glu Asn Leu
            660                 665                 670

Leu Asn Gln Ala Arg Glu Leu Gln Ala Lys Ala Glu Ser Ser Ser Asp
        675                 680                 685

Glu Ala Val Ala Asp Thr Ser Arg Arg Val Gly Gly Ala Leu Ala Arg
    690                 695                 700

Lys Ser Ala Leu Lys Thr Arg Leu Ser Asp Ala Val Lys Gln Leu Gln
705                 710                 715                 720

Ala Ala Glu Arg Gly Asp Ala Gln Gln Arg Leu Gly Gln Ser Arg Leu
                725                 730                 735

Ile Thr Glu Glu Ala Asn Arg Thr Thr Met Glu Val Gln Gln Ala Thr
            740                 745                 750

Ala Pro Met Ala Asn Asn Leu Thr Asn Trp Ser Gln Asn Leu Gln His
        755                 760                 765

Phe Asp Ser Ser Ala Tyr Asn Thr Ala Val Asn Ser Ala Arg Asp Ala
    770                 775                 780

Val Arg Asn Leu Thr Glu Val Val Pro Gln Leu Leu Asp Gln Leu Arg
785                 790                 795                 800

Thr Val Glu Gln Lys Arg Pro Ala Ser Asn Val Ser Ala Ser Ile Gln
                805                 810                 815

Arg Ile Arg Glu Leu Ile Ala Gln Thr Arg Ser Val Ala Ser Lys Ile
            820                 825                 830

Gln Val Ser Met Met Phe Asp Gly Gln Ser Ala Val Glu Val His Ser
        835                 840                 845

Arg Thr Ser Met Asp Asp Leu Lys Ala Phe Thr Ser Leu Ser Leu Tyr
    850                 855                 860

Met Lys Pro Pro Val Lys Arg Pro Glu Leu Thr Glu Thr Ala Asp Gln
865                 870                 875                 880

Phe Ile Leu Tyr Leu Gly Ser Lys Asn Ala Lys Lys Glu Tyr Met Gly
                885                 890                 895

Leu Ala Ile Lys Asn Asp Asn Leu Val Tyr Val Tyr Asn Leu Gly Thr
            900                 905                 910
```

```
Lys Asp Val Glu Ile Pro Leu Asp Ser Lys Pro Val Ser Ser Trp Pro
            915                 920                 925

Ala Tyr Phe Ser Ile Val Lys Ile Glu Arg Val Gly Lys His Gly Lys
        930                 935                 940

Val Phe Leu Thr Val Pro Ser Leu Ser Ser Thr Ala Glu Glu Lys Phe
945                 950                 955                 960

Ile Lys Lys Gly Glu Phe Ser Gly Asp Asp Ser Leu Leu Asp Leu Asp
                965                 970                 975

Pro Glu Asp Thr Val Phe Tyr Val Gly Val Pro Ser Asn Phe Lys
            980                 985                 990

Leu Pro Thr Ser Leu Asn Leu Pro Gly Phe Val Gly Cys Leu Glu Leu
        995                 1000                1005

Ala Thr Leu Asn Asn Asp Val Ile Ser Leu Tyr Asn Phe Lys His
    1010                1015                1020

Ile Tyr Asn Met Asp Pro Ser Thr Ser Val Pro Cys Ala Arg Asp
    1025                1030                1035

Lys Leu Ala Phe Thr Gln Ser Arg Ala Ala Ser Tyr Phe Phe Asp
    1040                1045                1050

Gly Ser Gly Tyr Ala Val Val Arg Asp Ile Thr Arg Arg Gly Lys
    1055                1060                1065

Phe Gly Gln Val Thr Arg Phe Asp Ile Glu Val Arg Thr Pro Ala
    1070                1075                1080

Asp Asn Gly Leu Ile Leu Leu Met Val Asn Gly Ser Met Phe Phe
    1085                1090                1095

Arg Leu Glu Met Arg Asn Gly Tyr Leu His Val Phe Tyr Asp Phe
    1100                1105                1110

Gly Phe Ser Gly Gly Pro Val His Leu Glu Asp Thr Leu Lys Lys
    1115                1120                1125

Ala Gln Ile Asn Asp Ala Lys Tyr His Glu Ile Ser Ile Ile Tyr
    1130                1135                1140

His Asn Asp Lys Lys Met Ile Leu Val Val Asp Arg Arg His Val
    1145                1150                1155

Lys Ser Met Asp Asn Glu Lys Met Lys Ile Pro Phe Thr Asp Ile
    1160                1165                1170

Tyr Ile Gly Gly Ala Pro Pro Glu Ile Leu Gln Ser Arg Ala Leu
    1175                1180                1185

Arg Ala His Leu Pro Leu Asp Ile Asn Phe Arg Gly Cys Met Lys
    1190                1195                1200

Gly Phe Gln Phe Gln Lys Lys Asp Phe Asn Leu Leu Glu Gln Thr
    1205                1210                1215

Glu Thr Leu Gly Val Gly Tyr Gly Cys Pro Glu Asp Ser Leu Ile
    1220                1225                1230

Ser Arg Arg Ala Tyr Phe Asn Gly Gln Ser Phe Ile Ala Ser Ile
    1235                1240                1245

Gln Lys Ile Ser Phe Phe Asp Gly Phe Glu Gly Gly Phe Asn Phe
    1250                1255                1260

Arg Thr Leu Gln Pro Asn Gly Leu Leu Phe Tyr Tyr Ala Ser Gly
    1265                1270                1275

Ser Asp Val Phe Ser Ile Ser Leu Asp Asn Gly Thr Val Ile Met
    1280                1285                1290

Asp Val Lys Gly Ile Lys Val Gln Ser Val Asp Lys Gln Tyr Asn
    1295                1300                1305

Asp Gly Leu Ser His Phe Val Ile Ser Ser Val Ser Pro Thr Arg
```

```
                1310                1315                1320
Tyr Glu Leu Ile Val Asp Lys Ser Arg Val Gly Ser Lys Asn Pro
    1325                1330                1335
Thr Lys Gly Lys Ile Glu Gln Thr Gln Ala Ser Glu Lys Lys Phe
    1340                1345                1350
Tyr Phe Gly Gly Ser Pro Ile Ser Ala Gln Tyr Ala Asn Phe Thr
    1355                1360                1365
Gly Cys Ile Ser Asn Ala Tyr Phe Thr Arg Val Asp Arg Asp Val
    1370                1375                1380
Glu Val Glu Asp Phe Gln Arg Tyr Thr Glu Lys Val His Thr Ser
    1385                1390                1395
Leu Tyr Glu Cys Pro Ile Glu Ser Ser Pro Leu Phe Leu Leu His
    1400                1405                1410
Lys Lys Gly Lys Asn Leu Ser Lys Pro Lys Ala Ser Gln Asn Lys
    1415                1420                1425
Lys Gly Gly Lys Ser Lys Asp Ala Pro Ser Trp Asp Pro Val Ala
    1430                1435                1440
Leu Lys Leu Pro Glu Arg Asn Thr Pro Arg Asn Ser His Cys His
    1445                1450                1455
Leu Ser Asn Ser Pro Arg Ala Ile Glu His Ala Tyr Gln Tyr Gly
    1460                1465                1470
Gly Thr Ala Asn Ser Arg Gln Glu Phe Glu His Leu Lys Gly Asp
    1475                1480                1485
Phe Gly Ala Lys Ser Gln Phe Ser Ile Arg Leu Arg Thr Arg Ser
    1490                1495                1500
Ser His Gly Met Ile Phe Tyr Val Ser Asp Gln Glu Glu Asn Asp
    1505                1510                1515
Phe Met Thr Leu Phe Leu Ala His Gly Arg Leu Val Tyr Met Phe
    1520                1525                1530
Asn Val Gly His Lys Lys Leu Lys Ile Arg Ser Gln Glu Lys Tyr
    1535                1540                1545
Asn Asp Gly Leu Trp His Asp Val Ile Phe Ile Arg Glu Arg Ser
    1550                1555                1560
Ser Gly Arg Leu Val Ile Asp Gly Leu Arg Val Leu Glu Glu Ser
    1565                1570                1575
Leu Pro Pro Thr Glu Ala Thr Trp Lys Ile Lys Gly Pro Ile Tyr
    1580                1585                1590
Leu Gly Gly Val Ala Pro Gly Lys Ala Val Lys Asn Val Gln Ile
    1595                1600                1605
Asn Ser Ile Tyr Ser Phe Ser Gly Cys Leu Ser Asn Leu Gln Leu
    1610                1615                1620
Asn Gly Ala Ser Ile Thr Ser Ala Ser Gln Thr Phe Ser Val Thr
    1625                1630                1635
Pro Cys Phe Glu Gly Pro Met Glu Thr Gly Thr Tyr Phe Ser Thr
    1640                1645                1650
Glu Gly Gly Tyr Val Val Leu Asp Glu Ser Phe Asn Ile Gly Leu
    1655                1660                1665
Lys Phe Glu Ile Ala Phe Glu Val Arg Pro Arg Ser Ser Ser Gly
    1670                1675                1680
Thr Leu Val His Gly His Ser Val Asn Gly Glu Tyr Leu Asn Val
    1685                1690                1695
His Met Lys Asn Gly Gln Val Ile Val Lys Val Asn Asn Gly Ile
    1700                1705                1710
```

| Arg | Asp | Phe | Ser | Thr | Ser | Val | Thr | Pro | Lys | Gln | Ser | Leu | Cys | Asp |
|-----|-----|-----|-----|-----|-----|-----|-----|-----|-----|-----|-----|-----|-----|-----|
| 1715 | | | | | 1720 | | | | 1725 | | | | | |

| Gly | Arg | Trp | His | Arg | Ile | Thr | Val | Ile | Arg | Asp | Ser | Asn | Val | Val |
| 1730 | | | | | 1735 | | | | 1740 | | | | | |

| Gln | Leu | Asp | Val | Asp | Ser | Glu | Val | Asn | His | Val | Val | Gly | Pro | Leu |
| 1745 | | | | | 1750 | | | | 1755 | | | | | |

| Asn | Pro | Lys | Pro | Ile | Asp | His | Arg | Glu | Pro | Val | Phe | Val | Gly | Gly |
| 1760 | | | | | 1765 | | | | 1770 | | | | | |

| Val | Pro | Glu | Ser | Leu | Leu | Thr | Pro | Arg | Leu | Ala | Pro | Ser | Lys | Pro |
| 1775 | | | | | 1780 | | | | 1785 | | | | | |

| Phe | Thr | Gly | Cys | Ile | Arg | His | Phe | Val | Ile | Asp | Gly | His | Pro | Val |
| 1790 | | | | | 1795 | | | | 1800 | | | | | |

| Ser | Phe | Ser | Lys | Ala | Ala | Leu | Val | Ser | Gly | Ala | Val | Ser | Ile | Asn |
| 1805 | | | | | 1810 | | | | 1815 | | | | | |

| Ser | Cys | Pro | Ala | Ala |
| 1820 | | | | |

<210> SEQ ID NO 5
<211> LENGTH: 5472
<212> TYPE: DNA
<213> ORGANISM: Artificial Sequence
<220> FEATURE:
<223> OTHER INFORMATION: DNA sequence of Laminin subunit alpha-4 (Homo sapiens)

<400> SEQUENCE: 5

| | | | | | |
|---|---|---|---|---|---|
| atggctttga | gctcagcctg | gcgctcggtt | ctgcctctgt | ggctcctctg | gagcgctgcc | 60 |
| tgctcccgcg | ccgcgtccgg | ggacgacaac | gcttttcctt | ttgacattga | agggagctca | 120 |
| gcggttggca | ggcaagaccc | gcctgagacg | agcgaacccc | gcgtggctct | gggacgcctg | 180 |
| ccgcctgcgg | ccgagaaatg | caatgctgga | ttctttcaca | ccctgtcggg | agaatgtgtg | 240 |
| ccctgcgact | gtaatggcaa | ttccaacgag | tgtttggacg | gctcaggata | ctgtgtgcac | 300 |
| tgccagcgga | acacaacagg | agagcactgt | gaaaagtgtc | tggatggtta | tatcggagat | 360 |
| tccatcaggg | gagcacccca | attctgccag | ccgtgccccc | tgtcccctgc | ccacttggcc | 420 |
| aattttgcag | aatcctgcta | taggaaaaat | ggagctgttc | ggtgcatttg | taacgaaaat | 480 |
| tatgctggac | taactgtgaa | agatgtgctc | cccggttact | atggaaaccc | cttactcatt | 540 |
| ggaagcacct | gtaagaaatg | tgactgcagt | ggaaattcag | atcccaacct | gatctttgaa | 600 |
| gattgtgatg | aagtcactgg | ccagtgtagg | aattgcttac | gcaacaccac | cggattcaag | 660 |
| tgtgaacgtt | gcgctcctgg | ctactatggg | gacgccagga | tagccaagaa | ctgtgcagtg | 720 |
| tgcaactgcg | ggggaggccc | catgtgacagt | gtaaccggag | aatgcttgga | agaaggtttt | 780 |
| gaaccccta | caggcatgga | ctgcccaacc | ataagctgtg | ataagtgcgt | ctgggaccTg | 840 |
| actgatgacc | tgcggttagc | agcgctctcc | atcgaggaag | gcaaatccgg | ggtgctgagc | 900 |
| gtatcctctg | gggccgccgc | tcataggcac | gtgaatgaaa | tcaacgccac | catctacctc | 960 |
| ctcaaaacaa | aattgtcaga | aagagaaaac | caatacgccc | taagaaagat | acaaatcaac | 1020 |
| aatgctgaga | cacgatgaa | aagccttctg | tctgacgtag | aggaattagt | tgaaaaggaa | 1080 |
| aatcaagcct | ccagaaaagg | acaacttgtt | cagaaggaaa | gcatggacac | cattaaccac | 1140 |
| gcaagtcagc | tggtagagca | agcccatgat | atgagggata | aatccaaga | gatcaacaac | 1200 |
| aagatgctct | attatggga | agagcatgaa | cttagcccca | aggaaatctc | tgagaagctg | 1260 |
| gtgttggccc | agaagatgct | tgaagagatt | agaagccgtc | aaccattttt | cacccaacgg | 1320 |

```
gagctcgtgg atgaggaggc agatgaggct tacgaactac tgagccaggc tgagagctgg    1380
cagcggctgc acaatgagac ccgcactctg tttcctgtcg tcctggagca gctggatgac    1440
tacaatgcta agttgtcaga tctccaggaa gcacttgacc aggcccttaa ctatgtcagg    1500
gatgccgaag acatgaacag ggccacagca gccaggcagc gggaccatga aaacaacag     1560 gaaagagtga gggaacaaat ggaagtggtg aacatgtctc tgagcacatc tgcggactct    1620
ctgacaacac ctcgtctaac tctttcagaa cttgatgata taataaagaa tgcgtcaggg    1680
atttatgcag aaatagatgg agccaaaagt gaactacaag taaaactatc taacctaagt    1740
aacctcagcc atgatttagt ccaagaagct attgaccatg cacaggacct tcaacaagaa    1800
gctaatgaat tgagcaggaa gttgcacagt tcagatatga acgggctggt acagaaggct    1860
ttggatgcat caaatgtcta tgaaaatatt gttaattatg ttagtgaagc caatgaaaca    1920
gcagaatttg ctttgaacac cactgaccga atttatgatg cggtgagtgg gattgatact    1980
caaatcattt accataaaga tgaaagtgag aacctcctca atcaagccag agaactgcaa    2040
gcaaaggcag agtctagcag tgatgaagca gtggctgaca ctagcaggcg tgtgggtgga    2100
gccctagcaa ggaaaagtgc ccttaaaacc agactcagtg atgccgttaa gcaactacaa    2160
gcagcagaga gagggatgc ccagcagcgc ctggggcagt ctagactgat caccgaggaa     2220
gccaacagga cgacgatgga ggtgcagcag gccactgccc ccatggccaa caatctaacc    2280
aactggtcac agaatcttca acattttgac tcttctgctt acaacactgc agtgaactct    2340
gctagggatg cagtaagaaa tctgaccgag gttgtccctc agctcctgga tcagcttcgt    2400
acggttgagc agaagcgacc tgcaagcaac gtttctgcca gcatccagag gatccgagag    2460
ctcattgctc agaccagaag tgttgccagc aagatccaag tctccatgat gtttgatggc    2520
cagtcagctg tggaagtgca ctcgagaacc agtatggatg acttaaaggc cttcacgtct    2580
ctgagcctgt acatgaaacc ccctgtgaag cggccggaac tgaccgagac tgcagatcag    2640
tttatcctgt acctcggaag caaaaacgcc aaaaaagagt atatgggtct tgcaatcaaa    2700
aatgataatc tggtatacgt ctataatttg ggaactaaag atgtggagat tcccctggac    2760
tccaagcccg tcagttcctg gcctgcttac ttcagcattg tcaagattga aagggtggga    2820
aaacatggaa aggtgttttt aacagtcccg agtctaagta gcacagcaga ggaaaagttc    2880
attaaaaagg gggaattttc gggagatgac tctctgctgg acctggaccc tgaggacaca    2940
gtgttttatg ttggtggagt gccttccaac ttcaagctcc ctaccagctt aaacctgcct    3000
ggctttgttg gctgcctgga actggccact ttgaataatg atgtgatcag cttgtacaac    3060
tttaagcaca tctataatat ggaccccctcc acatcagtgc catgtgcccg agataagctg    3120
gccttcactc agagtcgggc tgccagttac ttcttcgatg gctccggtta tgccgtggtg    3180
agagacatca aaggagagg gaaatttggt caggtgactc gctttgacat agaagttcga    3240
acaccagctg acaacggcct tattctcctg atggtcaatg aagtatgtt tttcagactg     3300 gaaatgcgca atggttacct acatgtgttc tatgattttg gattcagcgg tggccctgtg    3360
catcttgaag atacgttaaa gaaagctcaa attaatgatg caaaatacca tgagatctca    3420
atcatttacc acaatgataa gaaaatgatc ttggtagttg acagaaggca tgtcaagagc    3480
atggataatg aaaagatgaa aatacctttt acagatatat acattggagg agctcctcca    3540
gaaatcttac aatccaggggc cctcagcaca caccttcccc tagatatcaa cttcaggaga    3600
tgcatgaagg gcttccagtt ccaaaagaag gacttcaatt tactggagca gacagaaacc    3660
```

```
ctgggagttg gttatggatg cccagaagac tcacttatat ctcgcagagc atatttcaat    3720
ggacagagct tcattgcttc aattcagaaa atatctttct ttgatggctt tgaaggaggt    3780
tttaatttcc gaacattaca accaaatggg ttactattct attatgcttc agggtcagac    3840
gtgttctcca tctcactgga taatggtact gtcatcatgg atgtaaaggg aatcaaagtt    3900
cagtcagtag ataagcagta caatgatggg ctgtcccact cgtcattag ctctgtctca     3960 cccacaagat atgaactgat agtagataaa gcagagttg ggagtaagaa tcctaccaaa     4020
gggaaaatag aacagacaca agcaagtgaa aagaagtttt acttcggtgg ctcaccaatc    4080
agtgctcagt atgctaattt cactggctgc ataagtaatg cctactttac agggtggat    4140 agagatgtgg aggttgaaga tttccaacgg tatactgaaa aggtccacac ttctctttat    4200
gagtgtccca ttgagtcttc accattgttt ctcctccata aaaaggaaa aaatttatcc     4260 aagcctaaag caagtcagaa taaaagggga gggaaaagta aagatgcacc ttcatgggat    4320
cctgttgctc tgaaactccc agagcggaat actccaagaa actctcattg ccaccttcc     4380 aacagcccta gagcaataga gcacgcctat caatatggag aacagccaa cagccgccaa    4440 gagtttgaac acttaaaagg agattttggt gccaaatctc agttttccat tcgtctgaga    4500
actcgttcct cccatggcat gatcttctat gtctcagatc aagaagagaa tgacttcatg    4560
actctatttt tggcccatgg ccgcttggtt tacatgttta atgttggtca caaaaactg     4620 aagattagaa gccaggagaa atacaatgat ggcctgtggc atgatgtgat atttattcga    4680
gaaaggagca gtggccgact ggtaattgat ggtctccgag tcctagaaga aagtcttcct    4740
cctactgaag ctacctggaa aatcaagggt cccatttatt tgggaggtgt ggctcctgga    4800
aaggctgtga aaaatgttca gattaactcc atctacagtt ttagtggctg tctcagcaat    4860
ctccagctca atggggcctc catcacctct gcttctcaga cattcagtgt gacccccttgc   4920 tttgaaggcc ccatggaaac aggaacttac tttttcaacag aaggaggata cgtggttcta    4980
gatgaatctt tcaatattgg attgaagttt gaaattgcat ttgaagtccg tcccagaagc    5040
agttccggaa ccctggtcca cggccacagt gtcaatgggg agtacctaaa tgttcacatg    5100
aaaaatggac aggtcatagt gaaagtcaat aatggcatca gagatttttc cacctcagtt    5160
acacccaagc agagtctctg tgatggcaga tggcacagaa ttacagttat tagagattct    5220
aatgtggttc agttggatgt ggactctgaa gtgaaccatg tggttggacc cctgaatcca    5280
aaaccaattg atcacaggga gcctgtgttt gttggaggtg ttccagaatc tctactgaca    5340
ccacgcttgg ccccccagcaa acccttcaca ggctgcatac gccactttgt gattgatgga    5400
cacccagtga gcttcagtaa agcagccctg gtcagcggcg ccgtaagcat caactcctgt    5460
ccagcagcct ga                                                        5472
```

<210> SEQ ID NO 6
<211> LENGTH: 1798
<212> TYPE: PRT
<213> ORGANISM: Artificial Sequence
<220> FEATURE:
<223> OTHER INFORMATION: Amino acid sequence of Laminin subunit beta-2
      (Homo sapiens)

<400> SEQUENCE: 6

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

-continued

Gln Ala Pro Ala Pro Asp Val Pro Gly Cys Ser Arg Gly Ser Cys Tyr
                35                  40                  45

Pro Ala Thr Gly Asp Leu Leu Val Gly Arg Ala Asp Arg Leu Thr Ala
 50                  55                  60

Ser Ser Thr Cys Gly Leu Asn Gly Pro Gln Pro Tyr Cys Ile Val Ser
 65                  70                  75                  80

His Leu Gln Asp Glu Lys Lys Cys Phe Leu Cys Asp Ser Arg Arg Pro
                 85                  90                  95

Phe Ser Ala Arg Asp Asn Pro His Ser His Arg Ile Gln Asn Val Val
                100                 105                 110

Thr Ser Phe Ala Pro Gln Arg Arg Ala Ala Trp Trp Gln Ser Glu Asn
            115                 120                 125

Gly Ile Pro Ala Val Thr Ile Gln Leu Asp Leu Glu Ala Glu Phe His
        130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
                180                 185                 190

Pro Pro Arg His Trp Asp Asp Val Val Cys Glu Ser Arg Tyr Ser Glu
            195                 200                 205

Ile Glu Pro Ser Thr Glu Gly Glu Val Ile Tyr Arg Val Leu Asp Pro
        210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
                260                 265                 270

Ala Leu Tyr Glu Leu Val Val Arg Gly Asn Cys Phe Cys Tyr Gly His
            275                 280                 285

Ala Ser Glu Cys Ala Pro Ala Pro Gly Ala Pro Ala His Ala Glu Gly
        290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

Thr His Ser Cys His Phe Asp Met Ala Val Tyr Leu Ala Ser Gly Asn
        355                 360                 365

Val Ser Gly Gly Val Cys Asp Gly Cys Gln His Asn Thr Ala Gly Arg
    370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Asp Pro Ala Leu Gly
            420                 425                 430

Leu Val Ser Gly Gln Cys Arg Cys Lys Glu His Val Val Gly Thr Arg
        435                 440                 445

Cys Gln Gln Cys Arg Asp Gly Phe Phe Gly Leu Ser Ile Ser Asp Arg

-continued

```
            450                 455                 460
Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
                500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
        530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
                580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
        610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
        675                 680                 685

Tyr Lys Leu His Leu Lys Leu Val Arg Thr Gly Gly Ser Ala Gln Pro
        690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
        755                 760                 765

Leu Ile Ser Leu Ser Thr Leu Ile Tyr Asn Gly Ala Leu Pro Cys Gln
        770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
                805                 810                 815

Ala Pro Gly Tyr Tyr Gly Phe Gly Pro Thr Gly Cys Gln Ala Cys Gln
                820                 825                 830

Cys Ser His Glu Gly Ala Leu Ser Leu Cys Glu Lys Thr Ser Gly
        835                 840                 845

Gln Cys Leu Cys Arg Thr Gly Ala Phe Gly Leu Arg Cys Asp Arg Cys
        850                 855                 860

Gln Arg Gly Gln Trp Gly Phe Pro Ser Cys Arg Pro Cys Val Cys Asn
865                 870                 875                 880
```

-continued

```
Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
            900                 905                 910

His Gly Asp Pro Arg Leu Pro Tyr Gly Gly Gln Cys Arg Pro Cys Pro
        915                 920                 925

Cys Pro Glu Gly Pro Gly Ser Gln Arg His Phe Ala Thr Ser Cys His
    930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
                965                 970                 975

Ser Arg Pro Gly Gly Arg Cys Gln Leu Cys Glu Cys Ser Gly Asn Ile
            980                 985                 990

Asp Pro Met Asp Pro Asp Ala Cys  Asp Pro His Thr Gly  Gln Cys Leu
        995                 1000                1005

Arg Cys Leu His His Thr Glu  Gly Pro His Cys Ala  His Cys Lys
    1010                1015                1020

Pro Gly Phe His Gly Gln Ala  Ala Arg Gln Ser Cys  His Arg Cys
    1025                1030                1035

Thr Cys Asn Leu Leu Gly Thr  Asn Pro Gln Gln Cys  Pro Ser Pro
    1040                1045                1050

Asp Gln Cys His Cys Asp Pro  Ser Ser Gly Gln Cys  Pro Cys Leu
    1055                1060                1065

Pro Asn Val Gln Gly Pro Ser  Cys Asp Arg Cys Ala  Pro Asn Phe
    1070                1075                1080

Trp Asn Leu Thr Ser Gly His  Gly Cys Gln Pro Cys  Ala Cys His
    1085                1090                1095

Pro Ser Arg Ala Arg Gly Pro  Thr Cys Asn Glu Phe  Thr Gly Gln
    1100                1105                1110

Cys His Cys Arg Ala Gly Phe  Gly Gly Arg Thr Cys  Ser Glu Cys
    1115                1120                1125

Gln Glu Leu His Trp Gly Asp  Pro Gly Leu Gln Cys  His Ala Cys
    1130                1135                1140

Asp Cys Asp Ser Arg Gly Ile  Asp Thr Pro Gln Cys  His Arg Phe
    1145                1150                1155

Thr Gly His Cys Ser Cys Arg  Pro Gly Val Ser Gly  Val Arg Cys
    1160                1165                1170

Asp Gln Cys Ala Arg Gly Phe  Ser Gly Ile Phe Pro  Ala Cys His
    1175                1180                1185

Pro Cys His Ala Cys Phe Gly  Asp Trp Asp Arg Val  Val Gln Asp
    1190                1195                1200

Leu Ala Ala Arg Thr Gln Arg  Leu Glu Gln Arg Ala  Gln Glu Leu
    1205                1210                1215

Gln Gln Thr Gly Val Leu Gly  Ala Phe Glu Ser Ser  Phe Trp His
    1220                1225                1230

Met Gln Glu Lys Leu Gly Ile  Val Gln Gly Ile Val  Gly Ala Arg
    1235                1240                1245

Asn Thr Ser Ala Ala Ser Thr  Ala Gln Leu Val Glu  Ala Thr Glu
    1250                1255                1260

Glu Leu Arg Arg Glu Ile Gly  Glu Ala Thr Glu His  Leu Thr Gln
    1265                1270                1275
```

```
Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Asp Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
    1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470

Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530

Glu Met Val Ala Thr Arg Val Leu Glu Leu Ser Ile Pro Ala Ser
    1535                1540                1545

Ala Glu Gln Ile Gln His Leu Ala Gly Ala Ile Ala Glu Arg Val
    1550                1555                1560

Arg Ser Leu Ala Asp Val Asp Ala Ile Leu Ala Arg Thr Val Gly
    1565                1570                1575

Asp Val Arg Arg Ala Glu Gln Leu Leu Gln Asp Ala Arg Arg Ala
    1580                1585                1590

Arg Ser Trp Ala Glu Asp Glu Lys Gln Lys Ala Glu Thr Val Gln
    1595                1600                1605

Ala Ala Leu Glu Glu Ala Gln Arg Ala Gln Gly Ile Ala Gln Gly
    1610                1615                1620

Ala Ile Arg Gly Ala Val Ala Asp Thr Arg Asp Thr Glu Gln Thr
    1625                1630                1635

Leu Tyr Gln Val Gln Glu Arg Met Ala Gly Ala Glu Arg Ala Leu
    1640                1645                1650

Ser Ser Ala Gly Glu Arg Ala Arg Gln Leu Asp Ala Leu Leu Glu
    1655                1660                1665

Ala Leu Lys Leu Lys Arg Ala Gly Asn Ser Leu Ala Ala Ser Thr
```

Ala Glu Glu Thr Ala Gly Ser Ala Gln Gly Arg Ala Gln Glu Ala
                1685                1690                1695

Glu Gln Leu Leu Arg Gly Pro Leu Gly Asp Gln Tyr Gln Thr Val
                1700                1705                1710

Lys Ala Leu Ala Glu Arg Lys Ala Gln Gly Val Leu Ala Ala Gln
                1715                1720                1725

Ala Arg Ala Glu Gln Leu Arg Asp Glu Ala Arg Asp Leu Leu Gln
                1730                1735                1740

Ala Ala Gln Asp Lys Leu Gln Arg Leu Gln Glu Leu Glu Gly Thr
                1745                1750                1755

Tyr Glu Glu Asn Glu Arg Ala Leu Glu Ser Lys Ala Ala Gln Leu
                1760                1765                1770

Asp Gly Leu Glu Ala Arg Met Arg Ser Val Leu Gln Ala Ile Asn
                1775                1780                1785

Leu Gln Val Gln Ile Tyr Asn Thr Cys Gln
                1790                1795

<210> SEQ ID NO 7
<211> LENGTH: 5397
<212> TYPE: DNA
<213> ORGANISM: Artificial Sequence
<220> FEATURE:
<223> OTHER INFORMATION: DNA sequence of Laminin subunit beta-2 (Homo
      sapiens)

<400> SEQUENCE: 7

| | |
|---|---|
| atggagctga cctcaaggga agagggagg ggacagcctc tgccctggga acttcgactg | 60 |
| ggcctactgc taagcgtgct ggctgccaca ctggcacagg ccctgccccc ggatgtgcct | 120 |
| ggctgttcca ggggaagctg ctaccccgcc acgggcgacc tgctggtggg ccgagctgac | 180 |
| agactgactg cctcatccac ttgtggcctg aatggccccc agccctactg catcgtcagt | 240 |
| cacctgcagg acgaaaagaa gtgcttcctt tgtgactccc ggcgcccctt ctctgctaga | 300 |
| gacaacccac acagccatcg catccagaat gtagtcacca gctttgcacc acagcggcgg | 360 |
| gcagcctggt ggcagtcaga gaatggtatc cctgcggtca ccatccagct ggacctggag | 420 |
| gctgagtttc atttcacaca cctcattatg accttcaaga catttcgccc tgctgccatg | 480 |
| ctggtggaac gctcagcaga cttggccgc acctggcatg tgtaccgata tttctcctat | 540 |
| gactgtgggg ctgacttccc aggagtccca ctagcacccc cacggcactg ggatgatgta | 600 |
| gtctgtgagt cccgctactc agagattgag ccatccactg aaggcgaggt catctatcgt | 660 |
| gtgctggacc ctgccatccc tatcccagac ccctacagct cacggattca gaacctgttg | 720 |
| aagatcacca acctacgggt gaacctgact cgtctacaca cgttgggaga caacctactc | 780 |
| gacccacgga gggagatccg agagaagtac tactatgccc tctatgagct ggttgtacgt | 840 |
| ggcaactgct ctgctacgg acacgcctca gagtgtgcac cgccccagg gcaccagcc | 900 |
| catgctgagg gcatggtgca cggagcttgc atctgcaaac acaacacacg tggcctcaac | 960 |
| tgcgagcagt gtcaggattt ctatcgtgac ctgccctggc gtccggctga ggacggccat | 1020 |
| agtcatgcct gtaggaagtg tgagtgccat gggcacaccc acagctgcca cttcgacatg | 1080 |
| gccgtatacc tggcatctgg caatgtgagt ggaggtgtgt gtgatggatg tcagcataac | 1140 |
| acagctgggc gccactgtga gctcgtcgg cccttcttct accgtgaccc aaccaaggac | 1200 |
| ctgcgggatc cggctgtgtg ccgctcctgt gattgtgacc ccatggggtt caagacggt | 1260 |

-continued

```
ggtcgctgtg attcccatga tgaccctgca ctgggactgg tctccggcca gtgtcgctgc      1320
aaagaacatg tggtgggcac tcgctgccag caatgccgtg atggcttctt tgggctcagc      1380
atcagtgacc gtctgggctg ccggcgatgt caatgtaatg cacggggcac agtgcctggg      1440
agcactcctt gtgaccccaa cagtggatcc tgttactgca aacgtctagt gactggacgt      1500
ggatgtgacc gctgcctgcc tggccactgg ggcctgagcc acgacctgct cggctgccgc      1560
ccctgtgact gcgacgtggg tggtgctttg gatccccagt gtgatgaggg cacaggtcaa      1620
tgccactgcc gccagcacat ggttgggcga cgctgtgagc aggtgcaacc tggctacttc      1680
cggcccttcc tggaccacct aatttgggag gctgaggaca cccgagggca ggtgctcgat      1740
gtggtggagc gcctggtgac ccccggggaa actccatcct ggactggctc aggcttcgtg      1800
cggctacagg aaggtcagac cctggagttc ctggtggcct ctgtgccgaa ggctatggac      1860
tatgacctgc tgctgcgctt agagcccag gtccctgagc aatgggcaga gttggaactg      1920
attgtgcagc gtccagggcc tgtgcctgcc cacagcctgt gtgggcattt ggtgcccaag      1980
gatgatcgca tccaagggac tctgcaacca catgccaggt acttgatatt tcctaatcct      2040
gtctgccttg agcctggtat ctcctacaag ctgcatctga agctggtacg gacaggggga      2100
agtgcccagc ctgagactcc ctactctgga cctggcctgc tcattgactc gctggtgctg      2160
ctgccccgtg tcctggtgct agagatgttt agtggggtg atgctgctgc cctggagcgc      2220
caggccacct ttgaacgcta ccaatgccat gaggagggtc tggtgcccag caagacttct      2280
ccctctgagg cctgcgcacc cctcctcatc agcctgtcca ccctcatcta caatggtgcc      2340
ctgccatgtc agtgcaaccc tcaaggttca ctgagttctg agtgcaaccc tcatggtggt      2400
cagtgcctgt gcaagcctgg agtggttggg cgccgctgtg acctctgtgc ccctggctac      2460
tatggctttg gccccacagg ctgtcaagcc tgccagtgca gccacgaggg ggcactcagc      2520
agtctctgtg aaaagaccag tgggcaatgt ctctgtcgaa ctggtgcctt tgggcttcgc      2580
tgtgaccgct gccagcgtgg ccagtgggga ttccctagct gccggccatg tgtctgcaat      2640
gggcatgcag atgagtgcaa cacccacaca ggcgcttgcc tgggctgccg tgatcacaca      2700
gggggtgagc actgtgaaag gtgcattgct ggtttccacg gggacccacg gctgccatat      2760
gggggccagt gccggccctg tccctgtcct gaaggccctg ggagccaacg gcactttgct      2820
acttcttgcc accaggatga atattcccag cagattgtgt gccactgccg ggcaggctat      2880
acggggctgc gatgtgaagc ttgtgcccct gggcactttg ggacccatc aaggccaggt      2940 ggccggtgcc aactgtgtga gtgcagtggg aacattgacc caatggatcc tgatgcctgt      3000
gacccccaca cggggcaatg cctgcgctgt ttacaccaca cagagggtcc acactgtgcc      3060
cactgcaagc ctggcttcca tgggcaggct gcccgacaga gctgtcaccg ctgcacatgc      3120
aacctgctgg gcacaaatcc gcagcagtgc ccatctcctg accagtgcca ctgtgatcca      3180
agcagtgggc agtgcccatg cctccccaat gtccagggcc ctagctgtga ccgctgtgcc      3240
cccaacttct ggaacctcac cagtggccat ggttgccagc cttgtgcctg ccacccaagc      3300
cgggccagag gccccacctg caacgagttc acagggcagt gccactgccg tgccggcttt      3360
ggagggcgga cttgttctga gtgccaagag ctccactggg gagaccctgg gttgcagtgc      3420
catgcctgtg attgtgactc tcgtggaata gatacacctc agtgtcaccg cttcacaggt      3480
cactgcagct gccgcccagg ggtgtctggt gtgcgctgtg accagtgtgc ccgtggcttc      3540
tcaggaatct ttcctgcctg ccatcctctgc catgcatgct tcggggattg ggaccgagtg      3600
gtgcaggact tggcagccg tacacagcgc ctagagcagc gggcgcagga gttgcaacag      3660
```

-continued

```
acgggtgtgc tgggtgcctt tgagagcagc ttctggcaca tgcaggagaa gctgggcatt      3720
gtgcagggca tcgtaggtgc ccgcaacacc tcagccgcct ccactgcaca gcttgtggag      3780
gccacagagg agctgcggcg tgaaattggg gaggccactg agcacctgac tcagctcgag      3840
gcagacctga cagatgtgca agatgagaac ttcaatgcca accatgcact aagtggtctg      3900
gagcgagata ggcttgcact taatctcaca ctgcggcagc tcgaccagca tcttgacttg      3960
ctcaaacatt caaacttcct gggtgcctat gacagcatcc ggcatgccca tagccagtct      4020
gcagaggcag aacgtcgtgc caatacctca gccctggcag tacctagccc tgtgagcaac      4080
tcggcaagtg ctcggcatcg acagaggca ctgatggatg ctcagaagga ggacttcaac       4140
agcaaacaca tggccaacca gcgggcactt ggcaagctct ctgcccatac ccacaccctg      4200
agcctgacag acataaatga gctggtgtgt ggggcaccag gggatgcacc ctgtgctaca      4260
agcccttgtg ggggtgccgg ctgtcgagat gaggatgggc agccgcgctg tgggggcctc      4320
agctgcaatg gggcagcggc tacagcagac ctagcactgg gccgggcccg gcacacacag      4380
gcagagctgc agcgggcact ggcagaaggt ggtagcatcc tcagcagagt ggctgagact      4440
cgtcggcagg caagcgaggc acagcagcgg gcccaggcag ccctggacaa ggctaatgct      4500
tccagggac aggtggaaca ggccaaccag gaacttcaag aacttatcca gagtgtgaag       4560
gacttcctca accaggaggg ggctgatcct gatagcattg aaatggtggc cacacgggtg      4620
ctagagctct ccatcccagc ttcagctgag cagatccagc acctggcggg tgcgattgca      4680
gagcgagtcc ggagcctggc agatgtggat gcgatcctgg cacgtactgt aggagatgtg      4740
cgtcgtgccg agcagctact gcaggatgca cggcgggcaa ggagctgggc tgaggatgag      4800
aaacagaagg cagagacagt acaggcagca ctggaggagg cccagcgggc acagggtatt      4860
gcccagggtg ccatccgggg ggcagtggct gacacacggg acacagagca gaccctgtac      4920
caggtacagg agaggatggc aggtgcagag cgggcactga gctctgcagg tgaaagggct      4980
cggcagttgg atgctctcct ggaggctctg aaattgaaac gggcaggaaa tagtctggca      5040
gcctctacag cagaagaaac ggcaggcagt gcccagggtc gtgcccagga ggctgagcag      5100
ctgctacgcg gtcctctggg tgatcagtac cagacgtgaa aggccctagc tgagcgcaag      5160
gcccaaggtg tgctggctgc acaggcaagg gcagaacaac tgcgggatga ggctcgggac      5220
ctgttgcaag ccgctcagga caagctgcag cggctacagg aattggaagg cacctatgag      5280
gaaaatgagc gggcactgga gagtaaggca gcccagttgg acgggttgga ggccaggatg      5340
cgcagcgtgc ttcaagccat caacttgcag gtgcagatct acaacacctg ccagtga       5397
```

<210> SEQ ID NO 8
<211> LENGTH: 1609
<212> TYPE: PRT
<213> ORGANISM: Artificial Sequence
<220> FEATURE:
<223> OTHER INFORMATION: Amino acid sequence of Laminin subunit gamma-1
      (Homo sapiens)

<400> SEQUENCE: 8

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
                20                  25                  30

Ala Gln Ala Ala Met Asp Glu Cys Thr Asp Glu Gly Gly Arg Pro Gln
            35                  40                  45

Arg Cys Met Pro Glu Phe Val Asn Ala Ala Phe Asn Val Thr Val
            50                  55                  60

Ala Thr Asn Thr Cys Gly Thr Pro Pro Glu Glu Tyr Cys Val Gln Thr
 65                  70                  75                  80

Gly Val Thr Gly Val Thr Lys Ser Cys His Leu Cys Asp Ala Gly Gln
                 85                  90                  95

Pro His Leu Gln His Gly Ala Ala Phe Leu Thr Asp Tyr Asn Asn Gln
                100                 105                 110

Ala Asp Thr Thr Trp Trp Gln Ser Gln Thr Met Leu Ala Gly Val Gln
                115                 120                 125

Tyr Pro Ser Ser Ile Asn Leu Thr Leu His Leu Gly Lys Ala Phe Asp
        130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
                180                 185                 190

Phe Ile Arg Thr Gly Gly Asp Glu Gln Gln Ala Leu Cys Thr Asp Glu
                195                 200                 205

Phe Ser Asp Ile Ser Pro Leu Thr Gly Gly Asn Val Ala Phe Ser Thr
210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
                260                 265                 270

Tyr Tyr Tyr Ala Ile Ser Asp Phe Ala Val Gly Gly Arg Cys Lys Cys
            275                 280                 285

Asn Gly His Ala Ser Glu Cys Met Lys Asn Glu Phe Asp Lys Leu Val
290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
                340                 345                 350

Phe Asp Pro Glu Leu Tyr Arg Ser Thr Gly His Gly Gly His Cys Thr
            355                 360                 365

Asn Cys Gln Asp Asn Thr Asp Gly Ala His Cys Glu Arg Cys Arg Glu
        370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                405                 410                 415

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
                435                 440                 445

Pro Ser Gly Ser Ile Asp Glu Cys Asn Ile Glu Thr Gly Arg Cys Val
450                 455                 460

Cys Lys Asp Asn Val Glu Gly Phe Asn Cys Glu Arg Cys Lys Pro Gly

```
              465                 470                 475                 480
         Phe Phe Asn Leu Glu Ser Ser Asn Pro Arg Gly Cys Thr Pro Cys Phe
                         485                 490                 495

Cys Phe Gly His Ser Ser Val Cys Thr Asn Ala Val Gly Tyr Ser Val
                         500                 505                 510

Tyr Ser Ile Ser Ser Thr Phe Gln Ile Asp Glu Asp Gly Trp Arg Ala
                         515                 520                 525

Glu Gln Arg Asp Gly Ser Glu Ala Ser Leu Glu Trp Ser Ser Glu Arg
                         530                 535                 540

Gln Asp Ile Ala Val Ile Ser Asp Ser Tyr Phe Pro Arg Tyr Phe Ile
         545                 550                 555                 560

Ala Pro Ala Lys Phe Leu Gly Lys Gln Val Leu Ser Tyr Gly Gln Asn
                         565                 570                 575

Leu Ser Phe Ser Phe Arg Val Asp Arg Asp Thr Arg Leu Ser Ala
                         580                 585                 590

Glu Asp Leu Val Leu Glu Gly Ala Gly Leu Arg Val Ser Val Pro Leu
                         595                 600                 605

Ile Ala Gln Gly Asn Ser Tyr Pro Ser Glu Thr Thr Val Lys Tyr Val
         610                 615                 620

Phe Arg Leu His Glu Ala Thr Asp Tyr Pro Trp Arg Pro Ala Leu Thr
         625                 630                 635                 640

Pro Phe Glu Phe Gln Lys Leu Leu Asn Asn Leu Thr Ser Ile Lys Ile
                         645                 650                 655

Arg Gly Thr Tyr Ser Glu Arg Ser Ala Gly Tyr Leu Asp Asp Val Thr
                         660                 665                 670

Leu Ala Ser Ala Arg Pro Gly Pro Gly Val Pro Ala Thr Trp Val Glu
                         675                 680                 685

Ser Cys Thr Cys Pro Val Gly Tyr Gly Gly Gln Phe Cys Glu Met Cys
                         690                 695                 700

Leu Ser Gly Tyr Arg Arg Glu Thr Pro Asn Leu Gly Pro Tyr Ser Pro
         705                 710                 715                 720

Cys Val Leu Cys Ala Cys Asn Gly His Ser Glu Thr Cys Asp Pro Glu
                         725                 730                 735

Thr Gly Val Cys Asn Cys Arg Asp Asn Thr Ala Gly Pro His Cys Glu
                         740                 745                 750

Lys Cys Ser Asp Gly Tyr Tyr Gly Asp Ser Thr Ala Gly Thr Ser Ser
                         755                 760                 765

Asp Cys Gln Pro Cys Pro Cys Pro Gly Gly Ser Ser Cys Ala Val Val
                         770                 775                 780

Pro Lys Thr Lys Glu Val Val Cys Thr Asn Cys Pro Thr Gly Thr Thr
         785                 790                 795                 800

Gly Lys Arg Cys Glu Leu Cys Asp Asp Gly Tyr Phe Gly Asp Pro Leu
                         805                 810                 815

Gly Arg Asn Gly Pro Val Arg Leu Cys Arg Leu Cys Gln Cys Ser Asp
                         820                 825                 830

Asn Ile Asp Pro Asn Ala Val Gly Asn Cys Asn Arg Leu Thr Gly Glu
                         835                 840                 845

Cys Leu Lys Cys Ile Tyr Asn Thr Ala Gly Phe Tyr Cys Asp Arg Cys
                         850                 855                 860

Lys Asp Gly Phe Phe Gly Asn Pro Leu Ala Pro Asn Pro Ala Asp Lys
         865                 870                 875                 880

Cys Lys Ala Cys Asn Cys Asn Leu Tyr Gly Thr Met Lys Gln Gln Ser
                         885                 890                 895
```

```
Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
    930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
            995                 1000                1005

Gly Asn Arg Cys Asp Gln Cys Glu Glu Asn Tyr Phe Tyr Asn Arg
1010                1015                1020

Ser Trp Pro Gly Cys Gln Glu Cys Pro Ala Cys Tyr Arg Leu Val
1025                1030                1035

Lys Asp Lys Val Ala Asp His Arg Val Lys Leu Gln Glu Leu Glu
1040                1045                1050

Ser Leu Ile Ala Asn Leu Gly Thr Gly Asp Glu Met Val Thr Asp
1055                1060                1065

Gln Ala Phe Glu Asp Arg Leu Lys Glu Ala Glu Arg Glu Val Met
1070                1075                1080

Asp Leu Leu Arg Glu Ala Gln Asp Val Lys Asp Val Asp Gln Asn
1085                1090                1095

Leu Met Asp Arg Leu Gln Arg Val Asn Asn Thr Leu Ser Ser Gln
1100                1105                1110

Ile Ser Arg Leu Gln Asn Ile Arg Asn Thr Ile Glu Glu Thr Gly
1115                1120                1125

Asn Leu Ala Glu Gln Ala Arg Ala His Val Glu Asn Thr Glu Arg
1130                1135                1140

Leu Ile Glu Ile Ala Ser Arg Glu Leu Glu Lys Ala Lys Val Ala
1145                1150                1155

Ala Ala Asn Val Ser Val Thr Gln Pro Glu Ser Thr Gly Asp Pro
1160                1165                1170

Asn Asn Met Thr Leu Leu Ala Glu Glu Ala Arg Lys Leu Ala Glu
1175                1180                1185

Arg His Lys Gln Glu Ala Asp Asp Ile Val Arg Val Ala Lys Thr
1190                1195                1200

Ala Asn Asp Thr Ser Thr Glu Ala Tyr Asn Leu Leu Leu Arg Thr
1205                1210                1215

Leu Ala Gly Glu Asn Gln Thr Ala Phe Glu Ile Glu Glu Leu Asn
1220                1225                1230

Arg Lys Tyr Glu Gln Ala Lys Asn Ile Ser Gln Asp Leu Glu Lys
1235                1240                1245

Gln Ala Ala Arg Val His Glu Glu Ala Lys Arg Ala Gly Asp Lys
1250                1255                1260

Ala Val Glu Ile Tyr Ala Ser Val Ala Gln Leu Ser Pro Leu Asp
1265                1270                1275

Ser Glu Thr Leu Glu Asn Glu Ala Asn Asn Ile Lys Met Glu Ala
1280                1285                1290
```

```
Glu Asn Leu Glu Gln Leu Ile Asp Gln Lys Leu Lys Asp Tyr Glu
    1295                1300                1305

Asp Leu Arg Glu Asp Met Arg Gly Lys Glu Leu Glu Val Lys Asn
    1310                1315                1320

Leu Leu Glu Lys Gly Lys Thr Glu Gln Gln Thr Ala Asp Gln Leu
    1325                1330                1335

Leu Ala Arg Ala Asp Ala Ala Lys Ala Leu Ala Glu Glu Ala Ala
    1340                1345                1350

Lys Lys Gly Arg Asp Thr Leu Gln Glu Ala Asn Asp Ile Leu Asn
    1355                1360                1365

Asn Leu Lys Asp Phe Asp Arg Arg Val Asn Asp Asn Lys Thr Ala
    1370                1375                1380

Ala Glu Glu Ala Leu Arg Lys Ile Pro Ala Ile Asn Gln Thr Ile
    1385                1390                1395

Thr Glu Ala Asn Glu Lys Thr Arg Glu Ala Gln Gln Ala Leu Gly
    1400                1405                1410

Ser Ala Ala Ala Asp Ala Thr Glu Ala Lys Asn Lys Ala His Glu
    1415                1420                1425

Ala Glu Arg Ile Ala Ser Ala Val Gln Lys Asn Ala Thr Ser Thr
    1430                1435                1440

Lys Ala Glu Ala Glu Arg Thr Phe Ala Glu Val Thr Asp Leu Asp
    1445                1450                1455

Asn Glu Val Asn Asn Met Leu Lys Gln Leu Gln Glu Ala Glu Lys
    1460                1465                1470

Glu Leu Lys Arg Lys Gln Asp Asp Ala Asp Gln Asp Met Met Met
    1475                1480                1485

Ala Gly Met Ala Ser Gln Ala Gln Glu Ala Glu Ile Asn Ala
    1490                1495                1500

Arg Lys Ala Lys Asn Ser Val Thr Ser Leu Leu Ser Ile Ile Asn
    1505                1510                1515

Asp Leu Leu Glu Gln Leu Gly Gln Leu Asp Thr Val Asp Leu Asn
    1520                1525                1530

Lys Leu Asn Glu Ile Glu Gly Thr Leu Asn Lys Ala Lys Asp Glu
    1535                1540                1545

Met Lys Val Ser Asp Leu Asp Arg Lys Val Ser Asp Leu Glu Asn
    1550                1555                1560

Glu Ala Lys Lys Gln Glu Ala Ala Ile Met Asp Tyr Asn Arg Asp
    1565                1570                1575

Ile Glu Glu Ile Met Lys Asp Ile Arg Asn Leu Glu Asp Ile Arg
    1580                1585                1590

Lys Thr Leu Pro Ser Gly Cys Phe Asn Thr Pro Ser Ile Glu Lys
    1595                1600                1605

Pro
```

<210> SEQ ID NO 9
<211> LENGTH: 4830
<212> TYPE: DNA
<213> ORGANISM: Artificial Sequence
<220> FEATURE:
<223> OTHER INFORMATION: DNA sequence of Laminin subunit gamma-1 (Homo sapiens)

<400> SEQUENCE: 9

```
atgagaggga gccatcgggc cgcgccggcc ctgcggcccc gggggcggct ctggcccgtg    60
ctggccgtgc tggcggcggc cgccgcggcg ggctgtgccc aggcagccat ggacgagtgc   120
```

```
acggacgagg gcgggcggcc gcagcgctgc atgcccgagt tcgtcaacgc cgccttcaac    180
gtgactgtgg tggccaccaa cacgtgtggg actccgcccg aggaatactg tgtgcagacc    240
ggggtgaccg gggtcaccaa gtcctgtcac ctgtgcgacg ccgggcagcc ccacctgcag    300
cacggggcag ccttcctgac cgactacaac aaccaggccg acaccacctg gtggcaaagc    360
cagaccatgc tggccggggt gcagtacccc agctccatca acctcacgct gcacctggga    420
aaagcttttg acatcaccta tgtgcgtctc aagttccaca ccagccgccc ggagagcttt    480
gccatttaca agcgcacacg ggaagacggg ccctggattc cttaccagta ctacagtggt    540
tcctgtgaga cacctactc caaggcaaac cgcggcttca tcaggacagg aggggacgag    600
cagcaggcct tgtgtactga tgaattcagt gacatttctc ccctcactgg gggcaacgtg    660
gccttttcta ccctggaagg aaggcccagc gcctataact ttgacaatag ccctgtgctg    720
caggaatggg taactgccac tgacatcaga gtaactctta atcgcctgaa cactttggga    780
gatgaagtgt ttaacgatcc caaagttctc aagtcctatt attatgccat ctctgatttt    840
gctgtaggtg gcagatgtaa atgtaatgga cacgcaagcg agtgtatgaa gaacgaattt    900
gataagctgt gtgtaattg caaacataac acatatggag tagactgtga aaagtgtctt    960
cctttcttca atgaccggcc gtggaggagg gcaactgcgg aaagtgccag tgaatgcctg   1020
ccctgtgatt gcaatggtcg atcccaggaa tgctacttcg accctgaact ctatcgttcc   1080
actggccatg ggggccactg taccaactgc aggataaca cagatggcgc ccactgtgag   1140
aggtgccgag agaacttctt ccgccttggc aacaatgaag cctgctcttc atgccactgt   1200
agtcctgtgg gctctctaag cacacagtgt gatagttacg gcagatgcag ctgtaagcca   1260
ggagtgatgg gggacaaatg tgaccgttgc cagcctggat ccattctct cactgaagca   1320 ggatgcaggc catgctcttg tgatccctct ggcagcatag atgaatgtaa tattgaaaca   1380
ggaagatgtg tttgcaaaga caatgtcgaa ggcttcaatt gtgaaagatg caaacctgga   1440
ttttttaatc tggaatcatc taatcctcgg ggttgcacac cctgcttctg ctttgggcat   1500
tcttctgtct gtacaaacgc tgttggctac agtgtttatt ctatctcctc tacctttcag   1560
attgatgagg atgggtggcg tgcggaacag agagatggct ctgaagcatc tctcgagtgg   1620
tcctctgaga ggcaagatat cgccgtgatc tcagacagct actttcctcg gtacttcatt   1680
gctcctgcaa agttcttggg caagcaggtg ttgagttatg gtcagaacct ctccttctcc   1740
tttcgagtgg acaggcgaga tactcgcctc tctgcagaag accttgtgct tgagggagct   1800
ggcttaagag tatctgtacc cttgatcgct cagggcaatt cctatccaag tgagaccact   1860
gtgaagtatg tcttcaggct ccatgaagca acagattacc cttggaggcc tgctcttacc   1920
ccttttgaat tcagaagct cctaaacaac ttgacctcta tcaagatacg tgggacatac   1980
agtgagagaa gtgctggata tttggatgat gtcacccctgg caagtgctcg tcctgggcct   2040
ggagtccctg caactgggt ggagtcctgc acctgtcctg tgggatatgg agggcagttt   2100
tgtgagatgt gcctctcagg ttacagaaga gaaactccta atcttggacc atacagtcca   2160
tgtgtgcttt gcgcctgcaa tggacacagc gagacctgtg atcctgagac aggtgtttgt   2220
aactgcagag acaatacggc tggcccgcac tgtgagaagt gcagtgatgg gtactatgga   2280
gattcaactg caggcacctc ctccgattgc caaccctgtc cgtgtcctgg aggttcaagt   2340
tgtgctgttt ttcccaagac aaaggaggtg gtgtgcacca actgtcctac tggcaccact   2400
ggtaagagat gtgagctctg tgatgatggc tactttggag accccctggg tagaaacggc   2460
```

```
cctgtgagac tttgccgcct gtgccagtgc agtgacaaca tcgatcccaa tgcagttgga    2520
aattgcaatc gcttgacggg agaatgcctg aagtgcatct ataacactgc tggcttctat    2580
tgtgaccggt gcaaagacgg atttttttgga atcccctgg ctcccaatcc agcagacaaa    2640
tgcaaagcct gcaattgcaa tctgtatggg accatgaagc agcagagcag ctgtaacccc    2700
gtgacggggc agtgtgaatg tttgcctcac gtgactggcc aggactgtgg tgcttgtgac    2760
cctggattct acaatctgca gagtgggcaa ggctgtgaga ggtgtgactg ccatgccttg    2820
ggctccacca atgggcagtg tgacatccgc accggccagt gtgagtgcca gcccggcatc    2880
actggtcagc actgtgagcg ctgtgaggtc aaccactttg ggtttggacc tgaaggctgc    2940
aaaccctgtg actgtcatcc tgagggatct cttctacttc agtgcaaaga tgatggtcgc    3000
tgtgaatgca gagaaggctt tgtgggaaat cgctgtgacc agtgtgaaga aaactatttc    3060
tacaatcggt cttggcctgg ctgccaggaa tgtccagctt gttaccggct ggtaaaggat    3120
aaggttgctg atcatagagt gaagctccag gaattagaga gtctcatagc aaaccttgga    3180
actggggatg agatggtgac agatcaagcc ttcgaggata gactaaagga agcagagagg    3240
gaagttatgg acctccttcg tgaggcccag gatgtcaaag atgttgacca gaatttgatg    3300
gatcgcctac agagagtgaa taacactctg tccagccaaa ttagccgttt acagaatatc    3360
cggaatacca ttgaagagac tggaaacttg gctgaacaag cgcgtgccca tgtagagaac    3420
acagagcggt tgattgaaat cgcatccaga gaacttgaga aagcaaaagt cgctgctgcc    3480
aatgtgtcag tcactcagcc agaatctaca ggggacccaa acaacatgac tcttttggca    3540
gaagaggctc gaaagcttgc tgaacgtcat aaacaggaag ctgatgacat tgttcgagtg    3600
gcaaagacag ccaatgatac gtcaactgag gcatacaacc tgcttctgag gacactggca    3660
ggagaaaatc aaacagcatt tgagattgaa gagcttaata ggaagtatga acaagcgaag    3720
aacatctcac aggatctgga aaaacaagct gcccgagtac atgaggaggc caaaagggcc    3780
ggtgacaaag ctgtggagat ctatgccagc gtggctcagc tgagccctt ggactctgag    3840 acactggaga atgaagcaaa taacataaag atggaagctg agaatctgga caactgatt    3900 gaccagaaat taaagatta tgaggacctc agagaagata tgagagggaa ggaacttgaa    3960
gtcaagaacc ttctggagaa aggcaagact gaacagcaga ccgcagacca actcctagcc    4020
cgagctgatg ctgccaaggc cctcgctgaa gaagctgcaa agaagggacg ggatacctta    4080
caagaagcta atgacattct caacaacctg aaagattttg ataggcgtgt gaacgataac    4140
aagacggccg cagaggaggc actaaggaag attcctgcca tcaaccagac catcactgaa    4200
gccaatgaaa agaccagaga agcccagcag gccctgggca gtgctgcggc ggatgccaca    4260
gaggccaaga caaggccca tgaggcgag aggatcgcga gcgctgtcca aaagaatgcc    4320
accagcacca aggcagaagc tgaaagaact tttgcagaag ttacagatct ggataatgag    4380
gtgaacaata tgttgaagca actgcaggaa gcagaaaaag agctaaagag aaaacaagat    4440
gacgctgacc aggacatgat gatggcaggg atggcttcac aggctgctca agaagccgag    4500
atcaatgcca gaaaagccaa aaactctgtt actagcctcc tcagcattat taatgacctc    4560
ttggagcagc tggggcagct ggatacagtg gacctgaata agctaaacga gattgaaggc    4620
accctaaaca agccaaaga tgaaatgaag gtcagcgatc ttgataggaa agtgtctgac    4680
ctggagaatg aagccaagaa gcaggaggct gccatcatgg actataaccg agatatcgag    4740
gagatcatga ggacattccg caatctggag gacatcagga gaccttacc atctggctgc    4800 ttcaacaccc cgtccattga aaagccctag                                     4830
```

<210> SEQ ID NO 10
<211> LENGTH: 3122
<212> TYPE: PRT
<213> ORGANISM: Artificial Sequence
<220> FEATURE:
<223> OTHER INFORMATION: Amino acid sequence of Laminin subunit alpha-2
(Homo sapiens)

<400> SEQUENCE: 10

Met Pro Gly Ala Ala Gly Val Leu Leu Leu Leu Leu Ser Gly Gly
1               5                   10                  15

Leu Gly Gly Val Gln Ala Gln Arg Pro Gln Gln Gln Arg Gln Ser Gln
                20                  25                  30

Ala His Gln Gln Arg Gly Leu Phe Pro Ala Val Leu Asn Leu Ala Ser
            35                  40                  45

Asn Ala Leu Ile Thr Thr Asn Ala Thr Cys Gly Glu Lys Gly Pro Glu
        50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Ser Asn Pro Asn Gln Arg
                85                  90                  95

His Pro Ile Thr Asn Ala Ile Asp Gly Lys Asn Thr Trp Trp Gln Ser
            100                 105                 110

Pro Ser Ile Lys Asn Gly Ile Glu Tyr His Tyr Val Thr Ile Thr Leu
        115                 120                 125

Asp Leu Gln Gln Val Phe Gln Ile Ala Tyr Val Ile Val Lys Ala Ala
    130                 135                 140

Asn Ser Pro Arg Pro Gly Asn Trp Ile Leu Glu Arg Ser Leu Asp Asp
145                 150                 155                 160

Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
            180                 185                 190

Lys Asp Asp Glu Val Ile Cys Thr Ser Phe Tyr Ser Lys Ile His Pro
        195                 200                 205

Leu Glu Asn Gly Glu Ile His Ile Ser Leu Ile Asn Gly Arg Pro Ser
    210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Tyr Ser Val Lys Asp Ile Ser Val Gly Gly Met Cys Ile
        275                 280                 285

Cys Tyr Gly His Ala Arg Ala Cys Pro Leu Asp Pro Ala Thr Asn Lys
    290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile

```
                355                 360                 365
Arg Gly Lys Tyr Ile Gly Gly Val Cys Ile Asn Cys Thr Gln Asn
    370                 375                 380
Thr Ala Gly Ile Asn Cys Glu Thr Cys Thr Asp Gly Phe Phe Arg Pro
385                 390                 395                 400
Lys Gly Val Ser Pro Asn Tyr Pro Arg Pro Cys Gln Pro Cys His Cys
                405                 410                 415
Asp Pro Ile Gly Ser Leu Asn Glu Val Cys Val Lys Asp Glu Lys His
            420                 425                 430
Ala Arg Arg Gly Leu Ala Pro Gly Ser Cys His Cys Lys Thr Gly Phe
        435                 440                 445
Gly Gly Val Ser Cys Asp Arg Cys Ala Arg Gly Tyr Thr Gly Tyr Pro
    450                 455                 460
Asp Cys Lys Ala Cys Asn Cys Ser Gly Leu Gly Ser Lys Asn Glu Asp
465                 470                 475                 480
Pro Cys Phe Gly Pro Cys Ile Cys Lys Glu Asn Val Glu Gly Gly Asp
                485                 490                 495
Cys Ser Arg Cys Lys Ser Gly Phe Phe Asn Leu Gln Glu Asp Asn Trp
            500                 505                 510
Lys Gly Cys Asp Glu Cys Phe Cys Ser Gly Val Ser Asn Arg Cys Gln
        515                 520                 525
Ser Ser Tyr Trp Thr Tyr Gly Lys Ile Gln Asp Met Ser Gly Trp Tyr
    530                 535                 540
Leu Thr Asp Leu Pro Gly Arg Ile Arg Val Ala Pro Gln Gln Asp Asp
545                 550                 555                 560
Leu Asp Ser Pro Gln Gln Ile Ser Ile Ser Asn Ala Glu Ala Arg Gln
                565                 570                 575
Ala Leu Pro His Ser Tyr Tyr Trp Ser Ala Pro Ala Pro Tyr Leu Gly
            580                 585                 590
Asn Lys Leu Pro Ala Val Gly Gly Gln Leu Thr Phe Thr Ile Ser Tyr
        595                 600                 605
Asp Leu Glu Glu Glu Glu Asp Thr Glu Arg Val Leu Gln Leu Met
    610                 615                 620
Ile Ile Leu Glu Gly Asn Asp Leu Ser Ile Ser Thr Ala Gln Asp Glu
625                 630                 635                 640
Val Tyr Leu His Pro Ser Glu Glu His Thr Asn Val Leu Leu Leu Lys
                645                 650                 655
Glu Glu Ser Phe Thr Ile His Gly Thr His Phe Pro Val Arg Arg Lys
            660                 665                 670
Glu Phe Met Thr Val Leu Ala Asn Leu Lys Arg Val Leu Leu Gln Ile
        675                 680                 685
Thr Tyr Ser Phe Gly Met Asp Ala Ile Phe Arg Leu Ser Ser Val Asn
    690                 695                 700
Leu Glu Ser Ala Val Ser Tyr Pro Thr Asp Gly Ser Ile Ala Ala Ala
705                 710                 715                 720
Val Glu Val Cys Gln Cys Pro Pro Gly Tyr Thr Gly Ser Ser Cys Glu
                725                 730                 735
Ser Cys Trp Pro Arg His Arg Arg Val Asn Gly Thr Ile Phe Gly Gly
            740                 745                 750
Ile Cys Glu Pro Cys Gln Cys Phe Gly His Ala Glu Ser Cys Asp Asp
        755                 760                 765
Val Thr Gly Glu Cys Leu Asn Cys Lys Asp His Thr Gly Gly Pro Tyr
    770                 775                 780
```

```
Cys Asp Lys Cys Leu Pro Gly Phe Tyr Gly Glu Pro Thr Lys Gly Thr
785                 790                 795                 800

Ser Glu Asp Cys Gln Pro Cys Ala Cys Pro Leu Asn Ile Pro Ser Asn
            805                 810                 815

Asn Phe Ser Pro Thr Cys His Leu Asp Arg Ser Leu Gly Leu Ile Cys
        820                 825                 830

Asp Gly Cys Pro Val Gly Tyr Thr Gly Pro Arg Cys Glu Arg Cys Ala
    835                 840                 845

Glu Gly Tyr Phe Gly Gln Pro Ser Val Pro Gly Gly Ser Cys Gln Pro
850                 855                 860

Cys Gln Cys Asn Asp Asn Leu Asp Phe Ser Ile Pro Gly Ser Cys Asp
865                 870                 875                 880

Ser Leu Ser Gly Ser Cys Leu Ile Cys Lys Pro Gly Thr Thr Gly Arg
            885                 890                 895

Tyr Cys Glu Leu Cys Ala Asp Gly Tyr Phe Gly Asp Ala Val Asp Ala
        900                 905                 910

Lys Asn Cys Gln Pro Cys Arg Cys Asn Ala Gly Gly Ser Phe Ser Glu
    915                 920                 925

Val Cys His Ser Gln Thr Gly Gln Cys Glu Cys Arg Ala Asn Val Gln
930                 935                 940

Gly Gln Arg Cys Asp Lys Cys Lys Ala Gly Thr Phe Gly Leu Gln Ser
945                 950                 955                 960

Ala Arg Gly Cys Val Pro Cys Asn Cys Asn Ser Phe Gly Ser Lys Ser
            965                 970                 975

Phe Asp Cys Glu Glu Ser Gly Gln Cys Trp Cys Gln Pro Gly Val Thr
        980                 985                 990

Gly Lys Lys Cys Asp Arg Cys Ala His Gly Tyr Phe Asn Phe Gln Glu
    995                 1000                1005

Gly Gly Cys Thr Ala Cys Glu Cys Ser His Leu Gly Asn Asn Cys
1010                1015                1020

Asp Pro Lys Thr Gly Arg Cys Ile Cys Pro Pro Asn Thr Ile Gly
    1025                1030                1035

Glu Lys Cys Ser Lys Cys Ala Pro Asn Thr Trp Gly His Ser Ile
    1040                1045                1050

Thr Thr Gly Cys Lys Ala Cys Asn Cys Ser Thr Val Gly Ser Leu
1055                1060                1065

Asp Phe Gln Cys Asn Val Asn Thr Gly Gln Cys Asn Cys His Pro
    1070                1075                1080

Lys Phe Ser Gly Ala Lys Cys Thr Glu Cys Ser Arg Gly His Trp
    1085                1090                1095

Asn Tyr Pro Arg Cys Asn Leu Cys Asp Cys Phe Leu Pro Gly Thr
    1100                1105                1110

Asp Ala Thr Thr Cys Asp Ser Glu Thr Lys Lys Cys Ser Cys Ser
    1115                1120                1125

Asp Gln Thr Gly Gln Cys Thr Cys Lys Val Asn Val Glu Gly Ile
    1130                1135                1140

His Cys Asp Arg Cys Arg Pro Gly Lys Phe Gly Leu Asp Ala Lys
    1145                1150                1155

Asn Pro Leu Gly Cys Ser Ser Cys Tyr Cys Phe Gly Thr Thr Thr
    1160                1165                1170

Gln Cys Ser Glu Ala Lys Gly Leu Ile Arg Thr Trp Val Thr Leu
    1175                1180                1185
```

-continued

Lys Ala Glu Gln Thr Ile Leu Pro Leu Val Asp Glu Ala Leu Gln
1190                1195                1200

His Thr Thr Thr Lys Gly Ile Val Phe Gln His Pro Glu Ile Val
1205                1210                1215

Ala His Met Asp Leu Met Arg Glu Asp Leu His Leu Glu Pro Phe
1220                1225                1230

Tyr Trp Lys Leu Pro Glu Gln Phe Glu Gly Lys Lys Leu Met Ala
1235                1240                1245

Tyr Gly Gly Lys Leu Lys Tyr Ala Ile Tyr Phe Glu Ala Arg Glu
1250                1255                1260

Glu Thr Gly Phe Ser Thr Tyr Asn Pro Gln Val Ile Ile Arg Gly
1265                1270                1275

Gly Thr Pro Thr His Ala Arg Ile Ile Val Arg His Met Ala Ala
1280                1285                1290

Pro Leu Ile Gly Gln Leu Thr Arg His Glu Ile Glu Met Thr Glu
1295                1300                1305

Lys Glu Trp Lys Tyr Tyr Gly Asp Asp Pro Arg Val His Arg Thr
1310                1315                1320

Val Thr Arg Glu Asp Phe Leu Asp Ile Leu Tyr Asp Ile His Tyr
1325                1330                1335

Ile Leu Ile Lys Ala Thr Tyr Gly Asn Phe Met Arg Gln Ser Arg
1340                1345                1350

Ile Ser Glu Ile Ser Met Glu Val Ala Glu Gln Gly Arg Gly Thr
1355                1360                1365

Thr Met Thr Pro Pro Ala Asp Leu Ile Glu Lys Cys Asp Cys Pro
1370                1375                1380

Leu Gly Tyr Ser Gly Leu Ser Cys Glu Ala Cys Leu Pro Gly Phe
1385                1390                1395

Tyr Arg Leu Arg Ser Gln Pro Gly Gly Arg Thr Pro Gly Pro Thr
1400                1405                1410

Leu Gly Thr Cys Val Pro Cys Gln Cys Asn Gly His Ser Ser Leu
1415                1420                1425

Cys Asp Pro Glu Thr Ser Ile Cys Gln Asn Cys Gln His His Thr
1430                1435                1440

Ala Gly Asp Phe Cys Glu Arg Cys Ala Leu Gly Tyr Tyr Gly Ile
1445                1450                1455

Val Lys Gly Leu Pro Asn Asp Cys Gln Gln Cys Ala Cys Pro Leu
1460                1465                1470

Ile Ser Ser Ser Asn Asn Phe Ser Pro Ser Cys Val Ala Glu Gly
1475                1480                1485

Leu Asp Asp Tyr Arg Cys Thr Ala Cys Pro Arg Gly Tyr Glu Gly
1490                1495                1500

Gln Tyr Cys Glu Arg Cys Ala Pro Gly Tyr Thr Gly Ser Pro Gly
1505                1510                1515

Asn Pro Gly Gly Ser Cys Gln Glu Cys Glu Cys Asp Pro Tyr Gly
1520                1525                1530

Ser Leu Pro Val Pro Cys Asp Pro Val Thr Gly Phe Cys Thr Cys
1535                1540                1545

Arg Pro Gly Ala Thr Gly Arg Lys Cys Asp Gly Cys Lys His Trp
1550                1555                1560

His Ala Arg Glu Gly Trp Glu Cys Val Phe Cys Gly Asp Glu Cys
1565                1570                1575

Thr Gly Leu Leu Leu Gly Asp Leu Ala Arg Leu Glu Gln Met Val

```
            1580             1585              1590

Met Ser Ile Asn Leu Thr Gly Pro Leu Pro Ala Pro Tyr Lys Met
    1595             1600             1605

Leu Tyr Gly Leu Glu Asn Met Thr Gln Glu Leu Lys His Leu Leu
    1610             1615             1620

Ser Pro Gln Arg Ala Pro Glu Arg Leu Ile Gln Leu Ala Glu Gly
    1625             1630             1635

Asn Leu Asn Thr Leu Val Thr Glu Met Asn Glu Leu Leu Thr Arg
    1640             1645             1650

Ala Thr Lys Val Thr Ala Asp Gly Glu Gln Thr Gly Gln Asp Ala
    1655             1660             1665

Glu Arg Thr Asn Thr Arg Ala Lys Ser Leu Gly Glu Phe Ile Lys
    1670             1675             1680

Glu Leu Ala Arg Asp Ala Glu Ala Val Asn Glu Lys Ala Ile Lys
    1685             1690             1695

Leu Asn Glu Thr Leu Gly Thr Arg Asp Glu Ala Phe Glu Arg Asn
    1700             1705             1710

Leu Glu Gly Leu Gln Lys Glu Ile Asp Gln Met Ile Lys Glu Leu
    1715             1720             1725

Arg Arg Lys Asn Leu Glu Thr Gln Lys Glu Ile Ala Glu Asp Glu
    1730             1735             1740

Leu Val Ala Ala Glu Ala Leu Leu Lys Lys Val Lys Lys Leu Phe
    1745             1750             1755

Gly Glu Ser Arg Gly Glu Asn Glu Glu Met Glu Lys Asp Leu Arg
    1760             1765             1770

Glu Lys Leu Ala Asp Tyr Lys Asn Lys Val Asp Asp Ala Trp Asp
    1775             1780             1785

Leu Leu Arg Glu Ala Thr Asp Lys Ile Arg Glu Ala Asn Arg Leu
    1790             1795             1800

Phe Ala Val Asn Gln Lys Asn Met Thr Ala Leu Glu Lys Lys Lys
    1805             1810             1815

Glu Ala Val Glu Ser Gly Lys Arg Gln Ile Glu Asn Thr Leu Lys
    1820             1825             1830

Glu Gly Asn Asp Ile Leu Asp Glu Ala Asn Arg Leu Ala Asp Glu
    1835             1840             1845

Ile Asn Ser Ile Ile Asp Tyr Val Glu Asp Ile Gln Thr Lys Leu
    1850             1855             1860

Pro Pro Met Ser Glu Glu Leu Asn Asp Lys Ile Asp Asp Leu Ser
    1865             1870             1875

Gln Glu Ile Lys Asp Arg Lys Leu Ala Glu Lys Val Ser Gln Ala
    1880             1885             1890

Glu Ser His Ala Ala Gln Leu Asn Asp Ser Ser Ala Val Leu Asp
    1895             1900             1905

Gly Ile Leu Asp Glu Ala Lys Asn Ile Ser Phe Asn Ala Thr Ala
    1910             1915             1920

Ala Phe Lys Ala Tyr Ser Asn Ile Lys Asp Tyr Ile Asp Glu Ala
    1925             1930             1935

Glu Lys Val Ala Lys Glu Ala Lys Asp Leu Ala His Glu Ala Thr
    1940             1945             1950

Lys Leu Ala Thr Gly Pro Arg Gly Leu Leu Lys Glu Asp Ala Lys
    1955             1960             1965

Gly Cys Leu Gln Lys Ser Phe Arg Ile Leu Asn Glu Ala Lys Lys
    1970             1975             1980
```

```
Leu Ala Asn Asp Val Lys Glu Asn Glu Asp His Leu Asn Gly Leu
    1985            1990                1995

Lys Thr Arg Ile Glu Asn Ala Asp Ala Arg Asn Gly Asp Leu Leu
    2000            2005                2010

Arg Thr Leu Asn Asp Thr Leu Gly Lys Leu Ser Ala Ile Pro Asn
    2015            2020                2025

Asp Thr Ala Ala Lys Leu Gln Ala Val Lys Asp Lys Ala Arg Gln
    2030            2035                2040

Ala Asn Asp Thr Ala Lys Asp Val Leu Ala Gln Ile Thr Glu Leu
    2045            2050                2055

His Gln Asn Leu Asp Gly Leu Lys Lys Asn Tyr Asn Lys Leu Ala
    2060            2065                2070

Asp Ser Val Ala Lys Thr Asn Ala Val Val Lys Asp Pro Ser Lys
    2075            2080                2085

Asn Lys Ile Ile Ala Asp Ala Asp Ala Thr Val Lys Asn Leu Glu
    2090            2095                2100

Gln Glu Ala Asp Arg Leu Ile Asp Lys Leu Lys Pro Ile Lys Glu
    2105            2110                2115

Leu Glu Asp Asn Leu Lys Lys Asn Ile Ser Glu Ile Lys Glu Leu
    2120            2125                2130

Ile Asn Gln Ala Arg Lys Gln Ala Asn Ser Ile Lys Val Ser Val
    2135            2140                2145

Ser Ser Gly Gly Asp Cys Ile Arg Thr Tyr Lys Pro Glu Ile Lys
    2150            2155                2160

Lys Gly Ser Tyr Asn Asn Ile Val Val Asn Val Lys Thr Ala Val
    2165            2170                2175

Ala Asp Asn Leu Leu Phe Tyr Leu Gly Ser Ala Lys Phe Ile Asp
    2180            2185                2190

Phe Leu Ala Ile Glu Met Arg Lys Gly Lys Val Ser Phe Leu Trp
    2195            2200                2205

Asp Val Gly Ser Gly Val Gly Arg Val Glu Tyr Pro Asp Leu Thr
    2210            2215                2220

Ile Asp Asp Ser Tyr Trp Tyr Arg Ile Val Ala Ser Arg Thr Gly
    2225            2230                2235

Arg Asn Gly Thr Ile Ser Val Arg Ala Leu Asp Gly Pro Lys Ala
    2240            2245                2250

Ser Ile Val Pro Ser Thr His His Ser Thr Ser Pro Pro Gly Tyr
    2255            2260                2265

Thr Ile Leu Asp Val Asp Ala Asn Ala Met Leu Phe Val Gly Gly
    2270            2275                2280

Leu Thr Gly Lys Leu Lys Lys Ala Asp Ala Val Arg Val Ile Thr
    2285            2290                2295

Phe Thr Gly Cys Met Gly Glu Thr Tyr Phe Asp Asn Lys Pro Ile
    2300            2305                2310

Gly Leu Trp Asn Phe Arg Glu Lys Glu Gly Asp Cys Lys Gly Cys
    2315            2320                2325

Thr Val Ser Pro Gln Val Glu Asp Ser Glu Gly Thr Ile Gln Phe
    2330            2335                2340

Asp Gly Glu Gly Tyr Ala Leu Val Ser Arg Pro Ile Arg Trp Tyr
    2345            2350                2355

Pro Asn Ile Ser Thr Val Met Phe Lys Phe Arg Thr Phe Ser Ser
    2360            2365                2370
```

```
Ser Ala Leu Leu Met Tyr Leu Ala Thr Arg Asp Leu Arg Asp Phe
2375                2380                2385

Met Ser Val Glu Leu Thr Asp Gly His Ile Lys Val Ser Tyr Asp
2390                2395                2400

Leu Gly Ser Gly Met Ala Ser Val Val Ser Asn Gln Asn His Asn
2405                2410                2415

Asp Gly Lys Trp Lys Ser Phe Thr Leu Ser Arg Ile Gln Lys Gln
2420                2425                2430

Ala Asn Ile Ser Ile Val Asp Ile Asp Thr Asn Gln Glu Glu Asn
2435                2440                2445

Ile Ala Thr Ser Ser Ser Gly Asn Asn Phe Gly Leu Asp Leu Lys
2450                2455                2460

Ala Asp Asp Lys Ile Tyr Phe Gly Gly Leu Pro Thr Leu Arg Asn
2465                2470                2475

Leu Ser Met Lys Ala Arg Pro Glu Val Asn Leu Lys Lys Tyr Ser
2480                2485                2490

Gly Cys Leu Lys Asp Ile Glu Ile Ser Arg Thr Pro Tyr Asn Ile
2495                2500                2505

Leu Ser Ser Pro Asp Tyr Val Gly Val Thr Lys Gly Cys Ser Leu
2510                2515                2520

Glu Asn Val Tyr Thr Val Ser Phe Pro Lys Pro Gly Phe Val Glu
2525                2530                2535

Leu Ser Pro Val Pro Ile Asp Val Gly Thr Glu Ile Asn Leu Ser
2540                2545                2550

Phe Ser Thr Lys Asn Glu Ser Gly Ile Ile Leu Leu Gly Ser Gly
2555                2560                2565

Gly Thr Pro Ala Pro Pro Arg Arg Lys Arg Arg Gln Thr Gly Gln
2570                2575                2580

Ala Tyr Tyr Ala Ile Leu Leu Asn Arg Gly Arg Leu Glu Val His
2585                2590                2595

Leu Ser Thr Gly Ala Arg Thr Met Arg Lys Ile Val Ile Arg Pro
2600                2605                2610

Glu Pro Asn Leu Phe His Asp Gly Arg Glu His Ser Val His Val
2615                2620                2625

Glu Arg Thr Arg Gly Ile Phe Thr Val Gln Val Asp Glu Asn Arg
2630                2635                2640

Arg Tyr Met Gln Asn Leu Thr Val Glu Gln Pro Ile Glu Val Lys
2645                2650                2655

Lys Leu Phe Val Gly Gly Ala Pro Pro Glu Phe Gln Pro Ser Pro
2660                2665                2670

Leu Arg Asn Ile Pro Pro Phe Glu Gly Cys Ile Trp Asn Leu Val
2675                2680                2685

Ile Asn Ser Val Pro Met Asp Phe Ala Arg Pro Val Ser Phe Lys
2690                2695                2700

Asn Ala Asp Ile Gly Arg Cys Ala His Gln Lys Leu Arg Glu Asp
2705                2710                2715

Glu Asp Gly Ala Ala Pro Ala Glu Ile Val Ile Gln Pro Glu Pro
2720                2725                2730

Val Pro Thr Pro Ala Phe Pro Thr Pro Thr Pro Val Leu Thr His
2735                2740                2745

Gly Pro Cys Ala Ala Glu Ser Glu Pro Ala Leu Leu Ile Gly Ser
2750                2755                2760

Lys Gln Phe Gly Leu Ser Arg Asn Ser His Ile Ala Ile Ala Phe
```

Asp Asp Thr Lys Val Lys Asn Arg Leu Thr Ile Glu Leu Glu Val
2780            2785                    2790

Arg Thr Glu Ala Glu Ser Gly Leu Leu Phe Tyr Met Ala Arg Ile
2795            2800                    2805

Asn His Ala Asp Phe Ala Thr Val Gln Leu Arg Asn Gly Leu Pro
2810            2815                    2820

Tyr Phe Ser Tyr Asp Leu Gly Ser Gly Asp Thr His Thr Met Ile
2825            2830                    2835

Pro Thr Lys Ile Asn Asp Gly Gln Trp His Lys Ile Lys Ile Met
2840            2845                    2850

Arg Ser Lys Gln Glu Gly Ile Leu Tyr Val Asp Gly Ala Ser Asn
2855            2860                    2865

Arg Thr Ile Ser Pro Lys Lys Ala Asp Ile Leu Asp Val Val Gly
2870            2875                    2880

Met Leu Tyr Val Gly Gly Leu Pro Ile Asn Tyr Thr Thr Arg Arg
2885            2890                    2895

Ile Gly Pro Val Thr Tyr Ser Ile Asp Gly Cys Val Arg Asn Leu
2900            2905                    2910

His Met Ala Glu Ala Pro Ala Asp Leu Glu Gln Pro Thr Ser Ser
2915            2920                    2925

Phe His Val Gly Thr Cys Phe Ala Asn Ala Gln Arg Gly Thr Tyr
2930            2935                    2940

Phe Asp Gly Thr Gly Phe Ala Lys Ala Val Gly Gly Phe Lys Val
2945            2950                    2955

Gly Leu Asp Leu Leu Val Glu Phe Glu Phe Arg Thr Thr Thr Thr
2960            2965                    2970

Thr Gly Val Leu Leu Gly Ile Ser Ser Gln Lys Met Asp Gly Met
2975            2980                    2985

Gly Ile Glu Met Ile Asp Glu Lys Leu Met Phe His Val Asp Asn
2990            2995                    3000

Gly Ala Gly Arg Phe Thr Ala Val Tyr Asp Ala Gly Val Pro Gly
3005            3010                    3015

His Leu Cys Asp Gly Gln Trp His Lys Val Thr Ala Asn Lys Ile
3020            3025                    3030

Lys His Arg Ile Glu Leu Thr Val Asp Gly Asn Gln Val Glu Ala
3035            3040                    3045

Gln Ser Pro Asn Pro Ala Ser Thr Ser Ala Asp Thr Asn Asp Pro
3050            3055                    3060

Val Phe Val Gly Gly Phe Pro Asp Asp Leu Lys Gln Phe Gly Leu
3065            3070                    3075

Thr Thr Ser Ile Pro Phe Arg Gly Cys Ile Arg Ser Leu Lys Leu
3080            3085                    3090

Thr Lys Gly Thr Gly Lys Pro Leu Glu Val Asn Phe Ala Lys Ala
3095            3100                    3105

Leu Glu Leu Arg Gly Val Gln Pro Val Ser Cys Pro Ala Asn
3110            3115                    3120

<210> SEQ ID NO 11
<211> LENGTH: 3695
<212> TYPE: PRT
<213> ORGANISM: Artificial Sequence
<220> FEATURE:
<223> OTHER INFORMATION: Amino acid sequence of Laminin subunit alpha-5
      (Homo sapiens)

<400> SEQUENCE: 11

```
Met Ala Lys Arg Leu Cys Ala Gly Ser Ala Leu Cys Val Arg Gly Pro
1               5                   10                  15

Arg Gly Pro Ala Pro Leu Leu Val Gly Leu Ala Leu Leu Gly Ala
            20                  25                  30

Ala Arg Ala Arg Glu Glu Ala Gly Gly Phe Ser Leu His Pro Pro
        35                  40                  45

Tyr Phe Asn Leu Ala Glu Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Asp Pro Asn Gln
                85                  90                  95

Thr Ile Arg Gly Gln Tyr Cys Asp Ile Cys Thr Ala Ala Asn Ser Asn
                100                 105                 110

Lys Ala His Pro Ala Ser Asn Ala Ile Asp Gly Thr Glu Arg Trp Trp
            115                 120                 125

Gln Ser Pro Pro Leu Ser Arg Gly Leu Glu Tyr Asn Glu Val Asn Val
130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
            180                 185                 190

Arg Asp Cys Leu Glu Arg Phe Gly Pro Gln Thr Leu Glu Arg Ile Thr
        195                 200                 205

Arg Asp Asp Ala Ala Ile Cys Thr Thr Glu Tyr Ser Arg Ile Val Pro
210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
        355                 360                 365

Tyr Tyr Asp Pro Glu Val Asp Arg Arg Ala Ser Gln Ser Leu Asp
            370                 375                 380

Gly Thr Tyr Gln Gly Gly Val Cys Ile Asp Cys Gln His His Thr
385                 390                 395                 400

Thr Gly Val Asn Cys Glu Arg Cys Leu Pro Gly Phe Tyr Arg Ser Pro
```

```
                    405                 410                 415
Asn His Pro Leu Asp Ser Pro His Val Cys Arg Arg Cys Asn Cys Glu
                420                 425                 430

Ser Asp Phe Thr Asp Gly Thr Cys Glu Asp Leu Thr Gly Arg Cys Tyr
                435                 440                 445

Cys Arg Pro Asn Phe Ser Gly Glu Arg Cys Asp Val Cys Ala Glu Gly
            450                 455                 460

Phe Thr Gly Phe Pro Ser Cys Tyr Pro Thr Pro Ser Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
            515                 520                 525

Cys Ala Pro Gly Phe Tyr Gly Pro Gly Cys Gln Pro Cys Gln Cys Ser
            530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575

Gly Tyr Phe His Phe Pro Leu Cys Gln Leu Cys Gly Cys Ser Pro Ala
                580                 585                 590

Gly Thr Leu Pro Glu Gly Cys Asp Glu Ala Gly Arg Cys Leu Cys Gln
            595                 600                 605

Pro Glu Phe Ala Gly Pro His Cys Asp Arg Cys Arg Pro Gly Tyr His
            610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Gly Leu Cys Arg Cys Arg Pro Gly Tyr
                645                 650                 655

Thr Gly Thr Ala Cys Gln Glu Cys Ser Pro Gly Phe His Gly Phe Pro
                660                 665                 670

Ser Cys Val Pro Cys His Cys Ser Ala Glu Gly Ser Leu His Ala Ala
            675                 680                 685

Cys Asp Pro Arg Ser Gly Gln Cys Ser Cys Arg Pro Arg Val Thr Gly
            690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
                740                 745                 750

Pro Ser Cys Asp Arg Cys Lys Pro Gly Phe Trp Gly Leu Ser Pro Ser
            755                 760                 765

Asn Pro Glu Gly Cys Thr Arg Cys Ser Cys Asp Leu Arg Gly Thr Leu
            770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
                820                 825                 830
```

-continued

```
Ile Gly Gly Ala Leu Gly Gln Ser Cys Glu Pro Arg Thr Gly Val Cys
        835                 840                 845

Arg Cys Arg Pro Asn Thr Gln Gly Pro Thr Cys Ser Glu Pro Ala Arg
    850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
                900                 905                 910

Gln Pro Arg Ile Val Ala Arg Leu Asn Leu Thr Ser Pro Asp Leu Phe
            915                 920                 925

Trp Leu Val Phe Arg Tyr Val Asn Arg Gly Ala Met Ser Val Ser Gly
    930                 935                 940

Arg Val Ser Val Arg Glu Gly Arg Ser Ala Thr Cys Ala Asn Cys
945                 950                 955                 960

Thr Ala Gln Ser Gln Pro Val Ala Phe Pro Pro Ser Thr Glu Pro Ala
                965                 970                 975

Phe Ile Thr Val Pro Gln Arg Gly Phe Gly Pro Phe Val Leu Asn
            980                 985                 990

Pro Gly Thr Trp Ala Leu Arg Val  Glu Ala Glu Gly Val  Leu Leu Asp
    995                 1000                1005

Tyr Val  Val Leu Leu Pro Ser  Ala Tyr Glu Ala  Ala Leu Leu
    1010                1015                1020

Gln Leu Arg Val Thr Glu Ala  Cys Thr Tyr Arg Pro  Ser Ala Gln
    1025                1030                1035

Gln Ser  Gly Asp Asn Cys Leu  Leu Tyr Thr His Leu  Pro Leu Asp
    1040                1045                1050

Gly Phe  Pro Ser Ala Ala Gly  Leu Glu Ala Leu Cys  Arg Gln Asp
    1055                1060                1065

Asn Ser  Leu Pro Arg Pro Cys  Pro Thr Glu Gln Leu  Ser Pro Ser
    1070                1075                1080

His Pro  Pro Leu Ile Thr Cys  Thr Gly Ser Asp Val  Asp Val Gln
    1085                1090                1095

Leu Gln  Val Ala Val Pro Gln  Pro Gly Arg Tyr Ala  Leu Val Val
    1100                1105                1110

Glu Tyr  Ala Asn Glu Asp Ala  Arg Gln Glu Val Gly  Val Ala Val
    1115                1120                1125

His Thr  Pro Gln Arg Ala Pro  Gln Gln Gly Leu Leu  Ser Leu His
    1130                1135                1140

Pro Cys  Leu Tyr Ser Thr Leu  Cys Arg Gly Thr Ala  Arg Asp Thr
    1145                1150                1155

Gln Asp  His Leu Ala Val Phe  His Leu Asp Ser Glu  Ala Ser Val
    1160                1165                1170

Arg Leu  Thr Ala Glu Gln Ala  Arg Phe Phe Leu His  Gly Val Thr
    1175                1180                1185

Leu Val  Pro Ile Glu Glu Phe  Ser Pro Glu Phe Val  Glu Pro Arg
    1190                1195                1200

Val Ser  Cys Ile Ser Ser His  Gly Ala Phe Gly Pro  Asn Ser Ala
    1205                1210                1215

Ala Cys  Leu Pro Ser Arg Phe  Pro Lys Pro Pro Gln  Pro Ile Ile
    1220                1225                1230
```

```
Leu Arg Asp Cys Gln Val Ile Pro Leu Pro Pro Gly Leu Pro Leu
    1235                1240                1245

Thr His Ala Gln Asp Leu Thr Pro Ala Met Ser Pro Ala Gly Pro
    1250                1255                1260

Arg Pro Arg Pro Pro Thr Ala Val Asp Pro Asp Ala Glu Pro Thr
    1265                1270                1275

Leu Leu Arg Glu Pro Gln Ala Thr Val Val Phe Thr Thr His Val
    1280                1285                1290

Pro Thr Leu Gly Arg Tyr Ala Phe Leu Leu His Gly Tyr Gln Pro
    1295                1300                1305

Ala His Pro Thr Phe Pro Val Glu Val Leu Ile Asn Ala Gly Arg
    1310                1315                1320

Val Trp Gln Gly His Ala Asn Ala Ser Phe Cys Pro His Gly Tyr
    1325                1330                1335

Gly Cys Arg Thr Leu Val Val Cys Glu Gly Gln Ala Leu Leu Asp
    1340                1345                1350

Val Thr His Ser Glu Leu Thr Val Thr Val Arg Val Pro Lys Gly
    1355                1360                1365

Arg Trp Leu Trp Leu Asp Tyr Val Leu Val Val Pro Glu Asn Val
    1370                1375                1380

Tyr Ser Phe Gly Tyr Leu Arg Glu Glu Pro Leu Asp Lys Ser Tyr
    1385                1390                1395

Asp Phe Ile Ser His Cys Ala Ala Gln Gly Tyr His Ile Ser Pro
    1400                1405                1410

Ser Ser Ser Ser Leu Phe Cys Arg Asn Ala Ala Ala Ser Leu Ser
    1415                1420                1425

Leu Phe Tyr Asn Asn Gly Ala Arg Pro Cys Gly Cys His Glu Val
    1430                1435                1440

Gly Ala Thr Gly Pro Thr Cys Glu Pro Phe Gly Gly Gln Cys Pro
    1445                1450                1455

Cys His Ala His Val Ile Gly Arg Asp Cys Ser Arg Cys Ala Thr
    1460                1465                1470

Gly Tyr Trp Gly Phe Pro Asn Cys Arg Pro Cys Asp Cys Gly Ala
    1475                1480                1485

Arg Leu Cys Asp Glu Leu Thr Gly Gln Cys Ile Cys Pro Pro Arg
    1490                1495                1500

Thr Ile Pro Pro Asp Cys Leu Leu Cys Gln Pro Gln Thr Phe Gly
    1505                1510                1515

Cys His Pro Leu Val Gly Cys Glu Glu Cys Asn Cys Ser Gly Pro
    1520                1525                1530

Gly Ile Gln Glu Leu Thr Asp Pro Thr Cys Asp Thr Asp Ser Gly
    1535                1540                1545

Gln Cys Lys Cys Arg Pro Asn Val Thr Gly Arg Arg Cys Asp Thr
    1550                1555                1560

Cys Ser Pro Gly Phe His Gly Tyr Pro Arg Cys Arg Pro Cys Asp
    1565                1570                1575

Cys His Glu Ala Gly Thr Ala Pro Gly Val Cys Asp Pro Leu Thr
    1580                1585                1590

Gly Gln Cys Tyr Cys Lys Glu Asn Val Gln Gly Pro Lys Cys Asp
    1595                1600                1605

Gln Cys Ser Leu Gly Thr Phe Ser Leu Asp Ala Ala Asn Pro Lys
    1610                1615                1620

Gly Cys Thr Arg Cys Phe Cys Phe Gly Ala Thr Glu Arg Cys Arg
```

```
               1625                1630                1635

Ser  Ser  Ser  Tyr  Thr  Arg  Gln  Glu  Phe  Val  Asp  Met  Glu  Gly  Trp
     1640                1645                1650

Val  Leu  Leu  Ser  Thr  Asp  Arg  Gln  Val  Val  Pro  His  Glu  Arg  Gln
     1655                1660                1665

Pro  Gly  Thr  Glu  Met  Leu  Arg  Ala  Asp  Leu  Arg  His  Val  Pro  Glu
     1670                1675                1680

Ala  Val  Pro  Glu  Ala  Phe  Pro  Glu  Leu  Tyr  Trp  Gln  Ala  Pro  Pro
     1685                1690                1695

Ser  Tyr  Leu  Gly  Asp  Arg  Val  Ser  Ser  Tyr  Gly  Gly  Thr  Leu  Arg
     1700                1705                1710

Tyr  Glu  Leu  His  Ser  Glu  Thr  Gln  Arg  Gly  Asp  Val  Phe  Val  Pro
     1715                1720                1725

Met  Glu  Ser  Arg  Pro  Asp  Val  Val  Leu  Gln  Gly  Asn  Gln  Met  Ser
     1730                1735                1740

Ile  Thr  Phe  Leu  Glu  Pro  Ala  Tyr  Pro  Thr  Pro  Gly  His  Val  His
     1745                1750                1755

Arg  Gly  Gln  Leu  Gln  Leu  Val  Glu  Gly  Asn  Phe  Arg  His  Thr  Glu
     1760                1765                1770

Thr  Arg  Asn  Thr  Val  Ser  Arg  Glu  Glu  Leu  Met  Met  Val  Leu  Ala
     1775                1780                1785

Ser  Leu  Glu  Gln  Leu  Gln  Ile  Arg  Ala  Leu  Phe  Ser  Gln  Ile  Ser
     1790                1795                1800

Ser  Ala  Val  Phe  Leu  Arg  Arg  Val  Ala  Leu  Glu  Val  Ala  Ser  Pro
     1805                1810                1815

Ala  Gly  Gln  Gly  Ala  Leu  Ala  Ser  Asn  Val  Glu  Leu  Cys  Leu  Cys
     1820                1825                1830

Pro  Ala  Ser  Tyr  Arg  Gly  Asp  Ser  Cys  Gln  Glu  Cys  Ala  Pro  Gly
     1835                1840                1845

Phe  Tyr  Arg  Asp  Val  Lys  Gly  Leu  Phe  Leu  Gly  Arg  Cys  Val  Pro
     1850                1855                1860

Cys  Gln  Cys  His  Gly  His  Ser  Asp  Arg  Cys  Leu  Pro  Gly  Ser  Gly
     1865                1870                1875

Val  Cys  Val  Asp  Cys  Gln  His  Asn  Thr  Glu  Gly  Ala  His  Cys  Glu
     1880                1885                1890

Arg  Cys  Gln  Ala  Gly  Phe  Val  Ser  Ser  Arg  Asp  Asp  Pro  Ser  Ala
     1895                1900                1905

Pro  Cys  Val  Ser  Cys  Pro  Cys  Pro  Leu  Ser  Val  Pro  Ser  Asn  Asn
     1910                1915                1920

Phe  Ala  Glu  Gly  Cys  Val  Leu  Arg  Gly  Gly  Arg  Thr  Gln  Cys  Leu
     1925                1930                1935

Cys  Lys  Pro  Gly  Tyr  Ala  Gly  Ala  Ser  Cys  Glu  Arg  Cys  Ala  Pro
     1940                1945                1950

Gly  Phe  Phe  Gly  Asn  Pro  Leu  Val  Leu  Gly  Ser  Ser  Cys  Gln  Pro
     1955                1960                1965

Cys  Asp  Cys  Ser  Gly  Asn  Gly  Asp  Pro  Asn  Leu  Leu  Phe  Ser  Asp
     1970                1975                1980

Cys  Asp  Pro  Leu  Thr  Gly  Ala  Cys  Arg  Gly  Cys  Leu  Arg  His  Thr
     1985                1990                1995

Thr  Gly  Pro  Arg  Cys  Glu  Ile  Cys  Ala  Pro  Gly  Phe  Tyr  Gly  Asn
     2000                2005                2010

Ala  Leu  Leu  Pro  Gly  Asn  Cys  Thr  Arg  Cys  Asp  Cys  Thr  Pro  Cys
     2015                2020                2025
```

```
Gly Thr Glu Ala Cys Asp Pro His Ser Gly His Cys Leu Cys Lys
    2030            2035            2040

Ala Gly Val Thr Gly Arg Arg Cys Asp Arg Cys Gln Glu Gly His
    2045            2050            2055

Phe Gly Phe Asp Gly Cys Gly Cys Arg Pro Cys Ala Cys Gly
    2060            2065            2070

Pro Ala Ala Glu Gly Ser Glu Cys His Pro Gln Ser Gly Gln Cys
    2075            2080            2085

His Cys Arg Pro Gly Thr Met Gly Pro Gln Cys Arg Glu Cys Ala
    2090            2095            2100

Pro Gly Tyr Trp Gly Leu Pro Glu Gln Gly Cys Arg Arg Cys Gln
    2105            2110            2115

Cys Pro Gly Gly Arg Cys Asp Pro His Thr Gly Arg Cys Asn Cys
    2120            2125            2130

Pro Pro Gly Leu Ser Gly Glu Arg Cys Asp Thr Cys Ser Gln Gln
    2135            2140            2145

His Gln Val Pro Val Pro Gly Pro Val Gly His Ser Ile His
    2150            2155            2160

Cys Glu Val Cys Asp His Cys Val Val Leu Leu Leu Asp Asp Leu
    2165            2170            2175

Glu Arg Ala Gly Ala Leu Leu Pro Ala Ile His Glu Gln Leu Arg
    2180            2185            2190

Gly Ile Asn Ala Ser Ser Met Ala Trp Ala Arg Leu His Arg Leu
    2195            2200            2205

Asn Ala Ser Ile Ala Asp Leu Gln Ser Gln Leu Arg Ser Pro Leu
    2210            2215            2220

Gly Pro Arg His Glu Thr Ala Gln Gln Leu Glu Val Leu Glu Gln
    2225            2230            2235

Gln Ser Thr Ser Leu Gly Gln Asp Ala Arg Arg Leu Gly Gly Gln
    2240            2245            2250

Ala Val Gly Thr Arg Asp Gln Ala Ser Gln Leu Leu Ala Gly Thr
    2255            2260            2265

Glu Ala Thr Leu Gly His Ala Lys Thr Leu Leu Ala Ala Ile Arg
    2270            2275            2280

Ala Val Asp Arg Thr Leu Ser Glu Leu Met Ser Gln Thr Gly His
    2285            2290            2295

Leu Gly Leu Ala Asn Ala Ser Ala Pro Ser Gly Glu Gln Leu Leu
    2300            2305            2310

Arg Thr Leu Ala Glu Val Glu Arg Leu Leu Trp Glu Met Arg Ala
    2315            2320            2325

Arg Asp Leu Gly Ala Pro Gln Ala Ala Glu Ala Glu Leu Ala
    2330            2335            2340

Ala Ala Gln Arg Leu Leu Ala Arg Val Gln Glu Gln Leu Ser Ser
    2345            2350            2355

Leu Trp Glu Glu Asn Gln Ala Leu Ala Thr Gln Thr Arg Asp Arg
    2360            2365            2370

Leu Ala Gln His Glu Ala Gly Leu Met Asp Leu Arg Glu Ala Leu
    2375            2380            2385

Asn Arg Ala Val Asp Ala Thr Arg Glu Ala Gln Glu Leu Asn Ser
    2390            2395            2400

Arg Asn Gln Glu Arg Leu Glu Glu Ala Leu Gln Arg Lys Gln Glu
    2405            2410            2415
```

```
Leu Ser Arg Asp Asn Ala Thr Leu Gln Ala Thr Leu His Ala Ala
    2420                2425                2430

Arg Asp Thr Leu Ala Ser Val Phe Arg Leu Leu His Ser Leu Asp
    2435                2440                2445

Gln Ala Lys Glu Glu Leu Glu Arg Leu Ala Ala Ser Leu Asp Gly
    2450                2455                2460

Ala Arg Thr Pro Leu Leu Gln Arg Met Gln Thr Phe Ser Pro Ala
    2465                2470                2475

Gly Ser Lys Leu Arg Leu Val Glu Ala Ala Glu Ala His Ala Gln
    2480                2485                2490

Gln Leu Gly Gln Leu Ala Leu Asn Leu Ser Ser Ile Ile Leu Asp
    2495                2500                2505

Val Asn Gln Asp Arg Leu Thr Gln Arg Ala Ile Glu Ala Ser Asn
    2510                2515                2520

Ala Tyr Ser Arg Ile Leu Gln Ala Val Gln Ala Ala Glu Asp Ala
    2525                2530                2535

Ala Gly Gln Ala Leu Gln Gln Ala Asp His Thr Trp Ala Thr Val
    2540                2545                2550

Val Arg Gln Gly Leu Val Asp Arg Ala Gln Gln Leu Leu Ala Asn
    2555                2560                2565

Ser Thr Ala Leu Glu Glu Ala Met Leu Gln Glu Gln Gln Arg Leu
    2570                2575                2580

Gly Leu Val Trp Ala Ala Leu Gln Gly Ala Arg Thr Gln Leu Arg
    2585                2590                2595

Asp Val Arg Ala Lys Lys Asp Gln Leu Glu Ala His Ile Gln Ala
    2600                2605                2610

Ala Gln Ala Met Leu Ala Met Asp Thr Asp Glu Thr Ser Lys Lys
    2615                2620                2625

Ile Ala His Ala Lys Ala Val Ala Ala Glu Ala Gln Asp Thr Ala
    2630                2635                2640

Thr Arg Val Gln Ser Gln Leu Gln Ala Met Gln Glu Asn Val Glu
    2645                2650                2655

Arg Trp Gln Gly Gln Tyr Glu Gly Leu Arg Gly Gln Asp Leu Gly
    2660                2665                2670

Gln Ala Val Leu Asp Ala Gly His Ser Val Ser Thr Leu Glu Lys
    2675                2680                2685

Thr Leu Pro Gln Leu Leu Ala Lys Leu Ser Ile Leu Glu Asn Arg
    2690                2695                2700

Gly Val His Asn Ala Ser Leu Ala Leu Ser Ala Ser Ile Gly Arg
    2705                2710                2715

Val Arg Glu Leu Ile Ala Gln Ala Arg Gly Ala Ala Ser Lys Val
    2720                2725                2730

Lys Val Pro Met Lys Phe Asn Gly Arg Ser Gly Val Gln Leu Arg
    2735                2740                2745

Thr Pro Arg Asp Leu Ala Asp Leu Ala Ala Tyr Thr Ala Leu Lys
    2750                2755                2760

Phe Tyr Leu Gln Gly Pro Glu Pro Glu Pro Gly Gln Gly Thr Glu
    2765                2770                2775

Asp Arg Phe Val Met Tyr Met Gly Ser Arg Gln Ala Thr Gly Asp
    2780                2785                2790

Tyr Met Gly Val Ser Leu Arg Asp Lys Lys Val His Trp Val Tyr
    2795                2800                2805

Gln Leu Gly Glu Ala Gly Pro Ala Val Leu Ser Ile Asp Glu Asp
```

```
                    2810               2815               2820

Ile Gly Glu Gln Phe Ala Ala  Val Ser Leu Asp Arg  Thr Leu Gln
    2825               2830               2835

Phe Gly His Met Ser Val Thr  Val Glu Arg Gln Met  Ile Gln Glu
    2840               2845               2850

Thr Lys Gly Asp Thr Val Ala  Pro Gly Ala Glu Gly  Leu Leu Asn
    2855               2860               2865

Leu Arg Pro Asp Asp Phe Val  Phe Tyr Val Gly Gly  Tyr Pro Ser
    2870               2875               2880

Thr Phe Thr Pro Pro Leu Leu  Arg Phe Pro Gly  Tyr Arg Gly
    2885               2890               2895

Cys Ile Glu Met Asp Thr Leu  Asn Glu Glu Val Val  Ser Leu Tyr
    2900               2905               2910

Asn Phe Glu Arg Thr Phe Gln  Leu Asp Thr Ala Val  Asp Arg Pro
    2915               2920               2925

Cys Ala Arg Ser Lys Ser Thr  Gly Asp Pro Trp Leu  Thr Asp Gly
    2930               2935               2940

Ser Tyr Leu Asp Gly Thr Gly  Phe Ala Arg Ile Ser  Phe Asp Ser
    2945               2950               2955

Gln Ile Ser Thr Thr Lys Arg  Phe Glu Gln Glu Leu  Arg Leu Val
    2960               2965               2970

Ser Tyr Ser Gly Val Leu Phe  Phe Leu Lys Gln Gln  Ser Gln Phe
    2975               2980               2985

Leu Cys Leu Ala Val Gln Glu  Gly Ser Leu Val Leu  Leu Tyr Asp
    2990               2995               3000

Phe Gly Ala Gly Leu Lys Lys  Ala Val Pro Leu Gln  Pro Pro Pro
    3005               3010               3015

Pro Leu Thr Ser Ala Ser Lys  Ala Ile Gln Val Phe  Leu Leu Gly
    3020               3025               3030

Gly Ser Arg Lys Arg Val Leu  Val Arg Val Glu Arg  Ala Thr Val
    3035               3040               3045

Tyr Ser Val Glu Gln Asp Asn  Asp Leu Glu Leu Ala  Asp Ala Tyr
    3050               3055               3060

Tyr Leu Gly Gly Val Pro Pro  Asp Gln Leu Pro Pro  Ser Leu Arg
    3065               3070               3075

Arg Leu Phe Pro Thr Gly Gly  Ser Val Arg Gly Cys  Val Lys Gly
    3080               3085               3090

Ile Lys Ala Leu Gly Lys Tyr  Val Asp Leu Lys Arg  Leu Asn Thr
    3095               3100               3105

Thr Gly Val Ser Ala Gly Cys  Thr Ala Asp Leu Leu  Val Gly Arg
    3110               3115               3120

Ala Met Thr Phe His Gly His  Gly Phe Leu Arg Leu  Ala Leu Ser
    3125               3130               3135

Asn Val Ala Pro Leu Thr Gly  Asn Val Tyr Ser Gly  Phe Gly Phe
    3140               3145               3150

His Ser Ala Gln Asp Ser Ala  Leu Leu Tyr Tyr Arg  Ala Ser Pro
    3155               3160               3165

Asp Gly Leu Cys Gln Val Ser  Leu Gln Gln Gly Arg  Val Ser Leu
    3170               3175               3180

Gln Leu Leu Arg Thr Glu Val  Lys Thr Gln Ala Gly  Phe Ala Asp
    3185               3190               3195

Gly Ala Pro His Tyr Val Ala  Phe Tyr Ser Asn Ala  Thr Gly Val
    3200               3205               3210
```

```
Trp Leu Tyr Val Asp Asp Gln Leu Gln Gln Met Lys Pro His Arg
3215                3220                3225

Gly Pro Pro Pro Glu Leu Gln Pro Gln Pro Glu Gly Pro Pro Arg
3230                3235                3240

Leu Leu Leu Gly Gly Leu Pro Glu Ser Gly Thr Ile Tyr Asn Phe
3245                3250                3255

Ser Gly Cys Ile Ser Asn Val Phe Val Gln Arg Leu Leu Gly Pro
3260                3265                3270

Gln Arg Val Phe Asp Leu Gln Gln Asn Leu Gly Ser Val Asn Val
3275                3280                3285

Ser Thr Gly Cys Ala Pro Ala Leu Gln Ala Gln Thr Pro Gly Leu
3290                3295                3300

Gly Pro Arg Gly Leu Gln Ala Thr Ala Arg Lys Ala Ser Arg Arg
3305                3310                3315

Ser Arg Gln Pro Ala Arg His Pro Ala Cys Met Leu Pro Pro His
3320                3325                3330

Leu Arg Thr Thr Arg Asp Ser Tyr Gln Phe Gly Gly Ser Leu Ser
3335                3340                3345

Ser His Leu Glu Phe Val Gly Ile Leu Ala Arg His Arg Asn Trp
3350                3355                3360

Pro Ser Leu Ser Met His Val Leu Pro Arg Ser Ser Arg Gly Leu
3365                3370                3375

Leu Leu Phe Thr Ala Arg Leu Arg Pro Gly Ser Pro Ser Leu Ala
3380                3385                3390

Leu Phe Leu Ser Asn Gly His Phe Val Ala Gln Met Glu Gly Leu
3395                3400                3405

Gly Thr Arg Leu Arg Ala Gln Ser Arg Gln Arg Ser Arg Pro Gly
3410                3415                3420

Arg Trp His Lys Val Ser Val Arg Trp Glu Lys Asn Arg Ile Leu
3425                3430                3435

Leu Val Thr Asp Gly Ala Arg Ala Trp Ser Gln Glu Gly Pro His
3440                3445                3450

Arg Gln His Gln Gly Ala Glu His Pro Gln Pro His Thr Leu Phe
3455                3460                3465

Val Gly Gly Leu Pro Ala Ser Ser His Ser Ser Lys Leu Pro Val
3470                3475                3480

Thr Val Gly Phe Ser Gly Cys Val Lys Arg Leu Arg Leu His Gly
3485                3490                3495

Arg Pro Leu Gly Ala Pro Thr Arg Met Ala Gly Val Thr Pro Cys
3500                3505                3510

Ile Leu Gly Pro Leu Glu Ala Gly Leu Phe Phe Pro Gly Ser Gly
3515                3520                3525

Gly Val Ile Thr Leu Asp Leu Pro Gly Ala Thr Leu Pro Asp Val
3530                3535                3540

Gly Leu Glu Leu Glu Val Arg Pro Leu Ala Val Thr Gly Leu Ile
3545                3550                3555

Phe His Leu Gly Gln Ala Arg Thr Pro Pro Tyr Leu Gln Leu Gln
3560                3565                3570

Val Thr Glu Lys Gln Val Leu Leu Arg Ala Asp Asp Gly Ala Gly
3575                3580                3585

Glu Phe Ser Thr Ser Val Thr Arg Pro Ser Val Leu Cys Asp Gly
3590                3595                3600
```

```
Gln Trp His Arg Leu Ala Val Met Lys Ser Gly Asn Val Leu Arg
    3605                3610                3615

Leu Glu Val Asp Ala Gln Ser Asn His Thr Val Gly Pro Leu Leu
    3620                3625                3630

Ala Ala Ala Ala Gly Ala Pro Ala Pro Leu Tyr Leu Gly Gly Leu
    3635                3640                3645

Pro Glu Pro Met Ala Val Gln Pro Trp Pro Pro Ala Tyr Cys Gly
    3650                3655                3660

Cys Met Arg Arg Leu Ala Val Asn Arg Ser Pro Val Ala Met Thr
    3665                3670                3675

Arg Ser Val Glu Val His Gly Ala Val Gly Ala Ser Gly Cys Pro
    3680                3685                3690

Ala Ala
    3695

<210> SEQ ID NO 12
<211> LENGTH: 1786
<212> TYPE: PRT
<213> ORGANISM: Artificial Sequence
<220> FEATURE:
<223> OTHER INFORMATION: Amino acid sequence of Laminin subunit beta-1
      (Homo sapiens)

<400> SEQUENCE: 12

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255
```

```
Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
    290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
                340                 345                 350

Ala Thr Gly Asn Val Ser Gly Gly Val Cys Asp Asp Cys Gln His Asn
            355                 360                 365

Thr Met Gly Arg Asn Cys Glu Gln Cys Lys Pro Phe Tyr Tyr Gln His
    370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

Glu Gly Glu His Cys Asp Val Cys Lys Glu Gly Phe Tyr Asp Leu Ser
            435                 440                 445

Ser Glu Asp Pro Phe Gly Cys Lys Ser Cys Ala Cys Asn Pro Leu Gly
        450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
            485                 490                 495

His Trp Gly Leu Ser Asn Asp Leu Asp Gly Cys Arg Pro Cys Asp Cys
                500                 505                 510

Asp Leu Gly Gly Ala Leu Asn Asn Ser Cys Phe Ala Glu Ser Gly Gln
        515                 520                 525

Cys Ser Cys Arg Pro His Met Ile Gly Arg Gln Cys Asn Glu Val Glu
    530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
        580                 585                 590

Glu Gly Ala Tyr Leu Glu Phe Phe Ile Asp Asn Ile Pro Tyr Ser Met
    595                 600                 605

Glu Tyr Asp Ile Leu Ile Arg Tyr Glu Pro Gln Leu Pro Asp His Trp
        610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
            660                 665                 670
```

```
Glu Lys Gly Thr Asn Tyr Thr Val Arg Leu Glu Leu Pro Gln Tyr Thr
            675                 680                 685

Ser Ser Asp Ser Asp Val Glu Ser Pro Tyr Thr Leu Ile Asp Ser Leu
        690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
            740                 745                 750

Asp Val Cys Arg Asn Ile Ile Phe Ser Ile Ser Ala Leu Leu His Gln
        755                 760                 765

Thr Gly Leu Ala Cys Glu Cys Asp Pro Gln Gly Ser Leu Ser Ser Val
770                 775                 780

Cys Asp Pro Asn Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
            820                 825                 830

Cys Asn Pro Val Thr Gly Gln Cys His Cys Phe Gln Gly Val Tyr Ala
        835                 840                 845

Arg Gln Cys Asp Arg Cys Leu Pro Gly His Trp Gly Phe Pro Ser Cys
850                 855                 860

Gln Pro Cys Gln Cys Asn Gly His Ala Asp Asp Cys Asp Pro Val Thr
865                 870                 875                 880

Gly Glu Cys Leu Asn Cys Gln Asp Tyr Thr Met Gly His Asn Cys Glu
                885                 890                 895

Arg Cys Leu Ala Gly Tyr Tyr Gly Asp Pro Ile Ile Gly Ser Gly Asp
            900                 905                 910

His Cys Arg Pro Cys Pro Cys Pro Asp Gly Pro Asp Ser Gly Arg Gln
        915                 920                 925

Phe Ala Arg Ser Cys Tyr Gln Asp Pro Val Thr Leu Gln Leu Ala Cys
930                 935                 940

Val Cys Asp Pro Gly Tyr Ile Gly Ser Arg Cys Asp Cys Ala Ser
945                 950                 955                 960

Gly Tyr Phe Gly Asn Pro Ser Glu Val Gly Ser Cys Gln Pro Cys
                965                 970                 975

Gln Cys His Asn Asn Ile Asp Thr Thr Asp Pro Glu Ala Cys Asp Lys
            980                 985                 990

Glu Thr Gly Arg Cys Leu Lys Cys Leu Tyr His Thr Glu Gly Glu His
        995                 1000                1005

Cys Gln Phe Cys Arg Phe Gly Tyr Tyr Gly Asp Ala Leu Gln Gln
1010                1015                1020

Asp Cys Arg Lys Cys Val Cys Asn Tyr Leu Gly Thr Val Gln Glu
1025                1030                1035

His Cys Asn Gly Ser Asp Cys Gln Cys Asp Lys Ala Thr Gly Gln
1040                1045                1050

Cys Leu Cys Leu Pro Asn Val Ile Gly Gln Asn Cys Asp Arg Cys
1055                1060                1065

Ala Pro Asn Thr Trp Gln Leu Ala Ser Gly Thr Gly Cys Asp Pro
1070                1075                1080

Cys Asn Cys Asn Ala Ala His Ser Phe Gly Pro Ser Cys Asn Glu
```

-continued

```
                1085                1090                1095
Phe Thr Gly Gln Cys Gln Cys Met Pro Gly Phe Gly Gly Arg Thr
                1100                1105                1110
Cys Ser Glu Cys Gln Glu Leu Phe Trp Gly Asp Pro Asp Val Glu
                1115                1120                1125
Cys Arg Ala Cys Asp Cys Asp Pro Arg Gly Ile Glu Thr Pro Gln
                1130                1135                1140
Cys Asp Gln Ser Thr Gly Gln Cys Val Cys Val Glu Gly Val Glu
                1145                1150                1155
Gly Pro Arg Cys Asp Lys Cys Thr Arg Gly Tyr Ser Gly Val Phe
                1160                1165                1170
Pro Asp Cys Thr Pro Cys His Gln Cys Phe Ala Leu Trp Asp Val
                1175                1180                1185
Ile Ile Ala Glu Leu Thr Asn Arg Thr His Arg Phe Leu Glu Lys
                1190                1195                1200
Ala Lys Ala Leu Lys Ile Ser Gly Val Ile Gly Pro Tyr Arg Glu
                1205                1210                1215
Thr Val Asp Ser Val Glu Arg Lys Val Ser Glu Ile Lys Asp Ile
                1220                1225                1230
Leu Ala Gln Ser Pro Ala Ala Glu Pro Leu Lys Asn Ile Gly Asn
                1235                1240                1245
Leu Phe Glu Glu Ala Glu Lys Leu Ile Lys Asp Val Thr Glu Met
                1250                1255                1260
Met Ala Gln Val Glu Val Lys Leu Ser Asp Thr Thr Ser Gln Ser
                1265                1270                1275
Asn Ser Thr Ala Lys Glu Leu Asp Ser Leu Gln Thr Glu Ala Glu
                1280                1285                1290
Ser Leu Asp Asn Thr Val Lys Glu Leu Ala Glu Gln Leu Glu Phe
                1295                1300                1305
Ile Lys Asn Ser Asp Ile Arg Gly Ala Leu Asp Ser Ile Thr Lys
                1310                1315                1320
Tyr Phe Gln Met Ser Leu Glu Ala Glu Glu Arg Val Asn Ala Ser
                1325                1330                1335
Thr Thr Glu Pro Asn Ser Thr Val Glu Gln Ser Ala Leu Met Arg
                1340                1345                1350
Asp Arg Val Glu Asp Val Met Met Glu Arg Glu Ser Gln Phe Lys
                1355                1360                1365
Glu Lys Gln Glu Glu Gln Ala Arg Leu Leu Asp Glu Leu Ala Gly
                1370                1375                1380
Lys Leu Gln Ser Leu Asp Leu Ser Ala Ala Ala Glu Met Thr Cys
                1385                1390                1395
Gly Thr Pro Pro Gly Ala Ser Cys Ser Glu Thr Glu Cys Gly Gly
                1400                1405                1410
Pro Asn Cys Arg Thr Asp Glu Gly Glu Arg Lys Cys Gly Gly Pro
                1415                1420                1425
Gly Cys Gly Gly Leu Val Thr Val Ala His Asn Ala Trp Gln Lys
                1430                1435                1440
Ala Met Asp Leu Asp Gln Asp Val Leu Ser Ala Leu Ala Glu Val
                1445                1450                1455
Glu Gln Leu Ser Lys Met Val Ser Glu Ala Lys Leu Arg Ala Asp
                1460                1465                1470
Glu Ala Lys Gln Ser Ala Glu Asp Ile Leu Leu Lys Thr Asn Ala
                1475                1480                1485
```

```
Thr Lys Glu Lys Met Asp Lys Ser Asn Glu Glu Leu Arg Asn Leu
    1490            1495                1500

Ile Lys Gln Ile Arg Asn Phe Leu Thr Gln Asp Ser Ala Asp Leu
    1505            1510                1515

Asp Ser Ile Glu Ala Val Ala Asn Glu Val Leu Lys Met Glu Met
    1520            1525                1530

Pro Ser Thr Pro Gln Gln Leu Gln Asn Leu Thr Glu Asp Ile Arg
    1535            1540                1545

Glu Arg Val Glu Ser Leu Ser Gln Val Glu Val Ile Leu Gln His
    1550            1555                1560

Ser Ala Ala Asp Ile Ala Arg Ala Glu Met Leu Leu Glu Glu Ala
    1565            1570                1575

Lys Arg Ala Ser Lys Ser Ala Thr Asp Val Lys Val Thr Ala Asp
    1580            1585                1590

Met Val Lys Glu Ala Leu Glu Glu Ala Glu Lys Ala Gln Val Ala
    1595            1600                1605

Ala Glu Lys Ala Ile Lys Gln Ala Asp Glu Asp Ile Gln Gly Thr
    1610            1615                1620

Gln Asn Leu Leu Thr Ser Ile Glu Ser Glu Thr Ala Ala Ser Glu
    1625            1630                1635

Glu Thr Leu Phe Asn Ala Ser Gln Arg Ile Ser Glu Leu Glu Arg
    1640            1645                1650

Asn Val Glu Glu Leu Lys Arg Lys Ala Ala Gln Asn Ser Gly Glu
    1655            1660                1665

Ala Glu Tyr Ile Glu Lys Val Val Tyr Thr Val Lys Gln Ser Ala
    1670            1675                1680

Glu Asp Val Lys Lys Thr Leu Asp Gly Glu Leu Asp Glu Lys Tyr
    1685            1690                1695

Lys Lys Val Glu Asn Leu Ile Ala Lys Lys Thr Glu Glu Ser Ala
    1700            1705                1710

Asp Ala Arg Arg Lys Ala Glu Met Leu Gln Asn Glu Ala Lys Thr
    1715            1720                1725

Leu Leu Ala Gln Ala Asn Ser Lys Leu Gln Leu Leu Lys Asp Leu
    1730            1735                1740

Glu Arg Lys Tyr Glu Asp Asn Gln Arg Tyr Leu Glu Asp Lys Ala
    1745            1750                1755

Gln Glu Leu Ala Arg Leu Glu Gly Glu Val Arg Ser Leu Leu Lys
    1760            1765                1770

Asp Ile Ser Gln Lys Val Ala Val Tyr Ser Thr Cys Leu
    1775            1780                1785

<210> SEQ ID NO 13
<211> LENGTH: 25
<212> TYPE: RNA
<213> ORGANISM: Artificial Sequence
<220> FEATURE:
<223> OTHER INFORMATION: siRNA sequence of KRS

<400> SEQUENCE: 13
agaaguuuuc aucuaugaac auggc                                         25

<210> SEQ ID NO 14
<211> LENGTH: 24
<212> TYPE: RNA
<213> ORGANISM: Artificial Sequence
<220> FEATURE:
```

```
<223> OTHER INFORMATION: siRNA sequence of KRS

<400> SEQUENCE: 14
aucucuuucu ucaugacaaa cagc                                              24

<210> SEQ ID NO 15
<211> LENGTH: 25
<212> TYPE: RNA
<213> ORGANISM: Artificial Sequence
<220> FEATURE:
<223> OTHER INFORMATION: siRNA sequence of KRS

<400> SEQUENCE: 15
uaucucuuuc uucaugacaa acagc                                             25

<210> SEQ ID NO 16
<211> LENGTH: 21
<212> TYPE: RNA
<213> ORGANISM: Artificial Sequence
<220> FEATURE:
<223> OTHER INFORMATION: siRNA sequence of KRS

<400> SEQUENCE: 16
gcuguuucuc acugagcucu u                                                 21

<210> SEQ ID NO 17
<211> LENGTH: 21
<212> TYPE: RNA
<213> ORGANISM: Artificial Sequence
<220> FEATURE:
<223> OTHER INFORMATION: siRNA sequence of KRS

<400> SEQUENCE: 17
gaugcucagc ucacccuucu u                                                 21

<210> SEQ ID NO 18
<211> LENGTH: 21
<212> TYPE: RNA
<213> ORGANISM: Artificial Sequence
<220> FEATURE:
<223> OTHER INFORMATION: siRNA sequence of KRS

<400> SEQUENCE: 18
gagguucguu ucuggcagcu u                                                 21

<210> SEQ ID NO 19
<211> LENGTH: 21
<212> TYPE: RNA
<213> ORGANISM: Artificial Sequence
<220> FEATURE:
<223> OTHER INFORMATION: siRNA sequence of KRS

<400> SEQUENCE: 19
agugguugcu acauucuccu u                                                 21

<210> SEQ ID NO 20
<211> LENGTH: 25
<212> TYPE: RNA
<213> ORGANISM: Artificial Sequence
<220> FEATURE:
<223> OTHER INFORMATION: siRNA sequence of LRS

<400> SEQUENCE: 20
ccuugcaugg aucaugauag acaaa                                             25
```

<210> SEQ ID NO 21
<211> LENGTH: 446
<212> TYPE: PRT
<213> ORGANISM: Artificial Sequence
<220> FEATURE:
<223> OTHER INFORMATION: Amino acid sequence of N3 IgG heavy chain

<400> SEQUENCE: 21

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
                370             375             380
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 22
<211> LENGTH: 1338
<212> TYPE: DNA
<213> ORGANISM: Artificial Sequence
<220> FEATURE:
<223> OTHER INFORMATION: DNA sequence of N3 IgG heavy chain

<400> SEQUENCE: 22
gaggtgcagc tgttggagtc tgggggaggc ttggtacagc ctgggggtc cctgagactc        60 tcctgtgcag cctctggatt cacctttagc agttatgata tgagctgggt ccgccaggct      120
ccagggaagg ggctggagtg ggtctcagcg atctcttatg ataatggtaa tacatattac      180
gctgattctg taaaaggtcg gttcaccatc tccagagaca attccaagaa cacgctgtat      240
ctgcaaatga acagcctgag agccgaggac acggccgtgt attactctgc gagaatggcg      300
cttgatttcg actactgggg ccagggtaca ctggtcaccg tgagctcagc ctccaccaag      360
ggcccatcgg tcttccccct ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagaaag ttgagcccaa atcttgtgac      660
aaaactcaca catgcccacc gtgcccagca cctgaactcc tggggggacc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtataccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                   1338

<210> SEQ ID NO 23
<211> LENGTH: 217
<212> TYPE: PRT
<213> ORGANISM: Artificial Sequence
<220> FEATURE:
<223> OTHER INFORMATION: Amino acid sequence of N3 IgG light chain

<400> SEQUENCE: 23
```

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ala Tyr Val Phe Gly Gly Gly Thr Lys Leu Thr Val Leu Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 24
<211> LENGTH: 651
<212> TYPE: DNA
<213> ORGANISM: Artificial Sequence
<220> FEATURE:
<223> OTHER INFORMATION: DNA sequence of N3 IgG light chain

<400> SEQUENCE: 24
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat gataatagta tcggccaag cggggtccct      180 gaccgattct ctggctccaa gtctggcacc tcagcctccc tggccatcag tgggctccgg     240
tccgaggatg aggctgatta ttactgtgct tcttgggatg atagcctgag tgcttatgtc     300
ttcggcggag gcaccaagct gacggtccta cgtacggtgg ctgcaccatc tgtcttcatc     360
ttcccgccat ctgatgagca gttgaaatct ggaactgcct ctgttgtgtg cctgctgaat     420
aacttctatc cagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t              651
```

THERAPEUTIC AGENT FOR IMMUNE CELL MIGRATION-CAUSED DISEASE AND METHOD FOR SCREENING SAME

CROSS-REFERENCE TO RELATED APPLICATIONS

The present application is a continuation of PCT International Patent Application Serial No. PCT/KR2018/006820, filed Jun. 18, 2018, which claims priority from Korean Patent Application No. 10-2017-0076718, filed on Jun. 16, 2017, the entire contents of each of which are incorporated herein by reference.

TECHNICAL FIELD

The present invention relates to a therapeutic agent for an immune cell migration-caused disease and a method for screening the same and, more particularly, to a pharmaceutical composition comprising a KRS inhibitor (or expression or activity inhibitor) as an effective ingredient for preventing or treating an immune cell migration-related disease, a method for controlling the migration of immune cells by regulating a level of KRS in immune cells, a level of KRS specifically present at the plasma membrane location, or the translocation of KRS to the plasma membrane, and a method for screening a therapeutic agent for an immune cell migration-caused disease, using KRS.

BACKGROUND OF THE INVENTION

In many tissues of the body, each cell migrates in different ways depending on their genetic characteristics and environment. Uncontrolled cell migration involves various disease states such as inflammatory disease, cancer metastasis, etc., but the migration signaling and mechanism characteristics of each cell are not fully characterized. In particular, it is reported that different cells have different ways of relating to the same factors, which further increases difficulty in identifying signaling processes and mechanisms. For example, AQP1 (water channel aquaporin-1) is known to promote cell migration in the epithelial cells, and particularly cancer metastasis (Hara-Chikuma M et al., Aquaporin-1 facilitates epithelial cell migration in kidney proximal tubule, *J Am Soc Nephrol.* 2006 January, 17(1):39-45; Jiang Y, Aquaporin-1 activity of plasma membrane affects HT20 colon cancer cell migration, *IUBMB Life.* 2009 October, 61(10): 1001-9).

However, in the case of macrophages, expression of AQP1 rather suppresses the migration of these cells (Tyteca D et al., Regulation of Macrophage Motility by the Water Channel Aquaporin-1: Crucial Role of M0/M2 Phenotype Switch, *PLoS One.* 2015 Feb. 26, 10(2):e0117398). Likewise, since each cell has a variety of ways and characteristics of their migration, drugs designed to prevent the migration of specific cells have been very limited and insufficient. Therefore, there is a need for a new strategy to control the migratory switch (cell) of a cell and to treat migration-related diseases.

On the other hand, although immune cells are also the first line of defense network in the body, excessive activation of immune cells has recently been reported to be one of the major pathological mechanisms. Increased mobility of immune cells is generally observed upon activation of inflammatory immune cells. Specifically, it has been reported that the migration and infiltration of such immune cells are closely related to the pathology of the disease.

Cardiovascular diseases, for example, are diseases of the heart and major arteries, including atherosclerosis and coronary artery disease (Ross R et al., *New Engl J Med,* 1999, 340(2): 115-26; Poli G et al., *Redox Biol* 2013, 1(1):125-30; Libby P et al., *Circulation* 2002 5, 105(9):1135-43). Atherosclerosis is an inflammatory disease caused by cholesterol and is caused by atheroma consisting of cholesterol deposited on the inner artery membrane and immune cells that migrated from blood into the arteries. In other words, atheroma is formed by the migration of immune cells such as monocytes to the area where oxygenated cholesterol is evoking inflammation. When atheroma is formed, the inner surface of blood vessels becomes uneven and rough, and the wall becomes thick, and subsequently the diameter of the inside where blood flows is narrowed, which hinders blood circulation. When the fibrous membranes around the atheroma burst, blood clots develop in the blood vessels and bleeding into atheroma causes the vessel's internal diameter to narrow sharply or become blocked. Typically it occurs in the blood vessels that supply blood to the heart, brain, kidney, and peripheral blood vessels, causing ischemic heart diseases, ischemic cerebrovascular diseases (stroke), kidney failures, and ischemic limb arterial diseases. Previously, CCL2 (CCChemokine ligand 2, MCP-1), which causes inflammatory reactions by inducing monocyte migration, is known to play an important role in the occurrence and development of cardiovascular diseases, leading to a new proposal of methods for treating such cardiovascular diseases by suppressing the action of CCL2 and subsequent migration of monocytes (Gu L et al., *Mol Cell,* 1998, 2(2):275-81; Aiello R J et al., *Arterioscler Thromb Vasc Biol* 1999, 19(6): 1518-25; Gosling J I et al., *Clin Invest* 1999, 103(6):773-8; Harrington J R et al., *Stem Cells* 2000, 18(1): 65-6; Ikeda U et al., *Clin Cardiol* 2002, 25(4):143-7). In addition, even in high blood pressure, various immune cells that secrete inflammatory cytokines excessively migrate into the blood vessels, resulting in a thickened blood vessel wall, and a pathology of losing elasticity of the blood vessels.

In addition, pulmonary arterial hypertension (PAH) is classified as Group 1 of the World Health Organization (WHO) Clinical Classification System (ESC Guidelines, European Heart Journal 2015), and is a rare disease with common clinical features of elevation (mPAP>25 mmHg) of mean pulmonary artery pressure (mPAP). and right ventricular dysfunction. While many preexisting factors such as heredity, infection and related diseases are involved in the development of pulmonary arterial hypertension, immune responses due to the endothelial cell injury is known to be a key pathological factor (Huertas et al., *Circulation,* 129: 1332-1340, 2014). In this phenomenon, a series of processes due to infiltration and dysfunction of immune cells are known to be deeply associated with pathology. Especially, it is known that interactions between immune cells and blood vessel endothelial cells are important. Besides, there was a recent report suggesting that the infiltration of monocytes and macrophages promotes the diseases progression in Alport syndrome.

On the other hand, in fibrosis-related diseases, a persistent (chronic) inflammatory response activates a wound-healing program, which leads to fibrosis. After tissue damage, inflammatory immune cells such as monocytes/macrophages, neutrophils, eosinophils, and mast cells are activated, rapidly penetrating into the site of injury and secreting several cytokines, which further activates surrounding fibroblasts, epithelial cells, or smooth muscle cells, leading them to become myoblast type of cells. These cells produce and secrete large amounts of extracellular matrix proteins, ultimately resulting in excessive accumulation of such proteins in tissues, scarring as well as inducing tissue fibrosis or hypertrophy (Gurtner G C et al., *Trends Cell Biol.* 15:599-607, 2005). This pathological mechanism is one of the fundamental causes of scar formation in the skin tissue occurring during skin damages caused by wounds, burns, bedsores, etc., and sclerotic fibrosis of tissues such as the liver, kidney, blood vessels and lung. In addition, fibrosis appears as a major pathological feature in chronic autoimmune diseases such as scleroderma, rheumatoid arthritis, Crohn's disease, ulcerative colitis, myelofibrosis, and systemic lupus erythematosus. Further, activation of inflammatory immune cells is known to contribute to the pathology in atopic diseases, asthma, COPD, psoriasis, keloids, and proliferative retinopathy.

In particular, fibroblasts which are activated as myoblast type cells in the wound-healing program are called myofibroblasts. Since myofibroblast is central to all fibrosis-related disease pathologies, eliminating the molecular biological or immunological mechanisms that induce myofibroblast activity is a key component of disease treatment. It is well known that many innate or adaptive immunity is important for the activation and differentiation of fibroblasts. Accordingly, eliminating inflammatory responses in the injured area is a key element in stopping the tissue remodeling to fibrosis and maintaining normal tissue forms. In practice, however, elimination of inflammatory reactions is not easy, therefore understanding the mechanism of innate and adaptive immunity and finding key mediators is important in slowing down fibrosis.

While monocytes and macrophages do contribute to wound healing, they release reactive oxygens and nitrogens, which are harmful to surrounding cells. Therefore, without a rapid removal of monocytes and macrophages, it will cause more tissue damage and further fibrosis. Thus, limiting monocytes and macrophages that respond first in the early stages of the disease is considered a therapeutic strategy for various chronic inflammatory and fibrotic diseases.

When the wound-healing mechanism triggers a fibrosis reaction, it is understood that platelet-derived growth factor (PDGF), which is involved in hemagglutination, recruits other inflammatory immune cells to the wound area and TGF-β1 stimulates extracellular matrix synthesis from local fibroblasts. However, it has been reported that fibrosis is still induced even in the absence of these factors in the hemagglutination reaction.

As mentioned above, target factors have been suggested to prevent the migration (and infiltration) of immune cells in diseases in which excessive immune cell activation is a problem, and attempts to devise therapeutic methods using these factors for such diseases have been tried, however, the reality is that limitations for each approaches are being reported. Therefore, searching for the key mediators and the strategies to control these key players in the immune cell migration is an important challenge for effective disease treatment.

DETAILED DESCRIPTION OF THE INVENTION

Technical Problem

Accordingly, in search of a novel therapeutic strategy for immune cell migration (infiltration)-related diseases, the present inventors found out that lysyl-tRNA synthetase (KRS) has an activity of regulating the migration of immune cells, and in particular, the phenomenon of increasing a level of KRS specifically at the plasma membrane location of immune cells (monocytes/macrophages) is an important pathology for diseases related to the immune cell migration and invasion, which has a particular association with laminin (especially laminin subtype α4β2γ1). Based on these findings, the present inventors devised a new therapeutic strategy for those diseases, and also revealed that treatment of KRS inhibitors suppressing the expression or activity of KRS did have effects of preventing or treating various immune cell migration and infiltration-related diseases, such as fibrosis and pulmonary hypertension, thereby completing the present invention.

Thus, an aspect of the present invention is to provide a pharmaceutical composition for preventing or treating an immune cell migration-related disease comprising a lysyl tRNA synthetase (KRS) inhibitor as an active ingredient.

Another aspect of the present invention is to provide use of a lysyl tRNA synthetase (KRS) inhibitor for preparing a prophylactic or therapeutic agent for an immune cell migration-related disease.

Another aspect of the present invention is to provide a method for preventing or treating an immune cell migration-related disease comprising administrating an effective amount of a composition comprising a lysyl tRNA synthetase (KRS) inhibitor as an active ingredient to a subject in need thereof.

Another aspect of the present invention is to provide a method for controlling immune cell migration through regulation of a level of KRS in an immune cell, regulation of a level of KRS specifically present at the plasma membrane location, or regulation of KRS translocation to the plasma membrane.

Another aspect of the present invention is to provide a method for screening a prophylactic or therapeutic agent of an immune cell migration-related disease comprising (A) determining whether a test agent inhibits a lysyl tRNA synthetase (KRS);

(B) treating an immune cell with laminin; and (C) determining whether the test agent inhibits immune cell migration by treating the test agent identified as having an activity of KRS inhibition in step (A) to the immune cell of step (B).

Another aspect of the present invention is to provide a method for screening a prophylactic or therapeutic agent of an immune cell migration-related disease comprising (a) treating an immune cell with laminin and a test agent and monitoring a level of KRS at the plasma membrane location or translocation of KRS to the plasma membrane; and (b) determining the test agent as a therapeutic agent of the immune cell migration-related disease when the level of KRS at the plasma membrane or translocation of KRS to the plasma membrane is lower compared with a control group untreated with the test agent.

Technical Solution

An embodiment according to an aspect of the present invention provides a pharmaceutical composition for preventing or treating an immune cell migration-related disease comprising a lysyl tRNA synthetase (KRS) inhibitor as an active ingredient.

Another embodiment according to an aspect of the present invention provides use of a lysyl tRNA synthetase (KRS) inhibitor for preparing a prophylactic or therapeutic agent for an immune cell migration-related disease.

Another embodiment according to an aspect of the present invention provides a method for preventing or treating an immune cell migration-related disease comprising administrating an effective amount of a composition comprising a lysyl tRNA synthetase (KRS) inhibitor as an active ingredient to a subject in need thereof an.

Another embodiment according to an aspect of the present invention provides a method for controlling immune cell migration through regulation of a level of KRS in an immune cell, regulation of a level of KRS specifically present at the plasma membrane location, or regulation of KRS translocation to the plasma membrane.

Another embodiment according to an aspect of the present invention provides a method for screening a prophylactic or therapeutic agent of an immune cell migration-related disease comprising (A) determining whether a test agent inhibits a lysyl tRNA synthetase (KRS);

(B) treating an immune cell with laminin; and (C) determining whether the test agent inhibits immune cell migration by treating the test agent identified as having an activity of KRS inhibition in step (A) to the immune cell of step (B).

Another embodiment according to an aspect of the present invention provides a method for screening a prophylactic or therapeutic agent of an immune cell migration-related disease comprising (a) treating an immune cell with laminin and a test agent and monitoring a level of KRS at the plasma membrane location or translocation of KRS to the plasma membrane; and (b) determining the test agent as a therapeutic agent of the immune cell migration-related disease when the level of KRS at the plasma membrane location or translocation of KRS to the plasma membrane is lower compared with a control group untreated with the test agent.

Definitions

Unless defined otherwise, all technical and scientific terms used herein have the same meaning as commonly understood by one of ordinary skill in the art. The following references provide one of the skills having a general definition of several terms used in the specification of the present invention. Singleton et al., DICTIONARY OF MICROBIOLOGY AND MOLECULAR BIOLOTY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY. In addition, the following definitions are provided to assist the reader for practicing the present invention.

In the present invention, "expression" refers to the production of proteins or nucleic acids in a cell.

In the present invention, a "host cell" refers to a prokaryotic or eukaryotic cell containing heterologous DNA introduced into the cells by any means (e.g. electroporation, calcium phosphate precipitation, microinjection, transformation, viral infection, etc.).

The term "regulation" in the present invention is meant to include up-regulation (promotion, increase, enhancement) or down-regulation (suppression, decrease, inhibition).

In the present invention, "protein" is used interchangeably with "polypeptide" and refers to a polymer of amino acid residues, for example as commonly found in natural proteins.

In the present invention, "KRS protein" means polypeptides known as lysyl tRNA synthetases. KRS is an enzyme that mediates the aminoacylation of amino acid lysine and tRNA. In the present invention, as long as it is known in the art as lysyl tRNA synthase, its specific origin and sequence (amino acid sequence configuration) are not particularly limited, but for example, KRS of the present invention is derived from human (*Homo sapiens*) including those published as NCBI (Genbank) Accession No. NP_005539.1 and the like, and is derived from mouse (*Mus musculus*) including those published as NCBI (Genbank) Accession No. NP_444322.1 and the like, and is derived from rat (*Rattus norvegicus*) including those published as NCBI (Genbank) Accession No. XP_006255692.1 and the like, and may be referred to, but not limited to the following sequence information: XP_005004655.1 (guinea-pig: *Cavia porcellus*), XP_021503253.1 (gerbil, *Meriones unguiculatus*), XP_002711778.1 (rabbit, *Oryctolagus cuniculus*), XP_536777.2 (dog, *Canis lupus familiaris*), XP_003126904.2 (swine, *Sus scrofa*), XP_011755768.1 (monkey, *Macaca* nemestrina), XP_008984479.1 (marmoset, *Callithrix jacchus*), XP_019834275.1 (cow, Bos *indicus*), XP_511115.2 (chimpanzee, Pan troglodytes).

Preferably, KRS protein may comprise the amino acid sequence defined by SEQ ID NO: 1, more preferably may be a polypeptide consisting of the amino acid sequence of SEQ ID NO:1 (Genbank Accession No. NP_005539.1). Also in the present invention, KRS includes functional equivalents thereof.

In the present invention, KRS protein preferably refers to intracellular KRS or KRS inherent in the plasma membrane, which is distinct from KRS completely secreted extracellularly.

Intracellular KRS has two subtypes (isoforms): cytoplasmic form (lysyl-tRNA synthetase, cytoplasmic) and mitochondrial form (lysyl-tRNA synthetase, mitochondrial). KRS in the present invention is preferably a cytoplasmic form.

The functional equivalent refers to a polypeptide having sequence homology (i.e. identity) of at least 70%, preferably 80% or more, and more preferably 90% or more with an amino acid constituting a known KRS protein sequence (preferably, the amino acid sequence defined by SEQ ID NO:1). For example, it includes a polypeptide having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, referring to a polypeptide having substantially the same physiological activity as the known KRS protein (preferably, the polypeptide defined by SEQ ID NO: 1). Here, "substantially homogeneous physiological activity" means regulating the immune cell migration. Preferably, the functional equivalent of KRS in the present invention may be a result of the addition, substitution or deletion of a part of the amino acid sequence of SEQ ID NO: 1. Substitution of amino acids in the above is preferably a conservative substitution. Examples of conservative substitutions of amino acids present in nature are as follows; aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). The functional equivalent of KRS also includes variants in which some of the amino acids are deleted on the amino acid sequence of KRS protein. Deletion or substitution of the amino acid is preferably located in a region that is not directly related to the physiological activity of KRS. In addition, deletion of the amino acid is preferably located in a portion not directly involved in the physiological activity of KRS. Also variants in which some amino acids are added to both ends or within the amino acid sequence of KRS are included. In the scope of functional equivalents of the present invention, polypeptide derivatives in which some chemical structures of the polypeptide are modified while maintaining the basic backbone of KRS and its physiological activity are included as well. For example, this includes structural modifications to alter the stability, shelf life, volatility or solubility of the protein.

In this specification, sequence homology and identity are defined as the percentage of identical matching residues (amino acid residues or bases) of the candidate sequence relative to the original sequence obtained by aligning an original sequence (SEQ ID NO: 1 as a preferred example for amino acid sequences, or SEQ ID NO:2 as a preferred example for nucleic acid sequences) with a candidate sequence and introducing gaps. If necessary, conservative substitutions are not considered as part of sequence identity in order to obtain maximum percentage sequence identity. Also in the case of evaluating protein sequence homology or identity, the N-terminus, C-terminus or internal extension, deletion or insertion of the KRS amino acid sequence is not to be interpreted as a sequence affecting sequence homology or identity. In addition, the sequence identity can be determined by common standard methods used to compare similar portions of amino acid sequences of two polypeptides. Computer programs such as BLAST or FASTA align two polypeptides so that their respective amino acids are optimally matched (along the full length of one or two sequences or along the predicted portions of one or two sequences). The program provides a default opening penalty and default gap penalty and scoring metrics such as PAM250 which can be used in conjunction with a computer program (Standard Scoring Matrix; Dayhoff et al., In Atlas of Protein Sequence and Structure, vol 5, supp 3, 1978). For example, percentage identity can be calculated as follows. The total number of identical matches is multiplied by 100 and then divided by the sum of the length of the longer sequence in the corresponding span and the number of the gaps introduced into the longer sequence to align the two sequences.

In the present invention, the term "laminin" is a heterotrimeric molecule consisting of α, β, and γ chains, and is an extracellular matrix protein in which isoforms (subtypes) having different subunit chain compositions exist. Specifically, laminin is a heterotrimer having combination of 5 kinds of α chains, 4 kinds of β chains, and 3 kinds of γ chain, and has about 15 kinds of isoforms. Names of laminin are determined by combining the respective numbers of α chains (α1 to α5), β chains (β1 to β4) and γ chains (γ1 to γ3). For example, laminin having a combination of α1, β1 and γ1 chains is called LN111, and laminin having a combination of α5, β1, and γ1 chains is called LN511, and laminin having a combination of α5, β2, and γ1 chains is called LN521. In the present invention, the term laminin may mean a single component of one laminin subtype, or may mean a laminin mixture in which two or more laminin subtypes are mixed.

As laminin, laminin derived from a mammal can be used. For example, mammals include mice, rats, marmots, hamsters, rabbits, cats, dogs, sheep, pigs, cows, horses, goats, monkeys, and humans. Preferably human laminin can be used. Currently, 15 kinds of isoforms are known to human laminin. Preferably, the laminin isoform of the present invention may be in a form including α4, and more specifically, may be LN421.

Specifically, the "LN421 protein" refers to a polypeptide known as laminin subtype α4β2γ1, and if it is known in the art as LN421, its specific origin and sequence (amino acid sequence configuration) are not particularly limited, but preferably the α4 chain in LN421 may include the amino acid sequence defined by SEQ ID NO:4, β2 chain may include the amino acid sequence represented by SEQ ID NO:6, γ1 chain may include an amino acid sequence defined by SEQ ID NO:8. More preferably, in the LN421 α4 chain may consist of the amino acid sequence defined by SEQ ID NO:4, β2 chain may be consist of the amino acid sequence defined by SEQ ID NO:6, and γ1 chain may consist of the amino acid sequence defined by SEQ ID NO: 8 It may be made of a sequence.

In the present invention, LN421 also includes the functional equivalent thereof. The functional equivalent thereof means the same as explained in the functional equivalent of KRS above, where "substantially homogeneous physiological activity" refers to controlling or regulating the specific (selective) migration of immune cells such as monocytes, macrophages or neutrophils, and the like.

In the present invention, KRS protein or laminin protein may be extracted from nature or constructed by genetic engineering method. For example, first, a nucleic acid encoding KRS or a functional equivalent thereof (e.g. SEQ ID NO:2 (Genbank Accession No. D32053)) is constructed according to a conventional method. Or nucleic acids (e.g. SEQ ID NO:5, SEQ ID NO:7 and SEQ ID NO:9) encoding laminin or functional equivalent thereof is constructed according to conventional methods. Nucleic acids can be constructed by PCR amplification using appropriate primers. DNA sequences may be synthesized by different standard methods known in the art such as using automated DNA synthesizers (such as those sold by Biosearch or Applied Biosystems). The constructed nucleic acid is inserted into a vector comprising one or more expression control sequences (e.g. a promoter, enhancer, etc.) that is operatively linked to regulate expression of the nucleic acid, and the recombinant expression vector formed therefrom is transformed into the host cell. The resulting transformants are then cultured using media and conditions appropriate for the nucleic acid to be expressed. Polypeptides (proteins) expressed from the nucleic acid may be provided and used with cells without separate isolation and recovery process from the cell, or may require steps to recover substantially pure polypeptides expressed by the nucleic acid from culture, in accordance with embodiments of the invention provided herein. The recovery can be carried out using methods known in the art (e.g. chromatography). As used herein, "substantially pure polypeptide" means that the polypeptide according to the present invention is substantially free of any other proteins derived from a host cell. For genetic engineering methods for polypeptide synthesis of the present invention, reference may be made to the following literature: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y, Second (1998) and Third (2000) Editions; Gene Expression Technology, Method in Enzymology, Genetics and Molecular Biology, Method in Enzymology, Guthrie & Fink (eds.), Academic Press, San Diego, Calif., 1991; And Hitzeman et al., J. Biol. Chem., 255: 12073-12080, 1990.

In addition, polypeptides of the present invention may be readily prepared by chemical synthesis known in the art (Creighton, Proteins; Structures and Molecular Principles, W. H. Freeman and Co., NY, 1983). Representative methods include, but are not limited to, liquid or solid phase synthesis, fragment condensation, F-MOC or T-BOC chemistry (Chemical Approaches to the Synthesis of Peptides and Proteins, Williams et al., Eds., CRC Press, Boca Raton Fla., 1997; A Practical Approach, Athert on & Sheppard, Eds., IRL Press, Oxford, England, 1989).

As used herein, "nucleic acid", "DNA sequence" or "polynucleotide" refers to deoxyribonucleotides or ribonucleotides in the form of single- or double-stranded strands. Unless otherwise limited, known analogues of natural nucleotides that hybridize to nucleic acids in a manner similar to naturally occurring nucleotides are also included.

In the present invention, "polynucleotide encoding KRS" may have, for example, a base (nucleic acid) sequence encoding an amino acid sequence defined by SEQ ID NO: 1 or an amino acid sequence having at least 70% or more sequence homology thereto. The nucleic acid includes all DNA, cDNA and RNA sequences. That is, the polynucleotide may have a nucleotide sequence encoding the amino acid sequence of SEQ ID NO: 1 or a nucleotide sequence having at least 70% or more homology thereto, or may have a nucleotide sequence complementary thereto. Preferably, it may include the nucleotide sequence defined by SEQ ID NO:2, and most preferably, it may consist of the nucleotide sequence defined by SEQ ID NO:2. Such nucleic acid can be isolated in nature or produced by genetic engineering methods as described above.

In the present invention, "polynucleotide encoding laminin" is, for example, in the case of LN421, may have amino acid sequences defined by SEQ ID NO:4, SEQ ID NO:6 and SEQ ID NO:8 of each chain or it may have nucleotide sequences encoding amino acid sequences having at least 70% or more sequence homology and may also have nucleotide sequences complementary to those base (nucleic acid) sequence. Such nucleic acid includes all DNA, cDNA and RNA sequences. Preferably, each chain may comprise the nucleotide sequences defined by SEQ ID NO:5, SEQ ID NO:7 or SEQ ID NO:9, and most preferably it may consist of the nucleotide sequences defined by SEQ ID NO:5, SEQ ID NO:7 and SEQ ID NO:9. These nucleic acids can be isolated in nature or produced by genetic engineering methods as described above.

In the present invention, the term "analog" refers to a substance which is structurally similar to a reference molecule, but whose target or regulation is modified by replacing a specific substituent of the reference substance by substitution. Compared with the reference molecule, analogs have the same, similar or improved utility as would be expected by one skilled in the art. Synthesis and screening of analogs to identify known compound variants with improved properties (e.g. higher binding affinity for a target material) is a method known in the art of pharmacological chemistry.

As used herein, the term "homologues" refers to naturally or artificially derived from common ancestral proteins or protein sequences when referring to proteins and/or protein sequences. Similarly, nucleic acids and/or nucleic acid sequences are homologous when they are naturally or artificially derived from a common ancestral nucleic acid or nucleic acid sequence.

In the present invention, "contacting" has its normal meaning and combines two or more agents (e.g. two polypeptides), or agents and cells (e.g. proteins and cells). Contact can occur in vitro. For example, contact is to combine two or more agents in a test tube or other container, or to combine a test agent with a cell or cell lysate and a test agent. Contact may also occur in cells or in situ. For example, two polypeptides are contacted in a cell or cell lysate by coexpression of recombinant polynucleotides encoding the two polypeptides in a cell.

In the present invention, the term 'translocation of KRS to the plasma membrane', unless otherwise indicated, means that an endogenous protein of a cell (a protein made inside the cell, for example, present in the cytoplasm) moves to the plasma membrane (cell membrane) in the intracellular direction. In this case, KRS may be completely present only in the intracellular direction, or may be interposed between plasma membranes, and thus some (preferably, N-terminal part of KRS) may be exposed outside the cell, but in any case, it may be desirable to exclude proteins completely isolated from the cell where is produced. That is, in the present invention, movement to the plasma membrane is distinguished from the interaction between proteins completely separated and secreted extracellularly from any given cell in the extracellular space outside different cells or organs.

The term "plasma membrane location" in the present invention is meant to include both the plasma membrane itself and the neighboring (nearing) area that is very close to the plasma membrane, thereby recognized as substantially interacting with the plasma membrane.

In the present invention, the term "agent" or "test agent" means any substance, molecule, element, compound, entity, or their combinations. For example, it may include, but not limited to, proteins, polypeptides, small organic molecules, polysaccharides, polynucleotides, and the like. It may also be a natural product, synthetic compound or chemical compound or a combination of two or more substances. Unless otherwise specified, agents, materials, and compounds may be used interchangeably. Agent of the present invention includes, preferably and specifically, siRNA, shRNA, miRNA, ribozyme, DNAzyme, peptide nucleic acid (PNA), antisense nucleotides, antibodies, aptamers, peptides (peptides with binding domains specific for target material (e.g. KRS)), peptide mimetics, substrate analogs, natural extracts and compounds (natural and synthetic compounds).

More specifically, test agents that can be screened by the screening methods of the present invention include polypeptides, antibodies, beta-turn mimetics, polysaccharides, phospholipids, hormones, prostaglandins, steroids, aromatic compounds, heterocyclic compounds, benzodiazepines, oligomeric N-substituted glycines, oligocarbamates, sugars (saccharides), fatty acids, purines, pyrimidines or derivatives thereof, structural analogs or combinations thereof. Some test agent may be synthetic and others may be natural. Test agents can be obtained from a wide variety of sources, including libraries of synthetic or natural compounds. Combinatorial libraries can be produced with a variety of compounds that can be synthesized in a step-by-step fashion. Compounds of many combinatorial libraries can be prepared by encoded synthetic libraries (ESL) methods (WO95/12608, WO93/06121, WO94/08051, WO95/395503 and WO95/30642). Peptide libraries can be prepared by phage display methods (WO91/18980). Libraries of natural compounds in the form of bacterial, fungal, plant and animal extracts can be obtained from commercial sources or collected in the field. Known pharmacological agents can be subjected to directed or random chemical formulas such as acylation, alkylation, esterification, amidification to produce structural analogs.

A test agent may be a naturally occurring protein or fragment thereof. Such test agent may be obtained from natural sources such as cell or tissue lysates. Libraries of polypeptide agents can be obtained, for example, from cDNA libraries produced by conventional methods or commercially available sources. Such test agent may be a peptide having about 5-30, preferably about 5-20, and more preferably about 7-15 amino acids. The peptide may be a cleavage product of a naturally occurring protein, random peptide or "biased" random peptide.

And a test agent may also be a "nucleic acid." Nucleic acid agents may be naturally occurring nucleic acids, random nucleic acids, or "biased" random nucleic acids. For example, cleavage product of the prokaryotic or eukaryotic genome can be used similarly as described above.

A test agent may also be a small molecule (e.g. a molecule having a molecular weight of about 1,000 or less). The method for screening small molecule-modulating agents may preferably be subjected to a high throughput assay. Many assays are useful for such screening (Shultz, *Bioorg. Med. Chem. Lett.*, 8:2409-2414, 1998; Weller, *Mol. Drivers.*, 3:61-70, 1997; Fernandes, *Curr. Opin. Chem. Biol.*, 2:597-603, 1998; and Sittampalam, *Curr. Opin. Chem. Biol.*, 1:384-91, 1997).

Libraries of test agents screened in the methods of the invention can be prepared based on structural studies on KRS full-length proteins or fragments (fragment polypeptides) or analogs thereof. This structural study enables the identification of test agents that are likely to bind KRS. The three-dimensional structure of KRS can be studied in several ways, such as crystal structure and molecular modeling. Methods of studying protein structure using X-ray crystallography are well known in the literature: Physical Bio-Chemistry, Van Holde, K E (Prentice-Hall, New Jersey 1971), pp. 221-239, and Physical Chemistry with Applications to the Life Sciences, D. Eisenberg & D C Crothers (Benjamin Cummings, Menlo Park 1979). Computer modeling of the structure of KRS provides another means for the design of test agents for screening. Molecular modeling methods are described in the literature: U.S. Pat. Nos. 5,612,894 and 5,583,973. Protein structure can also be determined by neutron diffraction and nuclear magnetic resonance (NMR): Physical Chemistry, 4th Ed. Moore, W. J. (Prentice-Hall, New Jersey 1972) and NMR of Proteins and Nucleic Acids, K. Wuthrich (Wiley-Interscience, New York 1986).

In the present invention, "miRNA, siRNA or shRNA" means a nucleic acid molecule that mainly binds to mRNA transcribed from a gene of interest to mediate RNA interference or gene silencing, thereby inhibiting the translation of mRNA. Since siRNA or shRNA can inhibit the expression of the target gene at the translation level, it can be used for an efficient gene knockdown technique or gene therapy method, and for the purpose of the present invention, it can be used to suppress the expression of KRS.

In the present invention, 'siRNA' may be composed of a 15 to 30 mer sense sequence selected from a nucleotide sequence of mRNA transcribed from a gene encoding a protein of interest and an antisense sequence complementarily binding to the sense sequence. At this time, the sense sequence is not particularly limited thereto, but is preferably composed of 25 bases.

In the present invention, 'antisense nucleotide' is to hinder the flow of genetic information from DNA to a protein by binding to (hybridizing with) complementary sequences of DNA, immature mRNA or mature mRNA as defined by the Watson-click base pairs. The nature of antisense nucleotides specific to the target sequence makes them exceptionally multifunctional. Since antisense nucleotides are long chains of monomeric units, they can be easily synthesized for the target RNA sequence. Many recent studies have demonstrated the utility of antisense nucleotides as biochemical means for studying target proteins (Rothenberg et al., J. Natl. Cancer Inst., 81:1539-1544, 1999). The use of antisense nucleotides can be considered as a novel form of inhibitor because of many recent advances in the field of oligonucleotide chemistry and synthesis of nucleotides exhibiting improved cell adsorption, target binding affinity and nuclease resistance.

In the present invention, 'peptide mimetics' are to suppress the activity of KRS protein by inhibiting its binding domain. Peptide mimetics may be peptides or non-peptides, or may be constituted with amino acids bound by non-peptide bonds, such as psi bonds (Benkirane, N., et al. *J. Biol. Chem.*, 271:33218-33224, 1996). Furthermore, it may be cyclic mimetics comprising "conformationally constrained" peptides, cyclic mimetics having at least one exocyclic domain, a binding moiety (binding amino acid) and an active site. Peptide mimetics may be structured similar to the secondary structural properties of KRS proteins and may mimic inhibitory characteristics of macromolecules such as either antibodies (Park, B W et al. *Nat Biotechnol* 18, 194-198, 2000) or water soluble receptors (Takasaki, W. et al. *Nat Biotechnol* 15, 1266-1270, 1997), and may be novel small molecules that can act as equivalents to natural antagonists (Wrighton, N C et al. *Nat Biotechnol* 15, 1261-1265, 1997).

In the present invention, 'aptamer' refers to a nucleic acid molecule having binding activity to a predetermined target molecule. As single-stranded DNA or RNA molecules, oligomers binding to specific chemical or biological molecules with high affinity and selectivity can be isolated and obtained using evolutionary methods using oligonucleotide libraries called systemic evolution of ligands by exponential enrichment (SELEX) (C. Tuerand L. Gold, *Science* 249, 505-510, 2005; A D Ellington and J W Szostak, *Nature* 346, 818-822, 1990; M. Famulok, et. Al., *Acc. Chem Res.* 33, 591-599, 2000; D S Wilson and Szostak, *Annu. Rev Biochem.* 68, 611-647, 1999). Aptamers can bind specifically to the targets and modulate their activity, for example, by blocking the function of the targets through binding.

In the present invention, 'anti-KRS antibody' or 'antibody against KRS' means a specific protein molecule directed to the antigenic site of KRS. For the purposes of the present invention, the antibody refers to an antibody that specifically binds to a KRS protein, and includes all polyclonal antibodies, monoclonal antibodies and recombinant antibodies. It may be desirable for the purposes of the present invention to be a monoclonal antibody which is a population of antibodies in which the amino acid sequences of the heavy and light chains of the antibody are substantially identical.

Producing antibodies against KRS as described above can be readily prepared using techniques well known in the art. Polyclonal antibodies can be produced by methods well known in the art of injecting the KRS protein antigen into an animal and collecting blood from the animal to obtain a serum comprising the antibody. Such polyclonal antibodies can be prepared from the host of any animal species such as goat, rabbit, sheep, monkey, horse, pig, cow and dog.

Monoclonal antibodies may be prepared using methods well-known in the art such as a hybridoma method (see Kohler and Milstein (1976) *European Jounral of Immunology* 6:511-519), or phage antibody libraries (Clackson et al, *Nature*, 352:624-628, 1991; Marks et al, *J. Mol. Biol.*, 222:58, 1-597, 1991).

In addition, in the present invention, an antibody includes a functional fragment of an antibody molecule as well as a complete form having two full length light and heavy chains. A functional fragment of an antibody molecule means a fragment having at least antigen binding function, preferably said fragment is at least 50%, 60%, 70%, 80%, 90%, 95% or 100% or more of the KRS binding affinity of the parent antibody. Specifically, it may be in the form of Fab, F(ab)2, Fab', F (ab')2, Fv, diabody, scFv and the like. Fab (fragment antigen-binding) is an antigen-binding fragment of the antibody, consisting of one variable domain and a constant domain of each of the heavy and light chains. F(ab')2 is a fragment produced by hydrolyzing an antibody with pepsin, in which two Fabs are linked by disulfide bonds at the heavy chain hinges. Fab' is a monomeric antibody fragment in which a heavy chain hinge is added to a Fab separated by reducing the disulfide bond of the F(ab')2 fragment. Variable fragment (Fv) is an antibody fragment composed only of variable regions of heavy and light chains, respectively. A single chain variable fragment (scFv) is a recombinant antibody fragment in which a heavy chain variable region (VH) and a light chain variable region (VL) are linked by a flexible peptide linker. Diabody refers to a fragment of the VH and VL of the scFv linked by a very short linker so that they does not bind to each other, and forms a dimer by binding to the VL and VH of the other scFv of the same form, respectively.

The antibody applied to the present invention is not limited thereto, but may be one selected from the group consisting of IgG, IgA, IgM, IgE, and IgD, and may be preferably an IgG antibody.

As used herein, the term "immune cell" refers to a cell that participates in the immune response of the body, and its type is not particularly limited as long as it is known in the art as an immune cell, and in particular, if it is known as an immune cell present in the human body, but may include monocytes, macrophages, neutrophils, eosinophils, basophils, dendritic cells, natural killer cells, megakaryocytes, T cells and B cells and the like. Preferably it may mean monocytes, macrophages or neutrophils. Immune cells express KRS.

As used herein, 'treatment' refers to inhibiting the occurrence or recurrence of a disease, alleviating symptoms, reducing direct or indirect pathological consequences of the disease, decreasing the rate of disease progression, improving the disease state, improving, alleviating, improved prognosis and/or a concept that includes prevention. As used herein, the term "prevention" refers to any action that suppresses the onset of the disease or delays its progression.

The term 'comprising' of the present invention is used in the same way as 'including' or 'characterized by' and does not exclude additional component elements or method steps not mentioned in the composition or method. The term 'consisting of' means to exclude additional elements, steps or components, etc., unless otherwise noted. The term 'essentially consisting of' means within the scope of the composition or method, including the component elements or steps described, as well as the component elements or steps that do not substantially affect its basic properties.

In the present invention, the term 'agent or composition' may be in the form of a food composition, cosmetic composition, pharmaceutical composition, etc., and is not particularly limited.

Hereinafter, the present invention will be described in detail.

The inventors have revealed that KRS has immunoregulatory activity for the first time, and in particular, proved that the plasma membrane-specific elevation of the level of KRS as compared with the cytoplasm was a major pathology in relation to the pathological migration and infiltration of immune cells.

Thus the present inventors confirmed that the immune cell migration was inhibited when the expression of KRS was downregulated to reduce the (global) level in immune cells.

When the elevated level of KRS in the plasma membrane of the activated, migratory and invasive immune cells was reduced in a plasma membrane location-specific manner (e.g. induction of endocytosis), the immune cell migration was inhibited and therapeutic effects were shown for the diseases caused by excessive immune cell infiltration such as inflammatory disease, fibrotic disease, and pulmonary arterial hypertension in vivo. Moreover, it was verified that even suppression of the translocating activity of KRS to the plasma membrane also inhibited the immune cell migration, suggesting applicability in the prevention/treatment of the immune cell migration-associated diseases.

Accordingly, the present invention provides use of a lysyl tRNA synthetase (KRS) inhibitor for preparing a prophylactic or therapeutic agent for an immune cell migration-related disease.

The present invention provides a pharmaceutical composition for preventing or treating an immune cell migration-related disease comprising a lysyl tRNA synthetase (KRS) inhibitor as an active ingredient.

In addition, the present invention provides a pharmaceutical composition for preventing or treating an immune cell migration-related disease consisting of a lysyl tRNA synthetase (KRS) inhibitor as an active ingredient.

In addition, the present invention provides a pharmaceutical composition for preventing or treating an immune cell migration-related disease essentially consisting of a lysyl tRNA synthetase (KRS) inhibitor as an active ingredient.

In the present invention, the "KRS inhibition (agent)" is preferably meant to include both the inhibition (agent) or/and activity inhibition (agent) of KRS.

The inhibition of KRS expression includes inhibition of all of genes, mRNA and protein expression of KRS, meaning inhibition of synthesis of expression product at each step including a transcriptional step, a post-transcriptional step, a post-translational step, and the like, as described below with respect to a method for reducing the level of KRS in immune cells.

Inhibiting KRS activity preferably means all of reducing, stopping, preventing or blocking any activity (signal) of KRS related to the immune cell migration. KRS activity includes, but is not limited to, specifically an activity associated with intracellular level or stability of KRS, particularly an activity associated with increased level of KRS at the plasma membrane location associated with the immune cell migration. In this case, the activity is meant to include not only the activity that causes the plasma membrane-specific increase in the level of KRS in immune cells, but also the activity that is exerted and dependent on the location (presence) of KRS in the plasma membrane. For example, activities contributing to increase in the level of KRS in the plasma membrane may include phosphorylation of KRS and translocating activity of KRS to the plasma membrane. Activities which are exerted dependently when KRS is located (or present) in the plasma membrane include an activity of interaction between the plasma membrane and KRS, or interaction (or association) between KRS and its binding factor (or ligand) in the plasma membrane. Details of such embodiments of activity inhibition are understood with reference to the description of the method for regulating the migration of immune cells described below.

In the most preferred embodiment, the "inhibition of KRS" in the present invention may correspond to the following (i), (ii) and (iii).
  (i) inhibition of KRS expression;
  (ii) reduction of a level of KRS at the plasma membrane location; and (iii) inhibition of KRS translocation to the plasma membrane.

The KRS inhibitor may be one or more selected from
the group consisting of an antisense nucleotide, miRNA, siRNA, shRNA, ribozyme, DNAzyme and peptide nucleic acid (PNA), which complementarily binds to KRS mRNA; or
the group consisting of a compound, a peptide, a peptide mimetic, a substrate analog, an aptamer, an antibody, a natural extract and a synthetic compound, which specifically binds to a KRS protein, but is not limited hereto.

According to the present invention, when the expression of KRS in immune cells is suppressed, the migration of immune cells is suppressed. Therefore, as one specific aspect, the present invention provides a prophylactic or therapeutic composition for immune cell migration-related diseases comprising a recombinant expression vector including a promoter and a structural gene inhibiting the KRS expression operably linked thereto as an effective ingredient. The structural gene that inhibits the expression of KRS may be an antisense RNA, siRNA, shRNA or miRNA for a polynucleotide encoding KRS. In the present invention, siRNA (si-KRS) as a KRS inhibitor may consist of a sense sequence including a base sequence (nucleotide sequence) selected from the group consisting of SEQ ID NO: 13 to SEQ ID NO: 19 and antisense sequences complementary thereto.

The term 'promoter' refers to a DNA sequence that controls the expression of a nucleic acid sequence operably linked in a particular host cell. 'Operably linked' means that one nucleic acid fragment is combined with another nucleic acid fragment such that function or expression of one nucleic acid is affected by the other nucleic acid fragment. In addition, it may further comprise any operator sequence for regulating transcription, a sequence encoding a suitable mRNA ribosomal binding site and a sequence regulating termination of transcription and translation. The promoter may be a promoter (constitutive promoter) inducing the expression of the gene of interest continuously at all times or a promoter (inducible promoter) inducing the expression of the gene of interest at a specific position, time, for example, SV40 promoter, CMV promoter, CAG promoter (Hitoshi Niwa et al., *Gene,* 108:193-199, 1991; Monahan et al., *Gene Therapy,* 7:24-30, 2000), CaMV 35S promoter (Odell et al., *Nature* 313:810-812, 1985), Rsyn7 promoter (U.S. patent application Ser. No. 08/991,601), rice actin promoter (McElroy et al., *Plant Cell* 2:163-171, 1990), ubiquitin promoter (Christensen et al., *Plant Mol. Biol.* 12:619-632, 1989), and ALS promoter (U.S. patent application Ser. No. 08/409,297), etc. In addition, promoters disclosed in U.S. Pat. Nos. 5,608,149; 5,608,144; 5,604,121; 5,569,597; 5,466,785; 5,399,680; 5,268,463; 5,608,142; and the like can all be used.

Meanwhile, expression vectors may be introduced into the target cell for a phenotype by methods known in the art such as infection, transfection or transduction.

Gene delivery using plasmid expression vectors is a method for delivering plasmid DNA directly to mammalian cells, which can be used in humans approved by the FDA (Nabel, E G, et al., *Science,* 249:1285-1288, 1990). Plasmid DNA has the advantage that it can be homogeneously purified unlike viral vectors. As a plasmid expression vector that can be used in the present invention, mammalian expression plasmids known in the art can be used. For example, but not limited to, pRK5 (EP 307,247), pSV16B (WO 91/08291) and pVL1392 (Pharmingen) are representative. The plasmid expression vector may be introduced into the target cell using methods such as, but not limited to, transient transfection, microinjection, transduction, cell fusion, calcium phosphate precipitation liposome-mediated transfection, DEAE Dextran-mediated transfection, polybrene-mediated transfection, electroporation, gene guns and other known methods for introducing DNA into cells (Wu et al., *J. Bio. Chem.,* 267:963-967, 1992; Wu and Wu, *J. Bio. Chem.,* 263:14621-14624, 1988).

In addition, as an applicable method of the present invention, a viral expression vector including the nucleic acid is not limited thereto, but may be a retrovirus, adenovirus, herpes virus, and an avipoxvirus, *lenti* virus and the like. The retroviral vector is constructed such that all of the viral genes have been removed or altered, thereby allowing non-viral proteins to be produced in the cells infected by the viral vector. The main advantages of retroviral vectors for gene therapy are that large quantities of genes can be delivered into the cloned cells, and genes transferred into cellular DNA can be precisely integrated, and subsequent infections after gene transfection are not induced (Miller, A D, *Nature* 357:455-460, 1992). FDA-approved retroviral vectors were prepared using PA317 amphotropic retrovirus packaging cells (Miller, A. D. and Buttimore, C., *Molec. Cell Biol.,* 6:2895-2902, 1986). Non-retroviral vectors include adenoviruses as mentioned above (Rosenfeld et al., *Cell,* 68:143-155, 1992; Jaffe et al., *Nature Genetics,* 1:372-378, 1992; Lemarchand et al., *Proc. Natl. Acad. Sci. USA,* 89:6482-6486, 1992). The main advantages of adenoviruses include their ability to carry a large amount of DNA fragments (36 kb genome) and to infect non-replicating cells with very high titers. Herpes viruses can also be useful for human gene therapy (Wolfe, J. H., et al., *Nature Genetics,* 1:379-384, 1992). In addition, any appropriate viral vectors known in the art can be used in the present invention.

In addition, structural genes that inhibit the expression of KRS (e.g. antisense RNA, siRNA, shRNA or miRNA) may be administered by other methods, such as topical, oral (including sublingual application) and as a parenteral administration, nasal, intravenous, intramuscularly, subcutaneously or by other suitable means. Such parenteral administration includes injection and drip administration. In particular, vectors can be injected directly into a lesion of an immune cell migration-related disease in an effective amount for treating the target tissue. In particular, in the case of lesions in the body cavity such as the eye, gastrointestinal tract, urogenital organs, lungs and bronchial system, pharmaceutical compositions containing the structural gene of the present invention (or expression vectors containing the structural gene of the present invention) may be injected directly using a needle, catheter or other type of transport tube into the hollow organ affected by the lesion. At this time, an imaging device such as X-ray, sonogram, or fiber optic visualization system may be used for positioning of the target tissue and inserting a needle or conduit. In addition, in the case of lesions that cannot be reached directly or cannot be separated analytically, the composition of the present invention can be administered into the blood circulation system.

In another specific aspect, the present invention provides a prophylactic or therapeutic composition for preventing or treating immune cell migration-related diseases comprising an antibody against KRS as an active ingredient. In the present invention, the antibody as the KRS inhibitor may include, for example, a heavy chain comprising an amino acid sequence defined by SEQ ID NO:21 and a light chain comprising an amino acid sequence defined by SEQ ID NO:23.

In another specific aspect, the present invention provides a composition for preventing or treating immune cell migration-related diseases comprising a compound defined by the following <Chemical Formula 1> as a KRS inhibitor or a pharmaceutically acceptable salt thereof as an active ingredient. In one embodiment of the present invention, as a substance that inhibits the translocation of KRS to the plasma membrane, 4-({(7-fluorobenzo[d]thiazol-2-yl)[2-(4-methoxyphenyl)ethyl]amino}methyl)benzoic acid) defined by the following <Chemical Formula 1> has been applied to an in vivo disease model for various kinds of immune cell migration (and infiltration)-related diseases, and the effects of disease prevention and treatment have been confirmed. The compound of <Chemical Formula 1> is also referred to herein as 'BC-KI-00053'.

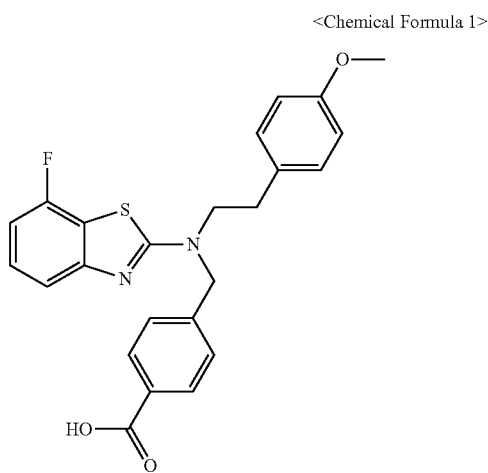 [SMILES: COc1ccc(CCN(Cc2ccc(C(=O)O)cc2)c2nc3cccc(F)c3s2)cc1]

<Chemical Formula 1>

The compound of Formula 1 or a salt thereof may have a substituent including an asymmetric atom, in which case the compound of <Chemical Formula 1> or a salt thereof may exist as an optical isomer such as (R), (S), or racemic (RS). Therefore, unless otherwise indicated, the compound of <Chemical Formula 1> or a salt thereof includes all optical isomers such as (R), (S), or racemic (RS).

The compound of <Chemical Formula 1> of the present invention may be in the form of a pharmaceutically acceptable salt. As used herein, "pharmaceutically acceptable (allowed)" refers to a nontoxic composition that is physiologically acceptable and does not normally cause an allergic reaction, such as a gastrointestinal disorder, dizziness, or the like, when administered to a human. The salts include salts derived from conventional acid addition salts, for example, salts derived from inorganic acids such as hydrochloric acid, bromic acid, sulfuric acid or phosphoric acid and salts derived from organic acids such as citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid or aspartic acid. The salts may also be in the form of conventional metal salts, for example alkali metal salts such as lithium, sodium, or potassium; alkaline earth metal salts such as calcium or magnesium salts; or chromium salts. Also included are salts formed with suitable organic ligands, such as quaternary ammonium salts, and dicyclohexylamine or N-methyl-D-glucamine salts and amino acid salts formed with arginine and lysine and the like.

The term "immune cell migration-related disease" in the present invention is not particularly limited as long as it is known in the art that excessive immune cell migration (or/and infiltration) is a major pathogenesis mechanism, for example, it may be selected from the group consisting of a cardiovascular disease, a fibrotic disease, an inflammatory disease and Alport syndrome.

The specific cardiovascular disease is not particularly limited, but for example, it may be selected from the group consisting of hypertension (including inflammatory complications caused by hypertension), pulmonary arterial hypertension, atherosclerosis, angina pectoris, myocardial infarction, an ischemic cerebrovascular disease, arteriosclerosis, and media sclerosis.

The fibrotic disease is not particularly limited in its specific kind, but for example, it may be selected from the group consisting of scleroderma, rheumatoid arthritis, Crohn's disease, ulcerative colitis, myelofibrosis, pulmonary fibrosis, hepatic fibrosis, liver cirrhosis, kidney fibrosis, glomerulosclerosis, myofibrosis, cardiac fibrosis, interstitial fibrosis, pancreatic fibrosis, splenic fibrosis, mediastinal fibrosis, vascular fibrosis, skin fibrosis, eye fibrosis, macular degeneration, joint fibrosis, thyroid fibrosis, endomyocardial fibrosis, peritoneal fibrosis, retroperitoneal fibrosis, progressive mass fibrosis, nephrogenic systemic fibrosis, systemic lupus erythematosus, hereditary fibrosis, infectious fibrosis, irritation fibrosis, chronic autoimmunity-associated fibrosis, antigen incompatibility during organ transplantation-associated fibrosis, fibrotic complication of surgery, hyperlipidemia-associated fibrosis, obesity-associated fibrosis, diabetes-associated fibrosis, hypertension-associated fibrosis and occlusion due to stent insertion-associated fibrosis.

The inflammatory disease in the present invention is not limited in its specific kind, but may be selected from the group consisting of an autoimmune disease, inflammatory bowel disease, dermatitis (e.g. atopic dermatitis, eczema, psoriasis), diabetic eye disease (diabetic retinopathy, etc.), peritonitis, osteomyelitis, cellulitis, meningitis, encephalitis, pancreatitis, trauma-induced shock, bronchial asthma, rhinitis, sinusitis, otitis media, pneumonia, gastritis, enteritis, cystic fibrosis, stroke (brain stroke, etc.), bronchitis, bronchiolitis, hepatitis (cirrhosis, non-alcoholic steatohepatitis, etc.), nephritis (diabetic renal failure, etc.), proteinuria, arthritis (psoriatic arthritis, osteoarthritis, etc.), neuritis (diabetic neuropathy, multiple sclerosis, etc.), gout, spondylitis, Reiter's syndrome, polyarteritis *nodosa*, vasculitis, Lou Gehrig's disease, Wegener's granulomatosis, hypercytokinemia, rheumatoid polymyalgia, giant cell arteritis, calcium crystal arthritis, pseudogout, non-articular rheumatism, bursitis, tendosynovitis, epicondylitis (tennis elbow), neuropathic arthropathy (Charcot's joint), hemarthrosis, Henoch-Schonlein purpura, hypertrophic osteoarthropathy, multicentric reticulohistiocytosis, sarcoidosis, hematochromatosis, sickle cell disease, hyperlipoproteinemia, hypogammaglobulinemia, hyperparathyroidism, acromegaly, familial Mediterranean fever, Behcet's disease, systemic lupus erythematosus, relapsing fever, psoriasis, multiple sclerosis, sepsis, septic shock, acute respiratory distress syndrome, multiple organ failure, chronic obstructive pulmonary disease, acute lung injury and broncho-pulmonary dysplasia, and include chronic inflammatory diseases as well.

The autoimmune disease in the present invention may be selected from the group consisting of rheumatoid arthritis, systemic scleroderma, systemic lupus erythematosus, psoriasis, asthma, ulcerative colitis, Behcet's disease, Crohn's disease, multiple sclerosis, dermatomyositis, collagen disease, vasculitis, arthritis, granulomatosis, organ-specific autoimmune lesion, ulcerative colitis and graft versus host disease.

The chronic inflammatory disease refers to a condition in which a disease become chronic with reference to the types of inflammatory diseases described above, and preferred examples thereof include asthma, atopic dermatitis, eczema, psoriasis, osteoarthritis, gout, psoriatic arthritis, cirrhosis, non-alcoholic fatty liver disease, chronic obstructive pulmonary disease, rhinitis, diabetic retinopathy, diabetic renal failure, diabetic neuropathy, and multiple sclerosis, but are not limited thereto.

The pharmaceutical composition according to the present invention may be formulated into various pharmaceutical formulations in a suitable form containing the KRS inhibitors alone or together with a pharmaceutically acceptable carrier, and may further contain excipients or diluents.

Pharmaceutically acceptable carriers may further include, for example, carriers for oral administration or carriers for parenteral administration. Pharmaceutically acceptable carriers may include binders, gliding agent (lubricant), disintegrants, excipients, solubilizers, dispersants, stabilizers, suspending agents, pigments and flavors in the case of oral administration. In the case of injections, buffers, preservatives, analgesics, solubilizers, isotonic agents and stabilizers can be used in combination, and in the case of topical administration agents, bases, excipients, lubricants and preservatives can be used. Specifically, carriers for oral administration may include lactose, starch, cellulose derivatives, magnesium stearate, stearic acid and the like. In addition, it may include various drug delivery materials used for oral administration. In addition, carriers for parenteral administration may include water, suitable oils, saline, aqueous glucose and glycols, and the like, and may further include stabilizers and preservatives. Suitable stabilizers include antioxidants such as sodium hydrogen sulfite, sodium sulfite or ascorbic acid. Suitable preservatives include benzalkonium chloride, methyl- or propyl-parabens and chlorobutanol. The pharmaceutical composition of the present invention may further include a lubricant, a humectant, a sweetener, a flavoring agent, an emulsifier, a suspending agent and the like in addition to the above components. Other pharmaceutically acceptable carriers and formulations may be referred to those described in Remington's Pharmaceutical Sciences, 19th ed., Mack Publishing Company, Easton, Pa., 1995.

As such, the formulation of the pharmaceutical composition comprising the KRS inhibitor of the present invention may be formulated in various forms by mixing with a pharmaceutically acceptable carrier as described above. In general, it can be formulated into a preparation for oral or parenteral administration according to the route of administration as described below.

In the case of preparations for oral administration, the compositions of the present invention may be formulated using methods known in the art as powders, granules, tablets, pills, dragees, capsules, solutions, gels, syrups, slurries, suspensions and the like. For example, oral formulations can be obtained as tablets or dragees by combining the active ingredients with solid excipients, milling them, adding suitable adjuvants and then processing them into granule mixtures. Examples of suitable excipients include sugars including lactose, dextrose, sucrose, sorbitol, mannitol, xylitol, erythritol and maltitol, and starch including corn starch, wheat starch, rice starch and potato starch, etc., and celluloses including methyl cellulose, sodium carboxymethylcellulose, hydroxypropylmethyl cellulose, and the like, fillers such as gelatin, polyvinylpyrrolidone, and the like, In addition, crosslinked polyvinylpyrrolidone, agar, alginic acid or sodium alginate and the like may optionally be added as a disintegrant. Furthermore, the pharmaceutical composition of the present invention may further include an anticoagulant, a lubricant, a humectant, a perfume, an emulsifier, a preservative, and the like.

Formulations for parenteral administration may be formulated by methods known in the art in the form of injections, creams, lotions, external ointments, oils, humectants, gels, aerosols and nasal inhalants. Injectables can be prepared in the form of unit dose ampoules or multiple dose inclusions. These formulations are described in Remington's Pharmaceutical Science, 19th ed., Mack Publishing Company, Easton, Pa., 1995, a prescription generally known in all pharmaceutical chemistries.

The KRS inhibitor of the present invention and/or the composition comprising the same may be administered in any possible way to any mammal, including humans. For example, it can be administered orally or parenterally. Oral administration also includes sublingual application.

Parenteral administration includes injections such as subcutaneous injection, intramuscular injection, and intravenous injection, and dripping method, while it is not limited hereto, but for example, injections or infusions by intravenous, intraperitoneal, intracranial, subcutaneous, intramuscular, intraocular, intraarterial, intraspinal, intramedullary, intradural, intracardiac, transdermal, subcutaneous, intranasal, intestinal, topical, sublingual, intrarectal or intralesional routes, or by a sustained release system described below. In one example, the KRS inhibitor or the composition containing the same may be administered systemically or locally.

The total effective amount of the composition of the present invention may be administered to a patient in a single dose, and may be administered by a fractionated treatment protocol that is administered in multiple doses for long periods of time. The pharmaceutical composition of the present invention may vary the content of the active ingredient depending on the extent of the disease. Preferably the preferred total dose of the pharmaceutical composition of the present invention may be about 0.01 µg to 10,000 mg, most preferably 0.1 µg to 500 mg per kg of patient body weight per day. However, the dosage of the pharmaceutical composition is determined in consideration of various factors such as the formulation method, route of administration and frequency of treatment, as well as various factors such as the patient's age, weight, health status, sex, severity of the disease, diet and excretion rate. In view of this, one of ordinary skill in the art will be able to determine an appropriate effective dosage of the compositions of the present invention. The pharmaceutical composition according to the present invention is not particularly limited to its formulation, route of administration and method of administration as long as the effect of the present invention is shown.

In addition, the present invention provides a method for preventing or treating an immune cell migration-related disease comprising administrating an effective amount of a composition comprising a lysyl tRNA synthetase (KRS) inhibitor as an active ingredient to a subject in need thereof.

In addition, the present invention provides a method for preventing or treating an immune cell migration-related disease comprising administrating an effective amount of a composition consisting of a lysyl tRNA synthetase (KRS) inhibitor as an active ingredient to a subject in need thereof.

In addition, the present invention provides a method for preventing or treating an immune cell migration-related disease comprising administrating an effective amount of a composition essentially consisting of a lysyl tRNA synthetase (KRS) inhibitor as an active ingredient to a subject in need thereof The 'effective amount' of the present invention refers to an amount that exhibits an effect of improving, treating, or preventing the immune cell migration, immune cell infiltration, or a disease caused therefrom, when administered to an individual, and is understood with reference to the foregoing with respect to the dosage.

The 'individual' may be an animal, preferably an animal including a mammal, especially a human, and may be a cell, tissue, organ or the like derived from the animal. The subject may be a patient in need of the effect.

The present inventors revealed that KRS has immune cell migration-regulating activity for the first time. Accordingly, the present invention discloses a method of regulating the immune cell migration through modulating the immune cell migration activity (signal) of KRS. In particular, it was confirmed that increase in the level of KRS specifically at the membrane location of immune cells is an important pathology for diseases related to the immune cell migration and infiltration. Accordingly, the present invention provides a method for regulating the migration of immune cells through regulation of the level of KRS (lysyl tRNA synthetase) in immune cells, regulation of the level of KRS in the plasma membrane location-specific manner, or regulation of KRS translocation to the plasma membranes.

In this case, the subject to which the method is performed is not particularly limited as long as the subject is in need of regulation of the immune cell migration, and the method may be used in a mammal including a human (*Homo sapiens*). Preferably the subject may be an animal other than a human.

When described in more detail with respect to the regulation of immune cell migration according to the regulation of the intracellular level of KRS, it is possible to inhibit the immune cell migration when reducing the level of lysyl tRNA synthetase (KRS) in immune cells, whereas increasing the level of lysyl tRNA synthetase (KRS) in immune cells can promote (enhance, increase) the immune cell migration.

Decrease or increase in the intracellular level can be controlled by various methods known to those skilled in the art, as described above. For example, but not limited thereto, the intracellular level can be regulated through regulation at the transcriptional step or regulation at the post-transcriptional step.

As a method of regulation at the transcriptional step, a method for enhancing expression of genes known to those skilled in the art, for example, by preparing a recombinant expression vector linking a polynucleotide encoding KRS or a functional equivalent thereof to a promoter to enhance the gene expression, or inserting an expression control sequence to enhance the gene expression around the gene encoding KRS or a functional equivalent thereof may be used, but is not limited thereto. Methods for inhibiting the gene expression include, for example, by inducing mutations in a promoter or gene region to inhibit promoter activity or protein function, expressing antisense genes, siRNA or microRNA (miRNA), but may not be limited thereto.

As a method of regulation at the post-transcriptional step, methods for enhancing or inhibiting protein expression known to those skilled in the art include, for example, enhancing or reducing the stability of mRNA transcribed from the gene encoding a KRS or a functional equivalent thereof, or enhancing or inhibiting the stability of the protein or polypeptide, or enhancing or inhibiting the activity of the protein or polypeptide.

More specific examples of the method may be transformation with DNA sequences encoding RNAs that act on transcribed mRNAs, such as group 1 intron type, M1 RNA type, hammerhead type, hairpin type or microRNA type, or cosuppression may be induced through transformation with DNA having a sequence identical or similar to a target gene sequence.

Preferably, in the present invention, regulating the level of KRS or a functional equivalent thereto in cells (immune cells) may be performed by a method of increasing or decreasing the expression of the KRS-encoding polynucleotide. For such increasing or decreasing methods, methods known to those skilled in the art may be used, respectively. For example, a recombinant expression vector may be prepared by linking a promoter to a polynucleotide encoding KRS or a functional equivalent thereof to enhance its expression. Alternatively, a recombinant expression vector can be prepared in which a promoter is linked to an antisense or siRNA-encoding polynucleotide against KRS to reduce its expression. At this time, the polynucleotide encoding KRS or a functional equivalent thereof may preferably comprise a nucleotide sequence defined by SEQ ID NO:2, but is not limited thereto. The siRNA-encoding polynucleotide for KRS may include, but is not limited to, a base sequence (nucleotide sequence) selected from the group consisting of SEQ ID NO:13 to SEQ ID NO:19.

When described in more detail with respect to the regulation of the immune cell migration according to the regulation of the level of KRS in the plasma membrane-specific manner, or regulation of the level of KRS specifically present at the plasma membrane location, it is possible to inhibit the immune cell migration when reducing the plasma membrane-specific exiting level of KRS, whereas increasing the plasma membrane-specific exiting level of KRS can promote (enhance, increase) the immune cell migration.

The plasma membrane-specific increase or reduction of the level of KRS can be controlled by a variety of methods known to those skilled in the art.

The plasma membrane-specific reduction of the level of KRS can be achieved by, for example, but not limited to, a method or means that inhibits the translocation of KRS to the plasma membrane. Specifically, in one embodiment of the present invention, it was confirmed that the immune cell migration is inhibited using a compound (BC-KI-00053 of <Chemical Formula 1>) that suppresses the translocation of KRS to the plasma membrane. Such translocation may also be inhibited by binding to an antibody against KRS (anti-KRS antibody), in which case additional treatment for intracellular penetration may be required depending on the specific target antigenic site of the antibody. Techniques for intracellular penetration of an antibody are well known in the art, and for example, means of attaching any cell permeable peptide can be used, which may be referred to literatures such as U.S. Pat. No. 9,598,465B2, US 20160009772A1. In addition, reference may be made to WO 2017204606A1, etc. for the infiltration of antibodies into cells.

In addition, decrease in the level of KRS in the plasma membrane-specific fashion may be achieved by, for example, a method or means for promoting endocytosis of KRS present in the plasma membrane location after KRS translocation to the plasma membrane occurs, but is not limited thereto. In addition, in one embodiment of the present invention, it was confirmed that the anti-KRS antibody bound to an extracellularly protruding N-terminal region of KRS (region corresponding to 1 to 72 amino acids of the KRS N-terminus) present in the plasma membrane, and induced endocytosis into the cell, thereby inhibiting the immune cell migration The plasma membrane-specific increase in the level of KRS may be achieved by, for example, but not limited to, a method or means that promotes the translocation of KRS to the plasma membrane. For example, it may be by means of treatment of laminin, in particular LN421. In one embodiment of the present invention, it was confirmed that the KRS level is specifically increased at the plasma membrane location when LN421 was treated to immune cells. As another example, any substance that causes or promotes phosphorylation of KRS may be used, but is not limited thereto, and a substance of a kinase class may be used.

When described in more detail with respect to the regulation of the immune cell migration according to the translocation of KRS to the plasma membrane, it is possible to inhibit the immune cell migration when reducing the translocation of KRS to the plasma membrane, whereas increasing the KRS translocation to the plasma membrane can promote (enhance, increase) the immune cell migration. This is understood with reference to the foregoing.

As described above, the inventors have identified that KRS has immune cell migration-regulating activity for the first time, and also confirmed that KRS has a special relation with laminin (particularly, laminin subtype α4132γ1) with respect to the behavioral patterns of KRS in immune cells. Based on these novel findings, the present invention provides new screening means for discovering therapeutic agents for diseases caused by immune cell migration and infiltration.

Accordingly, the present invention provides

A method for screening a prophylactic or therapeutic agent of an immune cell migration-related disease comprising (A) determining whether a test agent inhibits a lysyl tRNA synthetase (KRS);

(B) treating an immune cell with laminin; and (C) determining whether the test agent inhibits a migration of the immune cell by treating the test agent identified as having an activity of KRS inhibition in step (A) to the immune cell of step (B), and a prophylactic or pharmaceutical composition for a disease related to the immune cell migration comprising the agent selected by the screening method as an active ingredient.

The screening method can utilize a variety of biochemical and molecular biological techniques known in the art to implement the method. Such techniques are disclosed in the following literature: Sambrook et al., Molecular Cloning: A Laboratory Manual, Cold Spring Harbor Press, N.Y, Second (1998) and Third (2000) Editions; and Ausubel et al., Current Protocols in Molecular Biology, John Wiley & Sons, Inc., New York (1987-1999).

First, it is examined whether a test agent is capable of modulating the expression or (biological) activity of KRS (step (A), first assay step). Specifically, in the first step, the expression or biological activity of KRS is assayed in the presence of a test agent to identify a modulating agent that alters the expression or biological activity of KRS.

Specifically, in the first assay step, a test agent may be assayed to determine whether it is capable of regulating expression levels of KRS, such as, for example, the ability to modulate transcription or translation, but is not limited thereto. In this assay, known methods for measuring KRS expression levels can be used without limitation. In the present invention, the term 'KRS expression level measurement' is meant to include both measuring the expression level of the KRS protein itself or a polynucleotide (including a transcript such as a gene or mRNA) encoding KRS.

Measurement of protein expression level is not particularly limited as long as it is carried out by any protein expression measurement method known in the art, for example, any one of methods such as western blot, enzyme-linked immunosorbent assay (ELISA), radioimmunoassay, radioimmunodiffusion, Ouchterlony immunodiffusion, rocket immunoelectrophoresis, immunostaining (including immunohistochemistry and immunofluorescence staining), immunoprecipitation assay, complement fixation assay, fluorescence activated cell sorting (FACS), luminescence assay or protein chip method may be used.

Measurement of polynucleotide (including a transcript such as a gene or mRNA) gene expression level is not particularly limited as long as it is carried out by any gene expression measurement method known in the art, and preferably PCR (polymerase chain reaction), RNase protection assay, northern blotting, southern blotting, luminescence assay, and DNA chip may be used.

In the first assay step, it may also be assayed whether a test agent has a capacity to modulate various biological activities of KRS. For example, a test agent may be examined for its effect on the intracellular level or stability of KRS (such as post-translational modification), and the plasma membrane location-specific level or stability of KRS, whether it induces the endocytosis of KRS, whether it modulates the activity associated with migration to where KRS is activated, whether it translocates to the plasma membrane, whether it associates with binding factors, whether it changes the control of signals promoting the cell migration, and whether it has activity to interact with the plasma membrane. Selection of a test agent inhibiting KRS in the first assay step can be assessed with reference to the above-mentioned description in 'KRS inhibition.'

The first assay for the selection of test agents that affect KRS protein activity may first be assayed if the test agent has the ability to bind KRS. Binding of test agents to KRS can be assessed with variety of methods, for example, labeled in vitro protein-protein binding assays, electrophoretic mobility shift assays (EMSA), immunoassays for detecting protein binding, functional assays (phosphorylation assays, etc.), and the like. (U.S. Pat. Nos. 4,366,241; 4,376,110; 4,517,288 and 4,837,168; and Bevan et al., Trends in Biotechnology, 13:115-122, 1995; Ecker et al., Bio/Technology, 13:351-360, 1995; and Hodgson, Bio/Technology, 10:973-980, 1992). Test agents can be identified by detecting direct binding with KRS, such as co-immunoprecipitation with KRS polypeptides using antibodies against KRS. Test agents can also be identified by detecting signals that may indicate binding of KRS with a test agent, such as fluorescent quenching.

Various assays commonly practiced in the art can be used to identify agents that modulate KRS. Preferably, test agents may be screened in a cell-based assay system. For example, in a typical cell-based assay for screening, reporter gene activity (e.g. enzyme activity) is measured in the presence of a test agent and compared to that of the reporter gene in the absence of the test agent. The reporter gene may encode any detectable polypeptide (reaction or reporter polypeptide) known in the art, such as a polypeptide detectable by fluorescence or phosphorescence or a polypeptide detectable by the enzymatic activity it possesses. Detectable response polypeptides include, for example, luciferase, α-glucuronidase, α-galactosidase, chloramphenicol acetyl transferase, green fluorescent protein, enhanced green fluorescent protein and secreted human alkaline kinase.

In cell-based assays, test agents (e.g. peptides or polypeptides) may be expressed by other vectors present in the host cell. In some methods, the library of test agents is encoded by the library of said vectors (e.g. cDNA library). The library may be prepared using methods known in the art (Sambrook et al. And Ausubel et al., Supra), or may be obtained from various commercial sources.

In addition to the cell-based assays, they can also be screened by non-cell based methods. Those methods may include, for example, enzyme immunoassay (ELISA), surface plasmon resonance (SPR), assays using flow-cytometry analysis, and mobility shift DNA binding assays, methylation and uracil interference assays, DNase and hydroxyl radical footprinting analysis, fluorescence polarization and UV crosslinking or chemical cross-linkers. A general overview is disclosed in Ausubel et al. (Ausubel et al., Supra, chapter 12, DNA-Protein Interaction). Techniques for isolating co-associating proteins, including nucleic acids and DNA/RNA binding proteins, include cleavable crosslinkers, dithiobis (succinimidyl propionate) and UV-crosslinking or chemical crosslinking agents, including 3,3'-dithiobis (sulfosuccinimidyl-propionate) (McLaughlin, *Am. J. Hum. Genet.*, 59:561-569, 1996; Tang, *Biochemistry*, 35:8216-8225, 1996; Lingner, *Proc. Natl. Acad. Sci. USA*, 93:10712, 1996; and Chodosh, *Mol. Cell. Biol.*, 6:4723-4733, 1986).

Specifically, competition assays provide a suitable format for identifying test agents that specifically bind KRS. The present invention can be carried out in a high throughput manner according to various binding assays known in the art. In this format, a test agent is screened through competition with compounds already known to bind KRS. Known binding compounds can be synthetic compounds. It may also be an antibody that specifically recognizes KRS, such as a monoclonal antibody against KRS. If the test agent inhibits the binding of the known compound, the test agent also binds to KRS.

Various kinds of competition assays are known in the art, for example, solid phase direct or indirect radioimmunoassay (RIA), solid phase direct or indirect enzyme immunoassay (EIA), sandwich competition assay (Stahli et al., *Methods in Enzymology*, 9:242-2453, 1983); solid phase direct biotin-avidin EIA (Kirkland et al., *J. Immunol.*, 137:3614-3619, 1986); solid phase direct labeled assays, solid phase direct labeled sandwich assays (Harlow and Lane, Antibodies, A laboratory Manual, Cold Spring Harbor Press, 1988); solid phase direct labeling with $^{125}$I (Morel et al., *Mol. Immuno.*, 25 (1):7-15, 1988); solid phase direct biotin-avidin EIA (Cheung et al., *Virology*, 176:546-552, 1990); and directly labeled RIA (Moldenhauer et al., *Sacnd. J. Immunol.*, 32:77-82, 1990). Generally, these assays involve the use of purified polypeptide bound to a cell or solid surface containing an unlabeled test agent and a labeled control compound. Competitive inhibition is measured by determining the amount of label bound to a solid surface or cell in the presence of a test agent. Modulating agents identified by competition assays include agents that bind to the same epitope as the control compound, and agents that bind to the adjacent epitopes sufficiently close to the epitope bound by the control compound so that steric hindrance occurs. Typically, when excessive competition inhibition is present, specific binding of the control compound to the general target polypeptide will be inhibited by at least 50% to 75%.

The assay may be based on an insoluble or soluble format. One example of an insoluble assay is to immobilize KRS or a fragment thereof in a solid phase matrix. The solid phase matrix is then placed in contact with a test agent for a time sufficient for the test agent to bind. The unbound material is then washed off from the solid phase matrix, after which the presence of the bound agent in the solid phase is confirmed. The method may further comprise the step of isolating the agent by eluting the bound agent from the solid phase matrix. Alternatively, another method of immobilizing KRS is to bind the test agent to the solid phase matrix and then add KRS.

Soluble assays include several binding library screening methods described above. Under soluble assay format, neither test agents nor KRS are bound to the solid support. Binding of KRS or fragment thereof to the test agent can be measured, for example, by fluorescence of the KRS and/or test agent. Fluorescence may be intrinsic or imparted by labeling with components containing a fluorophore.

In the assay process, a test agent or KRS protein may be marked with a detectable label to facilitate its identification, detection and quantification under given conditions. For example, a detectable label may be a chemical label (e.g. biotin), an enzyme label (e.g. horseradish peroxidase, alkaline phosphatase, peroxidase, luciferase, α-glucuronidase, α-galactosidase, chloramphenicol acetyl transferase, β-galactosidase and β-glucosidase), a radiolabel (e.g. $^{14}$C, $^{125}$I, $^{32}$P and $^{35}$S), a fluorescent label (e.g. coumarin, fluorescein, fluorescein isothiocyanate (FITC), rhodamine 6G, rhodamine B, 6-carboxy-tetramethyl-rhodamine (TAMRA), Cy-3, Cy-5, Texas Red, Alexa Fluor, DAPI (4,6-diamidino-2-phenylindole), HEX, TET, Dansyl and FAM), a luminescent label, a chemiluminescent label, a fluorescence resonance energy transfer (FRET) label or a metal label (e.g. gold and silver). Similarly, a detectable group may be a substrate, cofactor, inhibitor or affinity ligand.

When using a KRS protein or test agent labeled with a detectable label, the binding between the KRS protein and the test agent can be analyzed by sensing signals from the label. For example, when alkaline phosphatase is used as a label, signals are detected using a color reaction substrate such as bromochloroindolyl phosphate (BCIP), nitro blue tetrazolium (NBT), naphthol-ASB1-phosphate and enhanced chemifluorescence (ECF). When hose radish peroxidase is used as a label, chloronaphthol, aminoethyl carbazole, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (tetramethylbenzidine), ABTS (2,2-azine-di[3-ethylbenzthiazoline sulfonate]), o-phenylenediamine (OPD), and substrates such as naphthol/pyronin are used to detect the signal.

Alternatively, binding of a test agent to a KRS protein may be assayed without labeling the interactants. For example, a microphysiometer may be used to analyze whether the test agent binds to the KRS protein. Microphysiometers are analytical tools that measure the rate at which cells acidify their environment using a light-addressable potentiometric sensor (LAPS). Changes in the acidification rate can be used as an indicator for binding between test agent and KRS protein (McConnell et al., *Science* 257:1906-1912 (1992)).

The ability of a test agent to bind to a KRS protein can be analyzed using real-time bimolecular interaction analysis (BIA). (Sjolander & Urbaniczky, *Anal. Chem.*, 63:2338-2345 (1991), and Szabo et al., *Curr. Opin. Struct. Biol.*

5:699-705 (1995)). BIA is a technique for analyzing specific interactions in real time, and can be performed without labeling of interactants (e.g. BIAcore™). Changes in surface plasmon resonance (SPR) can be used as indicators for real-time reactions between molecules.

In addition, the screening methods of the present invention may be carried out by applying a two-hybrid analysis or a three-hybrid analysis method (U.S. Pat. No. 5,283,317; Zervos et al., *Cell* 72:223-232, 1993; Madura et al., *J. Biol. Chem.* 268:12046-12054, 1993; Bartel et al., *BioTechniques* 14:920-924, 1993; Iwabuchi et al., *Oncogene* 8:1693-1696, 1993; and WO 94/10300). In this case, KRS protein can be used as a "bait" protein. According to this method, it is possible to screen substances, particularly proteins (peptides), which bind to KRS proteins. Two-hybrid systems are based on the modular nature of transcription factors composed of cleavable DNA-binding and activation domains. Briefly, this assay uses two DNA constructs. For example, in one construct, a KRS-encoding polynucleotide is fused to a DNA binding domain-encoding polynucleotide of a known transcription factor (e.g. GAL4). In another construct, a DNA sequence encoding a protein of interest ("prey" or "sample (test agent)") is fused to a polynucleotide encoding the activation domain of the known transcription factor. If bait and prey interact in vivo to form a complex, the DNA-binding and activation domains of the transcription factors becomes adjacent, which triggers transcription of the reporter gene (e.g. LacZ). Expression of the reporter gene can be detected, indicating that the protein of interest can bind to the KRS protein.

For the test agent thus identified as binding to the KRS protein, KRS proteins are treated with the test agent and changes in the activity is measured. As a result of the measurement, if the activity of KRS protein is down-regulated, the test agent may be determined as a candidate of prophylactic or therapeutic for preventing and treating immune cell migration-related diseases as an inhibitor of KRS activity.

After identifying the test agent that inhibits KRS (inhibiting KRS expression or activity) through the first assay step, whether the test agent has ability of suppressing the immune cell migration is further examined in the presence of KRS and laminin (particularly LN421) (steps (B) and (C), secondary assay). At this point, KRS may be provided in a form that is constantly expressed in immune cells, but is not limited thereto. In addition, treatment of laminin may be performed by treating separately isolated laminin proteins outside the immune cells (medium, etc.), or may be processed to be expressed in cells through a special genetic manipulation. In the present invention, it has been newly revealed that KRS has the ability to regulate the laminin-specific immune cell migration (particularly, LN421). In the second assay step, various cell migration assay methods, or cell invasion assays known in the art may be used.

As mentioned above, agents that inhibit KRS identified by the methods of the present invention can modulate (inhibit) the migration of immune cells. If the test agent selected in the first assay step modulates the intracellular level of KRS (e.g. by alteration of transcriptional activity), it can be immediately considered to be able to control the migration of immune cells.

On the other hand, if the test agent modulates activity other than the intracellular level of KRS, it may be necessary to confirm that the modulating effect of the test agent on KRS actually regulates the immune cell migration, in which case the second assay is preferred to be carried out additionally. In addition, the order of the first and second assays may be changed in order for efficient assays.

In addition, the present inventors found that increase in the KRS level specifically at the plasma membrane location of immune cells (monocytes/macrophages) is an important pathology for diseases related to immune cell migration and infiltration, in which laminin (particularly, laminin subtype α4β2γ1) has a special association. Based on these novel findings, the present invention provides new screening means for discovering therapeutic agents for diseases caused by immune cell migration and infiltration.

Therefore, the present invention provides a method for screening a prophylactic or therapeutic agent of an immune cell migration-related disease comprising (a) treating an immune cell with laminin and a test agent and monitoring a level of KRS at the plasma membrane or translocation of KRS to the plasma membrane; and (b) determining the test agent as a therapeutic agent of the immune cell migration-related disease when the level of KRS at the plasma membrane or translocation of KRS to the plasma membrane is lower compared with a control untreated with the test agent and a pharmaceutical composition for preventing or treating a disease related to the immune cell migration comprising the agent selected by the screening method as an active ingredient.

In step (a), immune cells may be treated with laminin and a test agent simultaneously or each substance may be sequentially processed. In the latter case, laminin may be treated first, followed by a test agent, or laminin may be treated after the test agent.

In step (b), the term "monitoring" means any means for measuring changes in the KRS level at the plasma membrane location, or the translocation and level (quantity) of KRS to the plasma membrane.

Such changes of KRS (presence) level at the plasma membrane location or the translocation and level (quantity) of KRS to the plasma membrane can be performed by any known protein level measurement method. It can be carried out using one or more of methods, while it is not limited thereto, selected from the group consisting of western blot, ELISA, radioimmunoassay, radioimmunodiffusion assay, Ouchterlony immunodiffusion, rocket immunoelectrophoresis, immunostaining (immunochemical staining, immunofluorescence staining, etc.), immunoprecipitation assay, complement fixation assay, luminescence assay and protein chip. Those skilled in the art may include any treatment process to measure the plasma membrane location-specific KRS levels and KRS translocation, depending on the nature of the protein level measurement method to be used. For example, in the case of using western blot methods, a separate process of preparing the membrane and cytosol fractions from the cells of interest may be implemented. In contrast, in the case of using immunostaining, it is possible to easily observe the migration behavior of the protein to the plasma membrane and the subsequent change of the protein level in the plasma membrane without preparing fractions as described above.

In addition, for detecting a compound that affects the movement of proteins in the cell when practicing the present invention, reference is made to Korean Patent Registration 10-0919637.

The 'control group' refers to a group of immune cells that have not been treated with a test agent (test preparation) and is the same type of immune cell as the cell used in step (a).

Immune cells used as the control group include both those treated with laminin (particularly, LN421) or those without laminin treatment.

The screening methods of the present invention may also include additional steps of 'administer the test agent determined (or identified) as a prophylactic or therapeutic agent for the immune cell migration (and infiltration)-related diseases to an animal and examine whether it shows a therapeutic effect.' In this case, the animal is preferably a non-human animal.

Advantageous Effect

When KRS is controlled according to the present invention, the migration of immune cells can be regulated, which can find very useful application in the prevention or treatment of immune cell migration-related diseases.

BRIEF DESCRIPTION OF DRAWINGS/FIGURES

The patent or application file contains at least one drawing executed in color. Copies of this patent or patent application publication with color drawing(s) will be provided by the Office upon request and payment of the necessary fee.

FIG. 1b is a graph showing the number of cells measured (quantified) in the microscope images of FIG. 1a.

FIG. 4b is a graph showing the number of cells measured (quantitative) in the microscopic images of FIG. 4a.

FIG. 6a shows microscope images of a transwell cell migration assay in which migration of monocytes/macrophages is noticeably suppressed by treatment of a compound (BC-KI-00053) inhibiting KRS translocation to the plasma membrane in a concentration-dependent manner.

FIG. 6b is a graph showing the number of cells measured (quantitative) in the microscopic images of FIG. 6a.

Figure 7A:
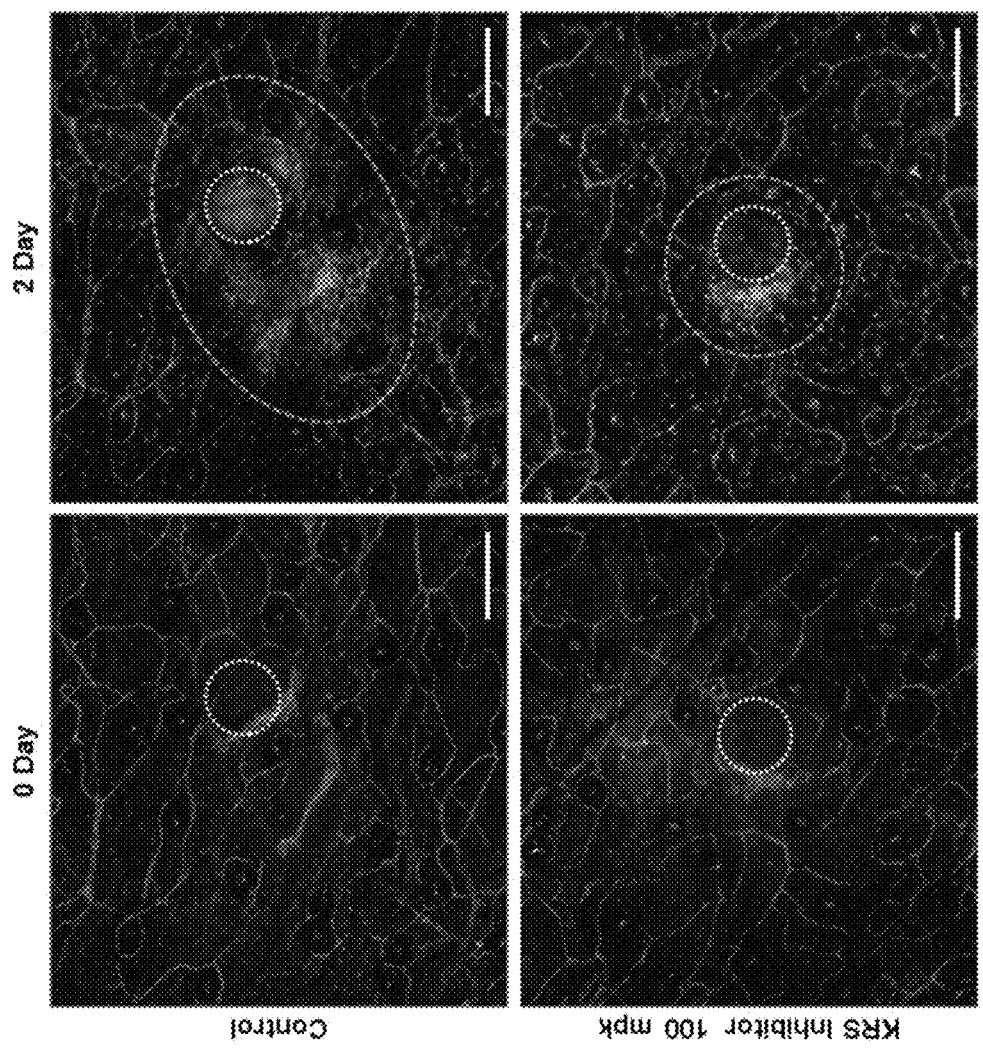

FIG. 7a shows the results of fluorescence microscopy to observe the degree of the infiltration of monocytes, macrophages and Langerhans cells upon treatment of BC-KI-00053 compound in acute inflammatory responses (ear skin wound model) (Upper panels shows the vehicle-treated group and lower panels BC-KI-00053 100 mg/kg treated groups. Green indicates monocytes, macrophages or Langerhans cells, and red indicates blood vessels stained for CD31. White circles denote the area of skin wound.)

FIG. 7b is a quantitative representation of the monocyte/macrophage infiltration at the periphery of the skin wound indicated by the blue circle in the fluorescence microscopy image of FIG. 7a.

Figure 8A:
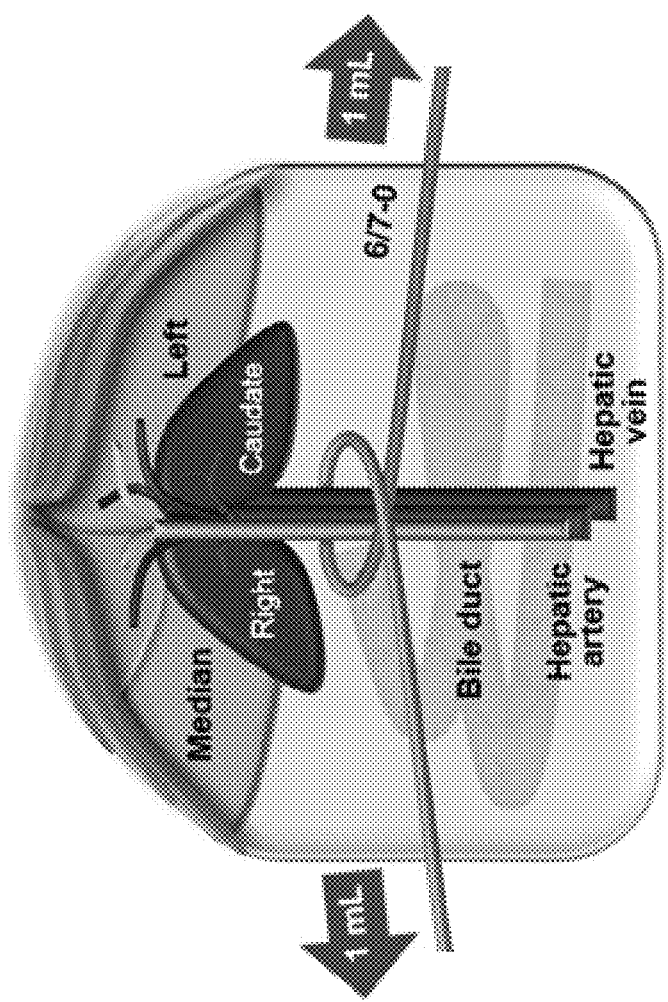

FIG. 8a is a schematic diagram of the triad (bile duct, hepatic artery, hepatic vein) occlusion procedure for the preparation of a liver ischemia-reperfusion injury model.

Figure 8B:
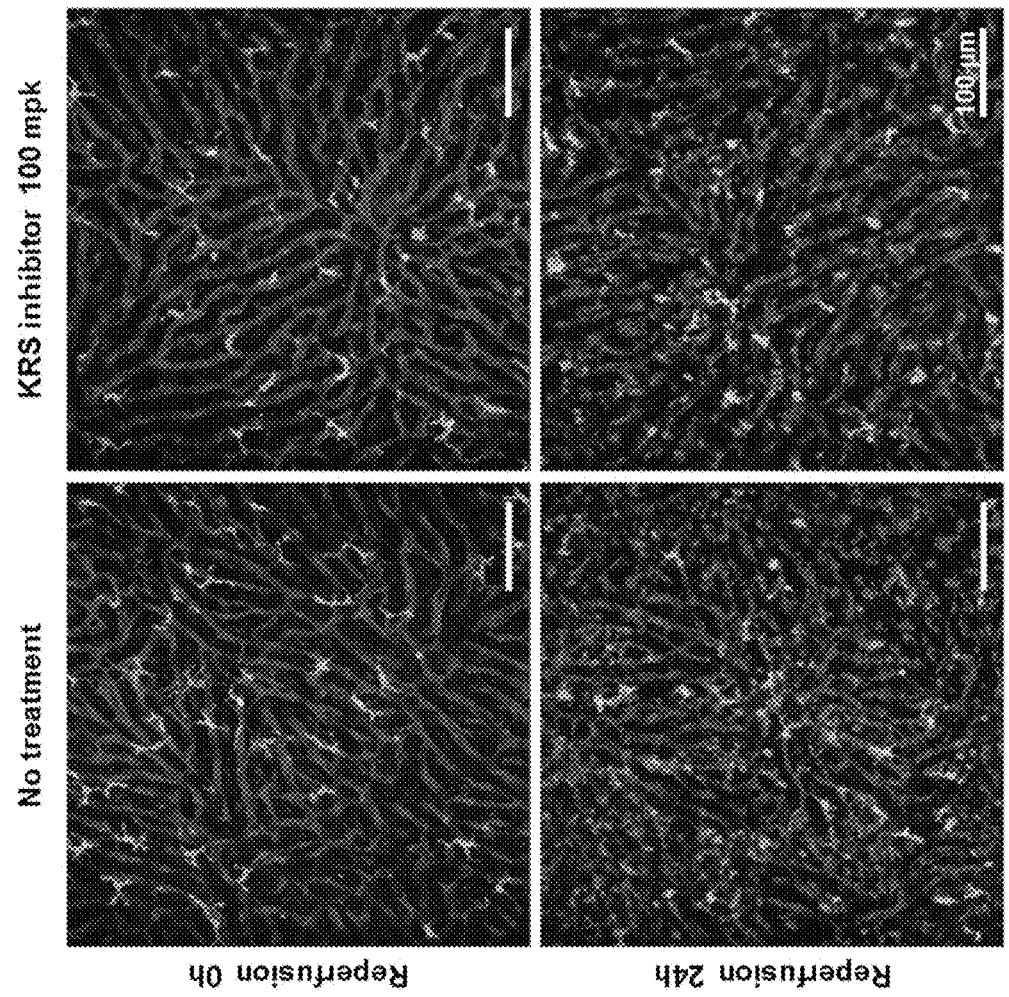

FIG. 8b shows the results of fluorescence microscopy to observe the degree of the infiltration of monocytes, macrophages and Kupffer's cells upon treatment with BC-KI-00053 compound in a liver ischemia-reperfusion injury model (Upper panels shows vehicle-treated groups and lower panels BC-KI-00053 100 mg/kg treated groups. Green indicates monocytes, macrophages or Kupffer's cells, and red indicates blood vessels stained for CD31).

Figure 8C:
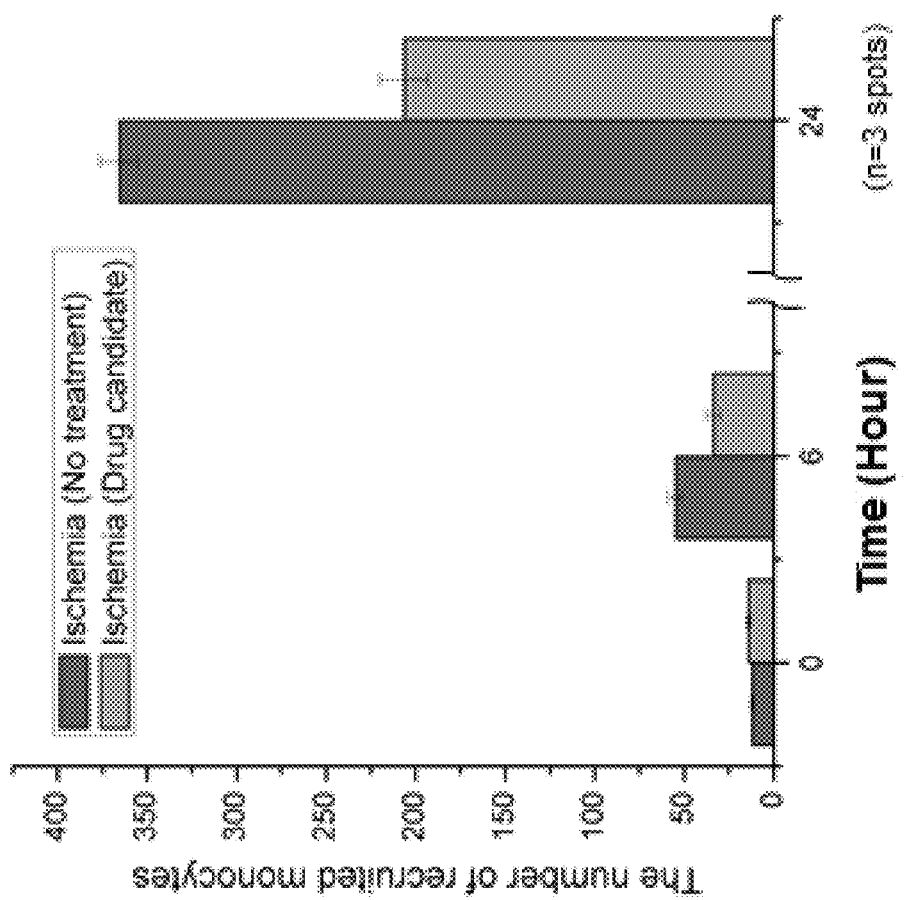

FIG. 8c shows the quantified degree of the monocyte/macrophage infiltration in the fluorescence microscopy image of FIG. 8b according to the time points after the ischemia-reperfusion injury. Red and green bars represent quantification of the vehicle-treated control group and the BC-KI-00053 100 mg/kg treated group, respectively.

Figure 9A:
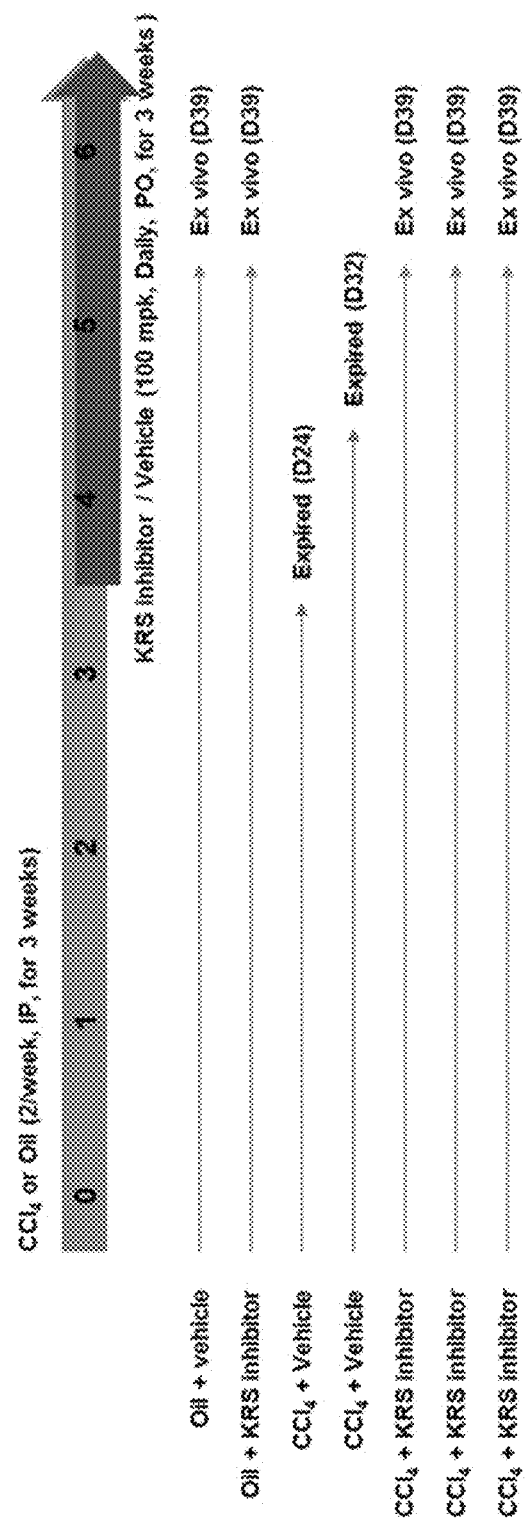

FIG. 9a is a diagram showing methods and schedule of the experiments to prepare a liver fibrosis animal model with $CCl_4$ (carbon tetrachloride) and to evaluate the therapeutic effect of BC-KI-00053 compound.

Figure 9B:
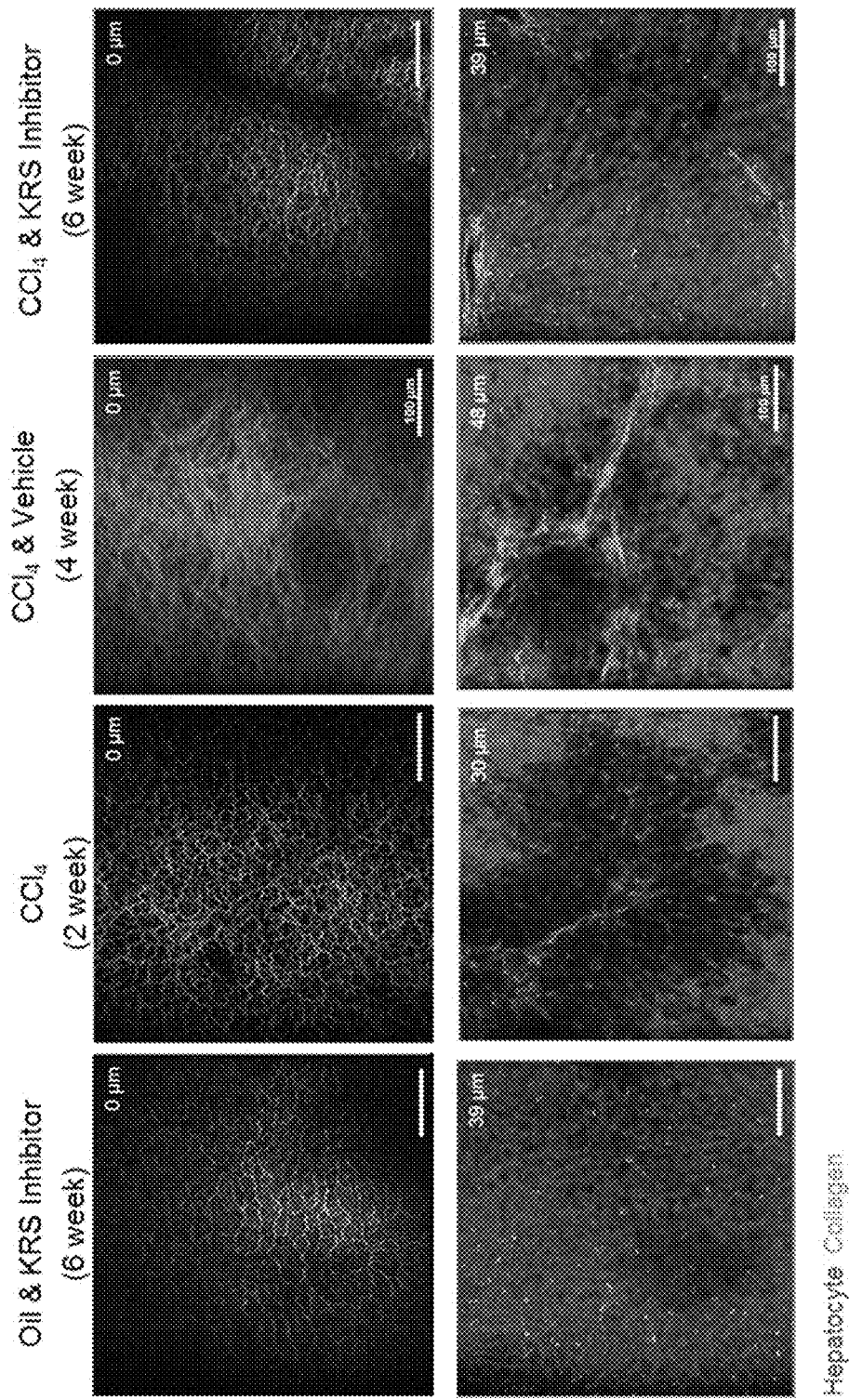

FIG. 9b shows fluorescence microscopic images to observe the degree of fibrosis in the surface and inside the liver in each experimental groups as results of evaluating the effect of BC-KI-00053 in $CCl_4$ (carbon tetrachloride)-induced liver fibrosis animal model (Upper panels visualize the liver surface, and lower panels visualize the inside of the liver. Green represents collagen and red represents hepatocytes).

FIG. 10a shows the changes in the right ventricular end-systolic pressure (RVESP) induced by BC-KI-00053 compound administration in the pulmonary arterial hypertension (PAH) model (MCT: monocrotaline treated pulmonary arterial hypertension (PAH) model, Tx25mpk: administration of BC-KI-00053 25 mg/kg in the PAH model, Tx50mpk: administration of BC-KI-00053 50 mg/kg in the PAH model).

Figure 10B:
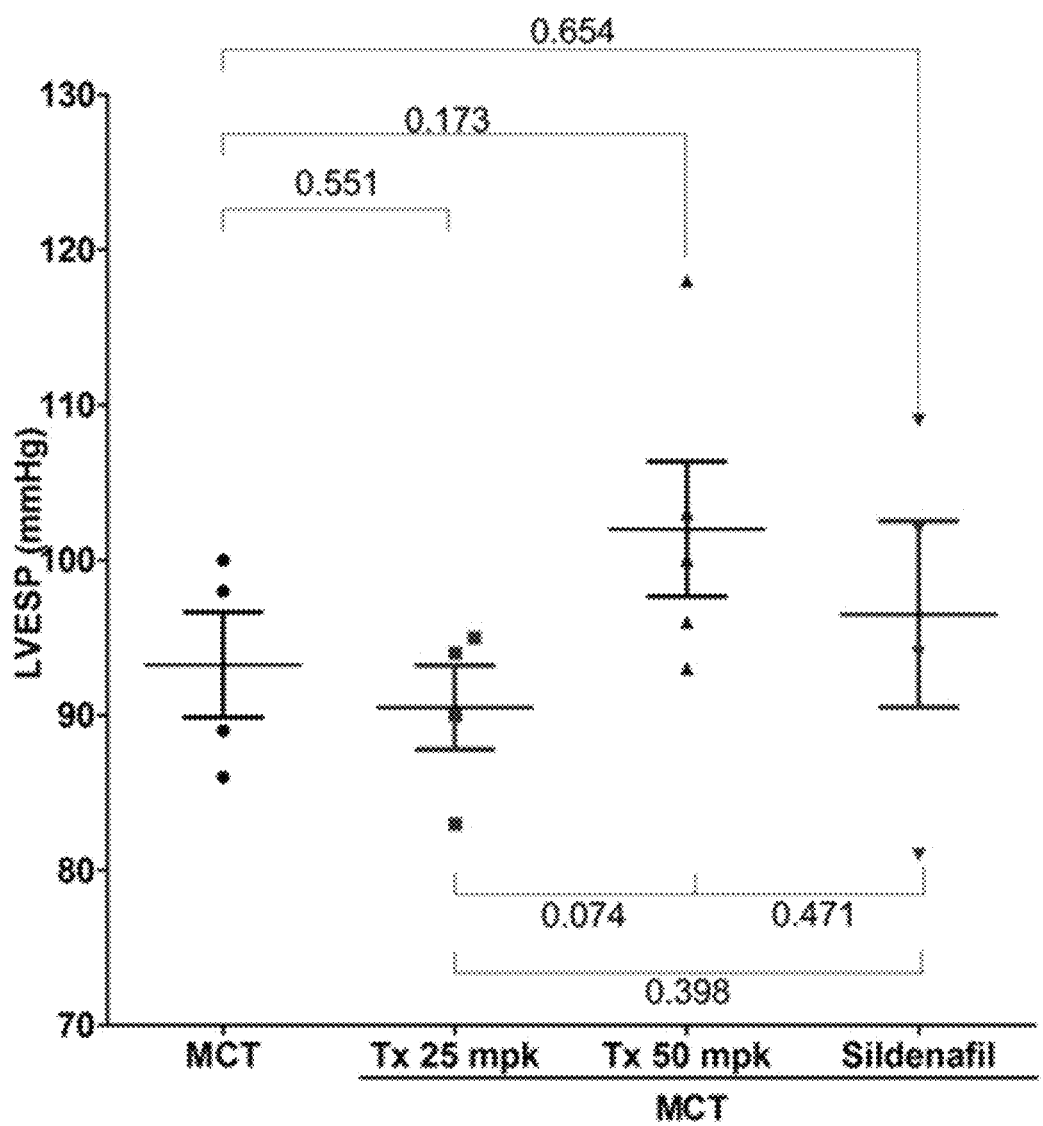

FIG. 10b shows the changes in the left ventricular end-systolic pressure (LVESP) induced by BC-KI-00053 compound administration in the pulmonary arterial hypertension (PAH) model (MCT: monocrotaline treated pulmonary arterial hypertension (PAH) model, Tx25mpk: administration of BC-KI-00053 25 mg/kg in the PAH model, Tx50mpk: BC-KI-00053 50 mg/kg in the PAH model).

Figure 10C:
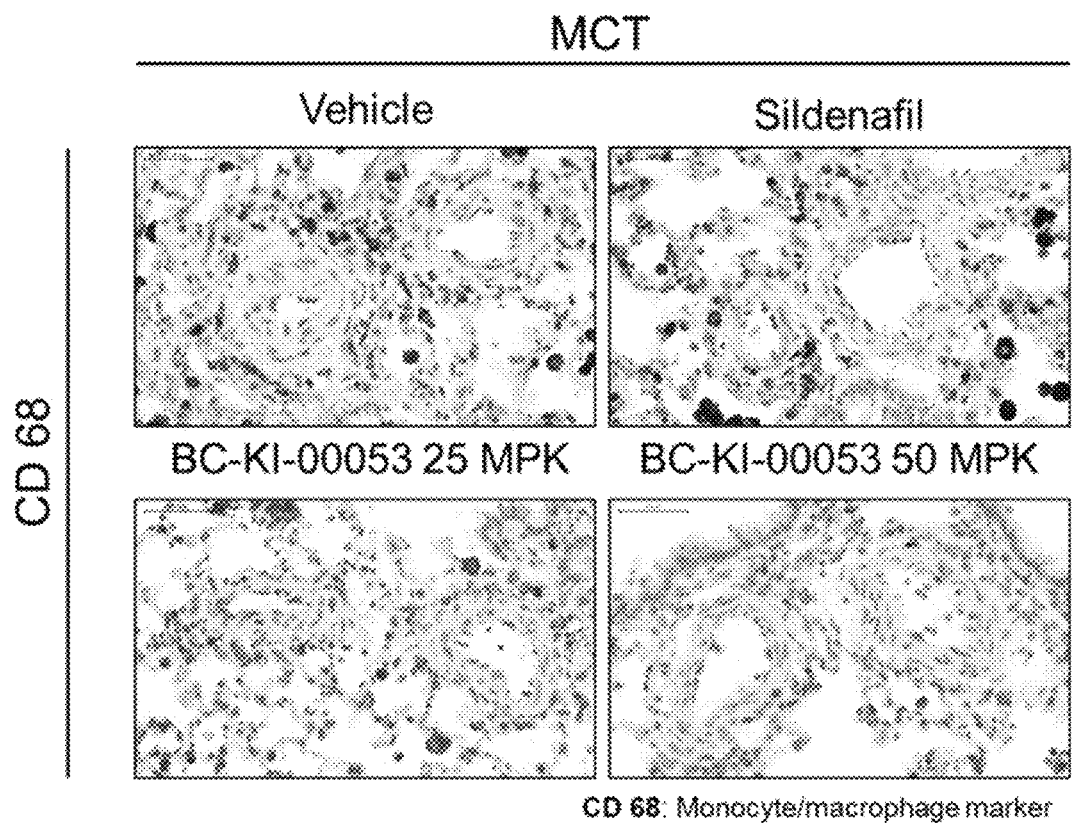

FIG. 10c shows the IHC staining results confirming that the migration and infiltration of immune cells of the lung tissue was reduced by BC-KI-00053 compound administration in the pulmonary arterial hypertension (PAH) model.

Figure 11A:
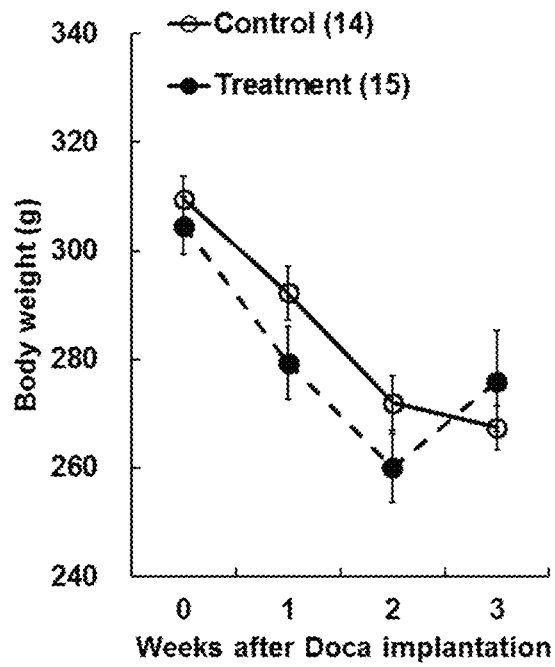

FIG. 11a shows the basal body weight and changes in the body weight during the experimental period in the vehicle-treated and BC-KI-00053-treated groups in FHH rats with superimposed hypertension (Numbers in parentheses represent the number of animals used to calculate the mean data in each group. same as below).

Figure 11B:
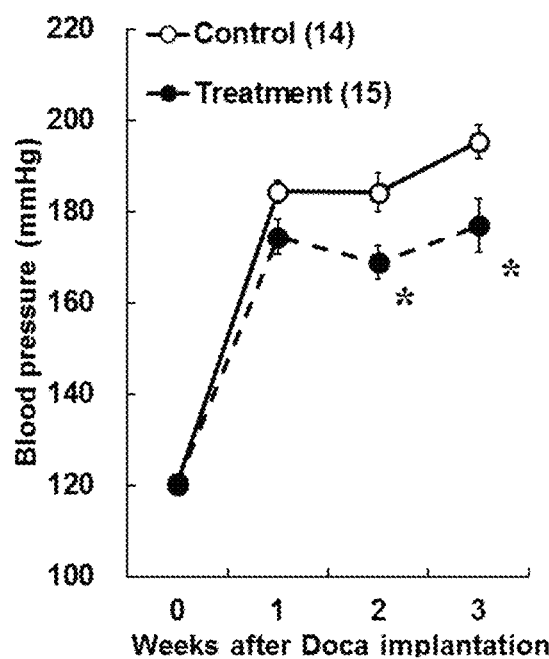

FIG. 11b shows the results measuring changes in MAP induced by BC-KI-00053 treatment in FHH rats with superimposed hypertension.

Figure 11C:
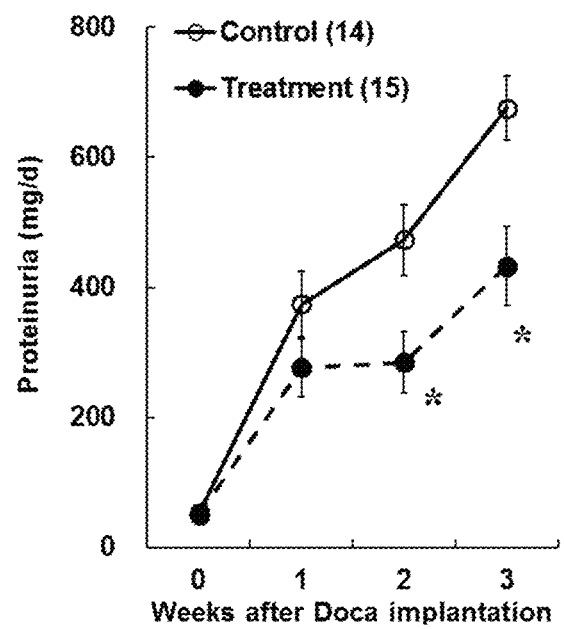

FIG. 11c shows the results measuring the degree of proteinuria (degree of protein excretion) induced by BC-KI-00053 treatment in FHH rats with superimposed hypertension.

Figure 11D:
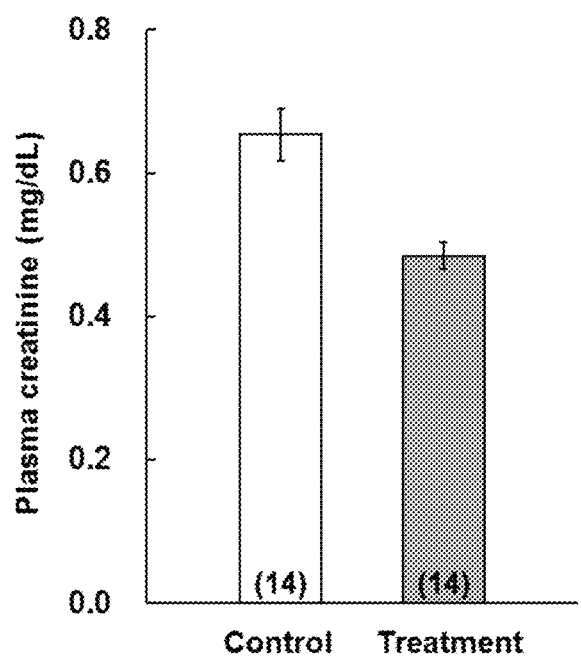

FIG. 11d shows the results measuring the changes in the plasma creatinine concentration induced by BC-KI-00053 treatment in FHH rats with superimposed hypertension.

Figure 11E:
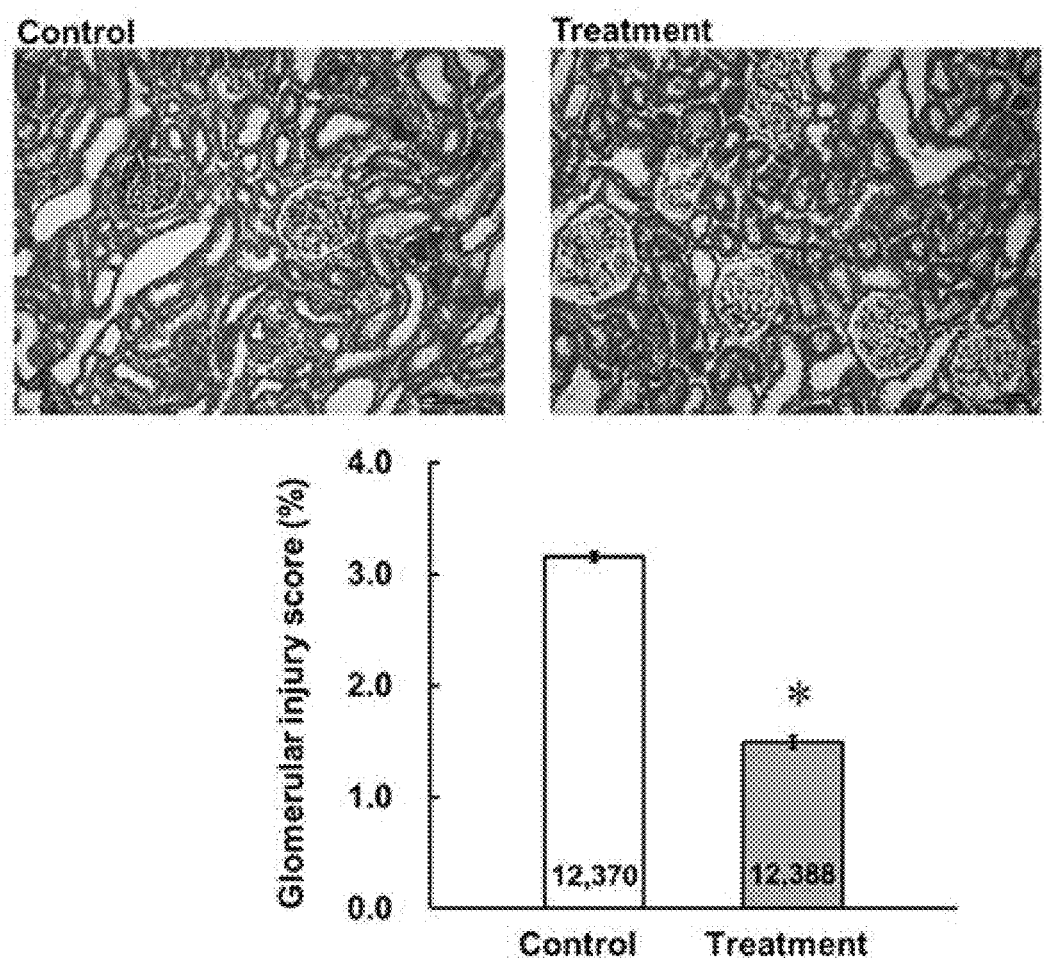

FIG. 11e shows the microscopic images (upper panels) of glomeruli and quantitative evaluation (bottom graph) of the degree of glomerulosclerosis in the vehicle-treated (control) and BC-KI-00053-treated (treatment) groups of FHH rats with superimposed hypertension (Numbers inside the graph represent the number of images used to measure the actual results).

Figure 11F:
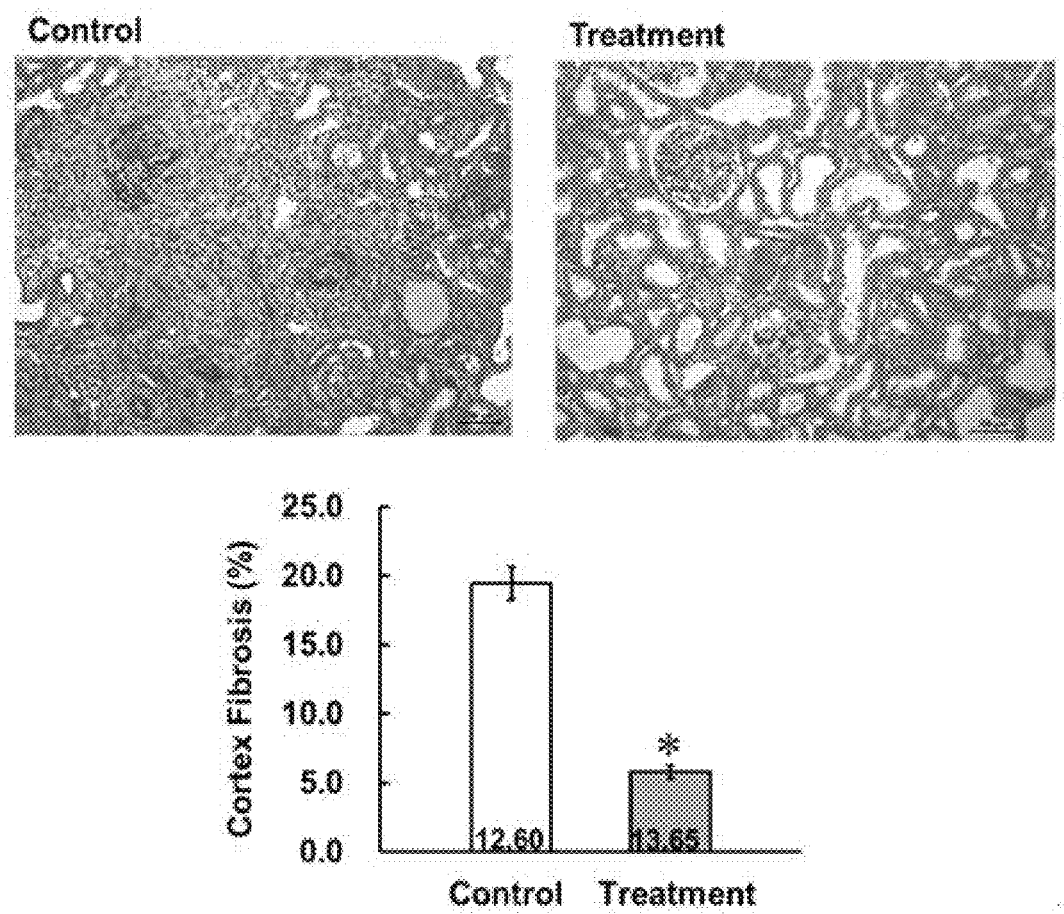

FIG. 11f shows the microscopic images (upper panels) of cortical fibrosis and quantitative representation (bottom graph) of the degree of cortical fibrosis in the vehicle-treated (control) and BC-KI-00053-treated (treatment) groups of FHH rats with superimposed hypertension (Numbers inside the graph represent the number of images used to measure the actual results).

Figure 11G:
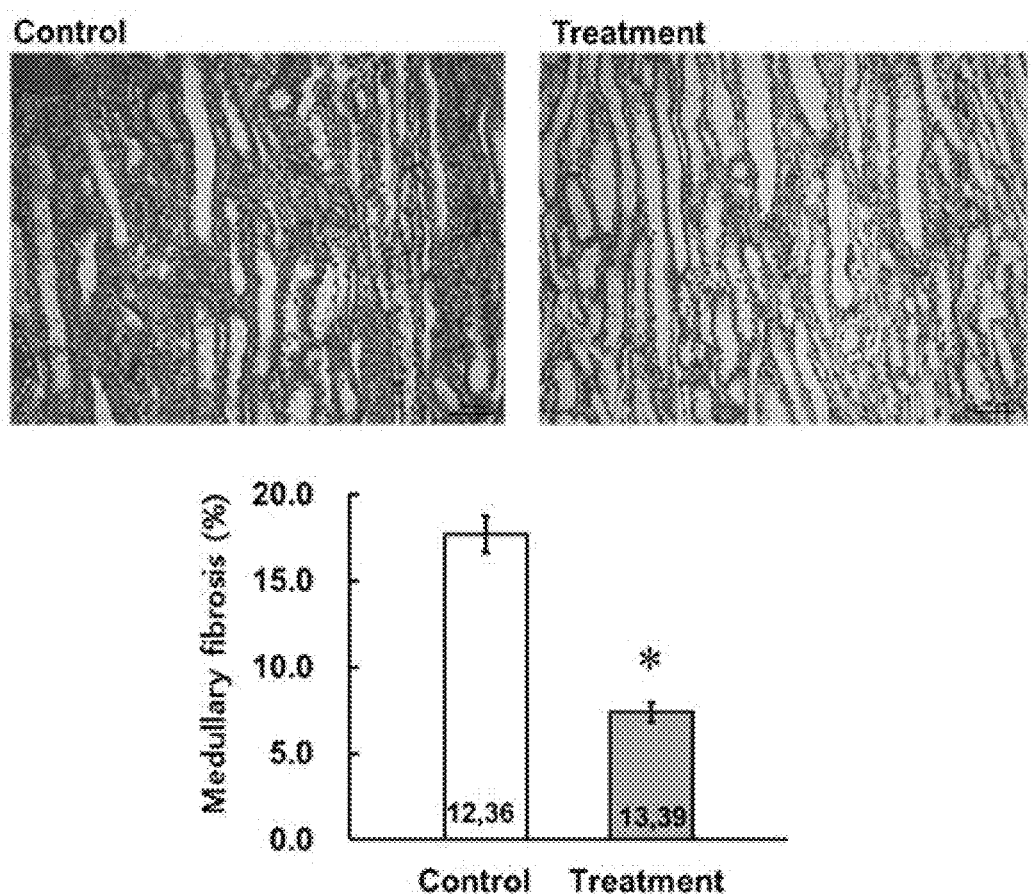

FIG. 11g shows the microscopic images (upper panels) of medullary fibrosis and quantitative representation (bottom graph) of the degrees of medullary fibrosis in the vehicle-treated (control) and BC-KI-00053-treated (treatment) groups of FHH rats with superimposed hypertension (Numbers inside the graph represent the number of images used to measure the actual results).

Figure 11H:
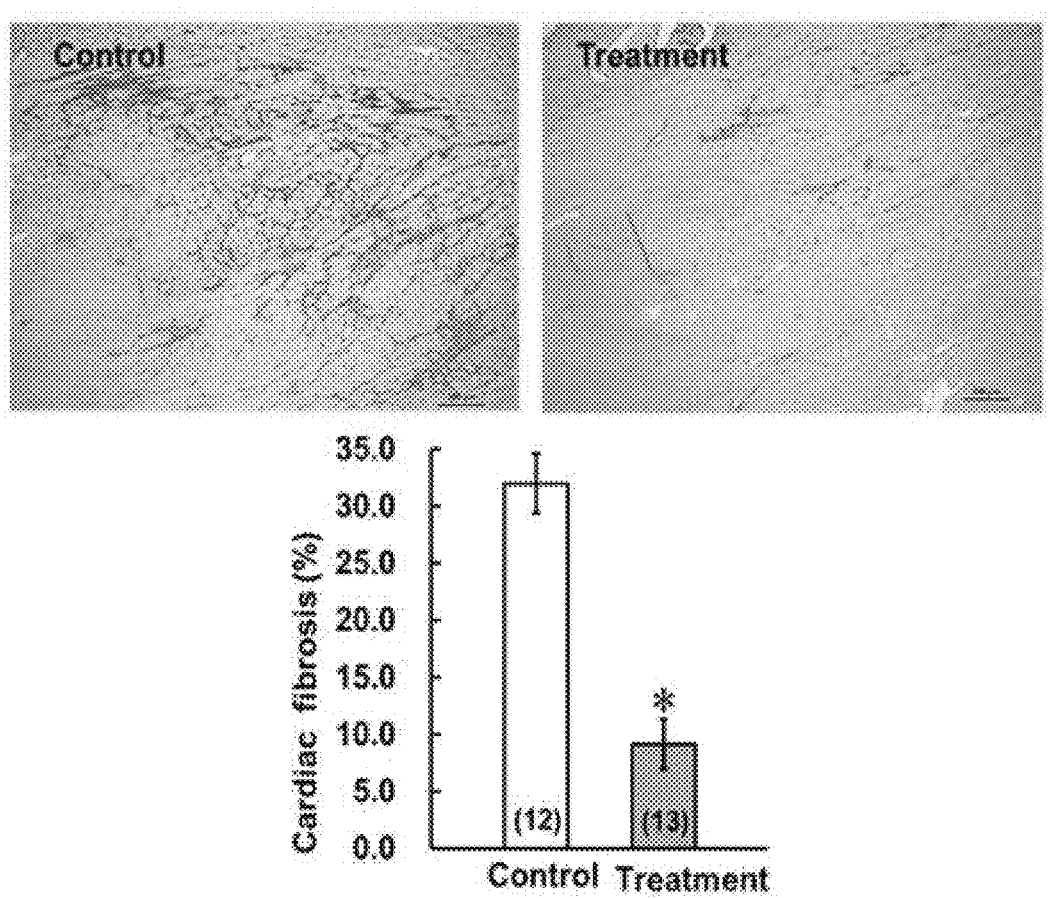

FIG. 11h shows the microscopic images (upper panels, right ventricular insertion point) of cardiac fibrosis and quantitative representation (bottom graph) of the degree of cardiac fibrosis in the vehicle-treated (control) and BC-KI-00053-treated (treatment) groups of FHH rats with superimposed hypertension (Numbers inside the graph represent the number of images used to measure the actual results).

Figure 11I:
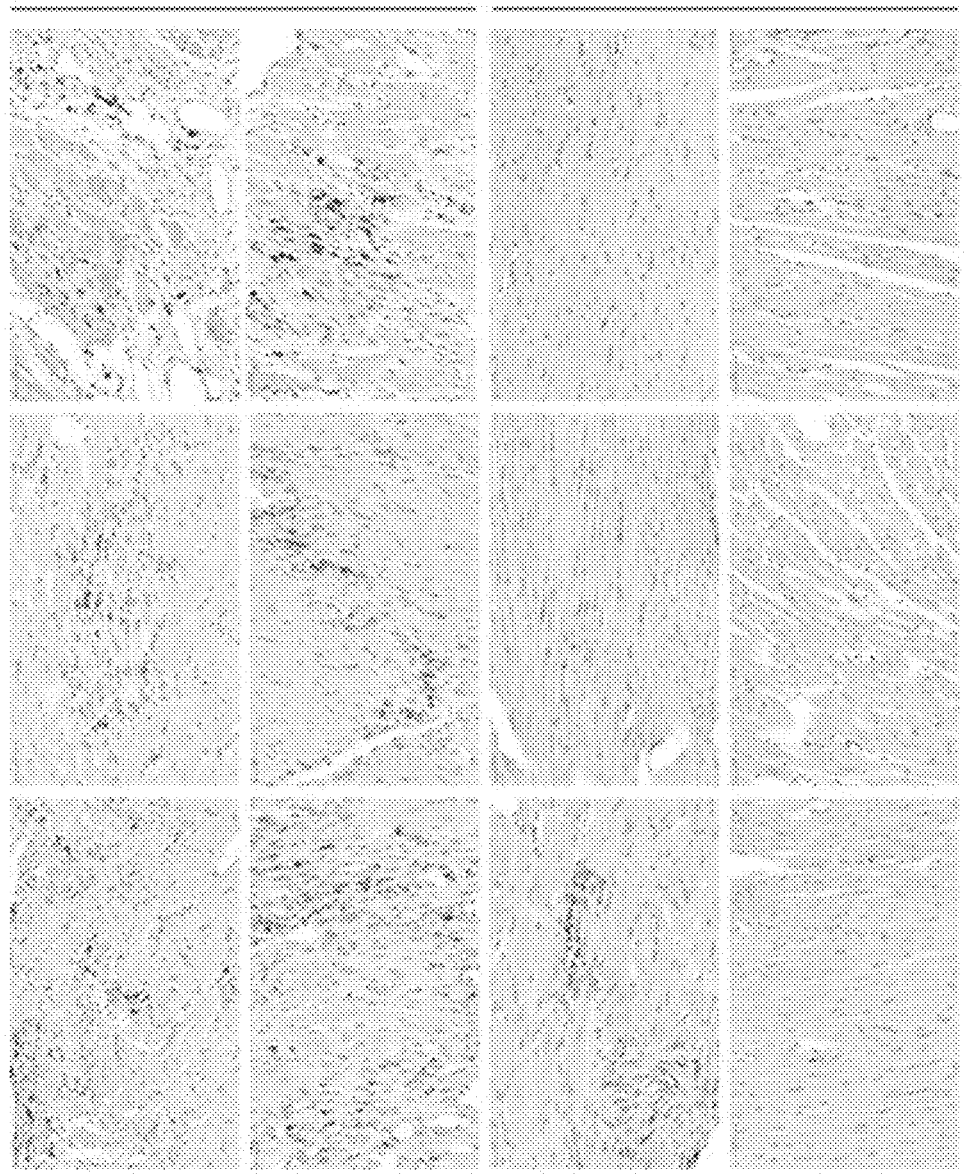

FIG. 11i shows the IHC staining results confirming that the migration and infiltration of immune cells of the kidney tissues are reduced by BC-KI-00053 compound administration in FHH rats with superimposed hypertension.

Figure 12A:
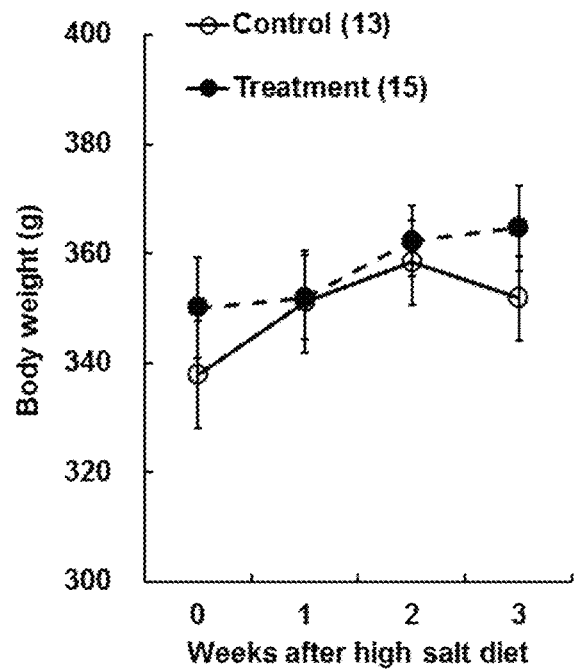

FIG. 12a shows the basal body weight and changes in the body weight during the experimental period in the vehicle-treated and BC-KI-00053-treated groups in Dahl salt-sensitive (SS) rats with hypertension, proteinuria, glomerulosclerosis and kidney interstitial fibrosis induced with high salt diet (Numbers in parentheses represent the number of animals used to calculate the mean data in each group. same as below).

Figure 12B:
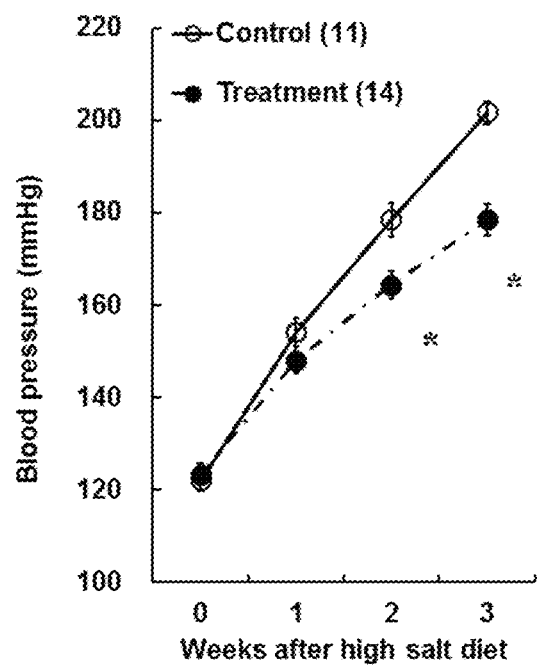

FIG. 12b shows the results measuring changes in MAP induced by BC-KI-00053 treatment in Dahl salt-sensitive (SS) rats with hypertension, proteinuria, glomerulosclerosis and kidney interstitial fibrosis induced with high salt diet.

Figure 12C:
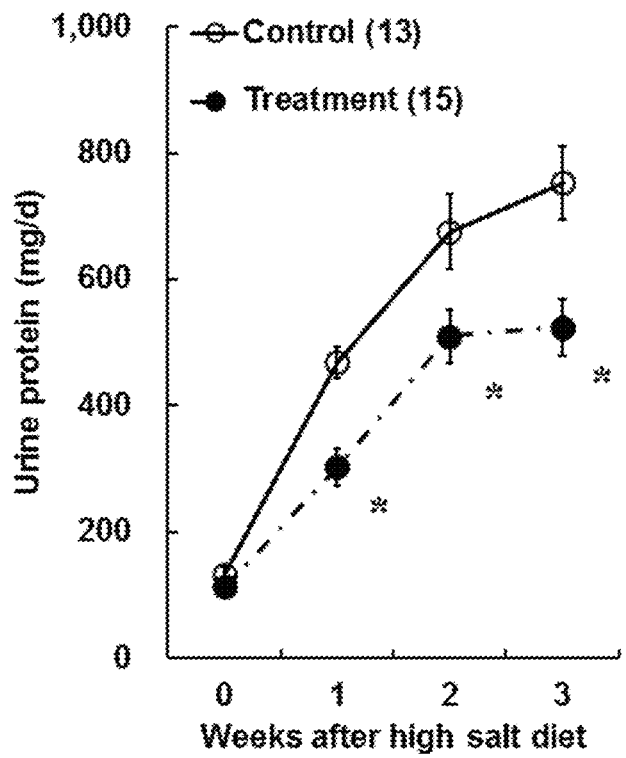

FIG. 12c shows the results measuring the degree of proteinuria (degree of protein excretion) induced by BC-KI-00053 treatment in Dahl salt-sensitive (SS) rats with hypertension, proteinuria, glomerulosclerosis and kidney interstitial fibrosis induced with high salt diet.

Figure 12D:
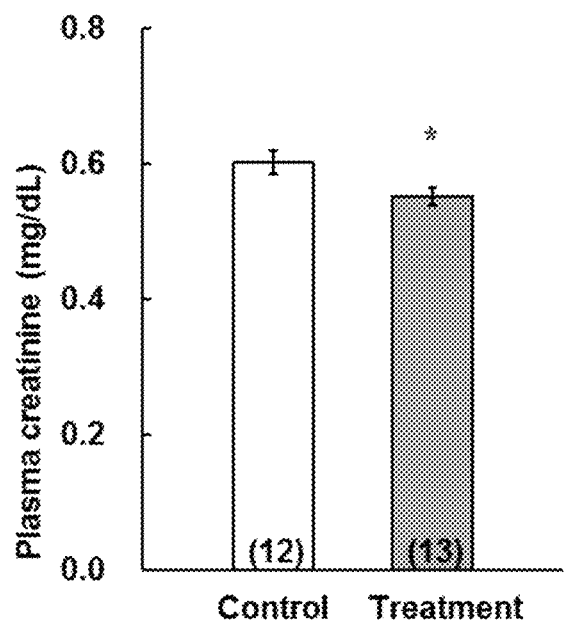

FIG. 12d shows the results measuring changes in the plasma creatinine concentration induced by BC-KI-00053 treatment in Dahl salt-sensitive (SS) rats with hypertension, proteinuria, glomerulosclerosis and kidney interstitial fibrosis induced with high salt diet.

Figure 12E:
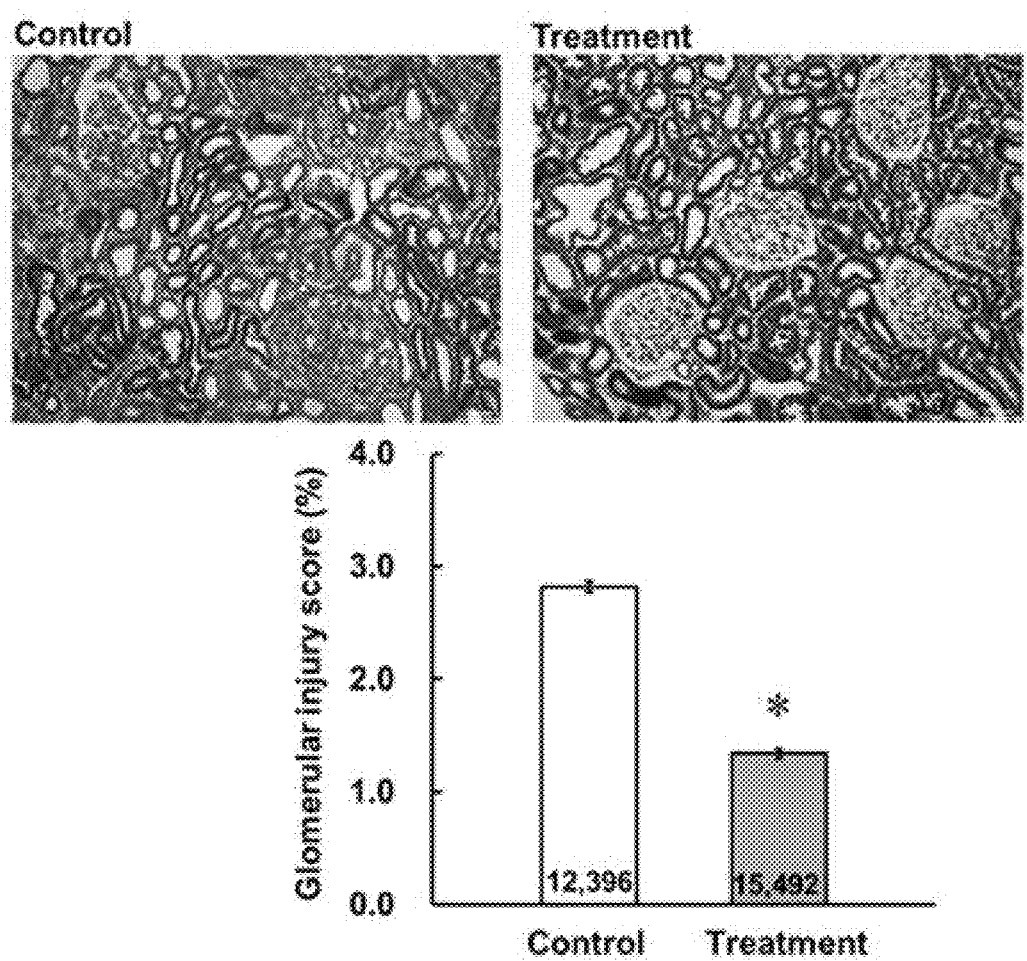

FIG. 12e shows the microscopic images (upper panels) of glomeruli and quantitative evaluation (bottom graph) of the degrees of glomerulosclerosis in the vehicle-treated (control) and BC-KI-00053-treated (treatment) groups of Dahl salt-sensitive (SS) rats with hypertension, proteinuria, glomerulosclerosis and kidney interstitial fibrosis induced with high salt diet (Numbers inside the graph represent the number of images used to measure the actual results).

Figure 12F:
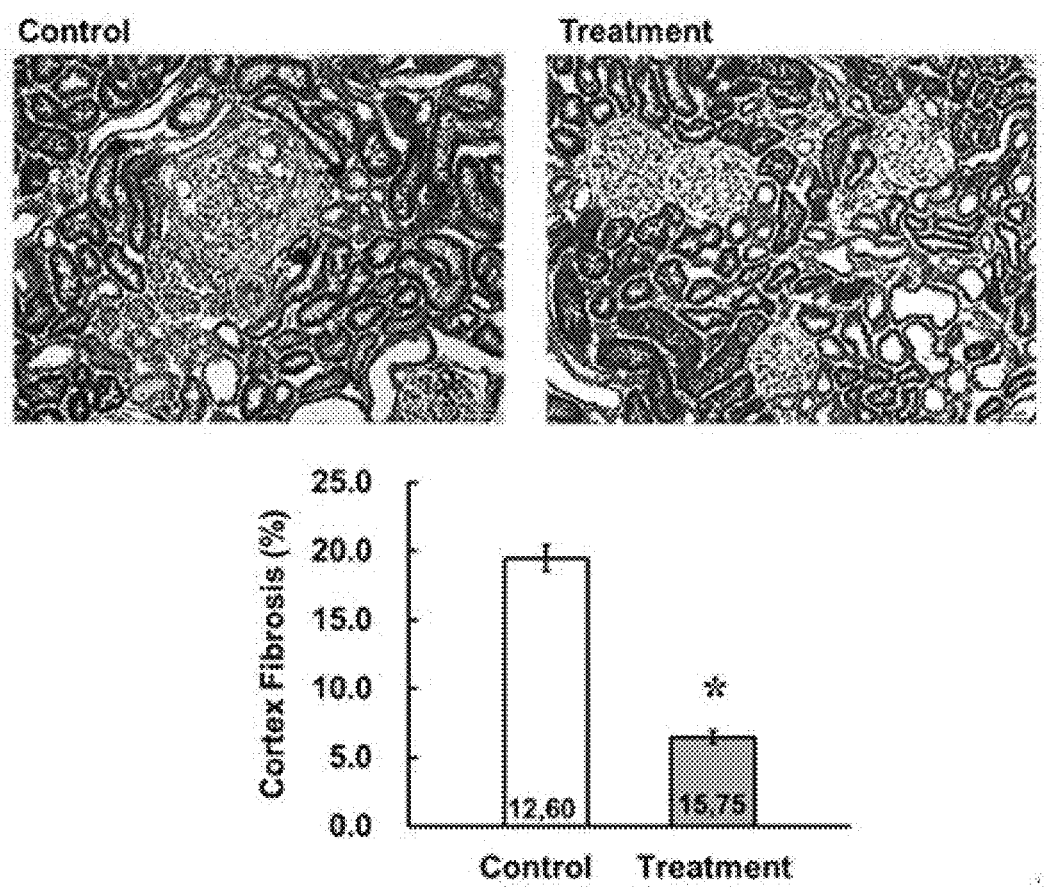

FIG. 12f shows the microscopic images (upper panels) of cortical fibrosis and quantitative representation (bottom graph) of the degree of cortical fibrosis in the vehicle-treated (control) and BC-KI-00053-treated (treatment) groups of Dahl salt-sensitive (SS) rats with hypertension, proteinuria, glomerulosclerosis and kidney interstitial fibrosis induced with high salt diet (Numbers inside the graph represent the number of images used to measure the actual results).

Figure 12G:
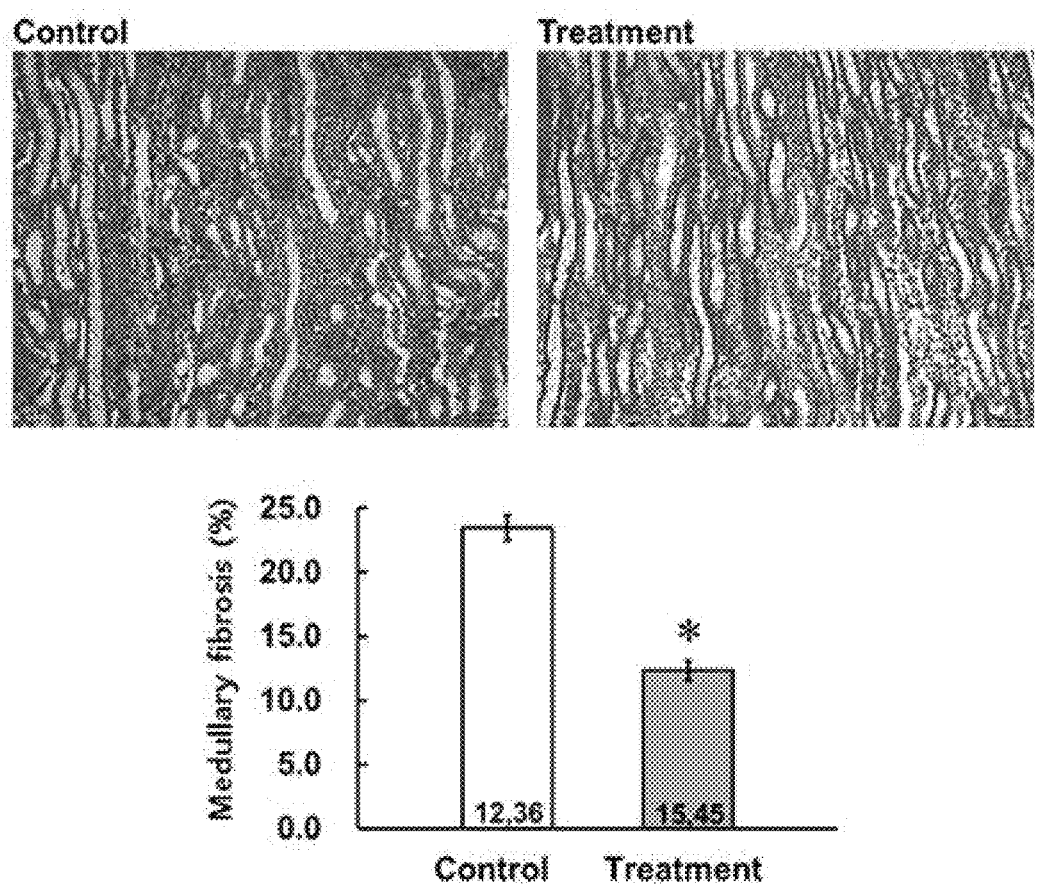

FIG. 12g shows the microscopic images (upper panels) of medullary fibrosis and quantitative representation (bottom graph) of the degree of medullary fibrosis in the vehicle-treated (control) and BC-KI-00053-treated (treatment) groups of Dahl salt-sensitive (SS) rats with hypertension, proteinuria, glomerulosclerosis and kidney interstitial fibrosis induced with high salt diet (the numbers inside the graph represent the number of images used to measure the actual results).

Figure 12H:
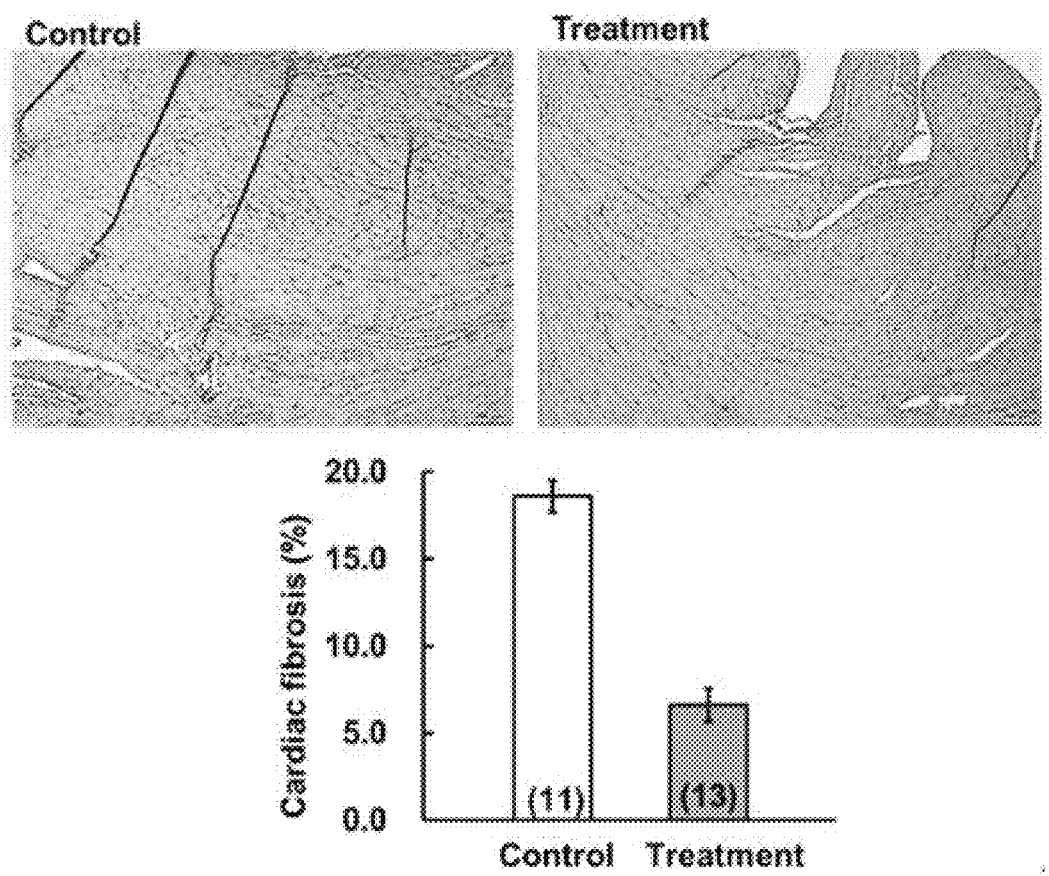

FIG. 12h shows the microscopic images (upper panels, right ventricular insertion point) of cardiac fibrosis and quantitative representation (bottom graph) of the degree of cardiac fibrosis in the vehicle-treated (control) and BC-KI-00053-treated (treatment) groups of Dahl salt-sensitive (SS) rats with hypertension, proteinuria, glomerulosclerosis and kidney interstitial fibrosis induced with high salt diet (Numbers inside the graph represent the number of images used to measure the actual results).

Figure 12I:
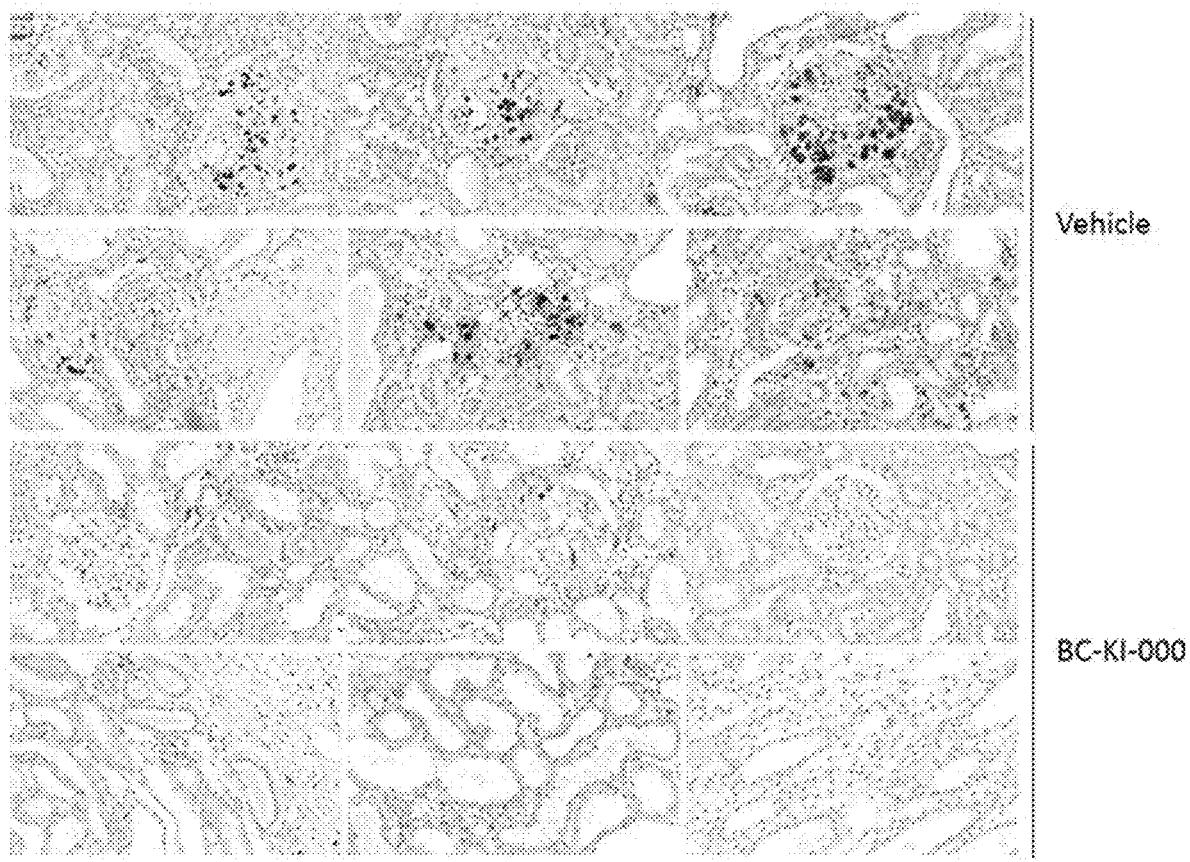

FIG. 12i shows the IHC staining results confirming that the migration and infiltration of immune cells of the kidney tissues are reduced by BC-KI-00053 compound administration in Dahl salt-sensitive (SS) rats with hypertension, proteinuria, glomerulosclerosis and kidney interstitial fibrosis induced with high salt diet.

Figure 13:
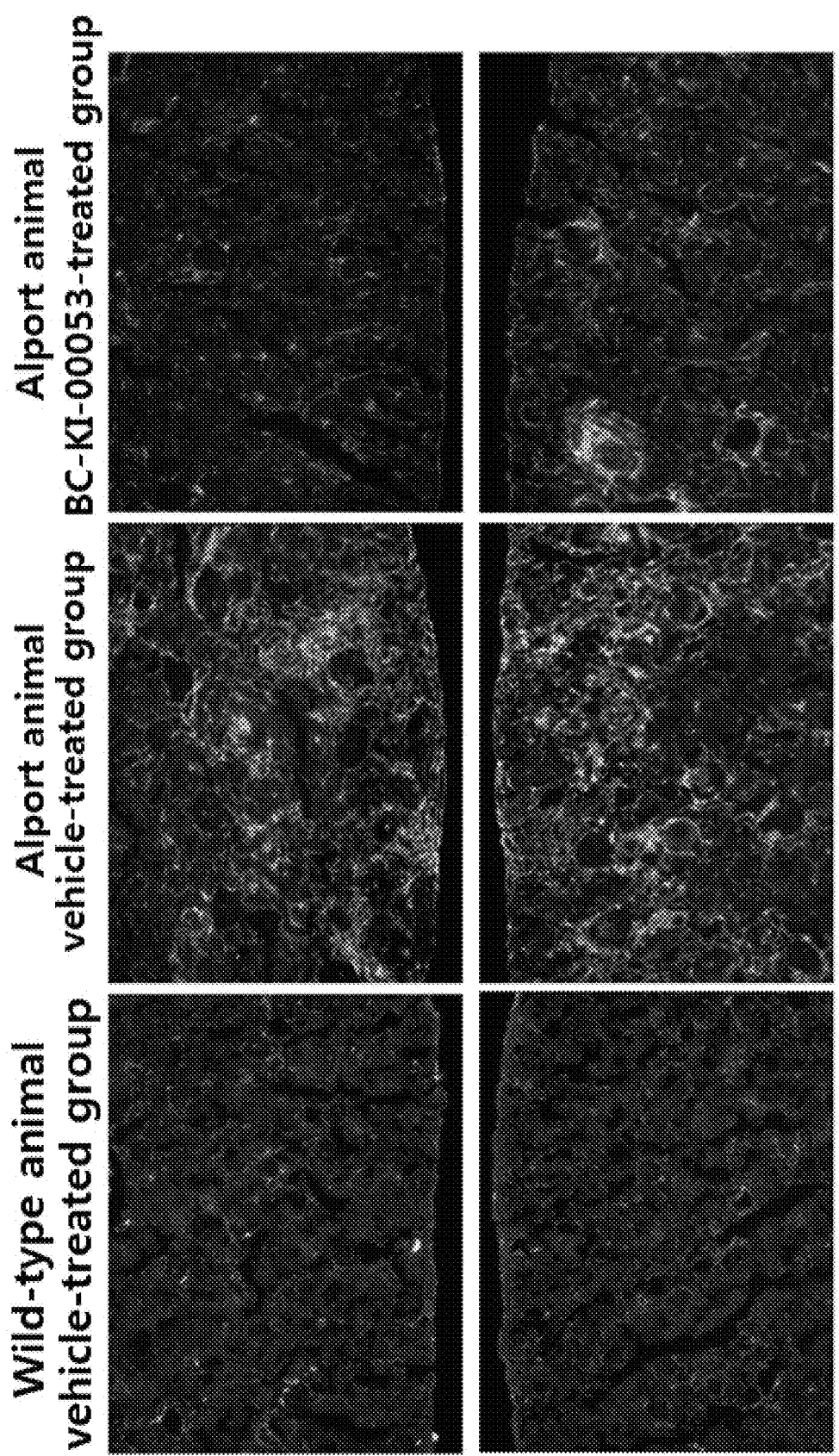

FIG. 13 shows the results of evaluating the degree of reduction in the leukocyte infiltration and fibrosis in the kidney when a control substance or BC-KI-00053 compound is administered in the animal model of Alport syndrome.

Figure 14A:
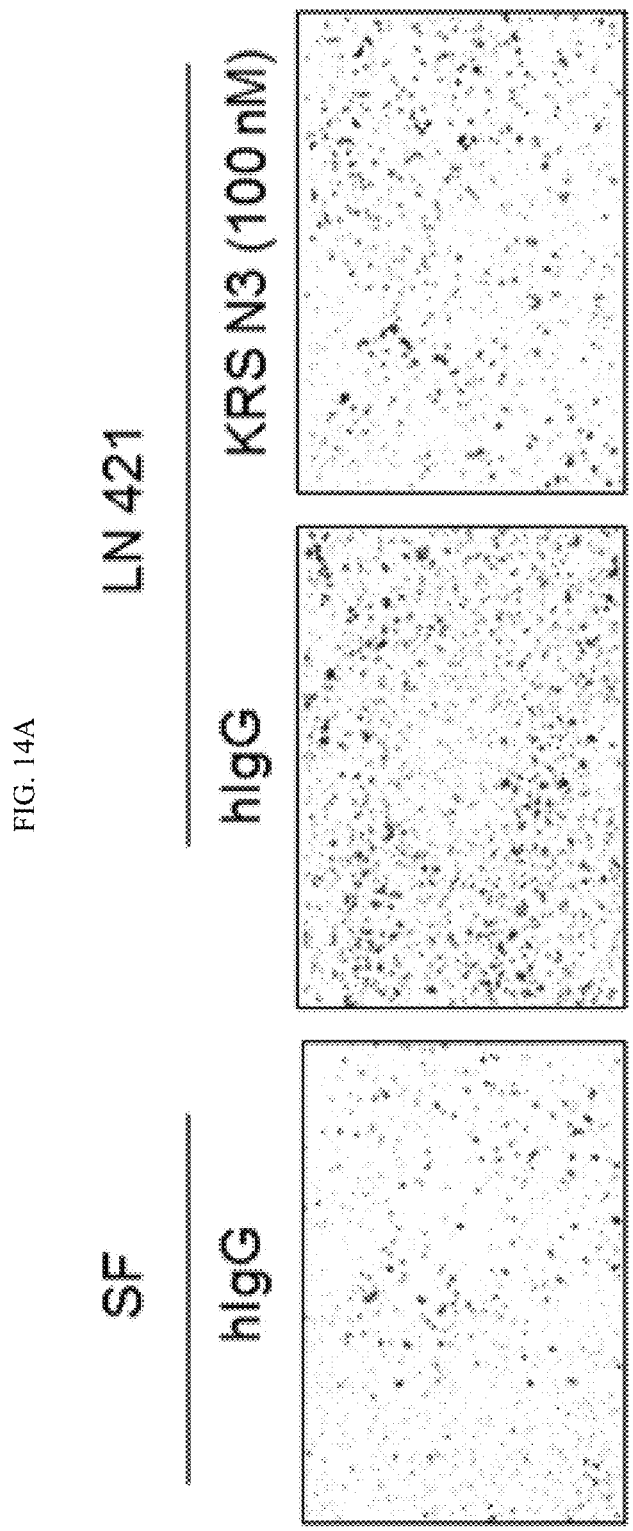

FIG. 14a shows microscopic images of migrating cells in a transwell migration assay as results of comparing the inhibitory effect of anti-KRS antibody on the LN421-specific monocyte/macrophage migration.

Figure 14B:
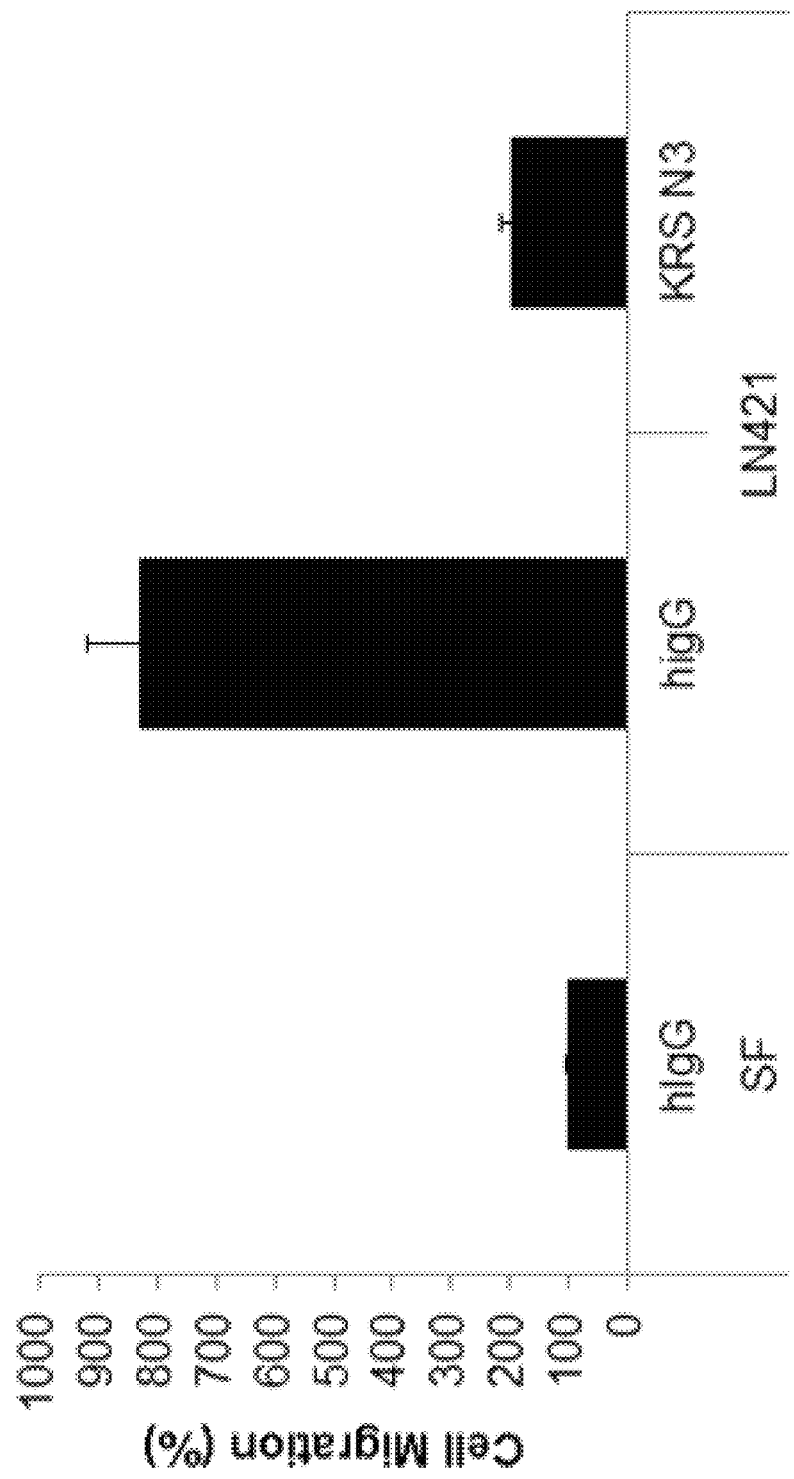

FIG. 14b is a graph representing the numbers of cells measured (quantified) in the microscope images of FIG. 14a.

Figure 14C:
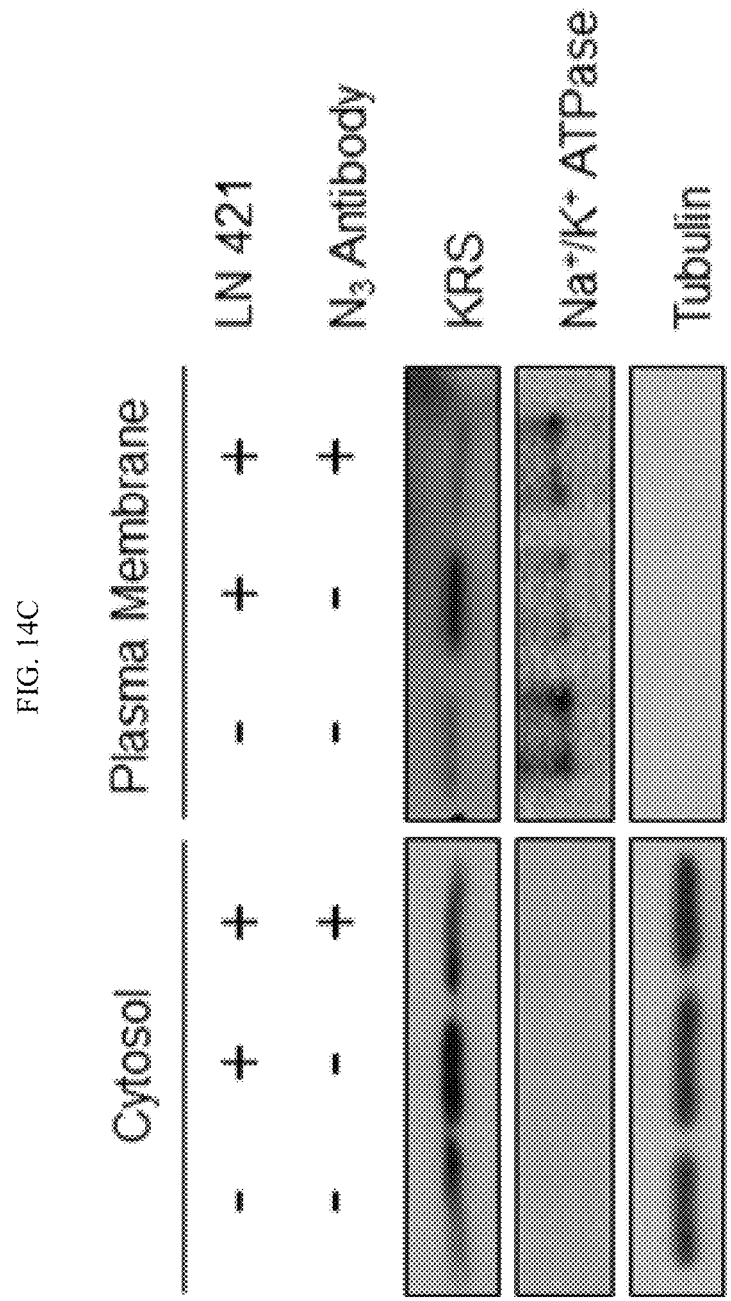

FIG. 14c shows the western blot results confirming that the LN421-induced increase of KRS level in the plasma membrane of monocytes/macrophages is reduced by anti-KRS antibody (e.g. N3 antibody) treatment.

Figure 15:
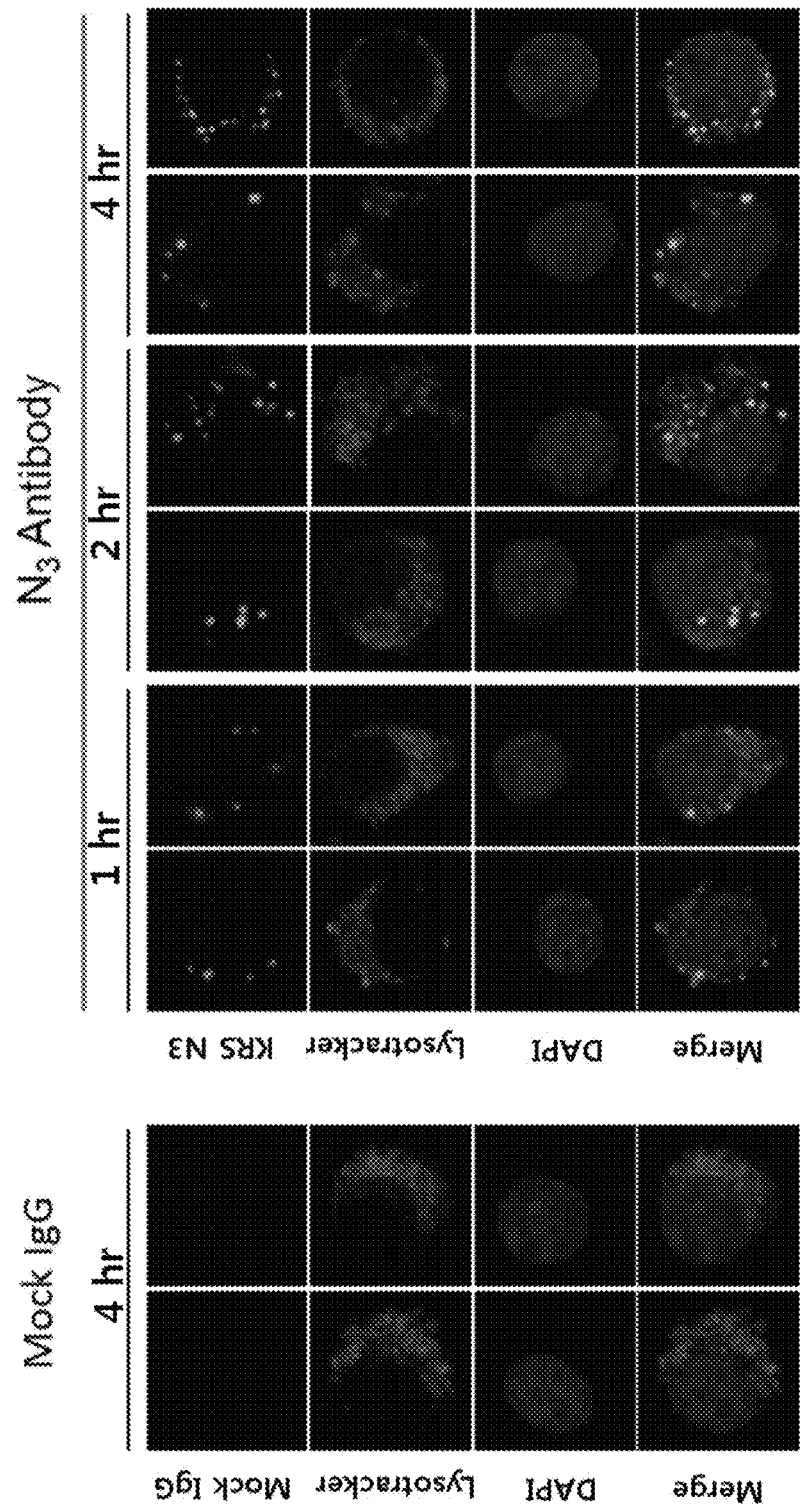

FIG. 15 shows the results confirming that KRS in the plasma membrane region is endocytosed by treatment with anti-KRS antibody (N3 antibody). Anti-KRS antibody labeled with Alexa fluor 488 (Thermofisher) fluorescence probe and mock IgG (Thermofisher), a control group, were treated and the movement of antibodies was monitored over time (Thermofisher), while Lysotracker (Thermofisher) was used to observe whether endocytosis occurred as a lysosomal marker.

Figure 16:
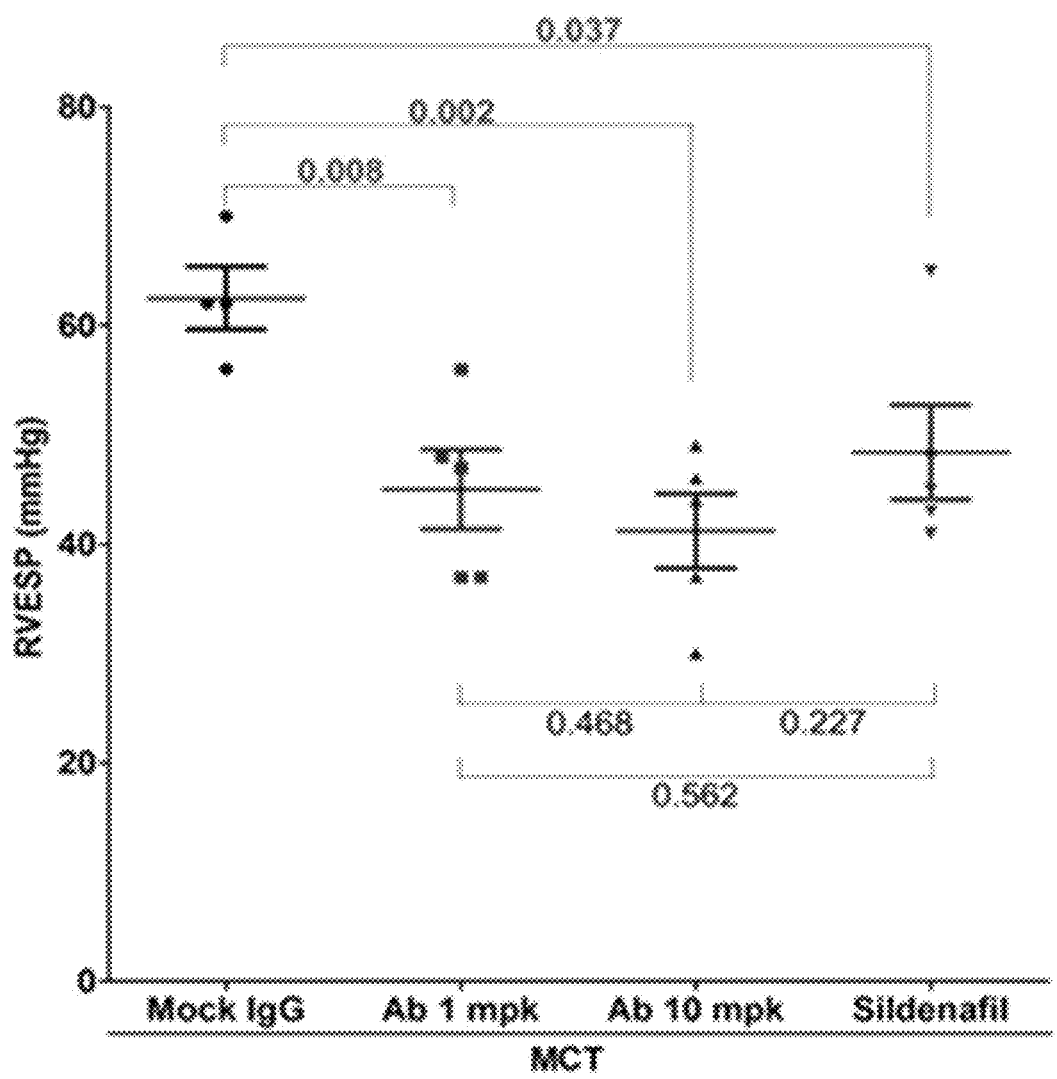

FIG. 16 shows the changes in the right ventricular end-systolic pressure (RVESP) induced by anti-KRS antibody (N3 antibody) administration in the pulmonary arterial hypertension (PAH) model (Mock IgG: negative control, Ab lmpk: N3 antibody 1 mpk, Ab 10 mpk: N3 antibody 10 mpk, sildenafil: positive control).

Figure 17:
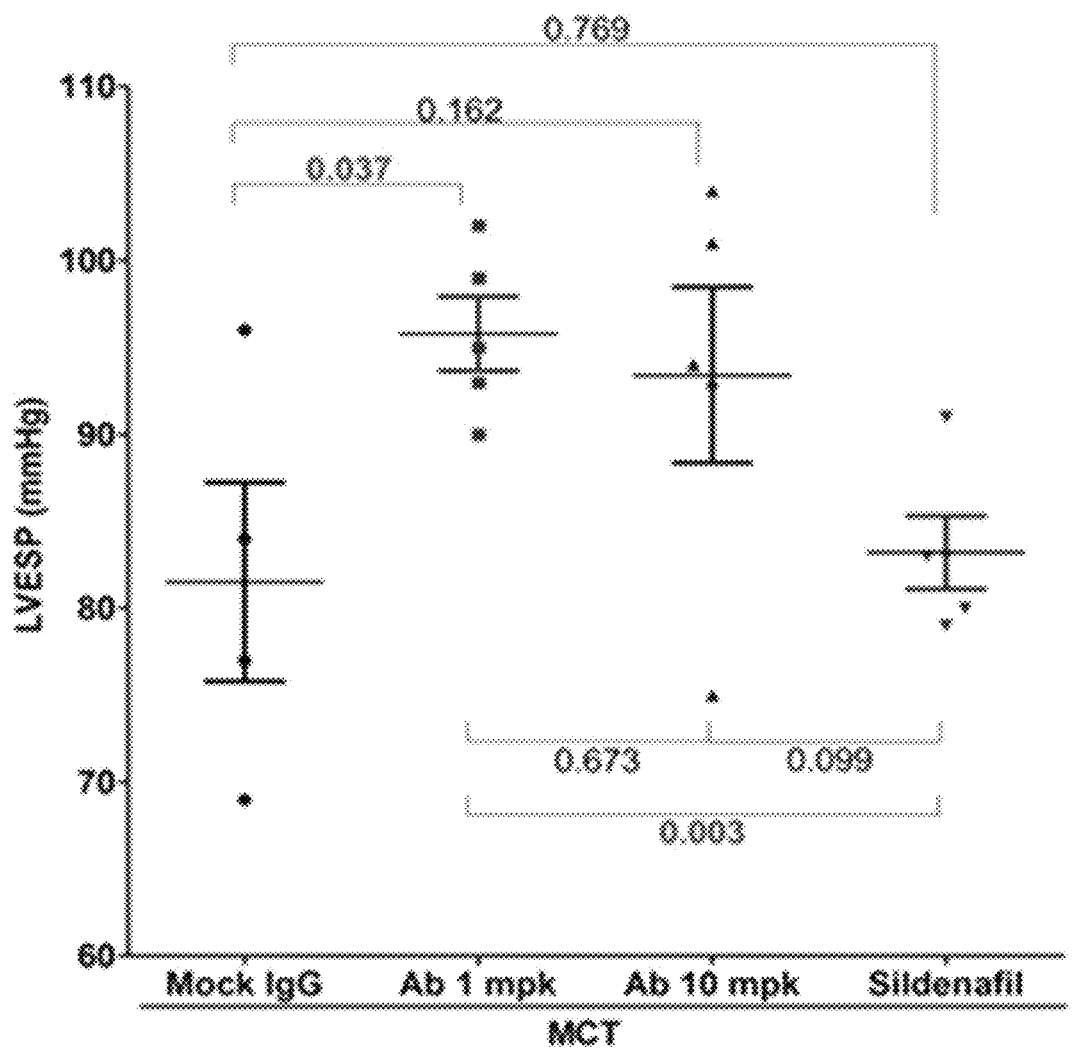

FIG. 17 shows the changes in the left ventricular end-systolic pressure (LVESP) induced by anti-KRS antibody (N3 antibody) administration in the pulmonary arterial hypertension (PAH) model (Mock IgG: negative control, Ab lmpk: N3 antibody 1 mpk, Ab 10 mpk: N3 antibody 10 mpk, sildenafil: positive control).

Figure 18:
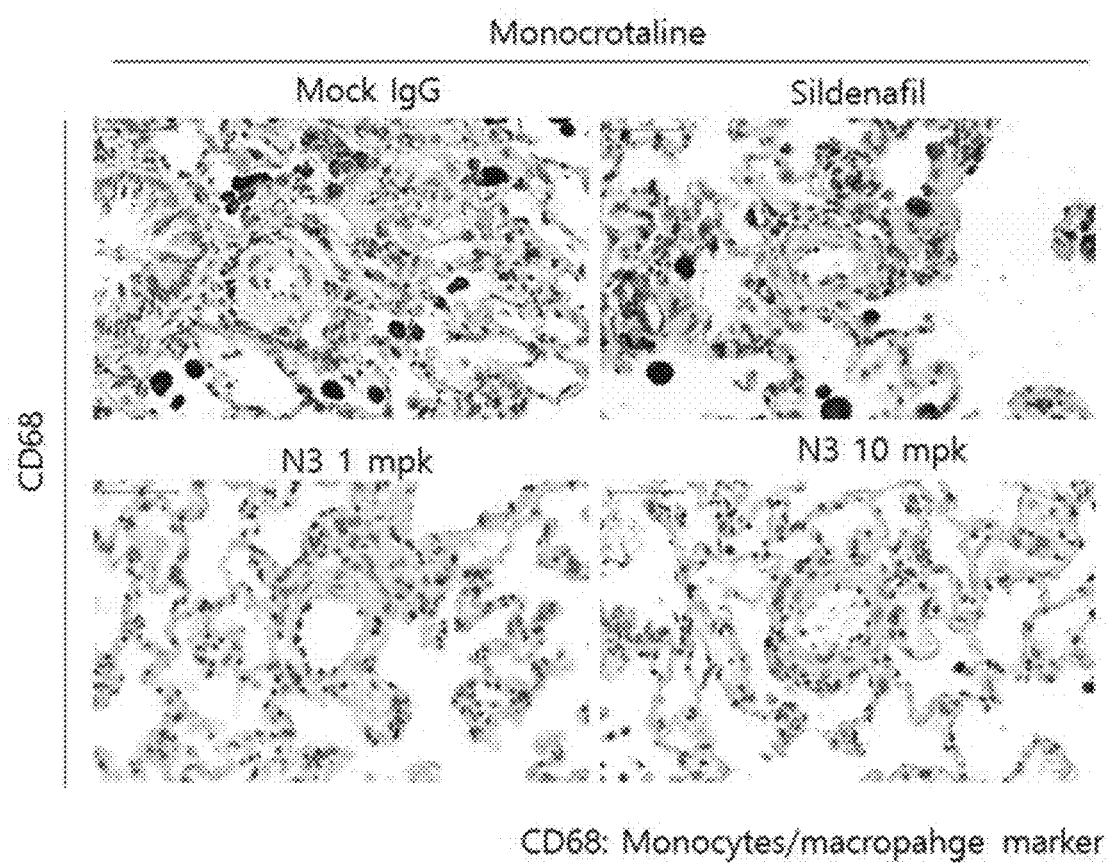

FIG. 18 shows the IHC staining results confirming that the degree of the migration and infiltration of immune cells in the lung tissues were reduced by anti-KRS antibody (N3 antibody) administration in the PAH model.

Figure 19:
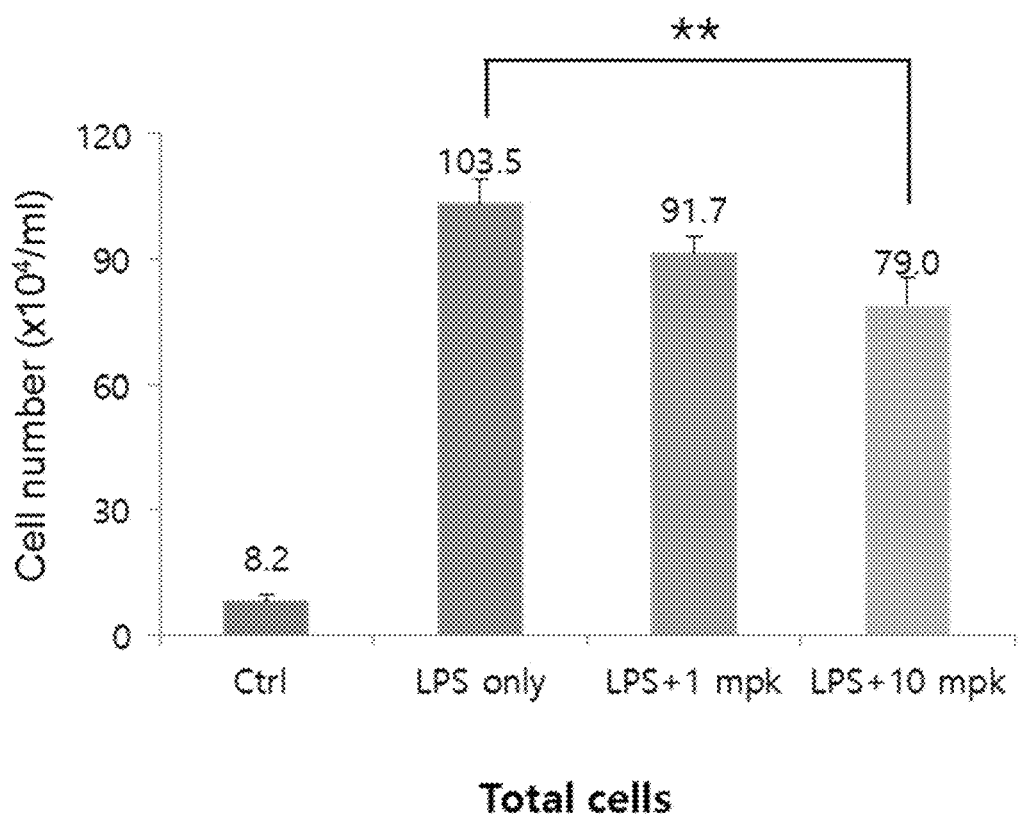

FIG. 19 shows the results confirming that the total number of immune cells increased in the bronchoalveolar lavage fluid (BALF) of the acute lung injury mouse model was reduced by anti-KRS antibody (N3 antibody) treatment in a concentration-dependent manner.

Figure 20:
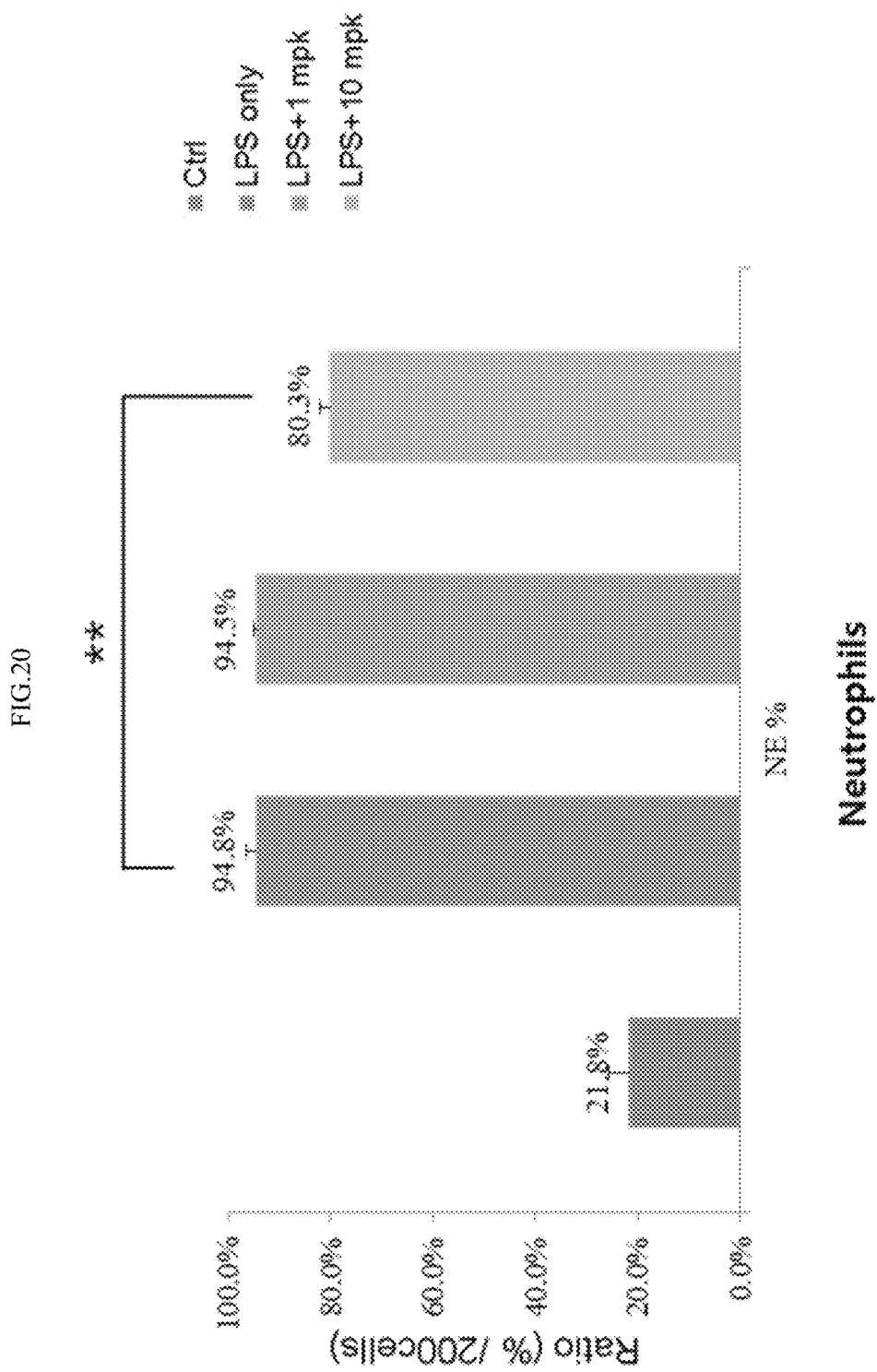

FIG. 20 shows the results confirming that the number of neutrophils particularly increased in the bronchoalveolar lavage fluid (BALF) of the acute lung injury mouse model was reduced by anti-KRS antibody (N3 antibody) treatment in a concentration-dependent manner.

Figure 21A:
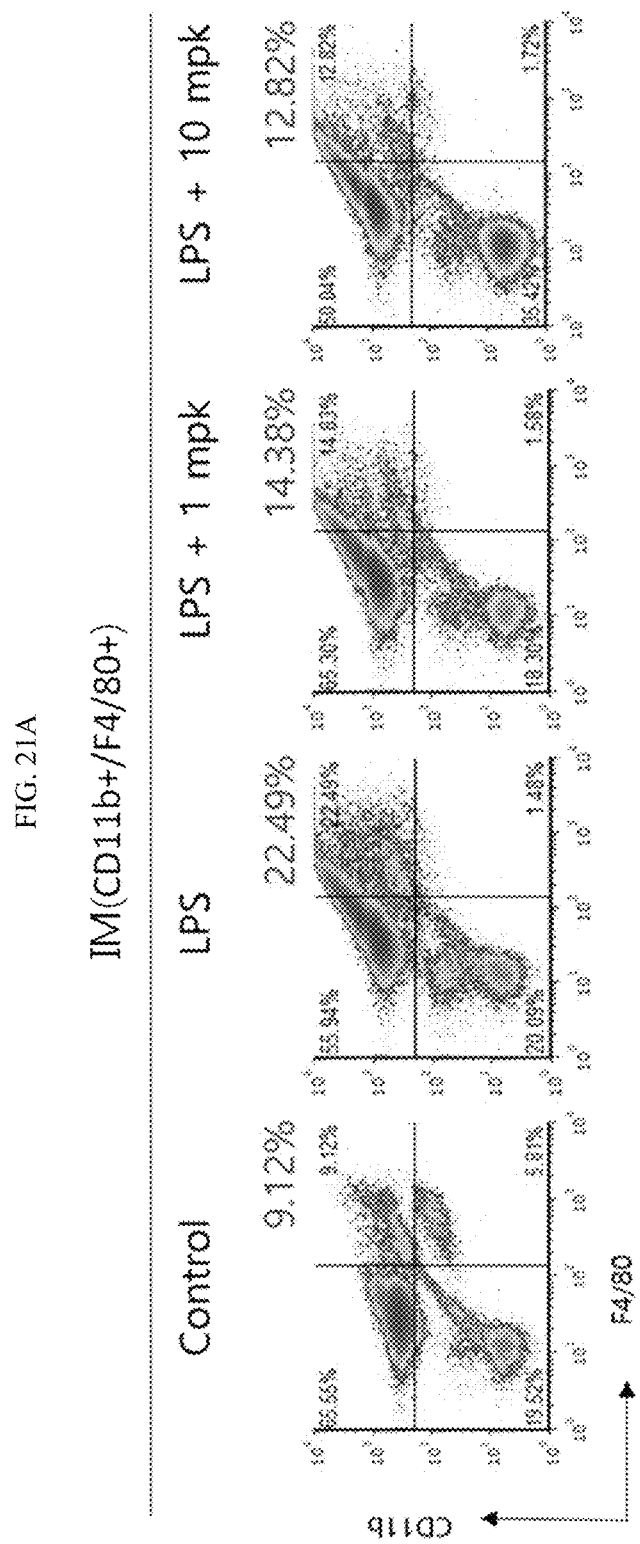

FIG. 21a shows the FACS results confirming that the migration and infiltration of macrophages (IM, CD11b+/F4/80+) increased in the lung tissues of the acute lung injury mouse model was reduced by anti-KRS antibody (N3 antibody) treatment in a concentration-dependent manner.

Figure 21B:
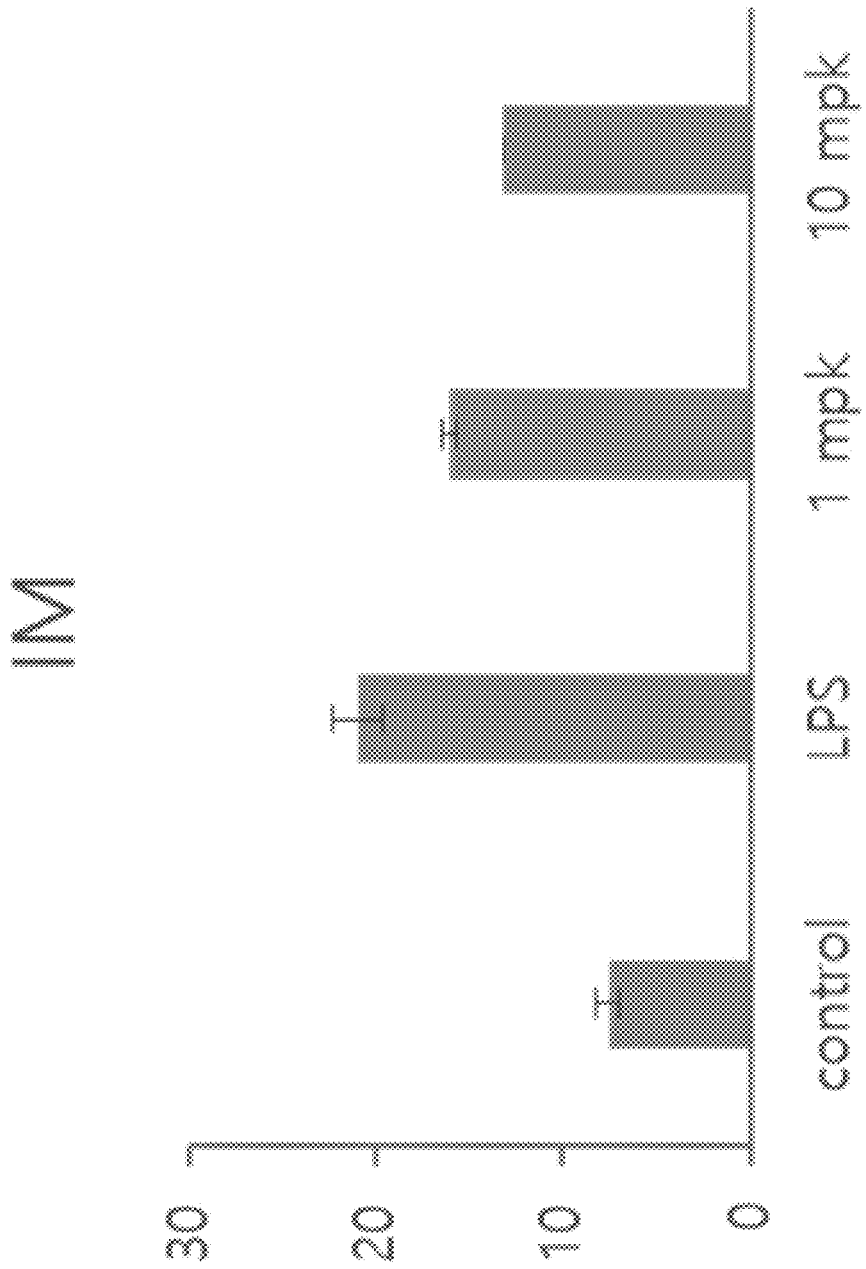

FIG. 21b is a graph quantifying the results of FIG. 21a.

Figure 22:
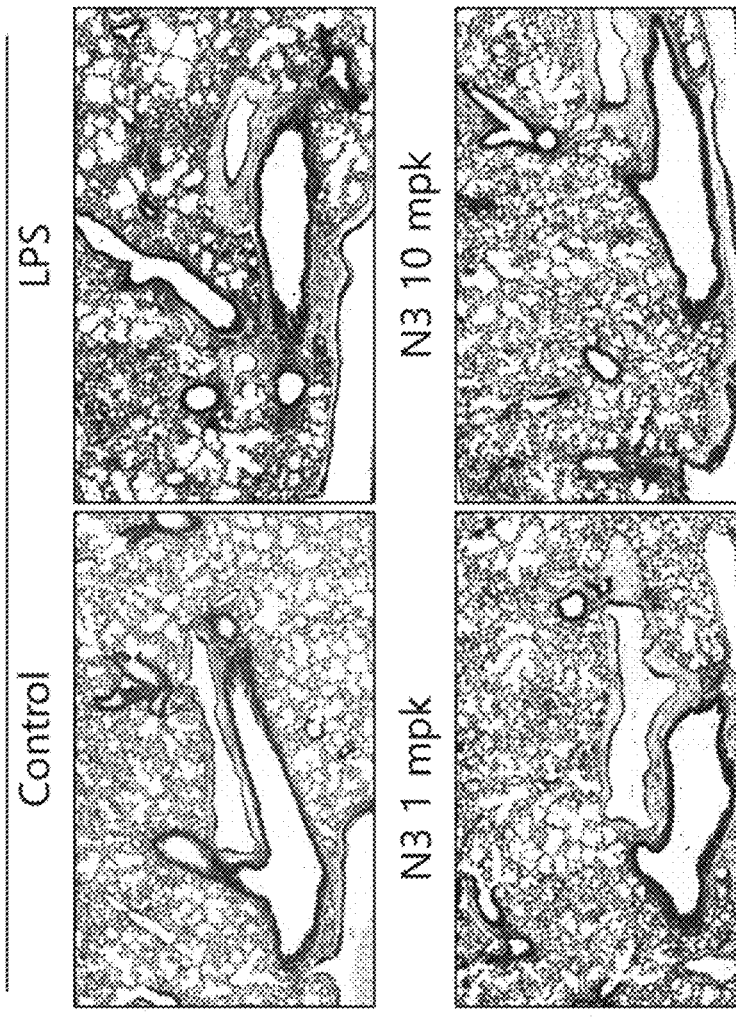

FIG. 22 shows tissue images indicating that tissues fibrosis progressed in the lung tissues of the acute lung injury mouse model was suppressed by treatment of anti-KRS antibody (N3 antibody). Tissues of each experimental and control groups were microscopically examined after Masson's trichrome staining.

MODE FOR CARRYING OUT INVENTION

Hereinafter, the present invention will be described in more detail with reference to examples, experimental examples and manufacturing examples. However, the following examples, experimental examples and preparation examples are illustrative of the present invention, and the present invention is not limited to the following examples, experimental examples and manufacturing examples.

Example 1: The Role of Laminin Signaling in the Immune Cell Migration and Infiltration Among several extracellular matrix (ECM), it was examined which ECM promotes the migration and infiltration of immune cells, typically monocytes/macrophages. A transwell migration assay was performed using collagen (Col), fibronectin (FN) and laminin (LN) as extracellular matrices, and detailed methods were as follows. Transwells (Corning, #3421-5 mm) were coated with gelatin (0.5 mg/ml) and RAW 264.7 cells (1×10$^5$ cells/well) were seeded into the top chambers. Serum free DMEM (500 μl) containing 10 μg/ml of laminin (laminin mixture, Biolamina), fibronectin or collagen, respectively, was placed in the bottom chambers. After 24 hours, cells were fixed with 70% methanol for 30 minutes and stained with 50% hematoxylin for 30 minutes. After removing non-migrating cells from the top of the membrane with a cotton swab, the membrane was taken and mounted on the slide. Migrating cells on the underside of the membrane were observed and quantified under a high magnification microscope.

Figure 1A:
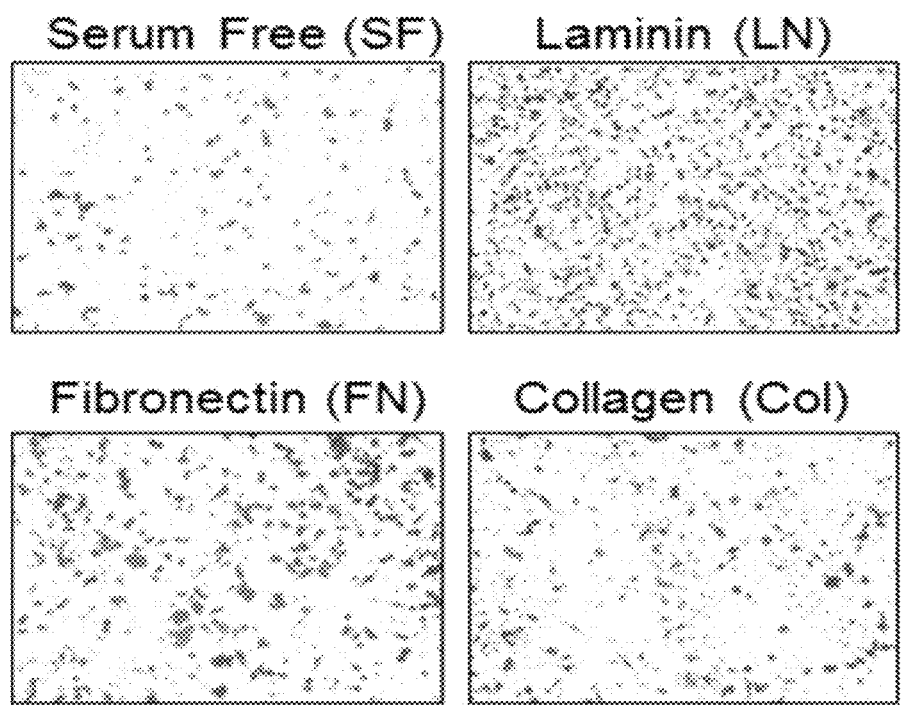
FIG. 1a shows microscope images of migrating cells as results of comparing the effects of collagen (Col), fibronectin (FN) and laminin (LN) on the immune cell (monocytes/macrophages) migration using a transwell migration assay.
Figure 1B:
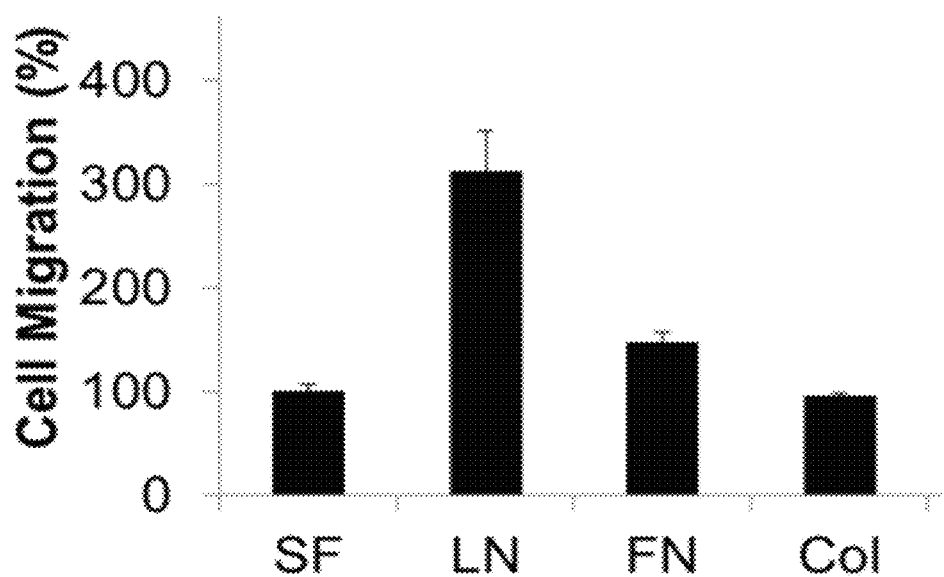

As shown in FIG. 1a and FIG. 1b, it was confirmed that laminin among various extracellular matrices most strongly promoted the migration of monocytes/macrophages. In other words, it was determined that the migration of monocytes/macrophages was most sensitive to the laminin (LN) signal among many extracellular matrices (ECM).

Figure 2A:
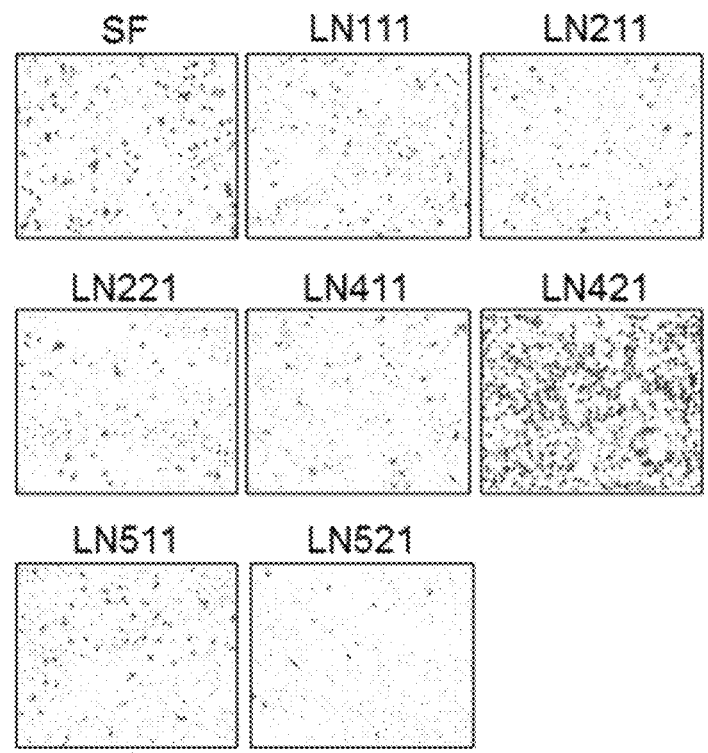
FIG. 2a shows microscope images of migrating cells as results of comparing the effects of various laminin subtypes (LN111, LN211, LN221, LN411, LN421, LN511, LN521) on the immune cell (monocytes/macrophages) migration by a transwell migration assay.
Figure 2B:
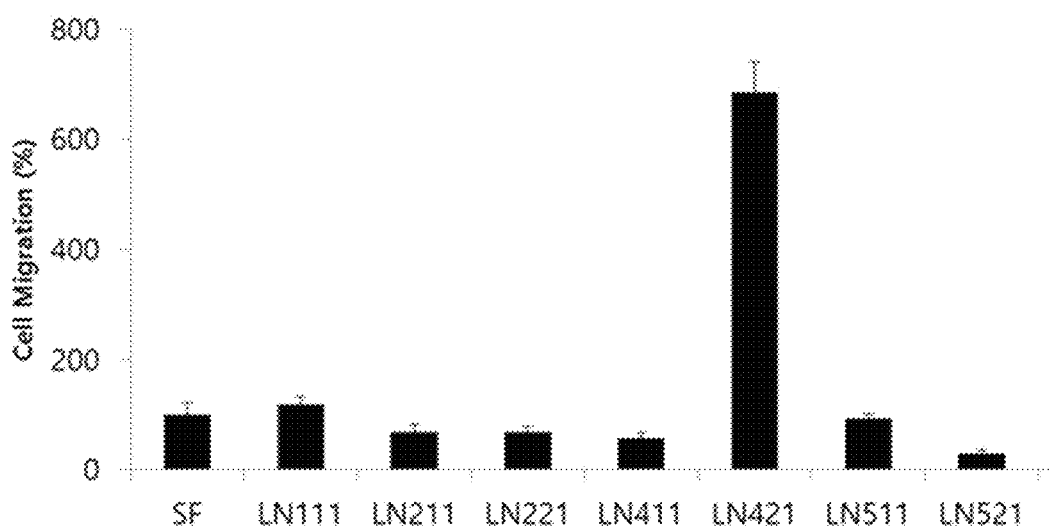
FIG. 2b is a graph showing the number of cells measured (quantitative) in the microscope image of FIG. 2A.

Example 2: Effect of Laminin Subtypes on the Immune Cell Migration and Infiltration Effect of laminin subtypes on the immune cell migration and infiltration was evaluated. A transwell migration assay was performed in the same manner as in Example 1 using LN111, LN211, LN221, LN411, LN421, LN511, and LN521 as various laminin subtype proteins (purchased from Biolamina). Specific sequences of laminin subtypes are referred to α4 chain of SEQ ID NO:4, α2 chain of SEQ ID NO: 10, α5 chain of SEQ ID NO: 11, β2 chain of SEQ ID NO:6, β1 chain of SEQ ID NO: 12, γ1 chain of SEQ ID NO: 8, according to the chain forming each laminin subtype, As shown in FIG. 2a and FIG. 2b, it was confirmed that monocytes/macrophages specifically reacted with α4β2γ1 subtype (LN421) among different laminins. That is, it was verified that the migration of monocytes/macrophages is specifically dependent on LN421 among various laminin types.

Example 3: Translocation of KRS from the Cytosol to the Plasma Membrane Induced by Treatment of Laminin in Immune Cells After dispensing RAW 264.7 cells (2×10$^6$ cells) in 100 mm dish and incubating for 18 hours, cells were treated with LN421 1 g/ml in serum free DMEM media and harvested at 0 hour, 12 hour, 24 hour. Proteins of RAW 264.7 cells were separated into the cytosol and membrane fractions using ProteoExtract Subcellular Proteome Extraction Kit (Calbiotech, cat #539790). Obtained proteins were electrophoresed and transferred to PVDF membrane (Milipore) and blocked with 3% skim milk. KRS was then detected by western blot. Specifically, KRS polyclonal antibody (rabbit, Neomics, Co. Ltd. #NMS-01-0005) was added and reacted for 1 hour. Unbound antibody was removed and the membrane was added and reacted with anti-rabbit secondary antibody (ThermoFisher Scientific, #31460). After reacting with the secondary antibody, films were exposed in the dark room using ECL reagent as a substrate. Photosensitized bands were compared to the standard molecular markers to identify the bands corresponding to the size of KRS. Antibodies against Na+/K+ ATPase (Abcam, ab76020) and tubulin (Santa cruz SC-5286) were used to identify the plasma membrane and cytosol markers, respectively.

Figure 3:
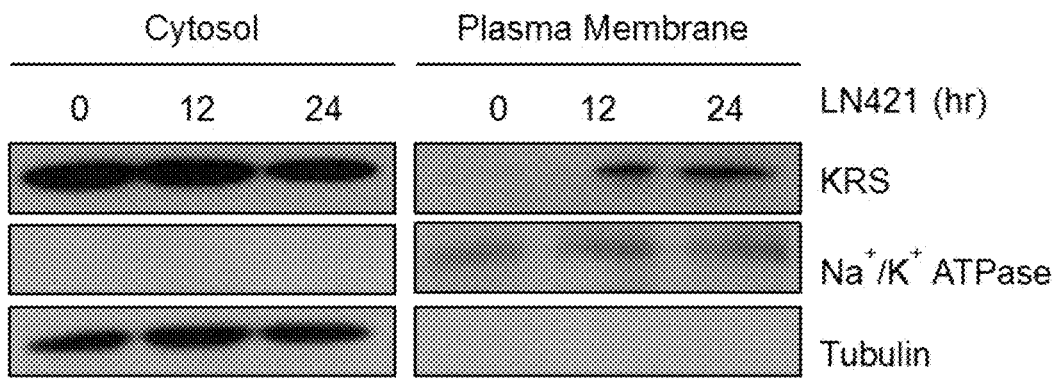
FIG. 3 shows the results of increase in the level of KRS in the plasma membrane of monocytes/macrophages by LN421 treatment using western blot.

As shown in FIG. 3, LN421 treatment in monocytes/macrophages increased the level of KRS detection in the plasma membrane fractions as compared with a partial decrease of KRS detection in the cytosol fractions. These results suggest that KRS, which is expressed in monocytes/macrophages and usually present in the cytoplasmic domain, translocates to the plasma membrane by LN421 treatment. This phenomenon of the plasma membrane-specific increase of KRS in immune cells is considered to be an important pathology for diseases related to the immune cell migration and invasion.

Example 4: Effect of KRS on the LN421-Dependent Immune Cell Migration and Infiltration To determine whether KRS influences the LN421-specific immune cell (especially monocyte/macrophage) migration, macrophages transformed to enhance or suppress KRS expression were treated with LN421, respectively, and a transwell migration assay was performed. As a control, leucyl-tRNA synthetase (LRS, SEQ ID NO:3), a protein similar to KRS, was used.

Specifically, KRS- or LRS-overexpressing macrophages were prepared as follows: KRS (SEQ ID NO:1)-Myc, LRS (SEQ ID NO:3)-Myc inserted in pcDNA3, respectively, were transfected into Raw 264.7 cells using Turbofect (ThermoFisher Scientific) (48 hours). Cells transfected with Ev (empty vector, pcDNA3)-Myc were prepared as a negative control.

Macrophages with suppressed KRS or LRS expression were prepared as follows: si-KRS (SEQ ID NO: 13) and si-LRS (SEQ ID NO:20) were transfected into Raw 264.7 cells, respectively, using Lipofectamin (ThermoFisher Scientific) (72 hours). As a negative control, cells transfected with si-control (si-RNA duplex with medium GC content (Invitrogen, Cat No. 12935-300)) were prepared.

Thus prepared transformed cells were examined and verified for upregulation or downregulation of KRS or LRS expression using western blot for each protein (data not shown).

For each of the transformed macrophages, a transwell migration assay was performed in the same manner as in Example 1 using 1 µg/ml of laminin 421.

Figure 4A:
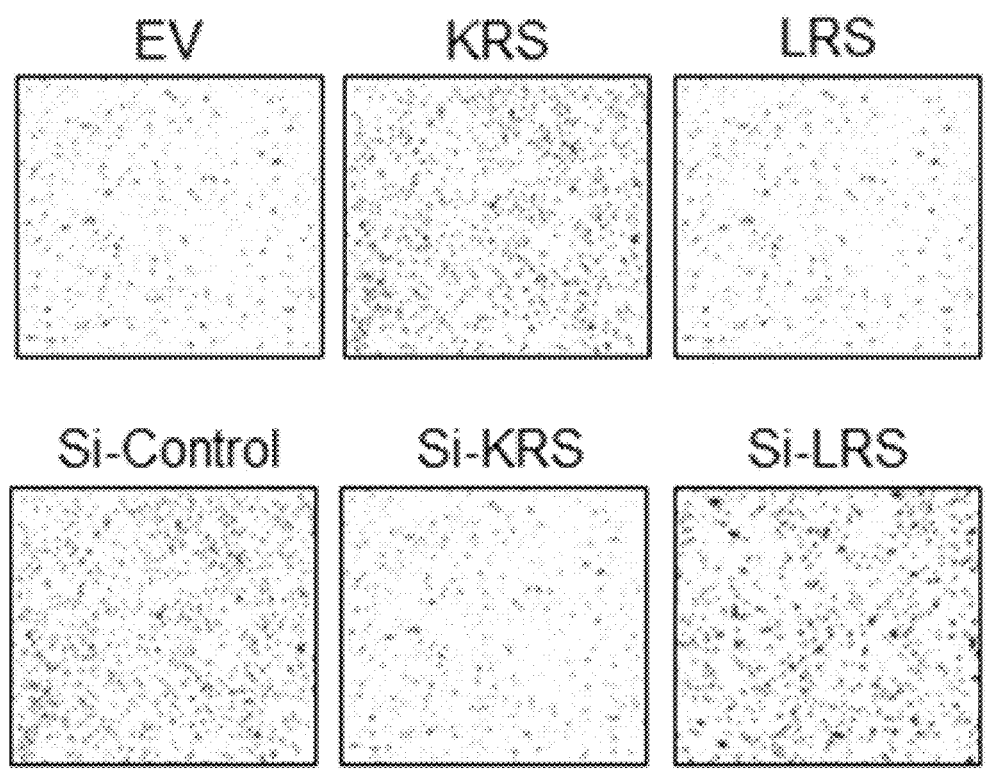
FIG. 4a shows microscope images of migrating cells as results of comparing the effect of the level of KRS expression on the LN421-specific migration of monocytes/macrophages using a transwell cell migration assay.
Figure 4B:
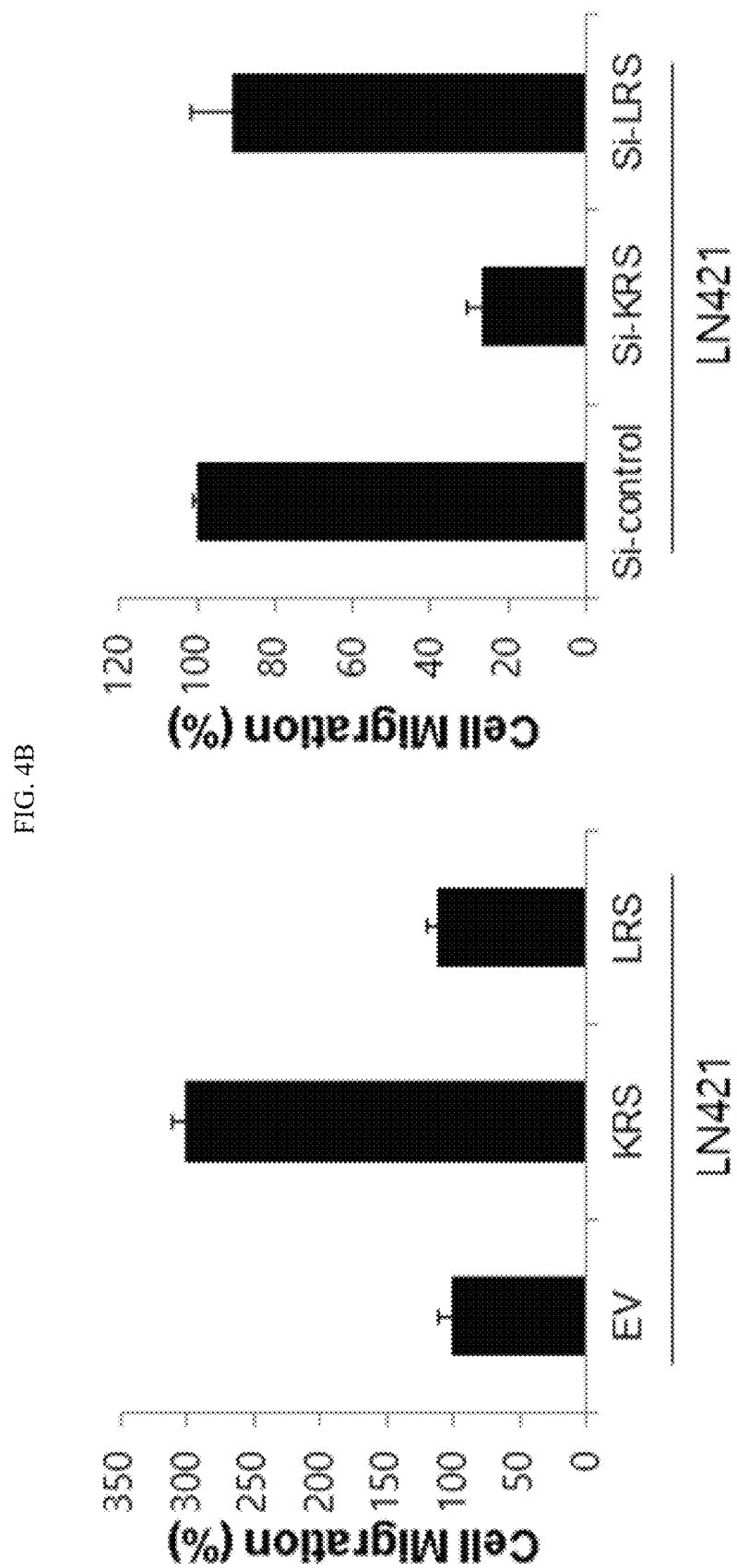

As shown in FIG. 4a and FIG. 4b, overexpression of KRS effectively increased the LN421-specific monocyte/macrophage migration, whereas downregulated KRS expression using si-RNA effectively prevented the LN421-specific monocyte/macrophage migration. In contrast, the expression of leucyl-tRNA synthetase (LRS), a KRS-like protein, did not affect monocyte/macrophage migration. This suggests that the LN421-dependent migration of monocyte/macrophage is strongly influenced by the level of KRS expression.

Example 5: Screening of Compounds Inhibiting the Immune Cell Migration: Compounds Inhibiting the Translocation of KRS to the Plasma Membrane Based on the results of Example 3 and Example 4, it was understood that not only the expression level of KRS but also the intracellular behavior of KRS significantly influences the LN421-dependent migration of monocyte/macrophage. In particular, the phenomenon in which KRS translocates to the plasma membrane, and increase its level in the membrane-specific manner in immune cells was considered to be an important pathology for the immune cell migration and infiltration-related diseases. Therefore, the aim of this study was to verify that inhibition of such pathological behavior of KRS could be one of the therapeutic strategies for immune cell migration and infiltration-related diseases. On the other hand, KRS is an organ necessary for synthesizing proteins in cells under normal conditions. Therefore, simply increasing or decreasing the amount of KRS is likely to be inadequate as a practical treatment strategy due to concerns about side effects on normal functioning. Thus, the present inventors screened compounds that affect intracellular kinetics, expression and activity in various aspects of KRS, and examined whether they can specifically inhibit the migration of monocyte/macrophage without side effects.

In particular, the screening method provided herein was used to find compounds that inhibit the translocation of KRS to the plasma membrane, and to identify and examine their therapeutic effects on diseases related to the immune cell migration. The specific methods are as follows.

First, in order to determine whether various KRS inhibitor candidates could exert inhibitory effect on the KRS translocation to the plasma membrane, RAW 264.7 cells ($2 \times 10^6$ cells) were dispensed in 100 mm dishes and incubated for 18 hours, followed by treatment with laminin 421 1 µg/ml in serum free DMEM, and 100 nM of each of various KRS inhibitor candidates, and cells were further incubated for 12 hours. After harvesting, proteins of RAW 264.7 cell were separated into the cytosol and membrane fractions using ProteoExtract Subcellular Proteome Extraction Kit (Calbiotech, cat #539790). Obtained proteins were electrophoresed and transferred to PVDF membrane (Milipore) and blocked with 3% skim milk. Afterwards, KRS was detected by western blot, and the specific method were as described in Example 3.

It was possible to determine tentatively that the inhibitor candidate actually suppressed the KRS translocation when the level of KRS was reduced specifically in the membrane fraction as relative to the cytosol fraction after the inhibitor treatment, by comparing the amount of KRS in each of the cytosol and membrane fractions before and after the treatment with inhibitor candidates.

Thus identified agents as inhibiting the translocation of KRS to the plasma membrane was added to the LN421-treated macrophages to perform a transwell migration assay. Through this, it was examined whether inhibition of KRS translocation to the plasma membrane had any inhibitory effect on the LN421-specific monocyte/macrophage migration. Specifically, transwells (Corning, #3421-5 mm) were coated with gelatin (0.5 mg/ml) and RAW 264.7 cells ($1 \times 10^5$ cells/well) were seeded in the top chambers. 500 µl of serum free DMEM containing 1 µg/ml of laminin 421 (LN421, Biolamina) was placed in the bottom chambers. Thereafter, DMSO, or KRS inhibitor compounds (in DMSO) were treated at various concentrations (30 nM, 100 nM, 300 nM, 1 µM, 3 µM, respectively) in the upper chambers. After 24 hours, cells were fixed with 70% methanol for 30 minutes and stained with 50% hematoxylin for 30 minutes. After removing non-migrating cells from the top of the membrane with a cotton swab, the membrane was taken and mounted on the slide. Migrating cells on the underside of the membrane were observed and quantified under a high magnification microscope.

Figure 5:
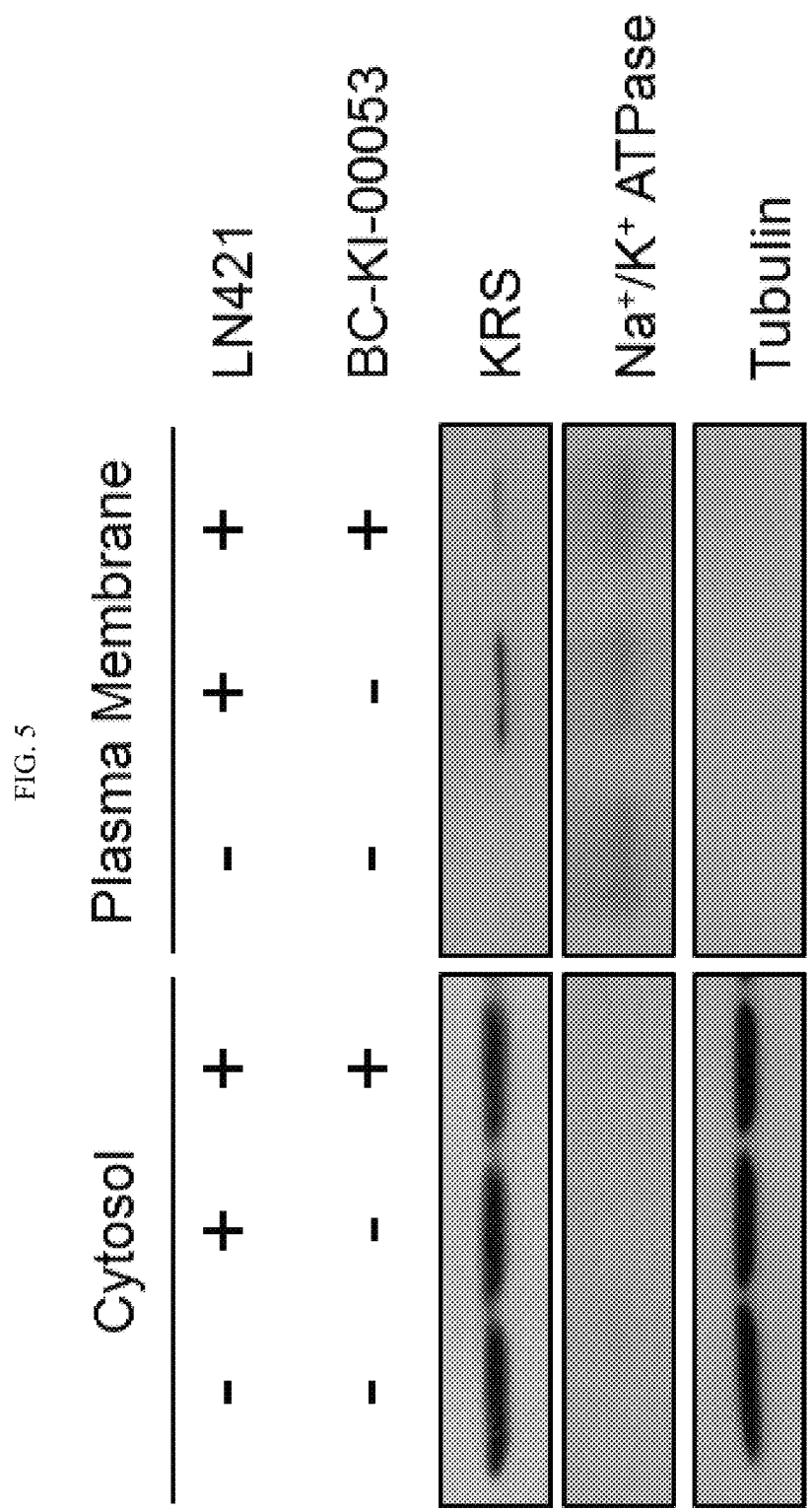
FIG. 5 shows the results that increase in the level of KRS in the plasma membrane induced by LN421 is reversed by treatment of a compound (BC-KI-00053) inhibiting KRS translocation to the plasma membrane.

FIG. 5 and FIG. 6 are results from experiments using representative examples of the compounds screened according to the present invention, BC-KI-00053 compound (4-({(7-fluorobenzo[d]thiazol-2-yl)[2-(4-methoxyphenyl)ethyl]amino}methyl)benzoic acid; Chemical Formula 1). As shown in FIG. 5, it was confirmed that the level of KRS in the plasma membrane region, previously increased by LN421 treatment, was significantly lowered by BC-KI-00053 treatment. This means that the level of KRS that was translocated to the plasma membrane of monocyte/macrophage by laminin (LN421) was reduced.

Figure 6B:
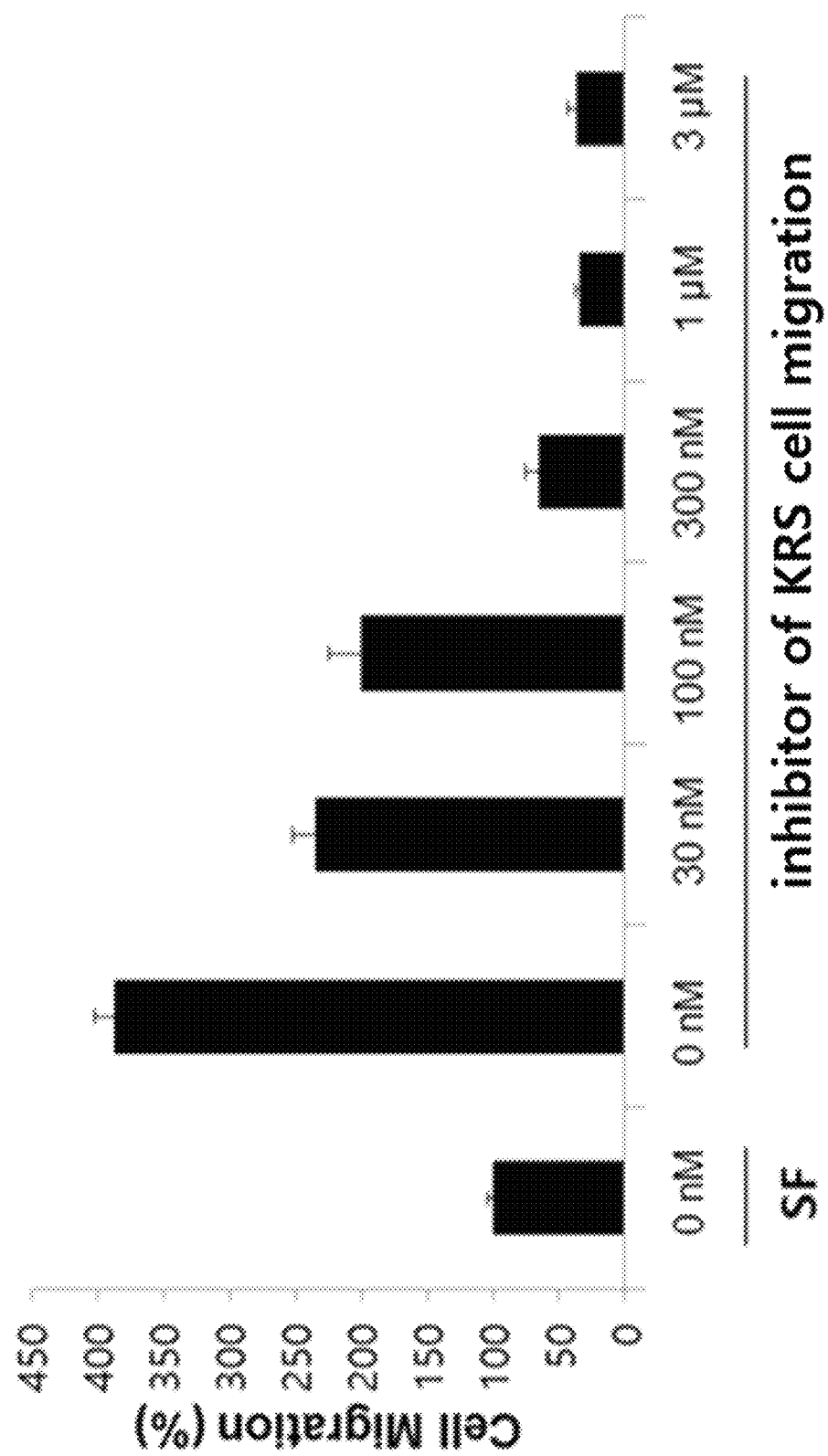

In addition, as shown in FIG. 6a and FIG. 6b, it was confirmed that the monocyte/macrophage migration was significantly inhibited depending on the concentration of BC-KI-00053 (compound inhibiting KRS translocation to the plasma membrane).

In the following in vivo experiments regarding immune cell migration-related diseases, BC-KI-00053 compound was used as a representative inhibitor candidate.

Example 6: Effect of the Inhibitor of KRS Translocation to the Plasma Membrane on the Monocyte/Macrophage Infiltration in the In Vivo Acute Inflammatory Responses Example 6-1: Ear Skin Wound Model To investigate the effect of the inhibitor of KRS translocation to the plasma membranes during monocyte infiltration in acute inflammatory responses, an ear skin wound model using CX3CR1-GFP mouse (Stock no. #005582, Jackson Laboratory, Bar Harbor, USA) was prepared. Monocytes, macrophages and Langerhans cells appear green in CX3R1-GFP mice. Mice were administered orally with vehicle or BC-KI-00053 (100 mg/kg, dissolved in vehicle, once daily) for a total of 4 days from 2 days prior to imaging (D−2, D−1, D−0, D+1). For a vehicle, corn oil:polyethylene glycol 400:Tween 80:methyl cellulose (1%)=20:30:1:49 was used. A 31G syringe was used to puncture the skin of the ear (time D−0) to induce acute inflammatory responses. Blood vessels were labeled using anti-CD31 antibody bound to Alexa Flour 555 (identifiable as red). Confocal microscopy was used as an imaging equipment.

As shown in FIG. 7a and FIG. 7b, it was observed that, in the vehicle-treated control group, monocytes and macrophages gathered around the wounded area (punctured ear area) indicated by the white circle, and infiltrated over a fairly wide range of area at a high level (blue circle). In contrast, infiltration of monocytes and macrophages was significantly reduced in mice administered with BC-KI-00053. Meanwhile, the green dots appearing to be scattered around the main tissue area rather than the main lesion (blue circle) in FIG. 7a and FIG. 7b are resident macrophages, Langerhans cells, the number of which was not affected by both in the vehicle- and BC-KI-00053-treated groups, suggesting that BC-KI-00053 treatment inhibited only the movement of migratory macrophages. From these results, it was confirmed that the migration and infiltration of immune cells induced during acute inflammatory responses were inhibited by administration of the inhibitor of KRS translocation to the plasma membrane (especially BC-KI-00053), which indicates that the compound can exert a prophylactic or therapeutic effect against inflammatory diseases by inhibiting the excessive migration of immune cells that secrete pro-inflammatory cytokines.

Example 6-2: Liver Ischemia-Reperfusion Injury Model

A liver ischemia-reperfusion injury model was prepared using CX3CR1-GFP mice to investigate the effect of inhibitors of KRS translocation to the plasma membrane on the monocyte infiltration during ischemic immune responses. Monocytes, macrophages and Kupffer's cells appear green in CX3CR1-GFP mice. Mice were orally administered with vehicle or BC-KI-00053 (100 mg/kg, dissolved in vehicle, once daily) for a total of three days beginning two days before imaging (D−2, D−1, D−0). For vehicle, corn oil: polyethylene glycol 400: Tween 80: methyl cellulose (1%)= 20:30:1:49 was used. On day 3 of oral administration (D−0), triad (bile duct, hepatic artery, hepatic vein) occlusion was performed using a 6-0 suture as shown in FIG. 8a. Triad occlusion was performed for 30 minutes to induce acute inflammation, and 3 g of Eppendorf tubes were suspended from both ends of the suture. Suture was removed and the ischemic inflammation site was observed immediately after reperfusion (0 hour) and 24 hours later. At this time, blood vessels were labeled with Alexa Flour 555-bound anti-CD31 antibody for repeated imaging (identifiable as red). Two-photon microscope was used as an imaging equipment.

As shown in FIG. 8b and FIG. 8c, it was observed in the vehicle-treated control mice that a large number of monocytes/macrophages were infiltrated into the wound site (occluded area) after 24 hours of reperfusion. In contrast, experimental group treated with BC-KI-00053 had significantly reduced monocyte/macrophage infiltration. In FIG. 8c, red bars are the quantified results of the control group and the green bars are of the BC-KI-00053 100 mg/kg administered group, respectively. Meanwhile, very bright green cells appearing to be scattered around the normal tissue mainly seen at reperfusion 0 hour in FIG. 8b are resident macrophages, Kupffer's cells, the number of which were not affect even at 24 hours after reperfusion in both control and BC-KI-00053-treated groups, suggesting that BC-KI-00053 treatment only suppressed the movement of migratory macrophages. In other words, the inhibitor of KRS translocation to the plasma membrane (particularly BC-KI-00053) have an excellent effect in inhibiting only monocyte/macrophage infiltration that migrates to the ischemia-induced liver.

Example 7: Therapeutic Effect of the Compound Inhibiting KRS Translocation to the Plasma Membrane in In Vivo Liver Fibrosis Hepatocytes appear red in Actin-DsRed mice (Stock no. #006051, Jackson Laboratory (Bar Harbor, USA)). In order to induce liver fibrosis in this mouse, $CCl_4$ (carbon tetrachloride) was dissolved in corn oil and injected intraperitoneally twice a week at a concentration of 20% for a total of 6 weeks. Three weeks after start of $CCl_4$ administration, vehicle and BC-KI-00053 (100 mg/kg) were administered orally, daily for three weeks. For vehicle, corn oil:polyethylene glycol 400:Tween 80:methyl cellulose (1%)=20:30:1: 49 was used. Animal groups were set up as shown in Table 1 below.

The degree of fibrosis on the surface and inside (area with a depth of 30-50 μm) of liver was detected by the Second Harmonic Generation (SHG) technique of intravial imaging (Excitation: 780 nm, Detection: 390 nm).

TABLE 1

| Group | | Treatment | Number of animals |
|---|---|---|---|
| Control | (1) | Corn oil-treated animal (normal) + vehicle administration | 1 |
| | (2) | Corn oil-treated animal (normal) + BC-KI-00053 administration | 1 |
| Experiment | (3) | $CCl_4$ liver fibrosis animal + vehicle administration | 2 |
| | (4) | $CCl_4$ liver fibrosis animal + BC-KI-00053 administration | 3 |

In the normal animal group administered with BC-KI-00053 (animal group (2) in Table 1), no weight loss was seen and no other symptoms occurred in the liver. Therefore, BC-KI-00053 compound was considered to be innocuous in vivo. Only the fibrosis animals administered with vehicle (animal group (3) in Table 1) died early 4 weeks after start of the experiment due to toxicity of $CCl_4$. Specifically, as shown in FIG. 9a, during the six weeks of the experiment, one died on day 24 and the other on day 32, and they showed significant weight loss. From these early deceased animals of experimental groups, fibrosis data of the surface and inside the liver were obtained at 2 weeks and 4 weeks before they died, and were used for data comparison after all experiments were completed, As shown in FIG. 9b, significant fibrosis was observed on the surface of the liver (FIG. 9b upper panel (0 μm)) after $CCl_4$ administration for 2 or 4 weeks. In particular, in the group administered with $CCl_4$ for 4 weeks, liver surface fibrosis was aggravated and portal-portal septa were observed as well, indicating that severe fibrosis had been progressing significantly. In addition, similar patterns of fibrosis were observed inside the liver (FIG. 9b bottom panel (30-48 μm)), and the serious extent of hepatocyte necrosis was found as well. On the other hand, the animal group treated with BC-KI-00053 for 3 weeks during treatment of CCl₄ for 6 weeks (animal group (4) in Table 1) exhibited greatly reduced fibrosis in the surface and inside the liver even compared to the group administer with CCl₄ for 2 weeks, expressing capsular collagen in a similar pattern to normal animals, and hepatocyte necrosis was noticeably reduced. In FIG. 9b, green represents collagen (fibrosis) and red represents hepatocytes. These experimental results show that the inhibitor of KRS translocation to the plasma membrane provided by the present invention (particularly, BC-KI-00053) has outstanding capacity of inhibiting fibrosis.

Example 8: Therapeutic Effect of an Inhibitor of KRS Translocation to the Plasma Membrane in In Vivo Liver Fibrosis Experimental Methods 1) Preparation of a Pulmonary Arterial Hypertension (PAH) Model and Administration of Test Compounds In order to induce PAH in 6-week-old female SD rats (Oriental Bio), 60 mg/kg of MCT (monocrotaline), a substance that causes pulmonary hypertension through pulmonary arterial injury, was injected subcutaneously. Then animals were divided into four groups (5 animals per group), and orally administered with vehicle, sildenafil (25 mg/kg, once daily) or BC-KI-00053 (25 or 50 mg/kg, dissolved in vehicle, once daily) for 3 weeks. Vehicle was corn oil: polyethylene glycol 400:Tween 80:methyl cellulose (1%)= 20:30:1:49.

2) Measurements of Blood Flow and Pressure

Three weeks later, rats were anesthetized with isoflurane, and blood flow and pressure were measured using an MPVS cardiovascular pressure and volume system (model name: MPVS Ultra, manufactured by Millar Instruments). Right ventricular systolic pressure (RVESP) and diastolic pressure, left ventricular systolic pressure and diastolic pressure were measured using a dedicated catheter (Mikro-Tip rat pressure catheter, manufactured by Millar Instruments). Cardiac output was measured using a perivascular blood flow probe (Transonic® Flowprobes, manufactured by Millar Instruments), and experimental techniques were performed in the same manner as described in the literature: Pacher P, Nagayama T, Mukhopadhyay P, Batkai S, Kass D A. Measurement of cardiac function using pressure-volume conductance catheter technique in mice and rats. *Nat Protoc* 2008, 3(9):1422-34.

3) Immunohistochemistry (IHC)

IHC staining for CD68, a monocyte/macrophage marker, was performed using lung tissues from each experimental group. Collected lungs were fixed in PFA (paraformaldehyde) according to the conventional procedure, and then embedded in paraffin through water washing, dehydration, and tissue clearing processes. Lung tissue paraffin blocks of rats were cut to a thickness of 6 m and slides were prepared. Thereafter, staining was performed as follows. First, three times for 5 minutes xylene treatment, 2 minutes in 100% ethanol twice, 95% ethanol, 90% ethanol, 70% ethanol, DW treatment for 2 minutes in this order and washed with PBS for 5 minutes (2 times). After treatment with 0.3% H₂O₂ (10 minutes), slides were washed twice with PBS for 5 minutes. Then slides were soaked in 0.01M citrate buffer of pH 6.0 and microwaved for 3 minutes and 30 seconds, then antigen retrieval of cooling for 10 seconds and reheating for 10 seconds was repeated for 10 minutes followed by 20 minutes of cooling at room temperature. Afterwards, slides were washed three times for 5 minutes with PBS-T (0.03% Triton-X). After 30 minutes blocking (2% BSA & 2% goat serum in PBS) at 4° C. anti-CD68 antibody (1:200, Abcam, ab31630) was treated overnight at 4° C. After washing three times with PBS-T for 5 minutes, slides were treated with polymer-HRP anti-mouse envision kit (DAKO) for 1 hour at 4° C. After washing 3 times with PBS-T for 5 minutes, 1 ml of DAB substrate buffer and 20 ul of DAB chromogen were mixed and treated with tissue. After 10 minutes when colors developed, slides were washed twice with tertiary distilled water. Stained tissues were treated with Mayer's hematoxylin (Sigma) for 1 minute, and then treated in the order of 70% ethanol, 90% ethanol, 95% ethanol, and 100% ethanol, twice for 2 minutes for each solution. Finally, after three times of xylene treatment for 5 minutes, cover slides were mounted using a mounting solution, and observed with an optical microscope.

Results

Pulmonary hypertension causes right ventricular pressure to rise due to narrowing of the pulmonary artery, resulting in right ventricular failure. In addition, if the reward mechanism is destroyed by persistent hypertension, right ventricular hypertrophy occurs followed by right ventricular enlargement. This results in compression of the left ventricle due to displacement of the ventricular septum and reduction of the left ventricular dilatation volume and cardiac output (Lee Woo-seok et al. Clinical Characteristics and Prognostic Factors in Patients with Severe Pulmonary Hypertension. *Korean Circulation J* 2007, 37:265-270). Ultimately, pulmonary hypertension is primarily associated with the right ventricle but also with the function of the left ventricle.

As shown in FIG. 10a, it was observed that RVESP (right ventricular systolic pressure) was increased in the PAH animal model, and treatment with BC-KI-00053 significantly reduced RVESP in a concentration dependent manner. In particular, the effect of lowering RVESP in BC-KI-00053 50 mg/kg treatment group was similar to that of sildenafil, one of the standard treatments.

In addition, there was no decrease in the left ventricular end systolic pressure (LVESP) following the treatment of BC-KI-00053, but rather, LVESP was increased in the BC-KI-00053 50 mg/kg administration group as shown in FIG. 10B. It was not statistically significant. This is in contrast to the risk of lowering systemic blood pressure in sildenafil, which is used as a treatment for pulmonary hypertension, causing expansion of the pulmonary artery as well as systemic artery. In other words, BC-KI-00053 showed a lower tendency to affect systemic artery pressure than sildenafil, and this effect is concerned with the risk of hypotension when sildenafil is administered in clinical settings. Considering this, it appears to be an advantageous property of therapeutic agent. In addition, when pulmonary hypertension is severe, as right ventricular failure occurs, low cardiac output and systemic hypotension may be accompanied. In contrast, treatment of BC-KI-00053 at higher concentrations may improve cardiac output and systemic blood pressure. If cardiac output and systemic blood pressure are lowered, patients may complain of general weakness or dizziness. Therefore, improvement of cardiac output and systemic blood pressure may be expected to improve these symptoms.

Taken together, administration of the inhibitor of KRS translocation to the plasma membranes (particularly BC-KI-00053) provided by the present invention not only exhibits therapeutic and alleviating effects on PAH, but also poses a relatively low risk of developing side effects of existing therapeutic drugs.

In addition, as shown in FIG. 10c, IHC staining of lung tissues from each experimental group for CD68, a monocyte/macrophage marker, showed that the lungs of PAH mice had high levels of monocyte/macrophage infiltration. In contrast, it was observed that treatment of the inhibitor of KRS translocation to the plasma membrane (especially BC-KI-00053) provided by the present invention clearly reduced lung tissue infiltration of monocytes/macrophages. These effects appeared to be noticeably superior to sildenafil which is previously known to have a therapeutic effect for PAH.

Example 9: Therapeutic Effect of the Inhibitor of KRS Translocation to the Plasma Membrane on In Vivo Hypertension-Induced Proteinuria, Glomerulosclerosis, Kidney and Heart Fibrosis Example 9-1: Effect of the Inhibitor of KRS Translocation to the Plasma Membrane on Hypertension Kidney Damage, Heart Damage and Fibrosis Development in the FHH Rat of Superimposed Hypertension Experimental Methods Experiments were performed using male FHH rats of 9-12 weeks of age. These animals were provided by the University of Mississippi Medical Center and approved by the American Association for Accreditation of Laboratory Animal Care (AAALAC). All protocols were approved by the Institutional Animal Care and Use Committee of the University of Mississippi Medical Center. Rats were fed ad libitum, and provided with a purified AIN-76 rodent feed containing 0.4% NaCl (Dyets, Bethlehem, Pa.) after weaning. Fawn-hooded hypertensive (FHH) rat is a genetic model of spontaneous hypertension associated with glomerular hyperfiltration and proteinuria. In order to promote glomerular damage in this rat, DOCA strips were implanted after single (one) kidney extraction.

Specifically, FHH rats were anesthetized with isoflurane and telemetry transmitters (model TA11PAC40, Data Sciences International, St. Paul, Minn.) were implanted as described in 'Williams, J. M. et al. *Im J Physiol Regul Integr Comp Physiol* (2012)'. Briefly, surgery was performed under 2% to 3% isoflurane-$O_2$, and the catheter of the device was inserted into the left femoral artery and guided upstream to the aorta. Body part of the telemetry unit was placed in the lateral cavity of the left leg and sutured with muscle tissue. Skin was then closed. To prevent infection, animals were given Baytril (10 mg/kg) and Rimadyl (5 mg/kg), a long-acting analgesic to control surgical pain. After surgery, rats were housed in individual cages in a quiet air-conditioned room environment with a 12:12 hour light-dark cycle and it took a week to fully recover from surgery. Thereafter, the basic mean arterial blood pressure (MAP) and proteinuria were measured for 4 hours (10 am to 2 μm) before the rats were housed in the metabolic cage. Proteinuria was measured using the Bradford method and BSA (Bio-Rad Laboratories, Hercules, Calif.) as a standard.

One week after the transmitter insertion, rats were uninephrectomized as described in Wang, X. et al. *Am J Physiol Renal Physiol* (2016). Briefly, rats were anesthetized with 2-3% isoflurane-$O_2$ and the right flank was dissected in aseptic condition. The right kidney was gently lifted and threaded tightly around the renal vessels and ureters. The right kidney was extracted by cutting the distal ends of the renal vessels and ureters. The incision was closed with a continuous subcutaneous stitch, after which the skin was further closed. After the rat's right kidney was removed, DOCA pellets (200 mg, Innovative Research of America) was subcutaneously implanted in the neck.

After single kidney extraction and DOCA transplant surgery, rats had recovery time for 3 days. Rats were provided with water containing 1% NaCl in place of distilled water, and randomly divided into two groups: Group 1 (n=15) was administered with BC-KI-00053 (25 mg/kg daily) by gastrointestinal gavage; Group 2 (n=15) was administered with the same volume (2.5 ml/kg daily) of vehicle (corn oil, polyethylene glycol 400, Tween 80 and methylcellulose) by gastrointestinal gavage. Blood pressure and proteinuria were measured weekly for 3 weeks in the experimental group. At the end of the experiment, rats were anesthetized with isoflurane and blood samples were taken to measure creatinine levels. Rats were then flushed with 50 ml of 0.9% NaCl through aorta and perfused with 20 ml of 4% paraformaldehyde. Kidneys and hearts were collected for histological evaluation.

Paraffin sections prepared with a thickness of 3 m were stained with Masson's trichrome to measure the degree of glomerular damage and renal interstitial fibrosis. Images were obtained using a Nikon Eclipse 55i microscope and NIS-Elements D 3.0 software equipped with Nikon DS-Fil color camera (Nikon, Melville, N.Y.). The degree of glomerular damage was assessed by the blinded experimenter, rating from 0 to 4+ for 30-40 μlomeruli/section. 0 represents normal glomeruli, 1+ represents 1~25% loss, 2+ represents 26~50% loss, 3+ represents 51~75% loss, and 4+ indicates more than 75% loss of capillaries in the tufts. Cortical and medulla fibrosis were analyzed using NIS-Elements automated measurement software after thresholding to determine the percentage of images stained in blue. In addition, immunohistochemical staining (IHC) for CD68, a monocyte/macrophage marker for kidney tissue, was performed in the same manner as in Example 8.

Statistics: Each data is expressed as mean±SEM. Comparisons between groups were analyzed by two-tailed test. P value $p<0.05$ was considered statistically significant.

Results

There was no difference in basal body weight between the vehicle treatment group and BC-KI-00053 treatment group (control group 309.57±4.14 g, experimental group 304.7±5.39 g, $p>0.05$). Body weight was reduced by approximately 10% in vehicle or BC-KI-00053-treated rats during the study period, but there was no statistical difference between the two groups (FIG. 11a).

MAP data measured via telemetry in control and experimental FHH rats are shown in FIG. 11b. There was no difference in basal MAP between two groups (control group 120.50±0.91 mmHg, experimental group 120.1±0.62 mmHg, $p>0.05$). MAP increased rapidly in both groups after uninephrectomy with DOCA pellet insertion and conversion to 1% NaCl water. Vehicle-treated group showed more abrupt increase in MAP than BC-KI-00053 treatment group. After one week of treatment, MAP of BC-KI-00053-treated group was statistically lower than vehicle-treated group (control group 184.34±2.46 mmHg, experimental group 174.4±3.83 mmHg, $p<0.05$). After two weeks of treatment, MAP results of vehicle-treated group appeared to be relatively stable compared to those of the first week. MAP in BC-KI-00053-treated group was further decreased, although temporarily, with a significant difference from vehicle-treated group (control group 184.22±4.21 mmHg, experimental group 168.8±3.74 mmHg, $p<0.05$). Three weeks later, mean MAP difference between the two groups widened (control group 195.30±3.68 mmHg, experimental group 176.9±5.83 mmHg, $p<0.05$).

Data for proteinuria in FHH rats of the control and experimental groups are shown in FIG. 11c. There was no difference in baseline proteinuria between two groups (control group 52.75±6.99 mg/day, experimental group 51.0±4.9 mg/day, p>0.05). After uninephrectomy with DOCA pellet insertion and conversion to 1% NaCl water, proteinuria increased in both groups. After two weeks of treatment, proteinuria in the BC-KI-00053-treated group was statistically lower than the vehicle-treated group (control group 472.99±53.81 mg/day, experimental group 285.5±47.48 mg/day, p<0.05). This trend continued until the study completed (control group 675.61±49.91 mg/day, experimental group 433.1±60.59 mg/day, p<0.05).

Data of plasma creatinine concentrations in FHH rats of the control and experimental are shown in FIG. 11d. Plasma creatinine concentration of vehicle-treated group was significantly higher than that of BC-KI-00053-treated group (control group 0.65±0.04 mg/dL, experimental group 0.48±0.02 mg/dL, p<0.05).

Uninephrectomy with DOCA pellet insertion followed by switching to 1% NaCl water in FHH rats had a morphologically significant effect on glomeruli and coronary injury (FIGS. 11e, 11f, 11g). Mean glomerular injury score (score) showed that the degree of injury was significantly reduced in the rats treated with BC-KI-00053 (control group 3.16±0.04, experimental group 1.49±0.05, p<0.05). In addition, fibrosis was significantly reduced in BC-KI-00053-treated group, whereas severe fibrosis progressed in the vehicle-treated group. Specifically, BC-KI-00053-treated rats showed significantly less cortical fibrosis (control group 19.46±1.18%, experimental group 5.79±0.48%, p<0.05), and loss of the straight arterioles (vasa recta) in renal medulla fibrosis and coronary injury was significantly reduced (control group 17.69±1.07%, experimental group 7.40±0.56%, p<0.05).

As seen in the sectioned tissue samples stained with Sirius red (FIG. 11h), control rats showed significant cardiac fibrosis, especially at the right ventricular insertion point. In contrast, the degree of cardiac fibrosis was significantly reduced in the rats treated with BC-KI-00053 (control group 31.97±2.62%, experimental group 9.14±2.18%, p<0.05).

In addition, as shown in FIG. 11i in which the degree of macrophage infiltration was examined IHC staining for CD68, a monocyte/macrophage marker, using kidney tissues indicated that high levels of monocyte/macrophage infiltration in the kidney tissues of the control group (vehicle treatment). With this finding, it was confirmed that the treatment of inhibitors of KRS translocation to the plasma membrane (especially BC-KI-00053) provided by the present invention significantly reduced renal tissue infiltration of monocytes/macrophages.

Example 9-2: Effect of the Inhibitor of KRS Translocation to the Plasma Membrane on Hypertension Kidney Damage, Heart Damage and Fibrosis Development in the Dahl SS (Salt Sensitive) Rat Experimental Methods Experiments were performed using male Dahl SS rats at 9-12 weeks of age. These animals were provided by the University of Mississippi Medical Center and approved by the American Association for Accreditation of Laboratory Animal Care (AAALAC). All protocols were approved by the Institutional Animal Care and Use Committee of the University of Mississippi Medical Center. Rats were fed ad libitum, and these rats were provided with a purified AIN-76 rodent feed containing 0.4% NaCl (Dyets, Bethlehem, Pa.) after weaning. Dahl salt-sensitive (SS) rat is an animal model that rapidly develops high hypertension, proteinuria, glomerulosclerosis and renal interstitial fibrosis on high salt (HS) diet.

Dahl SS rats were anesthetized with isoflurane and telemetry transmitters (model TA11PAC40, Data Sciences International, St. Paul, Minn.) were aseptically implanted in the same manner as described above. After surgery, rats were housed in individual cages in a quiet air-conditioned room environment with a 12:12 hour light-dark cycle and it took a week to fully recover from surgery. Then, the baseline mean arterial blood pressure (MAP) was measured before the rats were placed in the metabolic cage to measure urine protein excretion. Proteinuria was measured using the Bradford method and BSA (Bio-Rad Laboratories, Hercules, Calif.) as a standard.

Rats were then randomly divided into two experimental groups: Group 1 (n=15) was treated with BC-KI-00053 (25 mg/kg daily) by gastrointestinal gavage; Group 2 (n=15) was administered by gastrointestinal gavage with the same volume (2.5 ml/kg per day) of vehicle (corn oil, polyethylene glycol 400, Tween 80 and methyl cellulose). Simultaneously with the administration of agents, feed was changed to HS feed containing 8% NaCl (Dyets, Bethlehem, Pa.) and blood pressure and proteinuria were measured at 7, 14 and 21 days after starting HS feed. At the end of the experiment, rats were anesthetized with isoflurane and blood samples were taken to measure creatinine levels. Rats were then flushed with 50 ml of 0.9% NaCl through the aorta and perfused with 20 ml of 4% paraformaldehyde. Kidneys and hearts were collected for histological evaluation.

Paraffin section preparation and evaluations of the degree of glomerular damage, cortex and medulla fibrosis were performed as described above. In addition, immunohistochemical staining (IHC) for CD68, a monocyte/macrophage marker for kidney tissue, was performed in the same manner as in Example 8.

Statistics: Each data is expressed as mean±SEM. Comparison between groups was analyzed by two-tailed test. P value p<0.05 was considered statistically significant.

Results

There was no difference in baseline body weight between the vehicle- and BC-KI-00053-treated groups (control group 337.92±9.86 g, experimental group 350.13±9.173 g, p>0.05). Body weights were maintained or increased slightly in vehicle- or BC-KI-00053-treated rats, but there was no statistical difference between two groups during the entire study period (FIG. 12a).

MAP data measured via telemetry in the control and experimental Dahl SS rats are shown in FIG. 12b. There was no difference in baseline MAP between two groups (control group 122.13±2.31 mmHg, experimental group 123.45±2.36 mmHg, p>0.05). MAP increased continuously in both groups when Dahl SS rats were replaced with HS. Vehicle-treated group increased MAP more abruptly than BC-KI-00053-treated group. After 2 weeks of treatment, MAP of BC-KI-00053 treatment group was statistically decreased than the vehicle treated group (control group 178.51±3.71 mmHg, experimental group 164.43±3.00 mmHg, p<0.05), and this effect was seen continuously until the study completed (Control 201.65±2.54 mmHg, 178.48±3.49 mmHg, p<0.05).

Data of proteinuria in the control and experimental Dahl SS rats are shown in FIG. 12c. There was no difference in baseline proteinuria between two groups (control 133.82±10.50 mg/day, experimental group 113.27±8.06 mg/day, p>0.05). Conversion of Dahl SS rats into HS diet led to a sharp increase in proteinuria in both groups. In particular, vehicle-treated group was observed to increase proteinuria at a significantly higher degree than BC-KI-00053-treated group. After one week of treatment, proteinuria in BC-KI-00053-treated group was statistically lower than that of vehicle-treated group (control group 469.08±24.82 mg/day, experimental group 302.86±29.76 mg/day, p<0.05). After two weeks of treatment, the proteinuria levels in BC-KI-00053- and vehicle-treated groups were still clearly different (control group 675.61±59.67 mg/day, experimental group 510.64±42.42 mg/day, p<0.05), and this trend continued till the end of study (control group 752.97±57.80 mg/day, experimental group 524.55±44.70 mg/day, p<0.05).

Data of plasma creatinine concentrations in the control and experimental Dahl SS rats are shown in FIG. 12d. Plasma creatinine concentration in vehicle-treated group was significantly higher than BC-KI-00053-treated group (control group 0.60±0.02 mg/dL, experimental group 0.55±0.01 mg/dL, p<0.05).

Providing an HS diet had a significant effect on the glomerular and coronary injury morphologically in Dahl SS rats (FIGS. 12e, 12f, 12g). Mean glomerular injury score (score) showed that the degree of injury was significantly reduced in the rats treated with BC-KI-00053 (control group 2.82±0.05, experimental group 1.34±0.04, p<0.05). In addition, fibrosis was significantly reduced in the BC-KI-00053-treated group as well, whereas considerable fibrosis was progressed in the vehicle treatment group. Specifically, BC-KI-00053-treated rats showed significantly less cortical fibrosis (control group 19.48±0.96%, experimental group 6.47±0.46%, p<0.05), and loss of the straight arterioles (vasa recta) in renal medulla fibrosis and coronary injury was significantly reduced (control group 23.49±0.99%, experimental group 12.33±0.78%, p<0.05).

As seen in the sectioned samples stained with Sirius red (FIG. 12h), control rats showed significant cardiac fibrosis, especially at the right ventricular insertion point. In rats treated with BC-KI-00053, the rate of cardiac fibrosis was significantly reduced (control group 18.60±0.93%, experimental group 6.63±0.94%, p<0.05).

In addition, as shown in FIG. 12i, in which the degree of macrophage infiltration was examined, IHC staining for CD68, which is a monocyte/macrophage marker, using kidney tissues revealed that that the monocyte/macrophage infiltration occurred at a high level in the control kidneys (vehicle treatment). With this finding, it was confirmed that treatment of the inhibitor of KRS translocation to the plasma membrane (especially BC-KI-00053) provided by the present invention significantly reduced renal tissue infiltration of monocytes/macrophages.

Example 10: Effect of the Inhibitor of KRS Translocation to the Plasma Membrane on Kidney Fibrosis and Immune Cell Infiltration in the Animal Model of In Vivo Alport Syndrome The experiment was conducted using 129Sv/J mice (Boys town hospital). Animals groups were (i) 129Sv/J wild-type mice with vehicle administration (0.5% methyl cellulose suspension), (ii) 129Sv/J Alport mice (COL4A3 knockout mouse, Cosgrove D et al., Genes Dev. 1996 Dec. 1, 10(23): 2981-92) with vehicle administration (0.5% methyl cellulose suspension) (iii) 129Sv/J Alport mice with BC-KI-00053 administration. Each animal group consists of two mice. BC-KI-00053 was dissolved in 0.5% methyl cellulose suspension and orally administered at a concentration of 100 mg/kg, and kidney fibrosis and the immune cell infiltration were evaluated. Each animal group was treated with a control substance or a test agent once a day from 3 weeks of age for a total of 4 weeks. After 4 weeks of treatment, kidney paraffin sections were stained with collagen I (a marker of fibrosis) and CD45 to observe the extent of leukocyte infiltration. Evaluation of fibrosis and infiltration was performed in the same manner as in the above examples.

As can be seen in FIG. 13, the control group of Alport mice treat with vehicle (0.5% methyl cellulose) showed significantly progressed leukocyte infiltration and fibrosis in the kidneys. On the contrary, it was observed that the leukocyte infiltration and fibrosis were reduced down to the normal level (wild-type mouse-vehicle-administered group) in the kidneys of Alport mice treated with BC-KI-00053.

Example 11: Effect of Controlling the Immune Cell Migration/Infiltration by Anti-KRS Antibody It was examined whether an antibody specifically binding to KRS has an effect of controlling immune cell migration/infiltration. In this experiment, an antibody consisting of a heavy chain of SEQ ID NO:21 and a light chain of SEQ ID NO:23 was used representatively as an anti-KRS antibody. In the present specification, the antibody was referred to as N3 (monoclonal) antibody.

The specific experimental methods are as follows. Transwell (Corning #3421-5 mm) was coated with gelatin (0.5 mg/ml), and then RAW 264.7 cells ($1 \times 10^5$ cells/well) were seeded into the top chambers. Serum free DMEM (500 µl) containing laminin 421 (1 µg/ml) was placed in the bottom chambers. Anti-KRS antibody (N3 antibody) was treated at 100 nM concentration in the top chambers. After 24 hours, cells were fixed with 70% Methanol for 30 minutes and then stained with 50% hematoxylin for 30 minutes. After removing non-migrating cells in the upper part of the membrane with a cotton swab, the membrane was taken and mounted on the slide. Migrating cells present on the underside of the membrane were observed under a high magnification microscope (FIG. 14a), and the number of cells in the obtained image was measured and displayed graphically (FIG. 14b).

In addition, RAW 264.7 cells were treated with laminin 421 (1 µg/ml) and anti-KRS antibody (100 nM) for 24 hours and harvested. Then samples were prepared by separating into the cytosol and membrane fractions using ProteoExtract subcellular proteom extraction kit (Calbiochem), and subjected to western blot. Specific methods of western blot is as described in Example 3.

As a result, it was confirmed that anti-KRS antibody (N3 antibody) effectively inhibited the LN421-dependent monocyte/macrophage migration, which is shown in FIG. 14a and FIG. 14b. In addition, as shown in FIG. 14c, LN421 treatment increased the KRS level in the plasma membrane of monocytes/macrophage, whereas anti-KRS antibody (N3 antibody) treatment effectively downregulate the level of KRS on the plasma membrane. These findings suggest that anti-KRS antibody could be a novel therapeutic for diseases where the migration of immune cells, such as monocytes/macrophages, poses a problem.

On the other hand, the present inventors found out that KRS translocated from the cytoplasm to the plasma membrane, and KRS in the plasma membrane sometimes got embedded in the membrane with a part of N-terminal regions of the protein exposed to the extracellular space (typically 1 to 72 amino acid residues in the N-terminal regions of KRS (preferably, SEQ ID NO:1)). Accordingly, it is thought that an antibody which can bind to the N-terminus of KRS among anti-KRS antibodies could have significant advantages in vivo in terms of inhibiting the immune cell migration. Of course, it is apparent to those skilled in the art that even an anti-KRS antibody targeting different regions of KRS other than the extracellularly exposed region can be used for treatment because it can still inhibit KRS activity through further treatment for its intracellular penetration.

Representatively, N3 antibody is the antibody capable of binding to the N-terminus of KRS, and the treatment of this antibody specifically decreased KRS level in the plasma membrane of immune cells (FIG. 14c), and showed inhibitory effect on the immune cell migration (FIG. 14a and FIG. 14b). As shown in FIG. 15, endocytosis occurred when the antibody binds to an extracellularly exposed KRS region (particularly, N-terminal region). This suggest that active removal of KRS, which are already present in the plasma membrane, by applying substances (agents) specifically binding to KRS (particularly, N-terminus exposed to the outside the cell) can suppress the immune cell migration and treat associated diseases, as well as hindering KRS translocation from the cytoplasm to the plasma membrane.

Example 12: Therapeutic Effect of Anti-KRS Antibody in the In Vivo PAH Model

Experimental Methods
1) Preparation of a PAH Model and Administration of Test Compounds To induce PAH in 7-week-old SD rats (Orient bio), 60 mpk of MCT (monocrotaline) was subcutaneously injected. Then rats were divided into 4 groups (5 animals in each group), and administered with either of 1 mpk of mock human IgG (Thermo Fisher Scientific, negative control), 1 mpk or 10 mpk of anti-KRS antibody (N3 antibody), 25 mpk of sildenafil (positive control) for 3 weeks. All antibodies were intravenously injected twice a week and sildenafil was orally administered everyday.

2) Measurements of Blood Flow and Pressure

Three weeks later, rats were anesthetized with isoflurane, and blood flow and pressure were measured using an MPVS cardiovascular pressure and volume system (model name: MPVS Ultra, manufactured by Millar Instruments). Right ventricular systolic pressure (RVESP) and diastolic pressure, left ventricular systolic pressure and diastolic pressure were measured using a dedicated catheter (Mikro-Tip rat pressure catheter, manufactured by Millar Instruments). Cardiac output was measured using a perivascular blood flow probe (Transonic® Flowprobes, manufactured by Millar Instruments), and experimental techniques were performed in the same manner as described in the literature: Pacher P, Nagayama T, Mukhopadhyay P, Batkai S, Kass D A. Measurement of cardiac function using pressure-volume conductance catheter technique in mice and rats. *Nat Protoc* 2008, 3(9):1422-34.

3) Immunohistochemistry (IHC)

Collected lungs were fixed in PFA (paraformaldehyde) according to a conventional procedure, and then embedded in paraffin through water washing, dehydration, and tissue clearing processes. Lung tissue paraffin blocks of rats were cut to a thickness of 6 m and slides were prepared. Thereafter, staining was performed as follows. First, slides were treated with xylene 3 times for 5 minutes, followed by treatments with 100% ethanol, 95% ethanol, 90% ethanol, 70% ethanol, DW for 2 minutes in this order and washed with PBS for 5 minutes. After treatment with 0.3% $H_2O_2$, slides were washed twice with PBS for 5 minutes. After soaking in 0.01M citrate buffer and heating, slides were washed with PBS-T (0.03% tween 20). After 30 minutes blocking at room temperature (2% BSA & 2% goat serum in PBS), tissues were stained with anti-CD68 antibody (1:200, ED1 clone, Abcam) overnight at 4° C. After washing three times with PBS-T for 5 minutes, tissues were treated with polymer-HRP anti-mouse envision kit (DAKO) for 1 hour at 4° C. After washing three times with PBS-T, color was developed by treatment with DAB substrate buffer and DAB chromogen 20. Thus stained tissues were treated with Mayer's hematoxylin (Sigma) for 1 minute, and then treated twice for 2 minutes in the order of 70% ethanol, 90% ethanol, 95% ethanol, and 100% ethanol. Finally, xylene was treated three times for 5 minutes and observed with an optical microscope.

Results 12-1. Changes in the Blood Pressure and Cardiac Output

A PAH model, in which the immune cell infiltration is deeply related to pathology, was treated with anti-KRS antibody (N3 monoclonal antibody) at 1 mpk or 10 mpk for 3 weeks (i.e., twice a week). Subsequently, measurements of right ventricular end-systolic pressure (RVESP), right ventricular end-diastolic pressure (RVEDP), left ventricular end-systolic pressure (LVESP), left ventricular end-diastolic pressure (LVEDP) and cardiac output (CO) were carried out and the results are shown in Table 2.

TABLE 2

|  | MCT + Mock IgG (n = 4) | MCT + N3 Ab 1 mpk (n = 5) | MCT + N3 Ab 10 mpk (n = 5) | MCT ± sildenafil (n = 5) |
|---|---|---|---|---|
| RVESP (mmHg) | 62.5 ± 5.7 | 45.0 ± 8.1 | 41.2 ± 7.7 | 48.4 ± 9.6 |
| RVEDP (mmHg) | 2.8 ± 1.5 | 1.4 ± 2.2 | 3.8 ± 1.3 | 2.6 ± 1.3 |
| LVESP (mmHg) | 81.5 ± 11.4 | 95.8 ± 4.8 | 93.4 ± 11.3 | 83.2 ± 4.7 |
| LVEDP (mmHg) | 1.0 ± 0.8 | 2.6 ± 1.9 | 4.6 ± 3.9 | 3.6 ± 2.3 |
| CO (ml/min) | 58 ± 4.7 (n = 4) | 74.0 ± 10.9 (n = 5) | 59.8 ± 12.9 (n = 5) | 49.6 ± 17.7 (n = 4) |

(1 animal in MCT + mock IgG-treated group died during anesthetization. 1 animal in the sildenafil-treated group died during surgery and CO could not be measured.)

Pulmonary hypertension causes the right ventricular pressure to increase due to narrowing of the pulmonary artery, resulting in right ventricular failure. In addition, if the reward mechanism is destroyed by persistent hypertension, right ventricular enlargement is followed by right ventricular hypertrophy. This results in compression of the left ventricle due to displacement of the ventricular septum and reduction of the left ventricular dilatation volume and cardiac output (Lee Woo-seok et al. Clinical Characteristics and Prognostic Factors in Patients with Severe Pulmonary Hypertension. *Korean Circulation J* 2007, 37:265-270). As a result, pulmonary hypertension is primarily associated with the right ventricle but also with the function of the left ventricle.

RVESP is increased in PAH patients, which was also confirmed in the PAH animal model of this experiment. In contrast, as shown in FIG. 16, anti-KRS antibody (N3 antibody) significantly reduced RVESP at both concentrations, especially better than a positive control drug, sildenafil.

In addition, there was no decrease in left ventricular end systolic pressure (LVESP) following administration of anti-KRS antibody (N3 antibody), but rather significant increase in LVESP was observed as shown in FIG. 17. This is in contrast with the risk of lowering systemic blood pressure when causing expansion of not only the pulmonary arteries, but also the arteries in general as in the case of sildenafil, which is used as a conventional treatment for pulmonary hypertension. In other words, it is observed that N3 antibody tended to affect systemic artery pressure much less than sildenafil, which is considered to be a very advantageous characteristics of a therapeutic agent, given that there are situations when the risk of hypotension is concerned with sildenafil administration in the clinical settings. In addition, severe pulmonary hypertension may be accompanied by low cardiac output and systemic hypotension as systolic right ventricle failure occurs. Regarding this, anti-KRS antibody (especially N3 antibody) is expected to stabilize the blood pressure by increasing the cardiac output and systemic blood pressure by alleviating PAH.

Taken together, it was confirmed that administration of anti-KRS antibody (N3 antibody) has effects of alleviating and treating PAH symptoms, improving the possibility of side effects of existing therapeutic drugs.

12-2. Echocardiography

Findings of D-shaped left ventricle suggesting pressure overload in the right ventricle were observed in three mice treated with MCT alone (i.e., non-administered PAH model) and three mice treated with MCT+sildenafil, but non in the therapeutic antibody (anti-KRS antibody)-treated group.

In addition, as shown in Table 3 below, the body weight of each group was increased to a similar extent and there was no significant difference. In other words, no abnormal findings including abnormal weight loss by therapeutic antibody administration were observed.

TABLE 3

|  | MCT + Mock IgG (n = 4) | MCT + Ab 1 mpk (n = 5) | MCT + Ab 10 mpk (n = 5) | MCT + sildenafil (n = 5) |
|---|---|---|---|---|
| Absolute change (g) | 101.4 ± 14.2 | 113.5 ± 14.6 | 104.1 ± 12.3 | 104.1 ± 26.4 |
| Relative change (%) | 48.8 ± 7.8 | 43.6 ± 5.2 | 40.7 ± 5.0 | 49.8 ± 10.5 |

12-3. Monocyte/Macrophage Migration and Infiltration

IHC staining for CD68, a monocyte/macrophage marker, was performed using lung tissues from each experimental group. As shown in FIG. 18, it was observed that anti-KRS antibody (N3 antibody)-treated group had clearly reduced lung tissue infiltration of monocytes/macrophages, and this effect was remarkably superior to sildenafil.

Example 13: Effect of Anti-KRS Antibody in the In Vivo Acute Lung Injury Model

Experimental Methods

1) Preparation of an LPS-Induced Acute Lung Injury Model and Administration of Test Compounds The acute lung injury model was prepared by intratracheal injection of 2.5 mg/kg LPS (Sigma) into 7-week-old male C57BL/6 mice (DooYeol biotech).

In order to investigate the effect of KRS inhibitors on acute lung injury, C57BL/6 mice were first intravenously injected with N3 antibody at the concentration of 1 mg/kg or 10 mg/kg, and after 24 hours, LPS 2.5 mg/kg was intratracheally injected. After 24 hours of LPS injection, each mouse was sacrificed to collect and analyze lung tissues and bronchoalveolar lavage fluid (BALF).

2) Cell Counting of Immune Cells in BALF (Bronchoalveolar Lavage Fluid)

BALF obtained by washing the lungs with PBS was collected and centrifuged at 800×g for 10 minutes at 4° C. to collect pellets. After cells were suspended, red blood cells were removed using RBC lysis buffer (eBioscience cat no. 00-4333-57). After stopping the reaction with PBS, cells were washed twice, and resuspended in 400 µl PBS to measure the number of cells by hemocytometer. The number of neutrophils were counted by hema3 staining.

3) FACS of Immune Cells in the Lung Tissues

Lung tissues were collected and rotated at 37° C. for 45 minutes using gentleMACS Octo Dissociator (MACS Miltenyi Biotec, order no. 130-095-937) to smash the tissues. Tissues were then filtered using a cell strainer (40 m) and centrifuged at room temperature for 5 minutes at 1500 rpm. Pellet was collected and red blood cells were removed using RBC lysis buffer (eBioscience cat. no. 00-4333-57). Cells were collected and resuspended in FACS buffer (PBS containing 1% NaN3 and 3% FBS), and 50 µl of the cell suspension was placed in a tube, mixed well with the same amount of antibody, and stained at 4° C. for 1 hour, protecting from light. FITC rat anti-CD11b (BD Pharmingen) and PE rat anti-mouse F4/80 (BD Pharmingen) antibodies were used to analyze the migration of interstitial macrophage (IM) to the lung. After washing twice at 400×g for 5 minutes using FACS buffer, it was analyzed by Navios flow cytometer (Beckman).

4) Masson's Trichrome Staining of the Lung Tissues

Lung tissues were embedded in paraffin in the conventional manner and then sectioned. Thereafter, the tissue slides from which paraffin was removed using xylene was washed with DW, and then treated with Bouin fluid for 1 hour at 56-60° C. Tissues were then stained with Weigert's iron hematoxylin solution for 10 minutes, washed, and then stained again with Biebrich scarlet-acid fuchsin solution for 10-15 minutes and washed. Stained tissues were treated with phosphomolybdic-phosphotungstic acid solution for 10-15 minutes, transferred to aniline blue solution and stained for 5-10 minutes. After washing, stained tissues were treated with 1% acetic acid solution for 2-5 minutes. After washing and dehydration, stained tissues were treated with xylene and mounted.

Results 13-1. Inhibitory Effect on the Immune Cell Migration in BALF

As shown in FIG. 19, it was confirmed that the total immune cell counts in BALF were increased in mice with acute lung injury induced by LPS treatment, which were reduced by anti-KRS antibody (N3 antibody) treatment in a concentration-dependent manner.

In particular, as shown in FIG. 20, it was observed that a large increase in neutrophils in mice with LPS-induced acute lung injury, and again anti-KRS antibody (N3 antibody) treatment reduced these neutrophil counts. With this finding, it was confirmed that anti-KRS antibody treatment significantly inhibited the infiltration of immune cells in BALF, especially neutrophils into the lungs.

13-2. Inhibitory Effect on the Immune Cell Migration in the Lung Tissues

FIG. 21a and FIG. 21b show the results of FACS analysis of macrophages migrated to lung tissues due to acute lung injury. Interstitial macrophages (IM) are CD11b+/F4/80+ cells, which are migrating macrophages that do not reside in the lung but migrate to the lung in certain situations. LPS treatment increased the infiltration of IM into the lung, but anti-KRS antibody (N3 antibody) treatment reduced this in a concentration-dependent manner. Through this, it was confirmed that the migration and infiltration of immune cells such as macrophages/monocytes into the lung tissue is inhibited by Anti-KRS antibody treatment.

Excessive migration and infiltration of immune cells, such as macrophages/monocytes, is an important pathology in tissue fibrotic disease. As a result of Masson's trichrome staining of the lung tissues from the acute lung injury model (FIG. 22), it was also verified that fibrosis in the lung tissues proceeded considerably, but it was suppressed by anti-KRS antibody (N3 antibody) treatment.

INDUSTRIAL APPLICABILITY

As explained so far, the present invention relates to a therapeutic agent for immune cell migration-caused diseases and a method for screening the same and, more particularly, to a pharmaceutical composition comprising a KRS inhibitor (expression or activity inhibitor) as an effective ingredient for preventing or treating an immune cell migration-related disease, a method for controlling the migration of immune cells by regulating a level of KRS in immune cells, a level of KRS specifically present at a plasma membrane location or the translocation of KRS to the plasma membrane, and a method for screening a therapeutic agent for immune cell migration-caused diseases, using KRS. According to the present invention, the migration of immune cells can be controlled by means of KRS, which can find very useful application in the prevention, alleviation, and treatment of immune cell migration-related diseases, therefore industrial applicability is very high.

What is claimed is:

1. A method for identifying an agent for treating an immune cell migration-related disease selected from the group consisting of a cardiovascular disease, a fibrotic disease, an inflammatory disease, and Alport disease, the method comprising:
    contacting an immune cell selected from the group consisting of a monocyte, a macrophage, a neutrophil, an eosinophil, a basophil, a dendritic cell, a natural killer cell, a megakaryocyte, a T cell, and a B cell with a laminin and a candidate agent selected from the group consisting of a siRNA, shRNA, miRNA, ribozyme, DNAzyme, peptide nucleic acid (PNA), antisense nucleotide, antibody, aptamer, peptide, peptide mimetic, substrate analog, natural extract, and synthetic compound, wherein the immune cell is contacted with the laminin and the candidate agent simultaneously, or the immune cell is contacted sequentially with the candidate agent followed by the laminin or with the laminin followed by the candidate agent;
    performing an assay to measure a level of lysyl tRNA synthetase (KRS) at the plasma membrane of the immune cell or a level of KRS translocated to the plasma membrane of the immune cell, wherein the KRS comprises an amino acid sequence as set forth in SEQ ID NO: 1; and
    identifying an agent that lowers the level of KRS at the plasma membrane of the immune cell or the level of KRS translocated to the plasma membrane of the immune cell relative to the immune cell prior to the contacting step,
    whereby an agent for treating the immune cell migration-related disease is identified.

2. The method of claim 1, wherein the assay comprises separating the cytosol and membrane fraction of the immune cell after the contacting step and measuring a first level of KRS in the separated cytosol and a second level of KRS in the membrane fraction.

3. The method of claim 2, wherein measuring the first and second levels of the KRS comprises binding an anti-KRS antibody to KRS present in the separated cytosol and membrane fraction.

4. The method of claim 3, comprising transferring the separated cytosol and membrane fraction to a solid support and incubating the anti-KRS antibody with the solid support under conditions sufficient to bind the anti-KRS antibody to KRS present on the solid support.

5. A method for identifying an agent that reduces lysyl tRNA synthetase (KRS) at the plasma membrane of an immune cell, the method comprising:
    contacting an immune cell selected from the group consisting of a monocyte, a macrophage, a neutrophil, an eosinophil, a basophil, a dendritic cell, a natural killer cell, a megakaryocyte, a T cell, and a B cell with laminin and a candidate agent selected from the group consisting of a siRNA, shRNA, miRNA, ribozyme, DNAzyme, peptide nucleic acid (PNA), antisense nucleotide, antibody, aptamer, peptide, peptide mimetic, substrate analog, natural extract, and synthetic compound, wherein the immune cell is contacted with the laminin and the candidate agent simultaneously, or the immune cell is contacted sequentially with the candidate agent followed by the laminin or with the laminin followed by the candidate agent;
    performing an assay to measure a level of lysyl tRNA synthetase (KRS) at the plasma membrane of the immune cell or a level of KRS translocated to the plasma membrane of the immune cell, wherein the KRS comprises an amino acid sequence as set forth in SEQ ID NO: 1; and
    identifying an agent that reduces KRS at the plasma membrane of the immune cell or KRS translocated to the plasma membrane of the immune cell relative to the immune cell prior to the contacting step,
    whereby an agent that reduces lysyl tRNA synthetase (KRS) at the plasma membrane of the immune cell or KRS translocated to the plasma membrane of the immune cell is identified.

* * * * *